(12) United States Patent
Buchardt et al.

(10) Patent No.: US 6,710,163 B1
(45) Date of Patent: Mar. 23, 2004

(54) PEPTIDE NUCLEIC ACID SYNTHONS

(76) Inventors: Ole Buchardt, Søndergårdsvej 73, 3500 Værløse (DK); Michael Egholm, Sindshvilevej 5, 3. tv., 2000 Frederiksberg (DK); Peter Eigil Nielsen, Hjortevænget 509, 2980 Kokkedal (DK); Rolf Henrik Berg, Langelandsvej 20 B, 3. tv., 2000 Fredericksberg (DK)

( * ) Notice: Subject to any disclaimer, the term of this patent is extended or adjusted under 35 U.S.C. 154(b) by 348 days.

(21) Appl. No.: 08/468,719

(22) Filed: Jun. 6, 1995

Related U.S. Application Data

(62) Division of application No. 08/108,591, filed as application No. PCT/EP92/01219 on May 22, 1992, now Pat. No. 6,395,474.

(30) Foreign Application Priority Data

| May 24, 1991 | (DK) | 0986/91 |
| May 24, 1991 | (DK) | 0987/91 |
| Apr. 15, 1992 | (DK) | 0510/92 |

(51) Int. Cl.[7] .................. C12Q 1/68; A61K 38/00; C07H 21/00

(52) U.S. Cl. .................. 530/300; 435/6; 436/501; 536/23.1

(58) Field of Search ............... 435/5, 6, 810; 436/501; 536/22.1, 23.1, 24.1, 24.3–24.33, 25.3; 935/77, 78; 530/300

(56) References Cited

U.S. PATENT DOCUMENTS

| 5,340,716 A | | 8/1994 | Ullman et al. ............ 435/6 |
| 5,539,082 A | * | 7/1996 | Nielsen et al. ........... 530/300 |
| 5,773,571 A | * | 6/1998 | Nielsen et al. ........... 530/300 |
| 5,786,461 A | * | 7/1998 | Buchardt et al. .......... 536/18.7 |

FOREIGN PATENT DOCUMENTS

| WO | WO 86/05518 | 9/1986 |
| WO | WO 90/02749 | 3/1990 |
| WO | WO 92/20702 | 11/1992 |

OTHER PUBLICATIONS

Akashi et al. "New Aspects of Polymer Drugs", *Adv. Polym. Sci.*, 97:108–146, 1990.

Almarsson, O. et al., "Molecular Mechanics Calculations of the Structures of Polyamide Nucleic Acid DNA Duplexes and Triple Helical Hybrids", *PNAS USA* 1993, 90, 7518–7522.

Almarsson, O. and Bruice, "Peptide Nucleic Acid (PNA) Conformation and Polymorphism in PNA–DNA and PNA–RNA Hybrids", *PNAS USA* 1993, 90, 9542–9546.

Brady et al., "Large–Scale Synthesis of a Cyclic Hexapeptide Analogue of Somatostatin," *J. Org. Chem.*, 52:764–769, 1987.

Brown, S.C. et al., "NMR Solution Structure of a Peptide Nucliec Acid Complexed with RNA", *Science* 1994, 265, 777–780.

Buttrey et. al., "The Resolution of DL–β–(Thymin–1–YL)Alanine and Polymerisation of the β–(Thymin–1–YL) Alanines", *Tetrahedron*, 31:73–75, 1975.

Chen, S. et al., "Molecular Dynamics and NMR Studies of Single–Stranded PNAs", *Tetrahedron Letters* 1994, 35(29), 5105–5108.

(List continued on next page.)

*Primary Examiner*—Ardin H. Marschel
(74) *Attorney, Agent, or Firm*—Woodcock Washburn LLP

(57) ABSTRACT

A novel class of compounds, known as peptide nucleic acids, bind complementary ssDNA and RNA strands more strongly than a corresponding DNA. The peptide nucleic acids generally comprise ligands such as naturally occurring DNA bases attached to a peptide backbone through a suitable linker.

58 Claims, 31 Drawing Sheets

OTHER PUBLICATIONS

De Koning et. al. "Unconventional Nucleotide Analogues V. Derivatives of 6–(1–pyrimidinyl)–and 6–(9–purinyl)–2–aminocaproic acid.", *Recueil*, 90:874–884, 1971.

Demidov, V. et al., "Stability of Peptide Nucleic Acids in Human Serum and Cellular Extracts", *Biochem. Pharmacol.* 1994, 48(6), 1310–1313.

Demidov, V. et al., "Sequence Selective Double Strand DNA Cleavage by PNA Targeting Using Nuclease S1", *Nucleic Acids Res.* 1993, 21(9), 2103–2107.

Doel et al., "An Approach to the Synthesis of Peptide Analogues of Oligonucleotide (Nucleopeptides)", *Tetrahedron Letters*, 27:2285–2288, 1969.

Doel et al., "The Synthesis of Peptides Containing Purine and Pyrimidine Derivatives of DL–Alanine", *Tetrahedron*, 30:2755–2759, 1974.

Dueholm, K.L. et al., "An Efficient Synthetic Approach to Bocaminoacetaldehyde and Its Application in the Synthesis of 2–Boc–aminoethylglycine Methyl ester", *Org. Prep. Proc. Int.* 1993, 25, 457–461.

Dueholm, K.L. et al., "Peptide Nucleic Acid (PNA) with a Chiral Backbone Based on Alanine", *Bioorg. Med. Chem. Lett.* 1994, 4(8), 1077–1080.

Dueholm, K.L. et al., "Synthesis of Peptide Nucleic Acids Monomers Containing the Four Natural Nucleobases: Thymine, Cytosine, Adenine and Guanine, and Their Oligomerization", *J. Org. Chem.* 1994, 59(19), 5767–5773.

Egholm, M. et al., "Peptide Nucleic Acids (PNA). Oligonucleotide Analogues with an Achiral Peptide Backbone",*J. Am. Chem. Soc.* 1992, 114, 1895–1897.

Egholm, M. et al., Recognition of Guanine and Adenine in DNA by Cytosine and Thymine Containing Peptide Nucleic Acids (PNA), *J. Am. Chem. Soc.* 1992, 114, 9677–9678.

Egholm, M. et al., "Peptide Nucleic Acids Containing Adenine or Guanine Recognize Thymine and Cytosine in Complementary DNA Sequences", *J. Chem. Soc. Chem. COmm.* 1993, 800–801.

Flam, F., "Can DNA Mimics Improve on the Real Thing?", *Science* 1993, 262, 1647–1649.

Frank–Kamenetskii, M., "A Change of Backbone", *Nature* 1991, 354, 505.

Griffith, M.C. et al., "Single and Bis Peptide Nucliec Acids as Triplexing Agents: Binding and Stoichiometry", *J. Am. Chem. Soc.* 1995, 117(2), 831–832.

Hanvey et al., "Antisense and Antigene Properties of Peptide Nucleic Acids", *Science*, 258:1481–1485, 1992.

Hyrup, B. et al., "Modification of the Binding Affinity of Peptide Nucleic Acids (PNA). PNA with Extended Backbones Consisting of 2–aminoethyl–B–alanine or 3–aminopropylglycine Units",*J. Chem. Soc. Chem. Comm.* 1993, 6, 518–519.

Hyrup, B. et al., "Structure–activity Studies of the Binding of Modified Peptide Nucleic Acids (PNA) to DNA", *J. Am. Chem. Soc.* 1994, 116(18), 7964–7970.

Huang et al., "Acyclic Nucleic Acid Analogues: Synthesis and Oligomerization of γ,4–Diamino–2–oxo–1(2H)–pyrimidinepentanoic Acid and δ 4–Diamino–2–oxo–1(2H)–pyrimidinehexanoic Acid", *J. Org. Chem.*, 56:6007–6018, 1991.

Inaki et al., "Functionality and Applicability of Synthetic Nucleic Acid Analogs", *In Current Topics in Polymer Science*; Ottenbrite, Utracki, Inoue, Eds. New York : Macmillan Pub. Co., 1:80–100, 1987.

Inaki, Y., "Synthetic Nucleic Analogs", *Prog. Polym. Sci.*, 17:515–570, 1992.

Kosynkina, L. et al., "A Convenient Synthesis of Chiral Peptide Nucleic Acid (PNA) Monomers", *Tetrahedron Letters* 1994, 35(29), 5173–5176.

Lagriffoul, P.–H. et al., "The Synthesis, Cooligomerization and Hybridization of a Thymine–Thymine Heterodimer Containign PNA", *Bioorg. Med. Chem. Lett.* 1994, 4(8), 1081–1085.

Leijon, M. et al., "Structural Characterization of PNA–DNA Duplexes by NMR. Evidence for DNA in B–like Conformation", *Biochemistry* 1994, 33(33), 9820–9825.

Lu et al., "Synthesis of Polyesters Containing Nucleic Acid Base Derivatives as Pending Side Chains," *J. Polym. Sci.: Part A: Polymer Chemistry*, 24:526–536, 1986.

Mollegaard, N.E. et al., "Peptide Nucleic Acid–DNA Strand Displacement Loops as Artificial Promoters", *PNAS USA* 1994, 91, 3892–3895.

Nagae et. al., "Functional Monomers and Polymers. CLIV. Application of Nucleic Acid Base Containing Polymers to High Performance Liguid Chromatography," *J. Polym. Sci.: Part A: Polymer Chemistry*, 27:2593–2609, 1989.

Nielsen, P.E. et al., "Peptide Nucleic Acids (PNAs): Protein Antisense and Anti–gene Agents", *Anti–Cancer Drug Design* 1993, 8, 53–63.

Nielsen, P.E. et al., "Peptide Nucleic Acids (PNA): Potential Antiviral Agents", *Intl. Antiviral News* 1993, 1, 37–39.

Nielsen, P.E. et al,. "Peptide Nucleic Acids (PNA): Oligonucleotide Analogs witha Polyamide Backbone", *Antisense Research and Applications* 1993, Crooke and B. Lebleu (eds.), CRC Press, Boca Raton, FL 363–373.

Nielsen, P.E., "Peptide Nucleic Acid (PNA): A Model Structure for the Primoridal Genetic Material?" *Orig. Life Evol. Biosphere* 1993, 23, 323–327.

Nielsen, P.E., "Peptide Nucleic Acid (PNA). A DNA Mimic With a Peptide Backbone", *Bioconjugate Chem.* 1994, 5, 3–7.

Nielsen, P.E., "Sequence–specific Transcription Arrest by Peptide Nucleic Acid Bound to the DNA Template Strand", *Gene* 1994, 149, 139–145.

Matthews, J. and Kricka, "Analytical Strategies for the Use of DNA Probes", *Analytical Biochemistry* 1988, 169, 1–25.

Nollet et al., "Unconventional Nucleotide Analogues–III, 4–(N$_1$–Pyrimidyl)–2–Aminobutyric Acids", *Tetrahedron* 1968, 25, 5989–5994.

Nollet et al., "Unconventional Nucleotide Analogues–I, N$_9$–Purinyl α–Amino Acids", *Tetrahedron* 1969, 25, 5971–5981.

Nollet et al., "Unconventional Nucleotide Analogues–II, Synthesis of the Adenyl Analogue of Willardiine", *Tetrahedron* 1969, 25, 5983–5987.

Nollet et al., "Michael Addition of 4–O–Ethyluracil. A Method for Specific N$_1$–Alkylation of Hydroxpyrimidines", *Tetrahedron Letters* 1969, 53, 4605–4606.

Orum, et al., "Single Base Pair Mutation Analysis by PNA Directed PCR Clamping", *Nucleic Acids Res.*, 1993, 21(23):5332–5336.

Parkanyi, C. et al,. "Synthesis of Polymethylene Chain–Bridged 6–Substituted 8–Azapurines and Related Compounds", *Collect. Czech. Chem. Commun.* 1991, 56, 2382–2388.

Peffer, et al., "Strand–Invasion of Duplex DNA by Peptide Nucleic Acid Oligomers", *Proc. Natl. Acad. Sci. USA*, 1993, 90(22):10648–10652.

Pitha, J. et al., "Synthetic Analogs of Nucleic Acids", pp. 271–297 in "Biomedical Polymers", Goldberg and Nakajima, eds., Academic Press, New York, 1989.

Pitha et al., "Inhibition of Murine Leukemia Virus Replication by Poly(vinyluracil) and Poly(vinyladenine)", *Proc. Natl Acad. Sci. USA* 1973, 70, 1204–1208.

Pitha, J., "Physiological Activities of Synthethic Analogs of Polynucleotides", *Adv. Polym. Sci.* 1983, 50, 1–16.

Rose, D.J., "Characterization of Antisense Binding Properties of Peptide Nucleic Acids by Capillary Gel Electrophoresis", *Anal. Chem.*, 1993, 65(24):3545–3549.

Shvatschkin, Y.P. et al., "Uspechi i perspektivi chimij nikleoamniokislot i nikleopeptidov", *Isnechi Chimij* 1982, 2, 311–330.

Simon et al., "Peptoids: A modular approach to drug discovery", *Proc. Natl. Acad. Sci. USA* 1992, 89, 9367–9371.

Takemoto et al., "Synthetic Nucleic Acid Analogs. Preparation and Interactions", *Adv. Polym. Sci.* 1981, 1–51.

Takemoto, K., "Recent Problems Concerning Functional Monomers and Polymers Containing Nucleic Acid Bases", pp. 103–129 in "Polymeric Drugs", Donaruma and Vogl, eds., Academic Press, New York, 1978.

Uhlmann et al., "Antisense Oligonucleotides: A New Therapeutic Principle", *Chemical Reviews* 1990, 90, 544–583.

Weller et al., "Molecular Modeling of Acyclic Polyamide Oligonucleotide Analogues", *J. Org. Chem.* 1991, 6000–6006.

Wittung, et al., "DNA–like Double Helix Formed by Peptide Nucleic Acid", *Nature*, 1994, 368 (6471):561–563.

\* cited by examiner

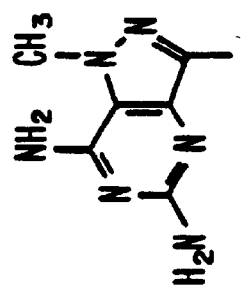 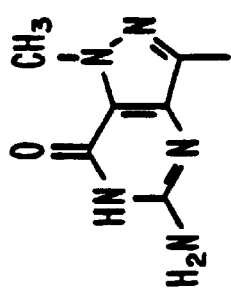 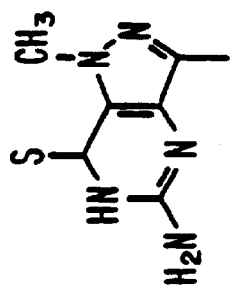
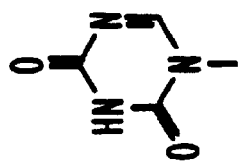 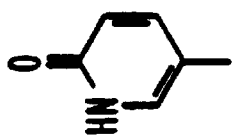 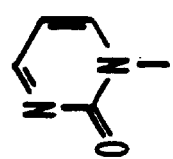
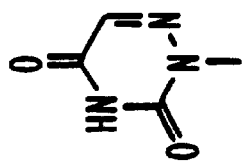 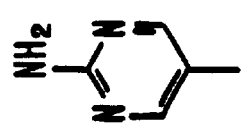 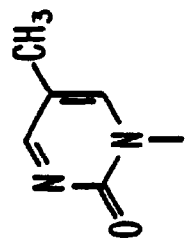
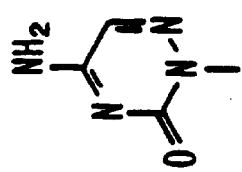 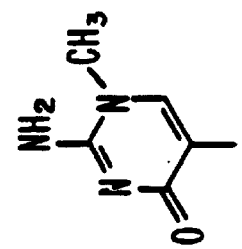 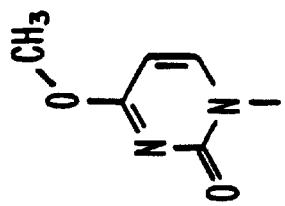
Fig. 2(B)

Fig. 3(a)

```
5'-GATCCAAAAAAAAAAGGATC
3'-CTAGGTTTTTTTTTTCCTAG
```

300 nm RADIATION PHOTOCLEAVAGE

Fig. 3(b)

DIAZOACRIDINE PHOTOFOOTPRINT

```
5'-GATCCAAAAAAAAAAGGATC
3'-CTAGGTTTTTTTTTTCCTAG
```

KMnO₄ CLEAVAGE

Fig. 3(c)

```
5'-GATCCAAAAAAAAAAGGATC
3'-CTAGGTTTTTTTTTTCCTAG
```

S₁-NUCLEASE CLEAVAGE

Fig. 3(d)

```
5'-GATCCAAAAAAAAAAGGATC
3'-CTAGGTTTTTTTTTTCCTAG
```

MICROCOCCUS NUCLEASE ENHANCEMENT

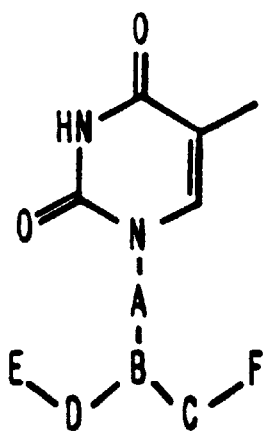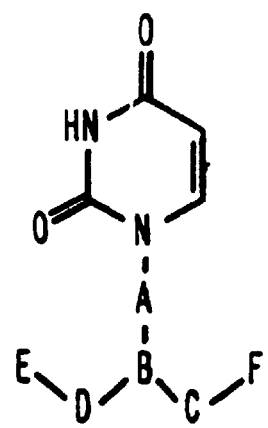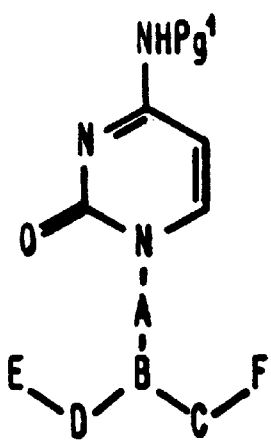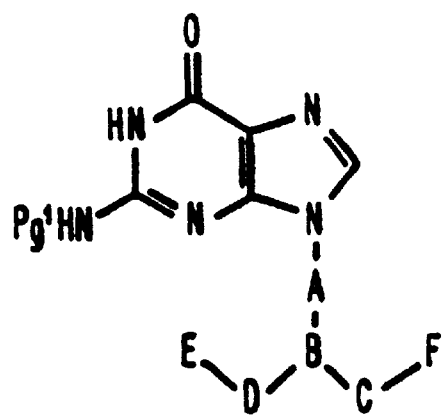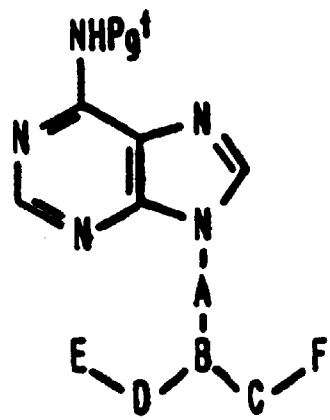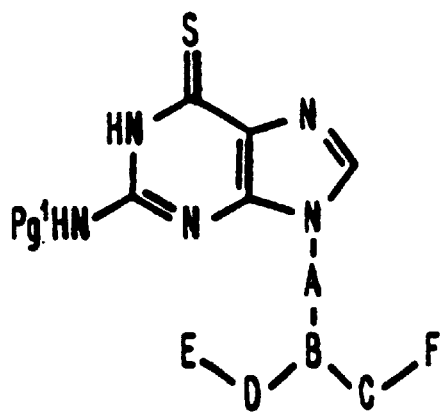
Fig. 4

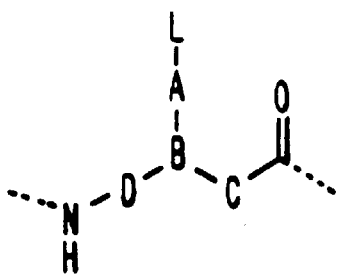
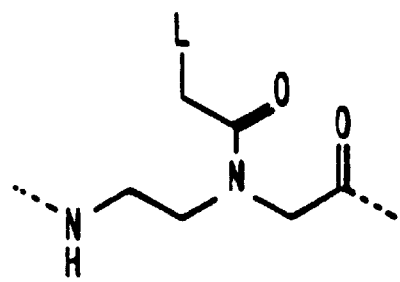
AMINOETHYL GLYCINE
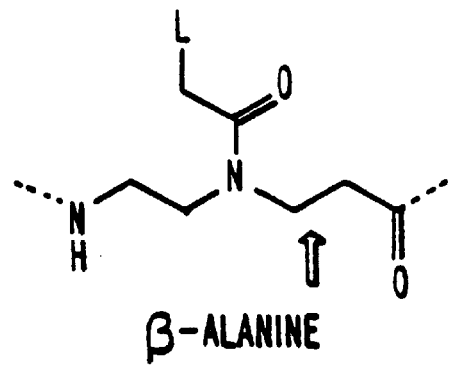
β-ALANINE
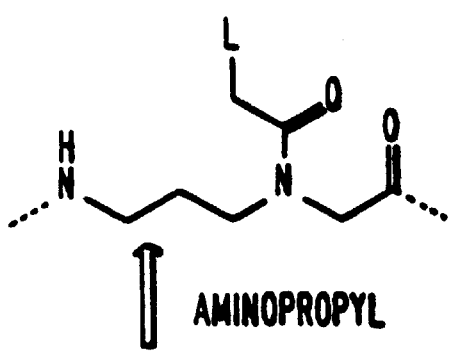
AMINOPROPYL
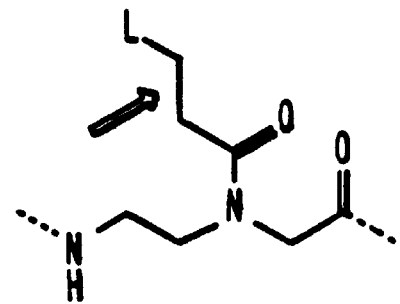
PROPIONYL
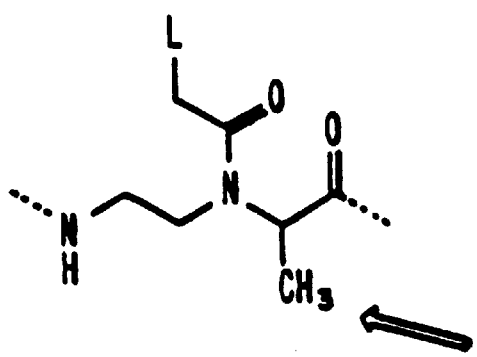
*Fig. 16*

R¹ = AMINO ACID SIDECHAIN
R² = METHYL, ETHYL ETC.

COMPOUND
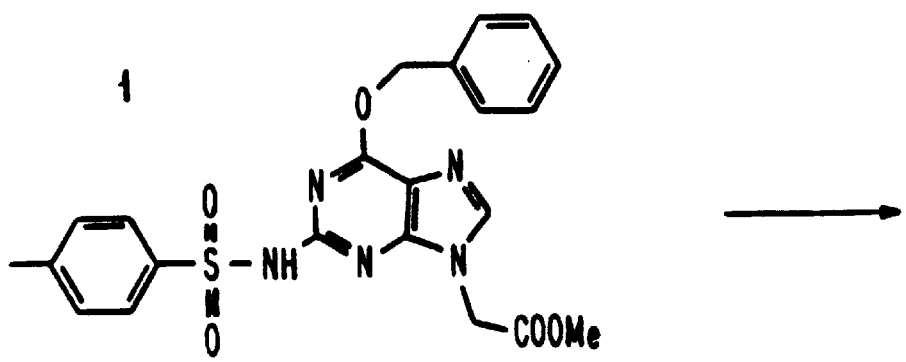
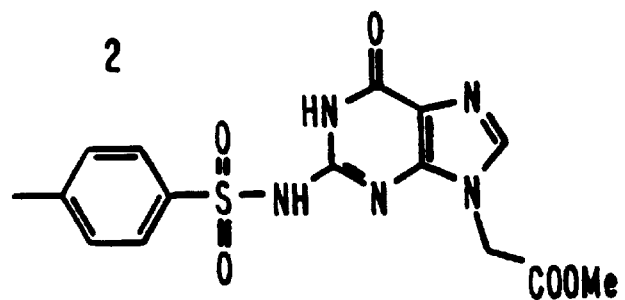
COMPOUND 1 IN
50% TFA: 50% METHYLENE CHLRIDE, 5h, rt.
QUANTITATIVE DE-BENZYLATION
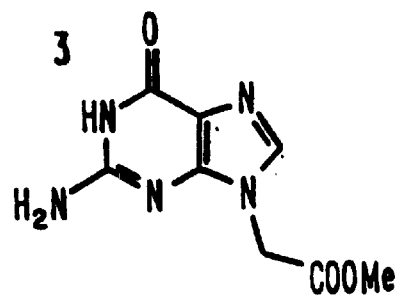
COMPOUND 1 IN
100% HF, 0°C, 1h
QUANTITATIVE DE-BENZYLATION
AND DE-SULFONYLATION
*Fig. 27*

PEPTIDE NUCLEIC ACID SYNTHONS

RELATED APPLICATIONS

This is a division, of application Ser. No. 08/108,591, filed Nov. 22, 1993 now U.S. Pat. No. 6,395,474; which is 371 filing of PCT/EP92/01219, filed May 22, 1992.

This application is a continuation-in-part of the following Danish Patent Applications: No. 986/91, filed May 24, 1991, No. 987/91, filed May 24, 1991, and No. 510/92, filed Apr. 15, 1992. The entire disclosure of each application is incorporated herein by reference.

FIELD OF THE INVENTION

This invention is directed to compounds that are not polynucleotides yet which bind to complementary DNA and RNA strands more strongly the corresponding DNA. In particular, the invention concerns compounds wherein naturally-occurring nucleobases or other nucleobase-binding moieties are covalently bound to a polyamide backbone.

BACKGROUND OF THE INVENTION

Oligodeoxyribonucleotides as long as 100 base pairs (bp) are routinely synthesized by solid phase methods using commercially available, fully automatic synthesis machines. The chemical synthesis of oligoribonucleotides, however, is far less routine. Oligoribonucleotides also are much less stable than oligodeoxyribonucleotides, a fact which has contributed to the more prevalent use of oligodeoxyribonucleotides in medical and biological research directed to, for example, gene therapy or the regulation of transcription or translation.

The function of a gene starts by transcription of its information to a messenger RNA (mRNA) which, by interaction with the ribosomal complex, directs the synthesis of a protein coded for by its sequence. The synthetic process is known as translation. Translation requires the presence of various co-factors and building blocks, the amino acids, and their transfer RNAs (tRNA), all of which are present in normal cells.

Transcription initiation requires specific recognition of a promoter DNA sequence by the RNA-synthesizing enzyme, RNA polymerase. In many cases in prokaryotic cells, and probably in all cases in eukaryotic cells, this recognition is preceded by sequence-specific binding of a protein transcription factor to the promoter. Other proteins which bind to the promoter, but whose binding prohibits action of RNA polymerase, are known as repressors. Thus, gene activation typically is regulated positively by transcription factors and negatively by repressors.

Most conventional drugs function by interaction with and modulation of one or more targeted endogenous proteins, e.g., enzymes. Such drugs, however, typically are not specific for targeted proteins but interact with other proteins as well. Thus, a relatively large dose of drug must be used to effectively modulate a targeted protein. Typical daily doses of drugs are from $10^{-5}-10^{-1}$ millimoles per kilogram of body weight or $10^{-3}-10$ millimoles for a 100 kilogram person. If this modulation instead could be effected by interaction with and inactivation of mRNA, a dramatic reduction in the necessary amount of drug necessary could likely bebachieved, along with a corresponding reduction in side effects. Further reductions could be effected if such interaction could be rendered site-specific. Given that a functioning gene continually produces mRNA, it would thus be even more advantageous if gene transcription could be arrested in its entirety.

Oligodeoxynucleotides offer such opportunities. For example, synthetic oligodeoxynucleotides could be used as antisense probes to block and eventually lead to the breakdown of mRNA. Thus, synthetic DNA could suppress translation in vivo. It also may be possible to modulate the genome of an animal by, for example, triple helix formation using oligonucleotides or other DNA recognizing agents. However, there are a number of drawbacks associated with triple helix formation. For example, it can only be used for homopurine sequences and it requires unphysiologically high ionic strength and low pH.

Furthermore, unmodified oligonucleotides are unpractical both in the antisense approach and in the triple helix approach because they have short in vivo half-lives, they are difficult to prepare in more than milligram quantities and, thus, are prohibitively costly, and they are poor cell membrane penetrators.

These problems have resulted in an extensive search for improvements and alternatives. For example, the problems arising in connection with double-stranded DNA (dsDNA) recognition through triple helix formation have been diminished by a clever "switch back" chemical linking whereby a sequence of polypurine on one strand is recognized, and by "switching back", a homopurine sequence on the other strand can be recognized. See, e.g., McCurdy, Moulds, and Froehler, Nucleosides, in press. Also, good helix formation has been obtained by using artificial bases, thereby improving binding conditions with regard to ionic strength and pH.

In order to improve half life as well as membrane penetration, a large number of variations in polynucleotide backbones has been undertaken, although so far not with desired results. These variations include the use of methylphosphonates, monothiophosphates, dithiophosphates, phosphoramidates, phosphate esters, bridged phosphoroamidates, bridged phosphorothioates, bridged methylenephosphonates, dephospho internucleotide analogs with siloxane bridges, carbonate bridges, carboxymethyl ester bridges, acetamide bridges, carbamate bridges, thioether, sulfoxy, sulfono bridges, various "plastic" DNAs, α-anomeric bridges, and borane derivatives.

International patent application WO 86/05518 broadly claims a polymeric composition effective to bind to a single-stranded polynucleotide containing a target sequence of bases. The composition is said to comprise non-homopolymeric, substantially stereoregular polymer molecules of the form:

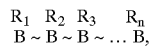

where:
(a) $R_1-R_n$ are recognition moieties selected from purine, purine-like, pyrimidine, and pyrimidine like heterocycles effective to bind by Watson/Crick pairing to corresponding, in-sequence bases in the target sequence;
(b) n is such that the total number of Watson/Crick hydrogen bonds formed between a polymer molecule and target sequence is at least about 15;
(c) B~B are backbone moieties joined predominantly by chemically stable, substantially uncharged, predominantly achiral linkages;
(d) the backbone moiety length ranges from 5 to 7 atoms if the backbone moieties have a cyclic structure, and ranges from 4 to 6 atoms if the backbone moieties have an acyclic structure; and (e) the backbone moieties support the recognition moieties at position which allow Watson/Crick base pairing between the recognition moieties and the corresponding, in-sequence bases of the target sequence.

According to WO 86/05518, the recognition moieties are various natural nucleobases and nucleobase-analogs and the backbone moieties are either cyclic backbone moieties comprising furan or morpholine rings or acyclic backbone moieties of the following forms:

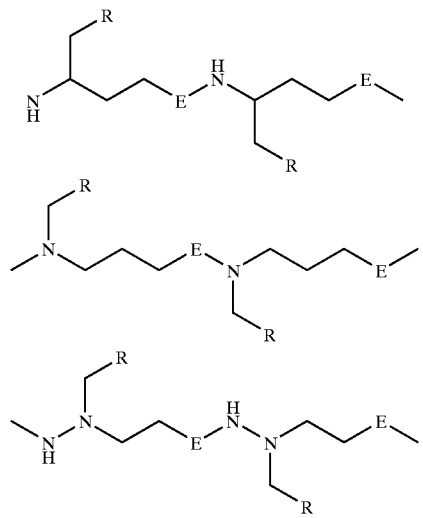

where E is —CO— or —SO$_2$—. The specification of the application provides general descriptions for the synthesis of subunits, for backbone coupling reactions, and for polymer assembly strategies. However, the specification provides no example wherein a claimed compound or structure is actually prepared. Although WO 86/05518 indicates that the claimed polymer compositions can bind target sequences and, as a result, have possible diagnostic and therapeutic applications, the application contains no data relating to the binding affinity of a claimed polymer.

International patent application WO 86/05519 claims diagnostic reagents and systems that comprise polymers described in WO 86/05518, but attached to a solid support. WO 86/05519 also provides no examples concerning actually preparation of a claimed diagnostic reagent, much less data showing the diagnostic efficiency of such a reagent.

International patent application WO 89/12060 claims various building blocks for synthesizing oligonucleotide analogs, as well as oligonucleotide analogs formed by joining such building blocks in a defined sequence. The building blocks may be either "rigid" (containing a ring) or "flexible" (lacking a ring). In both cases the building blocks contain a hydroxy group and a mercapto group, through which the building blocks are said to join to form oligonucleotide analogs. The linking moiety in the oligonucleotide analogs is selected from the group consisting of sulfide (—S—), sulfoxide (—SO—), and sulfone (—SO$_2$—). WO 89/12060 provides a general description concerning synthesis of the building blocks and coupling reactions for the synthesis of oligonucleotide analogs, along with experimental examples describing the preparation of building blocks. However, the application provides no examples directed to the preparation of a claimed oligonucleotide analog and no data confirming the specific binding of an oligonucleotide analog to a target oligonucleotide.

Furthermore, oligonucleotides or their derivatives have been linked to intercalators in order to improve binding, to polylysine or other basic groups in order to improve binding both to double-stranded and single-stranded DNA, and to peptides in order to improve membrane penetration. However, such linking has not resulted in satisfactory binding for either double-stranded or single-stranded DNA. Other problems which resulted from, for example, methylphosphonates and monothiophosphates were the occurrence of chirality, insufficient synthetic yield or difficulties in performing solid phase assisted syntheses.

In most cases only a few of these modifications could be used. Even then, only short sequences—often only dimers—or monomers could be generated. Furthermore, the oligomers actually produced have rarely been shown to bind to DNA or RNA or have not been examined biologically.

The great majority of these backbone modifications led to decreased stability for hybrids formed between the modified oligonucleotide and its complementary native oligonucleotide, as assayed by measuring $T_m$ values. consequently, it is generally understood in the art that backbone modifications destabilize such hybrids, i.e., result in lower $T_m$ values, and should be kept to a minimum.

OBJECTS OF THE INVENTION

It is one object of the present invention to provide compounds that bind ssDNA and RNA strands to form stable hybrids therewith.

It is a further object of the invention to provide compounds that bind ssDNA and RNA strands more strongly the corresponding DNA.

It is another object to provide compounds wherein naturally-occurring nucleobases or other nucleobase-binding moieties are covalently bound to a peptide backbone.

It is yet another object to provide compounds other than RNA that can bind one strand of a double-stranded polynucleotide, thereby displacing the other strand.

It is still another object to provide therapeutic and prophylactic methods that employ such compounds.

SUMMARY OF THE INVENTION

The present invention provides a novel class of compounds, known as peptide nucleic acids (PNAs), that bind complementary ssDNA and RNA strands more strongly than a corresponding DNA. The compounds of the invention generally comprise ligands linked to a peptide backbone via an aza nitrogen. Representative ligands include either the four main naturally occurring DNA bases (i.e., thymine, cytosine, adenine or guanine) or other naturally occurring nucleobases (e.g., inosine, uracil, 5-methylcytosine or thiouracil) or artificial bases (e.g., bromothymine, azaadenines or azaguanines, etc.) attached to a peptide backbone through a suitable linker.

In certain preferred embodiments, the peptide nucleic acids of the invention have the general formula (I):

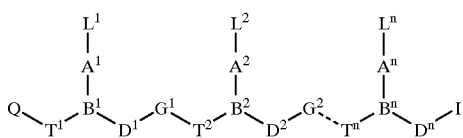

(I)

wherein:
n is at least 2,
each of $L^1-L^n$ is independently selected from the group consisting of hydrogen, hydroxy, $(C_1-C_4)$alkanoyl, naturally occurring nucleobases, non-naturally occurring nucleobases, aromatic moieties, DNA intercalators, nucleobase-binding groups, heterocyclic moieties, and reporter ligands, at least one of $L^1-L^n$ being a naturally occurring nucleobase, a non-naturally occurring nucleobase, a DNA intercalator, or a nucleobase-binding group;
each of $A^1-A^n$ is a single bond, a methylene group or a group of formula (IIa) or (IIb):

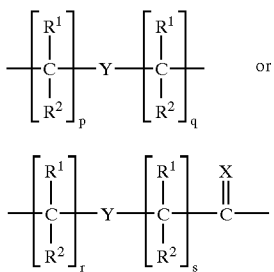

where:
X is O, S, Se, $NR^3$, $CH_2$ or $C(CH_3)_2$;
Y is a single bond, O, S or $NR^4$;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, $(C_1-C_4)$alkyl which may be hydroxy- or alkoxy- or alkylthio-substituted, hydroxy, alkoxy, alkylthio, amino and halogen; and
each $R^3$ and $R^4$ is independently selected from the group consisting of hydrogen, $(C_1-C_4)$alkyl, hydroxy- or alkoxy- or alkylthio-substituted $(C_1-C_4)$ alkyl, hydroxy, alkoxy, alkylthio and amino;
each of $B^1-B^n$ is N or $R^3N^+$, where $R^3$ is as defined above;
each of $T^1-T^n$ is $CR^6R^7$, $CHR^6CHR^7$ or $CR^6R^7CH_2$, where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$alkylthio, $NR^3R^4$ and $SR^5$, where $R^3$ and $R^4$ are as defined above, and $R^5$ is hydrogen, $(C_1-C_6)$alkyl, hydroxy-, alkoxy-, or alkylthio-substituted $(C_1-C_6)$alkyl, or $R^6$ and $R^7$ taken together complete an alicyclic or heterocyclic system;
each of $D^1-D^n$ is $CR^6R^7$, $CH_2CR^6R^7$ or $CHR^6CHR^7$, where $R^6$ and $R^7$ are as defined above;
each of $G^1-G^{n-1}$ is $-NR^3CO-$, $-NR^3CS-$, $-NR^3SO-$ or $-NR^3SO_2-$, Y in either orientation, where $R^3$ is as defined above;

Q is $-CO_2H$, $-CONR'R''$, $-SO_3H$ or $-SO_2NR'R''$ or an activated derivative of $-CO_2H$ or $-SO_3H$; and
I is $-NHR'''R''''$ or $-NR'''C(O)R''''$, where R', R'', R''' and R'''' are independently selected from the group consisting of hydrogen, alkyl, amino protecting groups, reporter ligands, intercalators, chelators, peptides, proteins, carbohydrates, lipids, steroids, oligonucleotides and soluble and non-soluble polymers.

The peptide nucleic acids of the invention differ from those disclosed in WO 86/05518 in that their recognition moieties are attached to an aza nitrogen atom in the backbone, rather than to an amide nitrogen atom, a hydrazine moiety or a carbon atom in the backbone.

Preferred peptide nucleic acids have general formula (III):

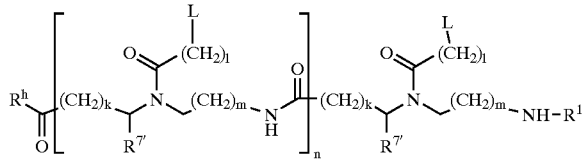

(III)

wherein:
each L is independently selected from the group consisting of hydrogen, phenyl, heterocyclic moieties, naturally occurring nucleobases, and non-naturally occurring nucleobases;
each $R^{7'}$ is independently selected from the group consisting of hydrogen and the side chains of naturally occurring alpha amino acids;
n is an integer from 1 to 60;
each of k, l and m is independently zero or an integer from 1 to 5;
$R^h$ is OH, $NH_2$ or $-NHLysNH_2$; and
$R^i$ is H or $COCH_3$.

Particularly preferred are compounds having formula (III) wherein each L is independently selected from the group consisting of the nucleobases thymine (T), adenine (A), cytosine (C), guanine (G) and uracil (U), k and m are zero or 1, and n is an integer from 1 to 30, in particular from 4 to 20. An example of such a compound is provided in FIG. 1, which shows the structural similarity between such compounds and single-stranded DNA.

The peptide nucleic acids of the invention are synthesized by adaptation of standard peptide synthesis procedures, either in solution or on a solid phase. The synthons used are specially designed monomer amino acids or their activated derivatives, protected by standard protecting groups. The oligonucleotide analogs also can be synthesized by using the corresponding diacids and diamines.

Thus, the novel monomer synthons according to the invention are selected from the group consisting of amino acids, diacids and diamines having general formulae:

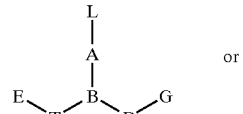

(IV)

or

-continued

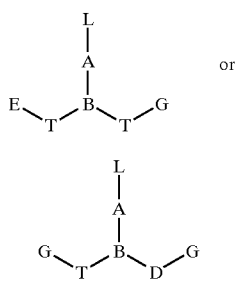
(V)
(VI)

wherein L, A, B, T and D are as defined above, except that any amino groups therein may be protected by amino protecting groups; E is COOH, CSOH, SOOH, SO$_2$OH or an activated derivative thereof; and G is NHR$^3$ or NPgR$^3$, where R$^3$ is as defined above and Pg is an amino protecting group.

Preferred monomer synthons according to the invention are amino acids having formula (VII):

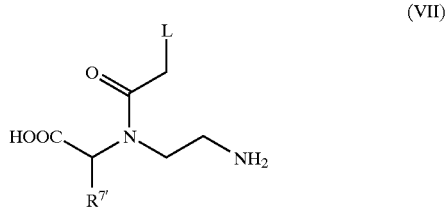
(VII)

or amino-protected and/or acid terminal activated derivatives thereof, wherein L is selected from the group consisting of hydrogen, phenyl, heterocyclic moieties, naturally occurring nucleobases, non-naturally occurring nucleobases, and protected derivatives thereof; and R$^{7'}$ is independently selected from the group consisting of hydrogen and the side chains of naturally occurring alpha amino acids. Especially preferred are such synthons having formula (VII) wherein R$^{7'}$ is hydrogen and L is selected from the group consisting of the nucleobases thymine (T), adenine (A), cytosine (C), guanine (G) and uracil (U) and protected derivatives thereof.

Unexpectedly, these compounds also are able to recognize duplex DNA by displacing one strand, thereby presumably generating a double helix with the other one. Such recognition can take place to dsDNA sequences 5–60 base pairs long. Sequences between 10 and 20 bases are of interest since this is the range within which unique DNA sequences of prokaryotes and eukaryotes are found. Reagents which recognize 17–18 bases are of particular interest since this is the length of unique sequences in the human genome. The compounds of the invention also should be able to form triple helices with dsDNA.

Whereas the improved binding of the compounds of the invention should render them efficient as antisense agents, it is expected that an extended range of related reagents may cause strand displacement, now that this surprising and unexpected new behavior of dsDNA has been discovered.

Thus, in one aspect, the present invention provides methods for inhibiting the expression of particular genes in the cells of an organism, comprising administering to said organism a reagent as defined above which binds specifically to sequences of said genes.

Further, the invention provides methods for inhibiting transcription and/or replication of particular genes or for inducing degradation of particular regions of double stranded DNA in cells of an organism by administering to said organism a reagent as defined above.

Still further, the invention provides methods for killing cells or virus by contacting said cells or virus with a reagent as defined above which binds specifically to sequences of the genome of said cells or virus.

BRIEF DESCRIPTION OF THE DRAWINGS

The numerous objects and advantages of the present invention may be better understood by those skilled in the art by reference to the accompanying figures, in which:

FIGS. 2(A) and 2(B) provide examples of naturally occurring and non-naturally occurring nucleobases for DNA recognition and reporter groups.

FIG. 3 provides a schematic illustration of (a) photocleavage by Acr$^1$-(Taeg)$_{10}$-Lys-NH$_2$ (Acr-T$_{10}$-LysNH$_2$) of 3'-CTAGGTTTTTTTTTTCCTAG (SEQ ID NO: 40)/3'-GATCCAAAAAAAAAAAGGATC (SEQ ID NO:41); (b) photofootprint by the diazo-linked acridine of Acr$^1$-(Taeg)$_{10}$-Lys-NH$_2$ and preferred KMnO$_4$-cleavage; (c) S$_1$ nuclease enhanced cleavage; and (d) micrococcus nuclease cleavage of Acr$^1$-(Taeg)$_{10}$-Lys-NH$_2$ binding site.

FIG. 4 provides examples of PNA monomer synthons of the invention.

FIG. 12b, lanes 1–3), photofootprinting (FIG. 12a, lanes 5–6), potassium permanganate probing (FIG. 12b, lanes 4–6) or probing by staphylococcus nuclease (FIG. 12b, lanes 8–10) or by nuclease S$_1$ (FIG. 12c). Either the A-strand (FIG. 12a) or the T-strand (FIGS. 12b,c) was probed.

FIG. 16 provides examples of PNA backbone alterations.

FIG. 27 provides a test for the tosyl group as a nitrogen protecting group in the synthesis of peptide nucleic acids.

DETAILED DESCRIPTION OF THE INVENTION

Figure 2A:
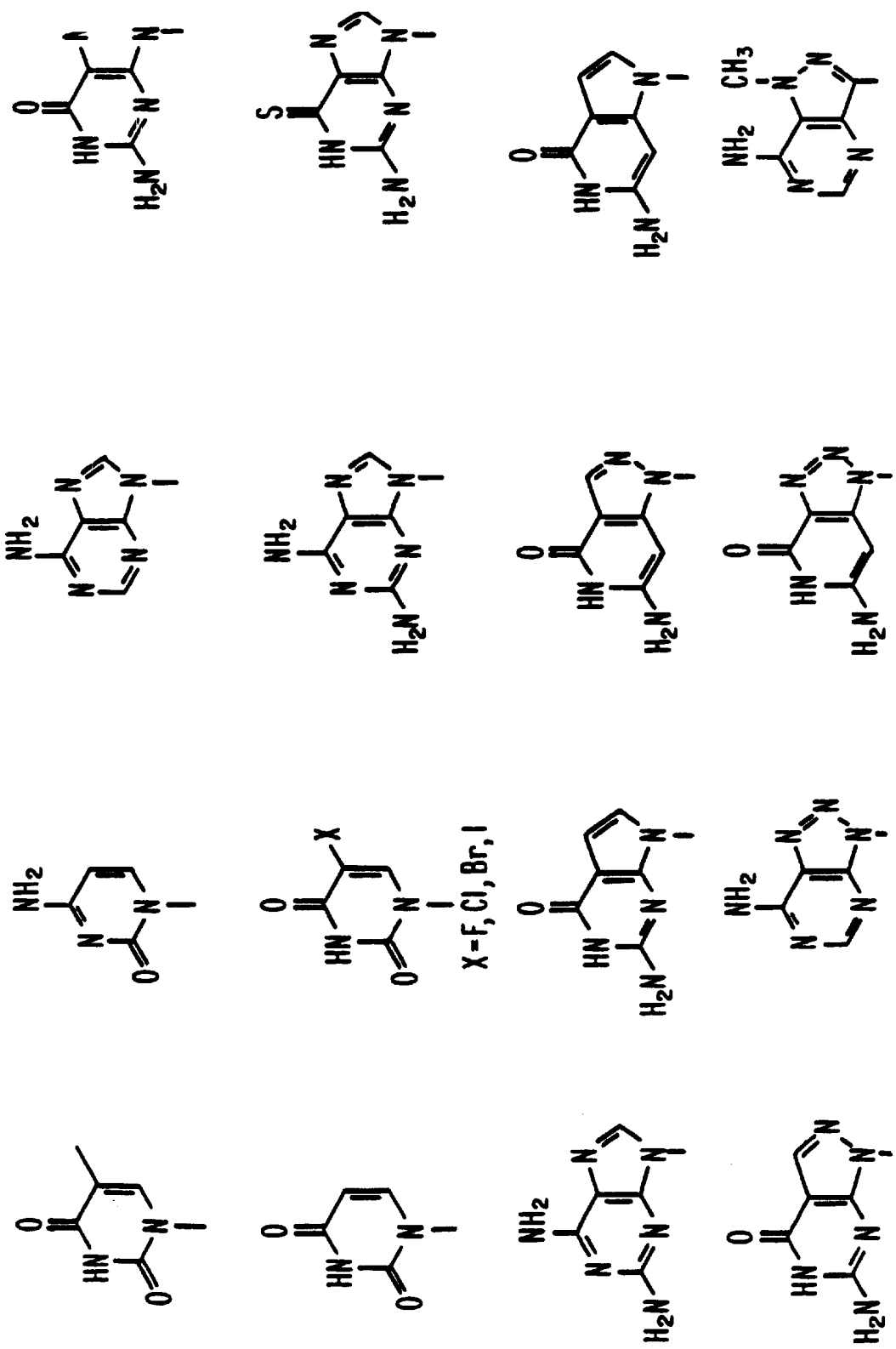

In the oligonucleotide analogs and monomer synthons according to the invention, ligand L is primarily a naturally occurring nucleobase attached at the position found in nature, i.e., position 9 for adenine or guanine, and position 1 for thymine or cytosine. Alternatively, L may be a non-naturally occurring nucleobase (nucleobase analog), another base-binding moiety, an aromatic moiety, ($C_1$–$C_4$)alkanoyl, hydroxy or even hydrogen. Some typical nucleobase ligands and illustrative synthetic ligands are shown in FIG. 2. Furthermore, L can be a DNA intercalator, a reporter ligand such as, for example, a fluorophor, radio label, spin label, hapten, or a protein-recognizing ligand such as biotin.

In monomer synthons, L may be blocked with protecting groups. This is illustrated in FIG. 4, where $Pg^1$ is an acid, a base or a hydrogenolytically or photochemically cleavable protecting group such as, for example, t-butoxycarbonyl (Boc), fluorenylmethyloxycarbonyl (Fmoc) or 2-nitrobenzyl (2Nb).

Linker A can be a wide variety of groups such as —$CR^1R^2CO$—, —$CR^1R^2CS$—, —$CR^1R^2CSe$—, —$CR^1R^2CNHR^3$—, —$CR^1R^2C$=$CH_2$— and —$CR^1R^2C$=$C(CH_3)_2$—, where $R^1$, $R^2$ and $R^3$ are as defined above. Preferably, A is methylenecarbonyl (—$CH_2CO$—). Also, A can be a longer chain moiety such as propanoyl, butanoyl or pentanoyl, or corresponding derivative, wherein O is replaced by another value of X or the chain is substituted with $R^1R^2$ or is heterogenous, containing Y. Further, A can be a ($C_2$–$C_6$)alkylene chain, a ($C_2$–$C_6$)alkylene chain substituted with $R^1R^2$ or can be heterogenous, containing Y. In certain cases, A can just be a single bond.

In the preferred form of the invention, B is a nitrogen atom, thereby presenting the possibility of an achiral backbone. B can also be $R^3N^+$, where $R^3$ is as defined above.

In the preferred form of the invention, T is —$CR^6R^7$—, but can also be a two carbon unit, i.e. —$CHR^6CHR^7$— or —$CR^6R^7CH_2$—, where $R^6$ and $R^7$ are as defined above. $R^6$ and $R^7$ also can be a heteroaryl group such as, for example, pyrrolyl, furyl, thienyl, imidazolyl, pyridyl, pyrimidinyl, indolyl, or can be taken together to complete an alicyclic system such as, for example, 1,2-cyclobutanediyl, 1,2-cyclopentanediyl or 1,2-cyclohexanediyl.

In the preferred form of the invention, E in the monomer synthon is COOH or an activated derivative thereof, and G in the oligomer is —$CONR^3$—. As defined above, E may also be CSOH, SOOH, $SO_2OH$ or an activated derivative thereof, whereby G in the oligomer becomes —$CSNR^3$—, —$SONR^3$— and —$SO_2NR^3$—, respectively. The activation may, for example, be achieved using an acid anhydride or an active ester derivative, wherein hydrogen in the groups represented by E is replaced by a leaving group suited for generating the growing backbone.

The amino acids which form the backbone may be identical or different. We have found that those based on 2-aminoethylglycine are especially well suited to the purpose of the invention.

In some cases it may be of interest to attach ligands at either terminus (Q, I) to modulate the binding characteristics of the PNAs. Representative ligands include DNA intercalators which will improve dsDNA binding or basic groups, such as lysine or polylysine, which will strengthen the binding of PNA due to electrostatic interaction. To decrease negatively charged groups such as carboxy and sulfo groups could be used. The design of the synthons further allows such other moieties to be located on non-terminal positions.

In a further aspect of the invention, the PNA oligomers are conjugated to low molecular effector ligands such as ligands having nuclease activity or alkylating activity or reporter ligands (fluorescent, spin labels, radioactive, protein recognition ligands, for example, biotin or haptens). In a further aspect of the invention, the PNAs are conjugated to peptides or proteins, where the peptides have signaling activity and the proteins are, for example, enzymes, transcription factors or antibodies. Also, the PNAs can be attached to water-soluble or water-insoluble polymers. In another aspect of the invention, the PNAs are conjugated to oligonucleotides or carbohydrates. When warranted, a PNA oligomer can be synthesized onto some moiety (e.g., a peptide chain, reporter, intercalator or other type of ligand-containing group) attached to a solid support.

Such conjugates can be used for gene modulation (e.g., gene targeted drugs), for diagnostics, for biotechnology, and for scientific purposes.

As a further aspect of the invention, PNAs can be used to target RNA and ssDNA to produce both antisense-type gene regulating moieties and hybridization probes for the identification and purification of nucleic acids. Furthermore, the PNAs can be modified in such a way that they can form triple helices with dsDNA. Reagents that bind sequence-specifically to dsDNA have applications as gene targeted drugs. These are foreseen as extremely useful drugs for treating diseases like cancer, AIDS and other virus infections, and may also prove effective for treatment of some genetic diseases. Furthermore, these reagents may be used for research and in diagnostics for detection and isolation of specific nucleic acids.

The triple helix principle is believed to be the only known principle in the art for sequence-specific recognition of dsDNA. However, triple helix formation is largely limited to recognition of homopurine-homopyrimidine sequences. Strand displacement is superior to triple helix recognition in that it allows for recognition of any sequence by use of the four natural bases. Also, in strand displacement recognition readily occurs at physiological conditions, that is, neutral pH, ambient (20–40 C.) temperature and medium (100–150 mM) ionic strength.

Gene targeted drugs are designed with a nucleobase sequence (containing 10–20 units) complementary to the regulatory region (the promoter) of the target gene. Therefore, upon administration of the drug, it binds to the promoter and block access thereto by RNA polymerase. Consequently, no mRNA, and thus no gene product (protein), is produced. If the target is within a vital gene for a virus, no viable virus particles will be produced. Alternatively, the target could be downstream from the promoter, causing the RNA polymerase to terminate at this position, thus forming a truncated mRNA/protein which is nonfunctional.

Sequence-specific recognition of ssDNA by base complementary hybridization can likewise be exploited to target specific genes and viruses. In this case, the target sequence is contained in the mRNA such that binding of the drug to the target hinders the action of ribosomes and, consequently, translation of the mRNA into protein. The peptide nucleic acids of the invention are superior to prior reagents in that they have significantly higher affinity for complementary ssDNA. Also, they possess no charge and water soluble, which should facilitate cellular uptake, and they contain amides of non-biological amino acids, which should make them biostable and resistant to enzymatic degradation by, for example, proteases.

Certain biochemical/biological properties of PNA oligomers are illustrated by the following experiments.

1. Sequence Discrimination at the dsDNA Level (Example 63, FIG. 20).

Using the $S_1$-nuclease probing technique, the discrimination of binding of the $T_{10}$, $T_5CT_4(T_9C)$ & $T_2CT_2CT_4(T_8C_2)$ PNA to the recognition sequences $A_{10}$, $A_5GA_4$ ($A_9G$) (SEQ ID NO:4) & $A_2GA_4GA_4$ ($A_8G_2$) (SEQ ID NO:5) cloned into the BamHI, SalI or PstI site of the plasmid pUC19 was analyzed. The results (FIG. 20) show that the three PNAs bind to their respective recognition sequences with the following relative efficiencies: PNA-T10: $A_{10}>A_9G>>A_8G_2$, PNA-T9C: $A_9G>A_{10}\sim A_8G_2$, PNA-T8C2: $A_8G_2 \geqq A_9G>>A_{10}$. Thus at 37° C. one mismatch out of ten gives reduced efficiency (5–10 times estimated) whereas two mismatches are not accepted.

2. Kinetics of PNA-$T_{10}$-dsDNA Strand Displacement Complex Formation (Example 66, FIG. 21).

Figure 21:
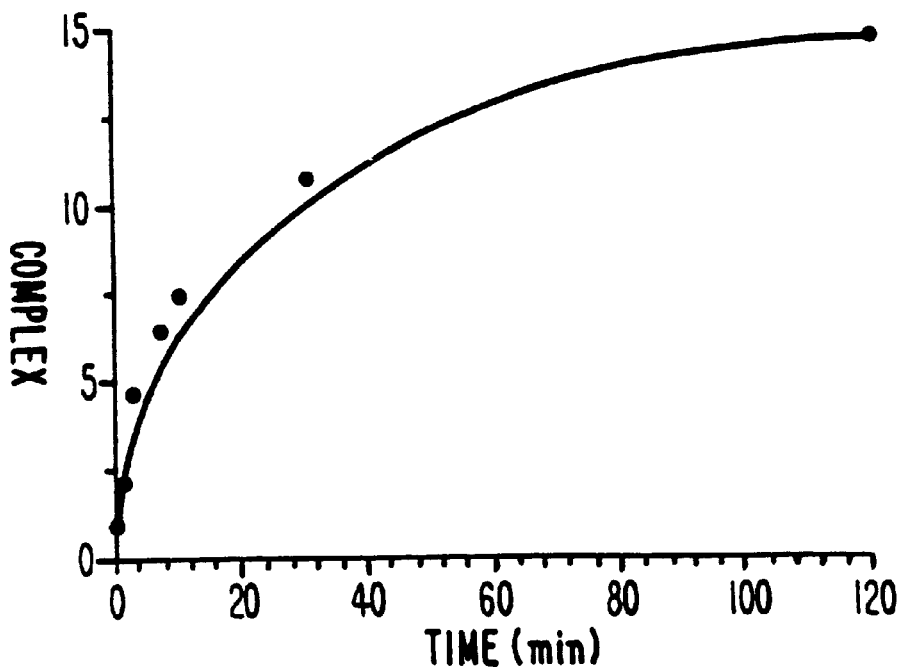
FIG. 21 shows a graph based on densitometric scanning of PAGE autoradiographs demonstrating the kinetics of the binding of PNA-$T_{10}$ to a double stranded target.

Complex formation was probed by $S_1$-nuclease at various times following mixing of PNA and $^{32}$P-endlabeled dsDNA fragment (FIG. 21).

3. Stability of PNA-dsDNA Complex (Example 67, FIG. 22)

Complexes between PNA-$T_n$ and $^{32}$P-dsDNA ($A_{10}/T_{10}$) target were formed (60 min, 37° C.). The complexes were then incubated at the desired temperature in the presence of excess oligo-$dA_{10}$ for 10 min, cooled to RT and probed with $KMnO_4$. The results (FIG. 22) show that the thermal stability of the PNA-dsDNA complexes mirror that of the PNA oligonucleotide complexes in terms of "$T_m$".

4. Inhibition of Restriction Enzyme Cleavage by PNA (Example 65, FIG. 23)

Figure 23:
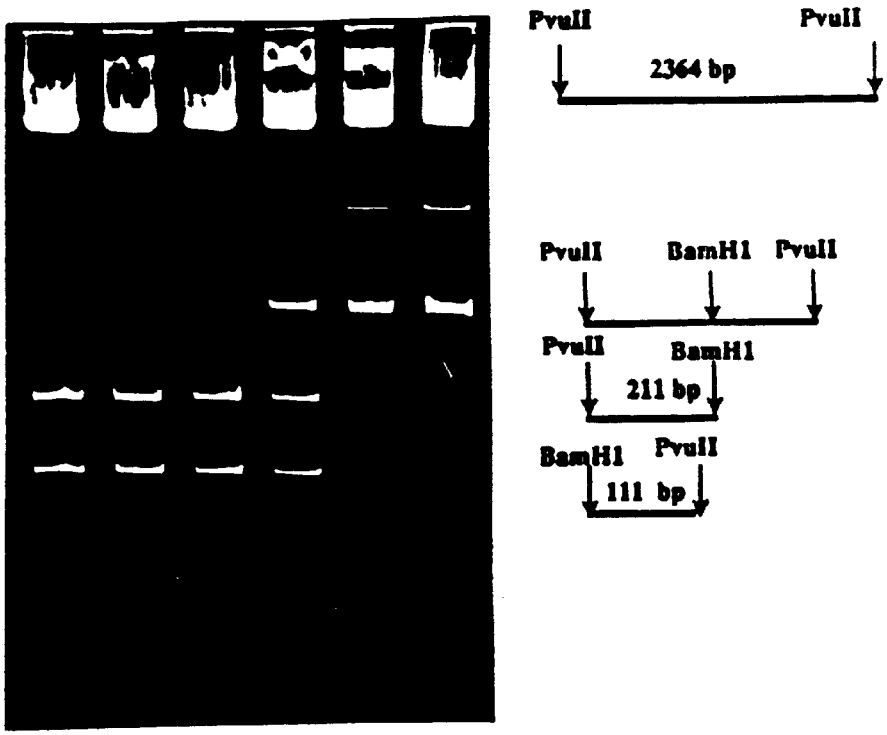
FIG. 23 shows an electrophoretic gel staining demonstrating that restriction enzyme activity towards DNA (5'-GGATCCAAAAAAAAAAAGGATCC (SEQ ID NO 42)/3'-CCTAGGTTTTTTTTTTCCTAGG (SEQ ID NO 43)) is inhibited when PNA is bound proximal to the restriction enzyme recognition site.

The plasmid construct, pT10, contains a $dA_{10}/dT_{10}$ tract cloned into the BamHI site in pUC19. Thus, cleavage of pT10 with BamHI and PvuII results in two small DNA fragments of 211 and 111 bp, respectively. In the presence of PNA-$T_{10}$, a 336 bp fragment is obtained corresponding to cleavage only by PvuII (FIG. 23). Thus cleavage by BamHI is inhibited by PNA bound proximal to the restriction enzyme site. The results also show that the PNA-dsDNA complex can be formed in 100% yield. Similar results were obtained using the pT8C2 plasmid and PNA-T8C2.

5. Binding of $^{125}$I-labeled PNA to Oligonucleotides (Example 63, FIG. 24)

Figure 24:
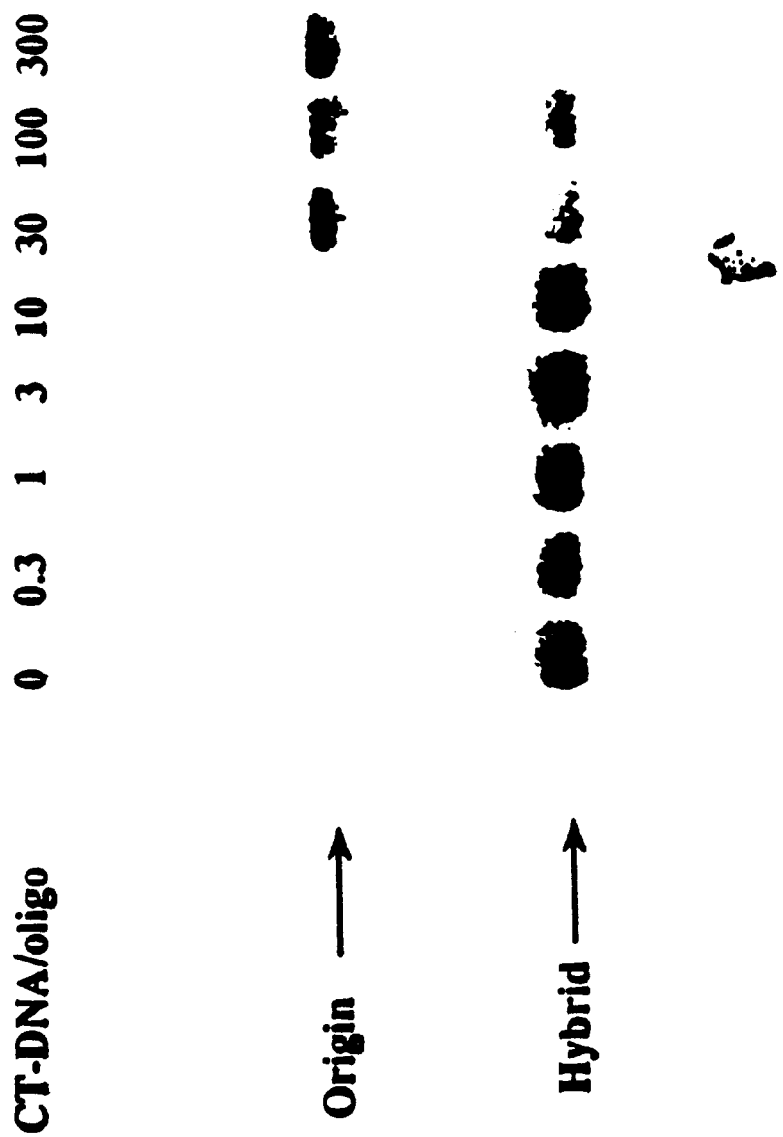
FIG. 24 shows a PAGE autoradiograph demonstrating that $^{125}$I-labeled PNA-$T_{10}$ binds to a complementary $dA_{10}$ (SEQ ID NO:3) oligonucleotide.

A Tyr-PNA-$T_{10}$-Lys-$NH_2$ was labeled with $^{125}$I using $Na^{125}$I and chloramine-T and purified by HPLC. The $^{125}$I-PNA-$T_{10}$ was shown to bind to oligo-$dA_{10}$ by PAGE and autoradiography (FIG. 24). The binding could be competed by excess denatured calf thymus DNA.

Figure 11A:
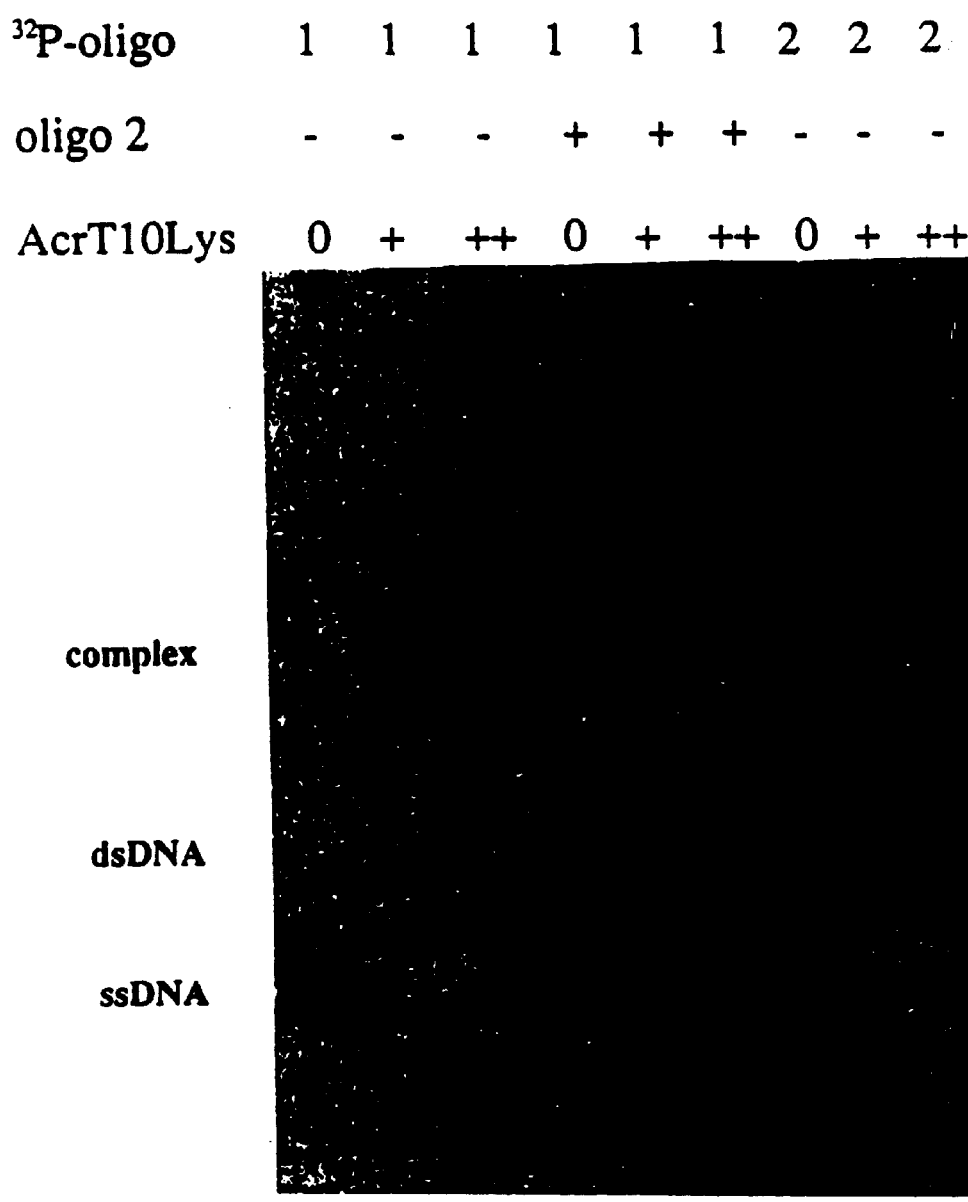
FIGS. 11A and 11B show binding of AcrT10-Lys to dA$_{10}$. 5'-$^{32}$P-labeled oligonucleotide (1) (5'-GATCCA$_{10}$G) (SEQ ID NO:1) was incubated in the absence or presence of Acr-T10-LysNH$_2$ and in the absence or presence of oligonucleotide (2) (5'-GATCCT$_{10}$G) (SEQ ID NO:2) and the samples were analyzed by polyacrylamide gel electrophoresis (PAGE) and autoradiography under "native conditions" (FIG. 11a) or under "denaturing conditions" (FIG. 11b).
Figure 11B:
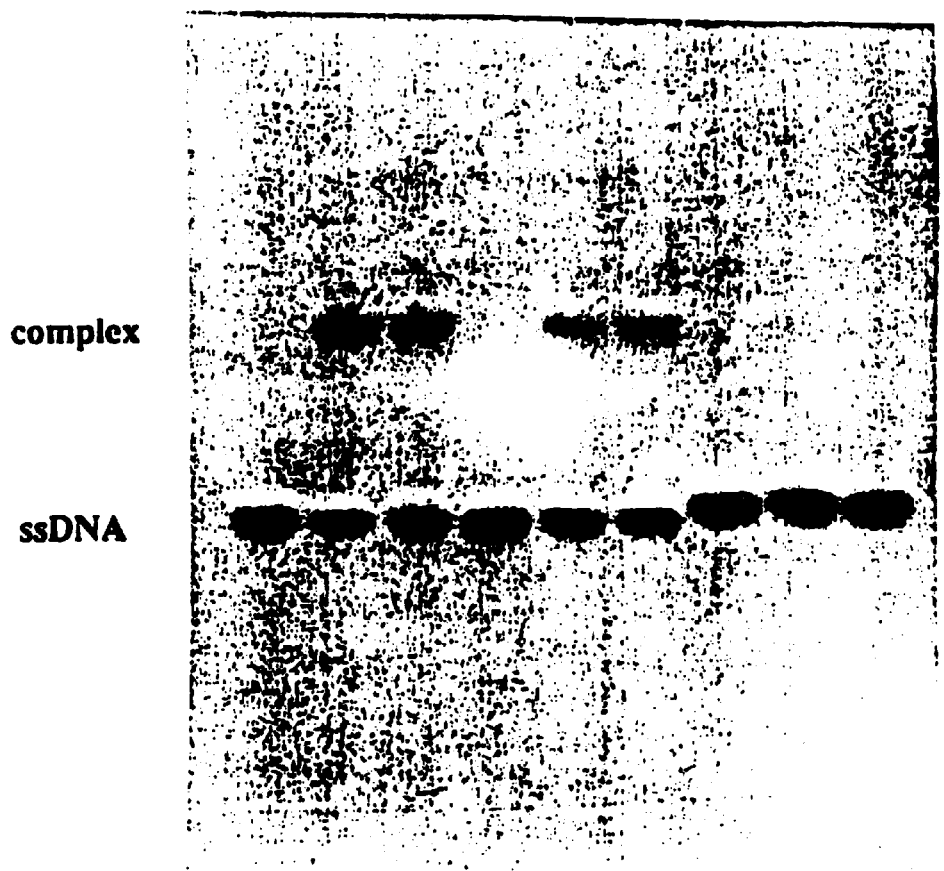

The sequence-specific recognition of dsDNA is illustrated by the binding of a PNA, consisting of 10 thymine substituted 2-aminoethylglycyl units, which C-terminates in a lysine amide and N-terminates in a complex 9-aminoacridine ligand (9-Acr$^1$-(Taeg)$_{10}$-Lys-$NH_2$, FIGS. 11a, 11b) to a $dA_{10}/dT_{10}$ target sequence. The target is contained in a 248 bp $^{32}$P-end-labelled DNA-fragment.

Figure 5:
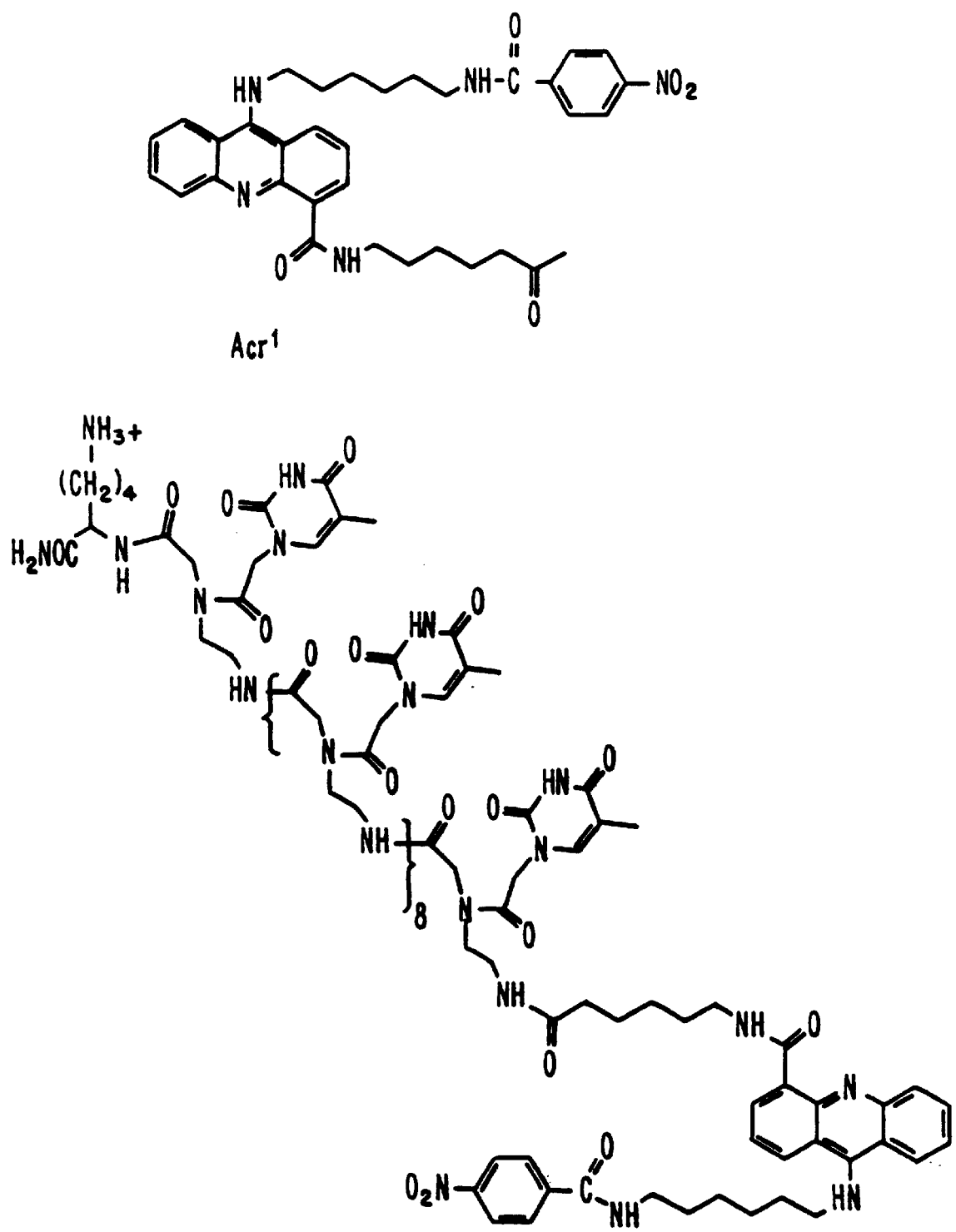
FIG. 5 shows the Acr$^1$ ligand and a PNA, Acr$^1$-(Taeg)$_{10}$-Lys-NH$_2$.
Figure 6:
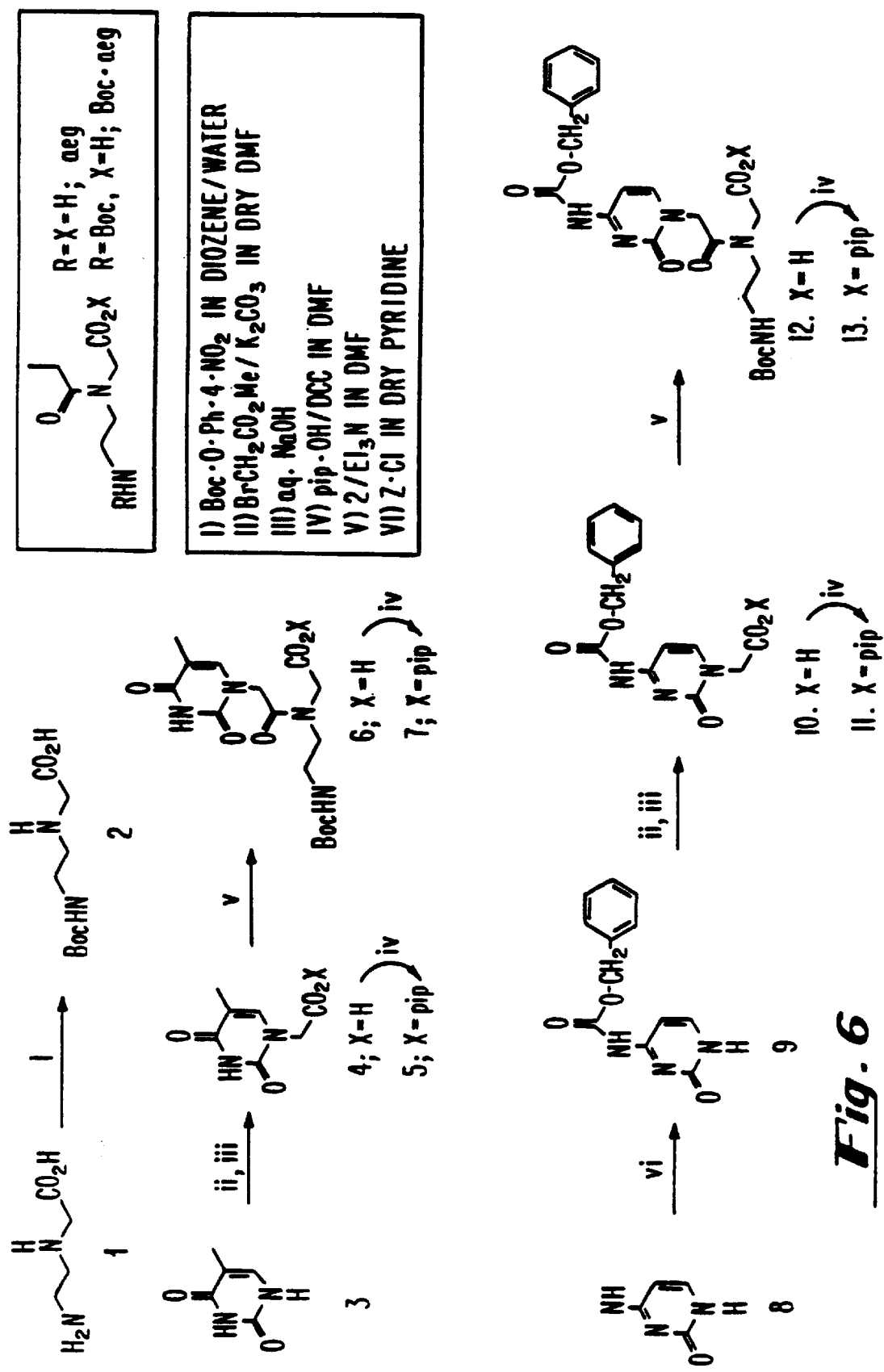
FIG. 6 provides a general scheme for the preparation of monomer synthons.
Figure 7:
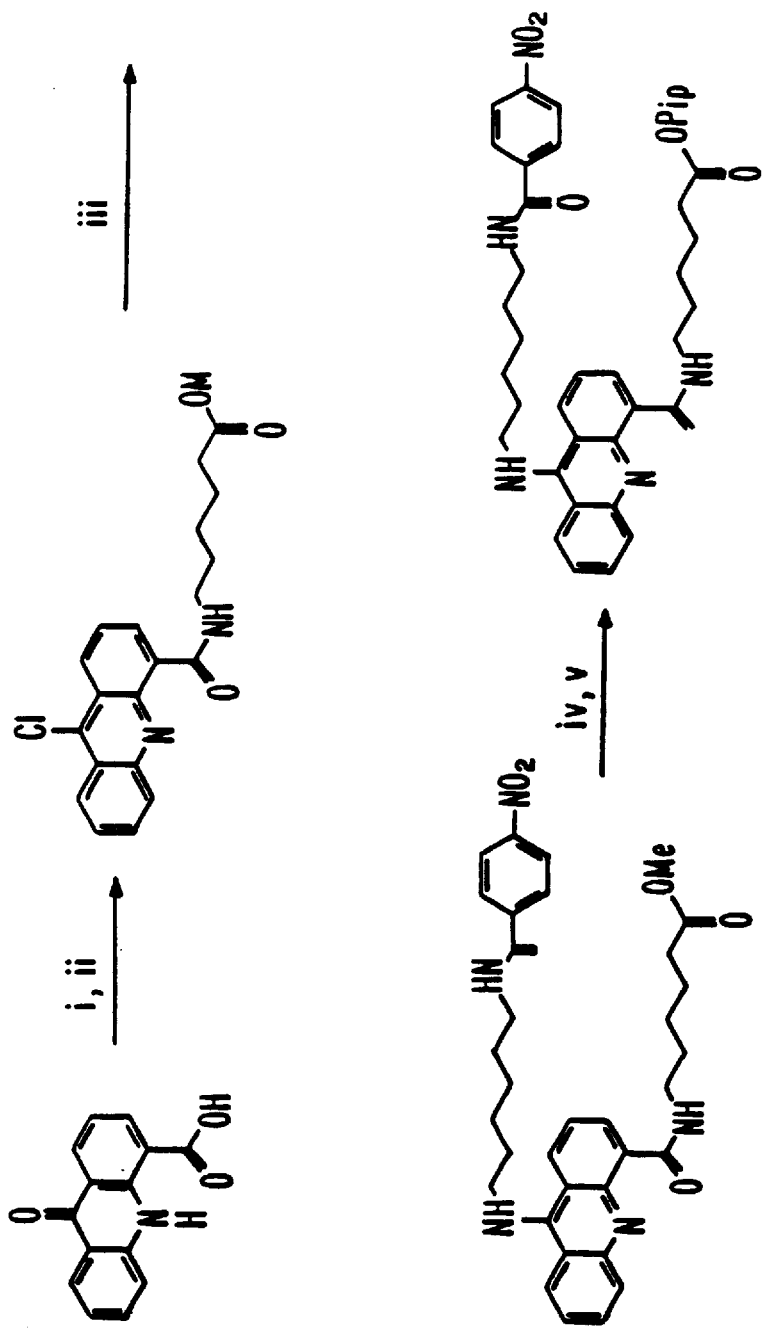
FIG. 7 provides a general scheme for the preparation of the Acr$^1$ ligand.

Strand displacement was ascertained by the following type of experiments:

1) The 9-Acr$^1$ ligand (FIG. 5), which is equipped with a 4-nitrobenzamido group to ensures cleavage of DNA upon irradiation, is expected only to cleave DNA in close proximity to its binding site. Upon irradiation of the PNA with the above 248 bp DNA fragment, selective cleavage at the $dA_{10}/dT_{10}$ sequence is observed (FIG. 3a).

2) In a so-called photofootprinting assay, where a synthetic diazo-linked acridine under irradiation cleaves DNA (except where the DNA is protected by said binding substance) upon interaction with DNA in the presence of a DNA-binding substance.

Such an experiment was performed with the above 248 bp dsDNA fragment, which showed clear protection against photocleavage of the PNA binding site (FIG. 3b).

3) In a similar type of experiment, the DNA-cleaving enzyme micrococcus nuclease, which is also hindered in its action by most DNA-binding reagents, showed increased cleavage at the $T_{10}$-target (FIG. 3c).

4) In yet another type of experiment, the well-known high susceptibility of single strand thymine ligands (as opposed to double strand thymine ligands) towards potassium permanganate oxidation was employed. Oxidation of the 248 bp in the presence of the reagent showed only oxidation of the $T_{10}$-strand of the target (FIG. 3b).

5) In a similar type of demonstration, the single strand specificity of $S_1$ nuclease clearly showed that only the $T_{10}$-strand of the target was attacked (FIG. 3d).

The very efficient binding of (Taeg)$_{10}$, (Taeg)$_{10}$-Lys-$NH_2$ and Acr$^1$-(Taeg)$_{10}$-Lys-$NH_2$ (FIGS. 11a. 11b) to the corresponding $dA_{10}$ was furthermore illustrated in two ways:

1. Ligand-oligonucleotide complexes will migrate slower than the naked oligonucleotide upon electrophoresis in polyacrylamide gels. Consequently, such experiments were performed with $Acr^1$-$(Taeg)_{10}$-Lys-$NH_2$ and $^{32}P$-end-labelled $dA_{10}$. This showed retarded migration under conditions where a normal $dA_{10}/dT_{10}$ duplex is stable, as well as under conditions where such a duplex is unstable (denaturing gel). A control experiment was performed with a mixture of $Acr^1$-$(Taeg)_{10}$-Lys-$NH_2$ and $^{32}P$-end-labelled $dT_{10}$ which showed no retardation under the above conditions.

2. Upon formation of DNA duplexes (dsDNA) from single strand DNA, the extinction coefficient decreases (hypochromicity). Thus, the denaturing of DNA can be followed by measuring changes in the absorbance, for example, as a function of $T_m$, the temperature where 50% of a duplex has disappeared to give single strands.

Duplexes were formed from the single-stranded oligodeoxyribonucleotides and the PNAs listed below. Typically 0.3 $OD_{260}$ of the T-rich strand was hybridized with 1 equivalent of the other strand by heating to 90 C. for 5 min, cooling to room temperature and kept for 30 min and finally stored in a refrigerator at 5 C. for at least 30 min. The buffers used were all 10 mM in phosphate and 1 mM in EDTA. The low salt buffer contained no sodium chloride, whereas the medium salt buffer contained 140 mM NaCl and the high salt buffer 500 mM NaCl. The pH of all the buffers was 7.2. The melting temperature of the hybrids were determined on a Gilford Response apparatus. The following extinction coefficients were used A: 15.4 ml/μmol.cm; T: 8.8; G: 11.7 and C: 7.3 for both normal oligonucleotides and PNA. The melting curves were recorded in steps of 0.5 C./min. The $T_m$ were determined from the maximum of the 1st derivative of the plot of $A_{260}$ vs temperature.

List of oligodeoxyribonucleotides:

| | | |
|---|---|---|
| 1. 5'-AAA-AAA-AA | (SEQ ID NO: 6) |
| 2. 5'-AAA-AAA-AAA-A | (SEQ ID NO: 3) |
| 3. 5'-TTT-TTT-TTT-T | (SEQ ID NO: 7) |
| 4. 5'-AAA-AAG-AAA-A | (SEQ ID NO: 8) |
| 5. 5'-AAG-AAG-AAA-A | (SEQ ID NO: 9) |
| 6. 5'-AAA-AGA-AAA-A | (SEQ ID NO: 10) |
| 7. 5'-AAA-AGA-AGA-A | (SEQ ID NO: 11) |
| 8. 5'-TTT-TCT-TTT-T | (SEQ ID NO: 12) |
| 9. 5'-TTT-TCT-TCT-T | (SEQ ID NO: 13) |
| 10. 5'-TTT-TTC-TTT-T | (SEQ ID NO: 14) |
| 11. 5'-TTT-TTC-TTC-T | (SEQ ID NO: 15) |
| 12. 5'-TTC-TTC-TTT-T | (SEQ ID NO: 16) |
| 13. 5'-TTT-TTT-TTT-TTT-TTT | (SEQ ID NO: 17) |
| 14. 5'-AAA-AAA-AAA-AAA-AAA | (SEQ ID NO: 18) |

List of PNAs a. TTT-TTT-TTT-T-Lys-$NH_2$ (SEQ ID NO: 44)
b. TTT-TTT-TT-Lys-$NH_2$ (SEQ ID NO: 45)
c. TTT-TTC-TTT-T-Lys-$NH_2$ (SEQ ID NO: 46)
d. TTC-TTC-TTT-T-Lys-$NH_2$ (SEQ ID NO: 47)
e. Acr-TTT-TTT-TTT-T-Lys-$NH_2$ (SEQ ID NO: 44)
f. Ac-TTT-TTT-TTT-T-Lys-$NH_2$ (SEQ ID NO: 44)

| Oligo/PNA | Low Salt | Medium Salt | High Salt |
|---|---|---|---|
| 1 + b | 56.0 | 51.5 | 50.0 |
| 2 + a | 73.0 | 72.5 | 73.0 |
| 2 + c | | 41.5 and 52.0* | |
| 2 + e | 84.5 | 86.0 | ≈90 |
| 2 + f | | 74 | |
| 4 + a | 60.0 | 59.0 | 61.5 |
| 4 + c | 74.5 | 72.0 | 72.5 |
| 4 + f | | 62.0 | |
| 5 + a | | 47.0 | |
| 5 + c | | 57.5 | |
| 5 + f | | 46.5 | |
| 7 + a | | 46.0 | |
| 7 + c | | 58.0 | |
| 7 + f | | 43.5 | |
| 7 + 12 | | 23.0 | |
| 13 + 14 | | 39.0 | |

*Two distinct melting temperatures are seen, indicating local melting before complete denaturation.

The hybrid formed between RNA-A (poly rA) and PNA-$T_{10}$-Lys-$NH_2$ melts at such high temperature that it cannot be measured (>90 C). But specific hybridization is demonstrated by the large drop in $A_{260}$ by mixing with RNA-A but not G,C and U. The experiment is done by mixing 1 ml of a solution of the PNA and 1 ml of a solution the RNA, each with $A_{260}$=0.6, and then measure the absorbance at 260 nm. Thereafter the sample is heated to 90 C. for 5 min, cooled to room temperature and kept at this temperature for 30 minutes and finally stored at 5 C. for 30 min.

| RNA | PNA | $A_{260}$ Before Mixing | $A_{260}$ After Mixing | $A_{260}$ After Mixing and Heating |
|---|---|---|---|---|
| RNA-A | PNA-$T_{10}$lys-$NH_2$ | 0.600 | 0.389 | 0.360 |
| RNA-U | PNA-$T_{10}$-lys-$NH_2$ | 0.600 | 0.538 | 0.528 |
| RNA-G | PNA-$T_{10}$-lys-$NH_2$ | 0.600 | 0.514 | 0.517 |
| RNA-C | PNA-$T_{10}$-lys-$NH_2$ | 0.600 | 0.540 | 0.532 |

From the above measurements the following conclusions can be made. There is base stacking, since a melting curve is observed. The PNA-DNA hybrid is more stable than a normal DNA-DNA hybrid, and the PNA-RNA is even more stable. Mismatches cause significant drops in the $T_m$-value, whether the mispaired base is in the DNA or in the PNA-strand. The $T_m$-value is only slightly dependent on ionic strength, as opposed to normal oligonucleotides.

Figure 1A:
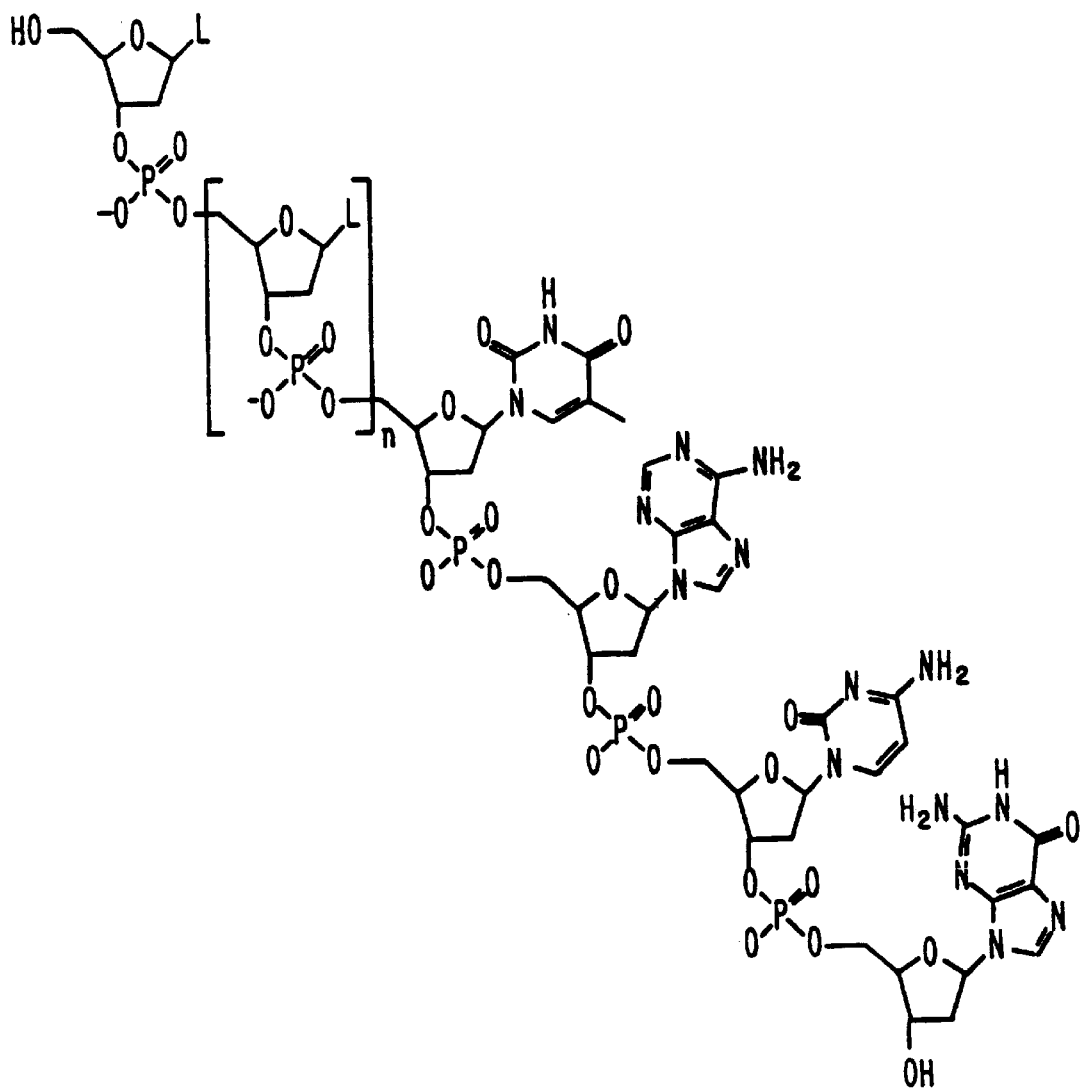
FIGS. 1(A) and 1(B) show a naturally occurring deoxyribooligonucleotide (A) and a peptide nucleic acid (PNA) of the invention (B).
Figure 1B:
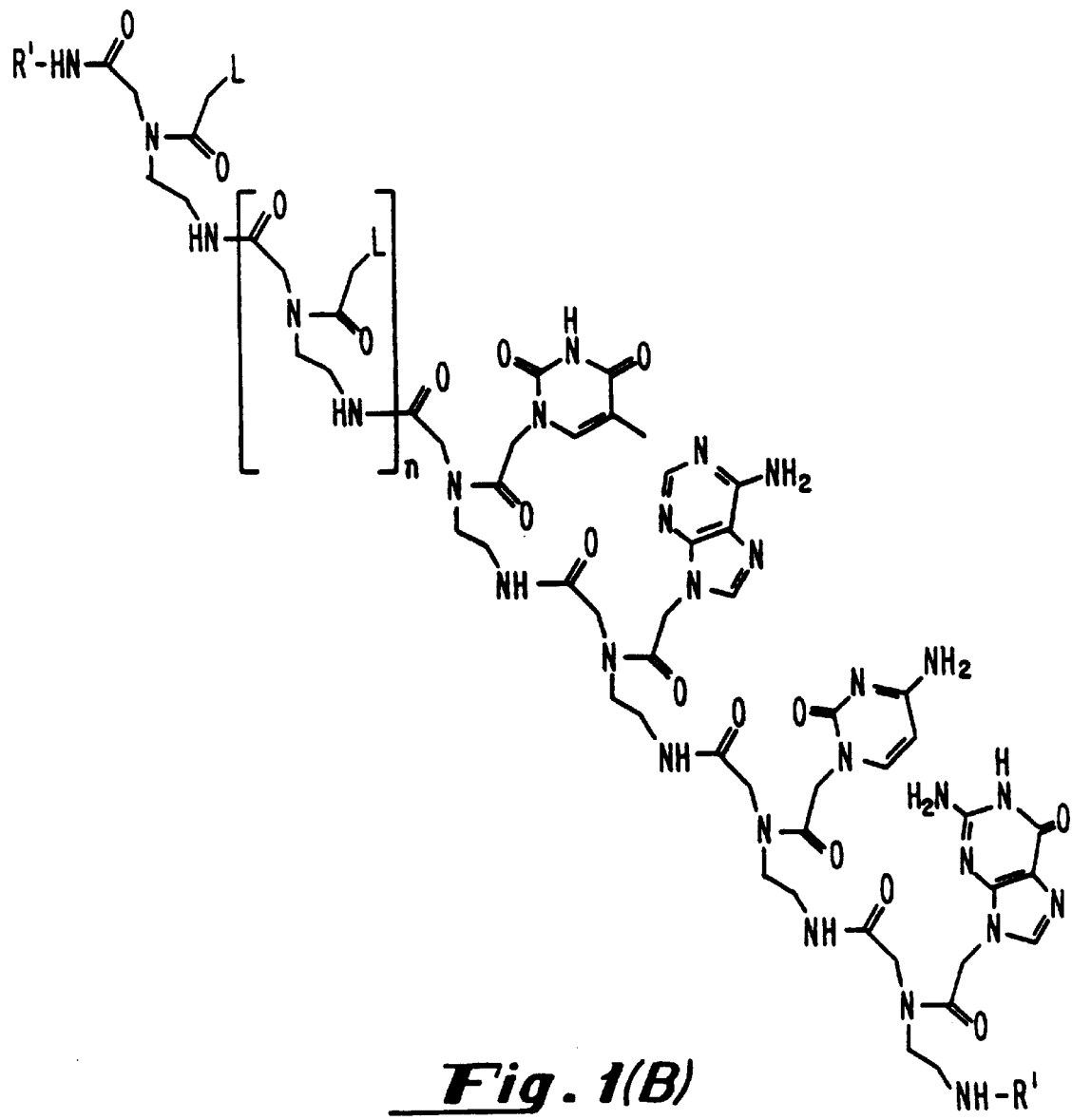

The synthesis of the PNAs according to the invention is discussed in detail in the following, where FIG. 1 illustrates one of the preferred PNA examples and compares its structure to that of a complementary DNA.

Synthesis of PNA Oligomers and Polymers

Figure 8:
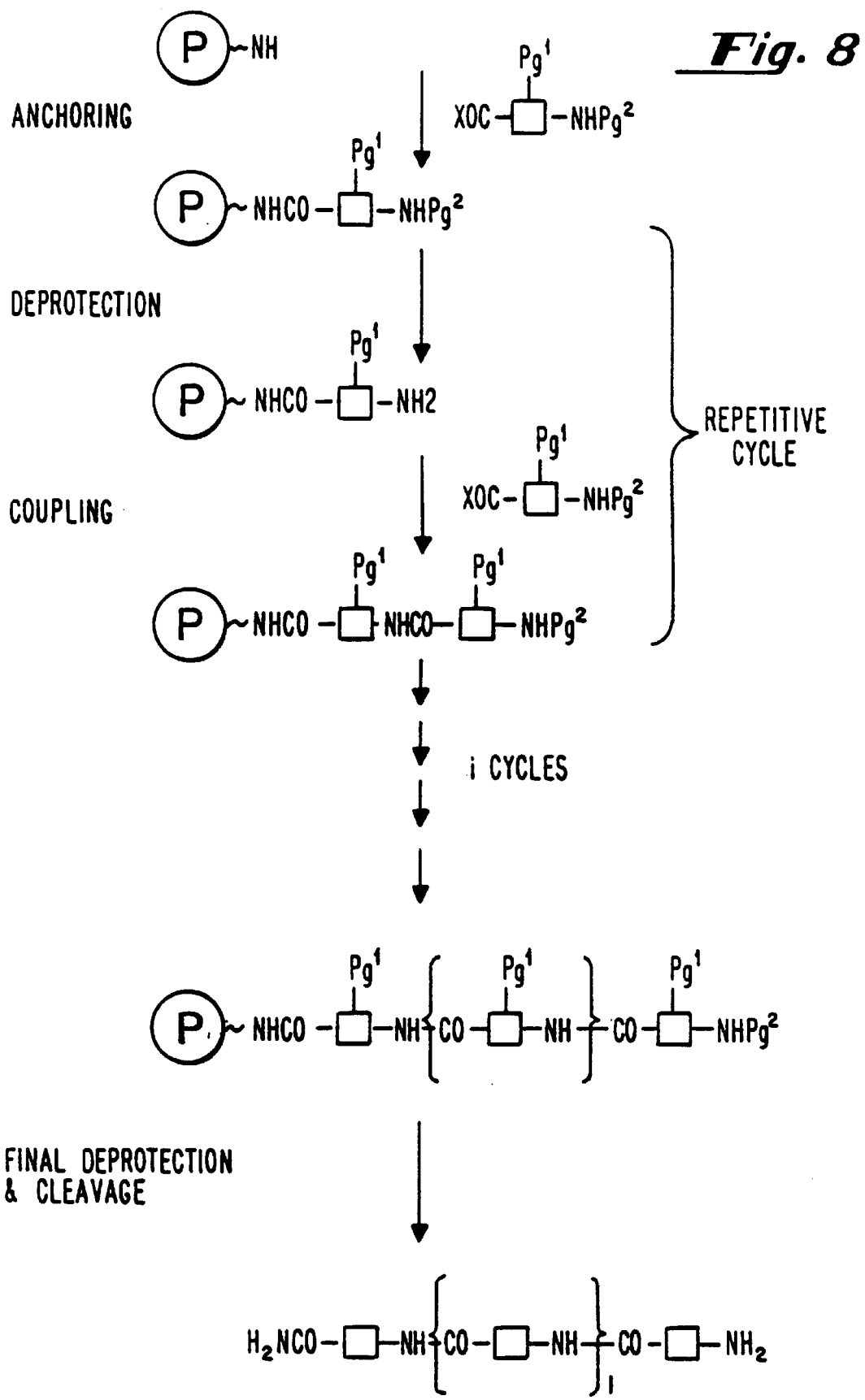
FIG. 8 provides a general scheme for solid-phase PNA synthesis illustrating the preparation of linear unprotected PNA amides.
Figure 9:
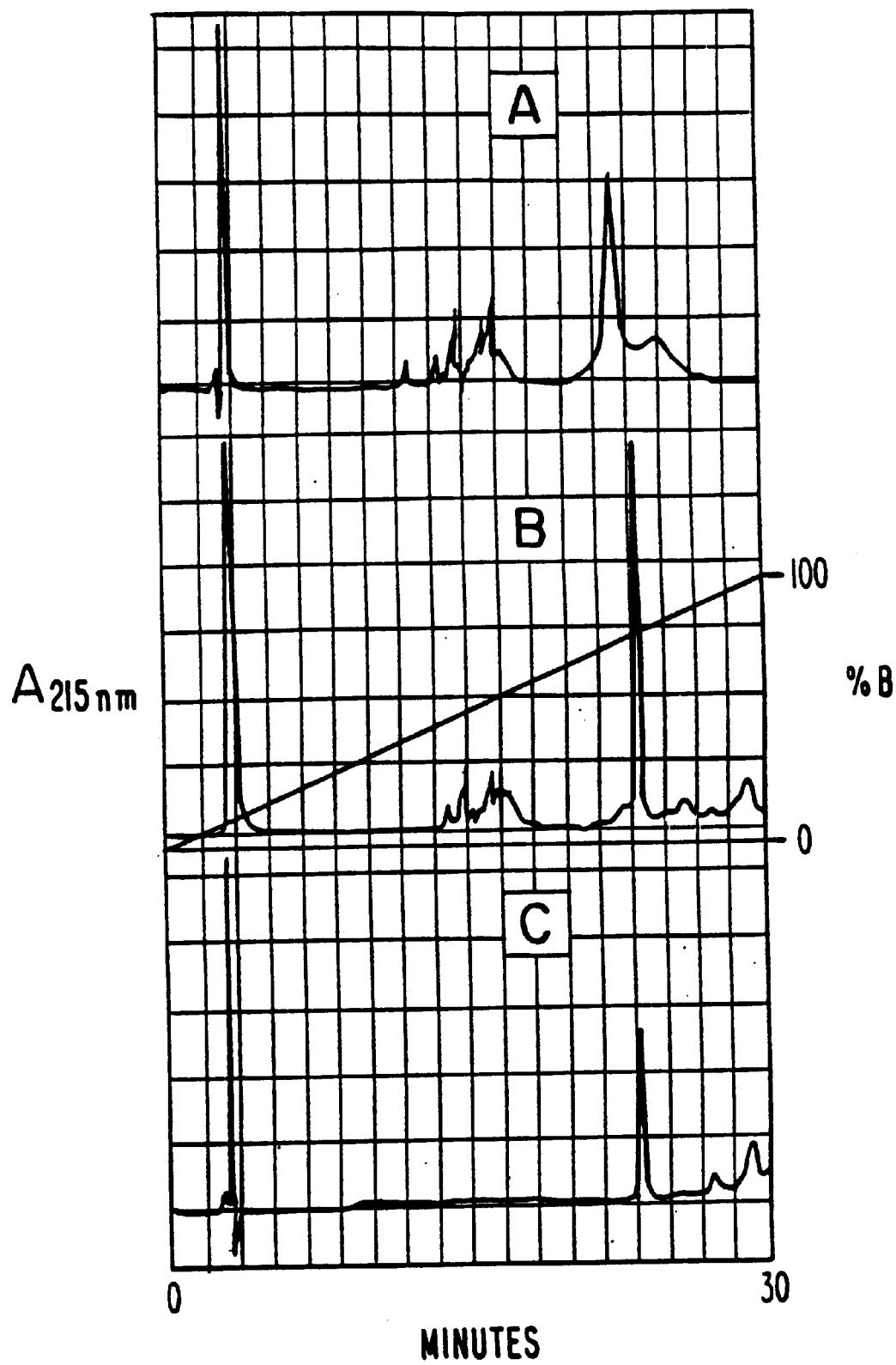
FIG. 9 shows analytical HPLC chromatograms of: (A) crude H-[Taeg]$_{15}$-NH$_2$ after HF-cleavage (before lyophilization); (B) crude Acr$^1$-[Taeg]$_{15}$-NH$_2$ after HF-cleavage (before lyophilization); and (C) purified Acr$^1$-[Taeg]$_{15}$-NH$_2$. Buffer A, 5% CH$_3$CN/95% H$_2$O/0.0445% TFA; buffer B, 60% CH$_3$CN/40% H$_2$O/0.0390% TFA; linear gradient, 0–100% of B in 30 min; flow rate, 1.2 ml/min; column, Vydac C$_{18}$ (5 µm, 0.46×25 cm).
Figure 10:
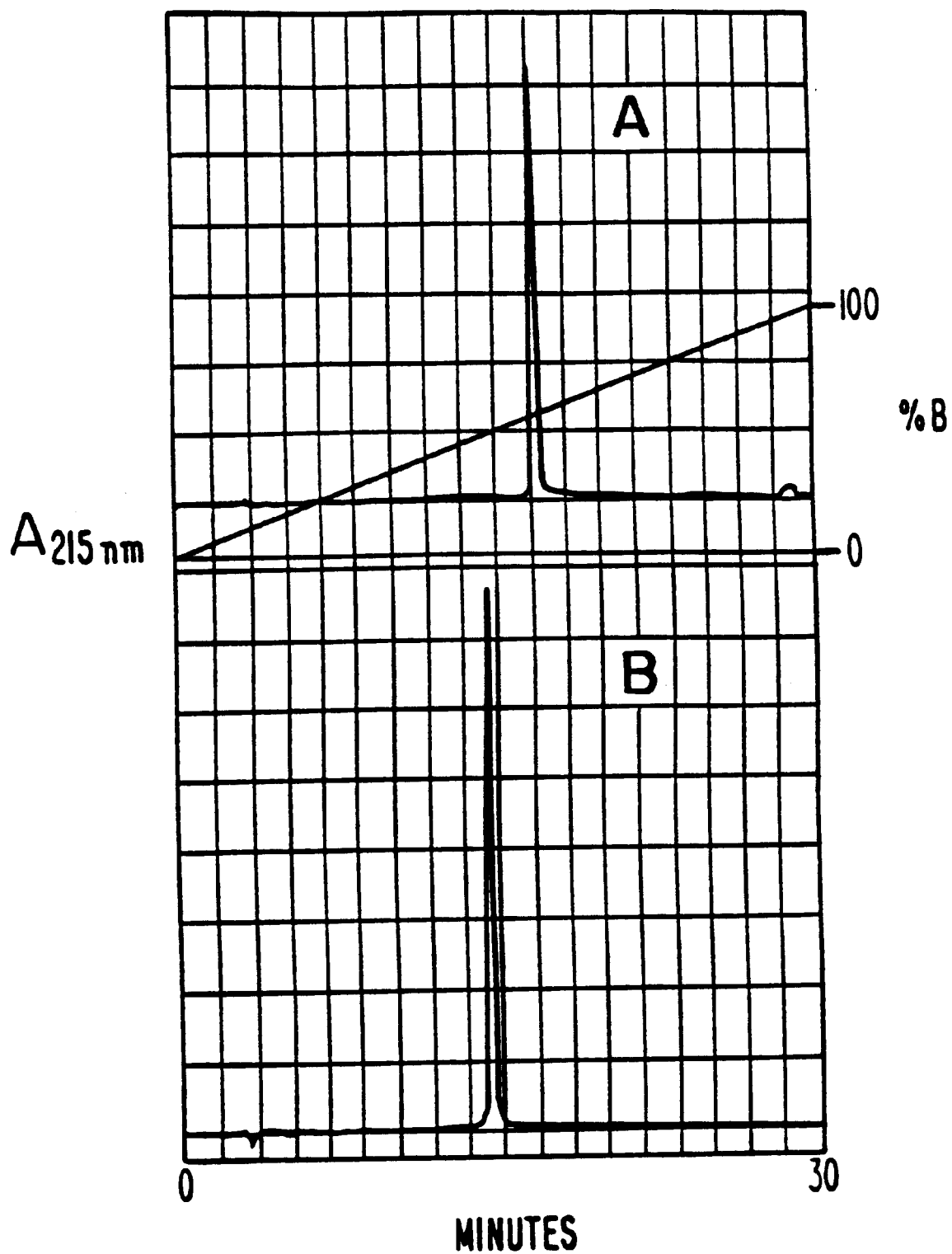
FIG. 10 shows analytical HPLC chromatograms of: (A) purified H-[Taeg]$_{10}$-Lys-NH$_2$ and (B) purified H-[Taeg]$_5$-Caeg-[Taeg]$_4$-Lys-NH$_2$ employing the same conditions as in FIG. 9.

The principle of anchoring molecules onto a solid matrix, which helps in accounting for intermediate products during chemical transformations, is known as Solid-Phase Synthesis or Merrifield Synthesis (see, e.g., Merrifield, *J. Am. Chem. Soc.*, 1963, 85, 2149 and *Science*, 1986, 232, 341). Established methods for the stepwise or fragmentwise solid-phase assembly of amino acids into peptides normally employ a beaded matrix of slightly cross-linked styrene-divinylbenzene copolymer, the cross-linked copolymer having been formed by the pearl polymerization of styrene monomer to which has been added a mixture of divinylbenzenes. A level of 1–2% cross-linking is usually employed. Such a matrix also can be used in solid-phase PNA synthesis in accordance with the present invention (FIG. 8).

Concerning the initial functionalization of the solid phase, more than fifty methods have been described in connection with traditional solid-phase peptide synthesis (see, e.g., Barany and Merrifield in "The Peptides" Vol. 2, Academic Press, New York, 1979, pp. 1–284, and Stewart and Young, "Solid Phase Peptide Synthesis", 2nd Ed., Pierce Chemical Company, Illinois, 1984). Reactions for the introduction of chloromethyl functionality (Merrifield resin; via a chloromethyl methyl ether/$SnCl_4$ reaction), aminomethyl functionality (via an N-hydroxymethylphthalimide reaction; see, Mitchell, et al., *Tetrahedron Lett.*, 1976, 3795), and benzhydrylamino functionality (Pietta, et al., *J. Chem. Soc.*, 1970, 650) are the most widely applied. Regardless of its nature, the purpose of the functionality is normally to form an anchoring linkage between the copolymer solid support and the C-terminus of the first amino acid to be coupled to the solid support. As will be recognized, anchoring linkages also can be formed between the solid support and the amino acid N-terminus. It is generally convenient to express the "concentration" of a functional group in terms of millimoles per gram (mmol/g). Other reactive functionalities which have been initially introduced include 4-methylbenzhydrylamino and 4-methoxybenzhydrylamino. All of these established methods are in principle useful within the context of the present invention. Preferred methods for PNA synthesis employ aminomethyl as the initial functionality, in that aminomethyl is particularly advantageous with respect to the incorporation of "spacer" or "handle" groups, owing to the reactivity of the amino group of the aminomethyl functionality with respect to the essentially quantitative formation of amide bonds to a carboxylic acid group at one end of the spacer-forming reagent. A vast number of relevant spacer- or handle-forming bifunctional reagents have been described (see, Barany, et al., *Int. J. Peptide Protein Res.*, 1987, 30, 705), especially reagents which are reactive towards amino groups such as found in the aminomethyl function. Representative bifunctional reagents include 4-(haloalkyl)aryl-lower alkanoic acids such as 4-(bromomethyl)phenylacetic acid, Boc-aminoacyl-4-(oxymethyl)aryl-lower alkanoic acids such as Boc-aminoacyl-4-(oxymethyl)phenylacetic acid, N-Boc-p-acylbenzhydrylamines such as N-Boc-p-glutaroylbenzhydrylamine, N-Boc-4'-lower alkyl-p-acylbenzhydrylamines such as N-Boc-4'-methyl-p-glutaroylbenzhydrylamine, N-Boc-4'-lower alkoxy-p-acylbenzhydrylamines such as N-Boc-4'-methoxy-p-glutaroyl-benzhydrylamine, and 4-hydroxymethylphenoxy-acetic acid. One type of spacer group particularly relevant within the context of the present invention is the phenylacetamidomethyl (Pam) handle (Mitchell and Merrifield, *J. Org. Chem.*, 1976, 41, 2015) which, deriving from the electron withdrawing effect of the 4-phenylacetamidomethyl group, is about 100 times more stable than the classical benzyl ester linkage towards the Boc-amino deprotection reagent trifluoroacetic acid (TFA).

Certain functionalities (e.g., benzhydrylamino, 4-methylbenzhydrylamino and 4-methoxybenzhydrylamino) which may be incorporated for the purpose of cleavage of a synthesized PNA chain from the solid support such that the C-terminal of the PNA chain is in amide form, require no introduction of a spacer group. Any such functionality may advantageously be employed in the context of the present invention.

An alternative strategy concerning the introduction of spacer or handle groups is the so-called "preformed handle" strategy (see, Tam, et al., *Synthesis*, 1979, 955–957), which offers complete control over coupling of the first amino acid, and excludes the possibility of complications arising from the presence of undesired functional groups not related to the peptide or PNA synthesis. In this strategy, spacer or handle groups, of the same type as described above, are reacted with the first amino acid desired to be bound to the solid support, the amino acid being N-protected and optionally protected at the other side-chains which are not relevant with respect to the growth of the desired PNA chain. Thus, in those cases in which a spacer or handle group is desirable, the first amino acid to be coupled to the solid support can either be coupled to the free reactive end of a spacer group which has been bound to the initially introduced functionality (for example, an aminomethyl group) or can be reacted with the spacer-forming reagent. The space-forming reagent is then reacted with the initially introduced functionality. Other useful anchoring schemes include the "multidetachable" resins (Tam, et al., *Tetrahedron Lett.*, 1979, 4935 and *J. Am. Chem. Soc.*, 1980, 102, 611; Tam, *J. Org. Chem.*, 1985, 50, 5291), which provide more than one mode of release and thereby allow more flexibility in synthetic design.

Suitable choices for N-protection are the tert-butyloxycarbonyl (Boc) group (Carpino, *J. Am. Chem. Soc.*, 1957, 79, 4427; McKay, et al., *J. Am. Chem. Soc.*, 1957, 79, 4686; Anderson, et al., *J. Am. Chem. Soc.*, 1957, 79, 6180) normally in combination with benzyl-based groups for the protection of side chains, and the 9-fluorenylmethyloxycarbonyl (Fmoc) group (Carpino, et al., *J. Am. Chem. Soc.*, 1970, 92, 5748 and *J. Org. Chem.*, 1972, 37, 3404), normally in combination with tert-butyl (tBu) for the protection of any side chains, although a number of other possibilities exist which are well known in conventional solid-phase peptide synthesis. Thus, a wide range of other useful amino protecting groups exist, some of which are Adoc (Hass, et al., *J. Am. Chem. Soc.*, 1966, 88, 1988), Bpoc (Sieber, *Helv. Chem. Acta.*, 1968, 51, 614), Mcb (Brady, et al., *J. Org. Chem.*, 1977, 42, 143), Bic (Kemp, et al., *Tetrahedron*, 1975, 4624), the o-nitrophenylsulfenyl (Nps) (Zervas, et al., *J. Am. Chem. Soc.*, 1963, 85, 3660), and the dithiasuccinoyl (Dts) (Barany, et al., *J. Am. Chem. Soc.*, 1977, 99, 7363). These amino protecting groups, particularly those based on the widely-used urethane functionality, successfully prohibit racemization (mediated by tautomerization of the readily formed oxazolinone (azlactone) intermediates (Goodman, et al., *J. Am. Chem. Soc.*, 1964, 86, 2918)) during the coupling of most α-amino acids. In addition to such amino protecting groups, a whole range of otherwise "worthless" nonurethane-type of amino protecting groups are applicable when assembling PNA molecules, especially those built from achiral units. Thus, not only the above-mentioned amino protecting groups (or those derived from any of these groups) are useful within the context of the present invention, but virtually any amino protecting group which largely fulfills the following requirements: (1) stability to mild acids (not significantly attacked by carboxyl groups); (2) stability to mild bases or nucleophiles (not significantly attacked by the amino group in question); (3) resistance to acylation (not significantly attacked by activated amino acids). Additionally: (4) the protecting group must be close to quantitatively removable, without serious side reactions, and (5) the optical integrity, if any, of the incoming amino acid should preferably be highly preserved upon coupling. Finally, the choice of side-chain protecting groups, in general, depends on the choice of the amino protecting group, since the protection of side-chain functionalities must withstand the conditions of the repeated amino deprotection cycles. This is true whether the overall strategy for chemically assembling PNA molecules relies on, for example, differential acid stability of amino and side-chain protecting groups (such as is the case for the above-mentioned "Boc-benzyl" approach) or employs an orthogonal, that is, chemoselective, protection scheme (such as is the case for the above-mentioned "Fmoc-tBu" approach), Following coupling of the first amino acid, the next stage of solid-phase synthesis is the systematic elaboration of the desired PNA chain. This elaboration involves repeated deprotection/coupling cycles. The temporary protecting group, such as a Boc or Fmoc group, on the last-coupled amino acid is quantitatively removed by a suitable treatment, for example, by acidolysis, such as with trifluoroacetic acid, in the case of Boc, or by base treatment, such as with piperidine, in the case of Fmoc, so as to liberate the N-terminal amine function.

The next desired N-protected amino acid is then coupled to the N-terminal of the last-coupled amino acid. This coupling of the C-terminal of an amino acid with the N-terminal of the last-coupled amino acid can be achieved in several ways. For example, the carboxyl group of the incoming amino acid can be reacted directly with the N-terminal of the last-coupled amino acid with the assistance of a condensation reagent such as, for example, dicyclohexylcarbodiimide (DCC) (Sheehan & Hess, et al., *J. Am. Chem. Soc.*, 1955, 77, 1067) and diisoproplycarbodiimide (DIC) (Sraantakis et al., *Biochem. biophys. res. Commun.*, 1976, 73, 336) or derivatives thereof. Alternatively, it can be bound by providing the incoming amino acid in a form with the carboxyl group activated by any of several methods, including the initial formation of an active ester derivative such as a 2,4,5-trichlorophenyl ester (Pless, et al., *Helv. Chim. Acta*, 1963, 46, 1609), a phthalimido ester (Nefkens, et al., *J. Am. Chem. Soc.*, 1961, 83, 1263), a pentachlorophenyl ester (Kupryszewski, *Rocz. Chem.*, 1961, 35, 595), a pentafluorophenyl ester (Kovacs, et al., *J. Am. Chem. Soc.*, 1963, 85, 183), an o-nitrophenyl ester (Bodanzsky, *Nature*, 1955, 175, 685), an imidazole ester (Li, et al., *J. Am. Chem. Soc.*, 1970, 92, 7608), and a 3-hydroxy-4-oxo-3,4-dihydroquinazoline (Dhbt-OH) ester (Konig, et al., *Chem. Ber.*, 1973, 103, 2024 and 2034), or the initial formation of an anhydride such as a symmetrical anhydride (Wieland, et al., *Angew. Chem., Int. Ed. Engl.*, 1971, 10, 336). Benzotriazolyl N-oxytrisdimethylaminophosphonium hexafluorophosphate (BOP), "Castro's reagent" (see, e.g., Rivaille, et al., *Tetrahedron*, 1980, 36, 3413) is recommended when assembling PNA molecules containing secondary amino groups. Finally, activated PNA monomers analogous to the recently-reported amino acid fluorides (Carpino, *J. Am. Chem. Soc.*, 1990, 112, 9651) hold considerable promise to be used in PNA synthesis as well.

Following assembly of the desired PNA chain, including protecting groups, the next step will normally be deprotection of the amino acid moieties of the PNA chain and cleavage of the synthesized PNA from the solid support. These processes can take place substantially simultaneously, thereby providing the free PNA molecule in the desired form. Alternatively, in cases in which condensation of two separately synthesized PNA chains is to be carried out, it is possible by choosing a suitable spacer group at the start of the synthesis to cleave the desired PNA chains from their respective solid supports (both peptide chains still incorporating their side-chain protecting groups) and finally removing the side-chain protecting groups after, for example, coupling the two side-chain protected peptide chains to form a longer PNA chain.

In the above-mentioned "Boc-benzyl" protection scheme, the final deprotection of side-chains and release of the PNA molecule from the solid support is most often carried out by the use of strong acids such as anhydrous HF (Sakakibara, et al., *Bull. Chem. Soc. Jpn.*, 1965, 38, 4921), boron tris (trifluoroacetate) (Pless, et al., *Helv. Chim. Acta*, 1973, 46, 1609), and sulfonic acids such as trifluoromethanesulfonic acid and methanesulfonic acid (Yajima, et al., *J. Chem. Soc., Chem. Comm.*, 1974, 107). This conventional strong acid (e.g., anhydrous HF) deprotection method, produces very reactive carbocations that may lead to alkylation and acylation of sensitive residues in the PNA chain. Such side-reactions are only partly avoided by the presence of scavengers such as anisole, phenol, dimethyl sulfide, and mercaptoethanol and, therefore, the sulfide-assisted acidolytic $S_N2$ deprotection method (Tam, et al., *J. Am. Chem. Soc.*, 1983, 105, 6442 and *J. Am. Chem. Soc.*, 1986, 108, 5242), the so-called "low", which removes the precursors of harmful carbocations to form inert sulfonium salts, is frequently employed in peptide and PNA synthesis, either solely or in combination with "high" methods. Less frequently, in special cases, other methods used for deprotection and/or final cleavage of the PNA-solid support bond are, for example, such methods as base-catalyzed alcoholysis (Barton, et al., *J. Am. Chem. Soc.*, 1973, 95, 4501), and ammonolysis as well as hydrazinolysis (Bodanszky, et al., *Chem. Ind.*, 1964 1423), hydrogenolysis (Jones, *Tetrahedron Lett.* 1977 2853 and Schlatter, et al., *Tetrahedron Lett.* 1977 2861)), and photolysis (Rich and Gurwara, *J. Am. Chem. Soc.*, 1975 97, 1575)).

Finally, in contrast with the chemical synthesis of "normal" peptides, stepwise chain building of achiral PNAs such as those based on aminoethylglycyl backbone units can start either from the N-terminus or the C-terminus, because the coupling reactions are free of racemization. Those skilled in the art will recognize that whereas syntheses commencing at the C-terminus typically employ protected amine groups and free or activated acid groups, syntheses commencing at the N-terminus typically employ protected acid groups and free or activated amine groups.

Based on the recognition that most operations are identical in the synthetic cycles of solid-phase peptide synthesis (as is also the case for solid-phase PNA synthesis), a new matrix, PEPS, was recently introduced (Berg, et al., *J. Am. Chem. Soc.*, 1989, 111, 8024 and International Patent Application WO 90/02749) to facilitate the preparation of large numbers of peptides. This matrix is comprised of a polyethylene (PE) film with pendant long-chain polystyrene (PS) grafts (molecular weight on the order of $10^6$). The loading capacity of the film is as high as that of a beaded matrix, but PEPS has the additional flexibility to suit multiple syntheses simultaneously. Thus, in a new configuration for solid-phase peptide synthesis, the PEPS film is fashioned in the form of discrete, labeled sheets, each serving as an individual compartment. During all the identical steps of the synthetic cycles, the sheets are kept together in a single reaction vessel to permit concurrent preparation of a multitude of peptides at a rate close to that of a single peptide by conventional methods. It was reasoned that the PEPS film support, comprising linker or spacer groups adapted to the particular chemistry in question, should be particularly valuable in the synthesis of multiple PNA molecules, these being conceptually simple to synthesize since only four different reaction compartments are normally required, one for each of the four "pseudo-nucleotide" units. Thus, the PEPS film support has been successfully tested in a number of PNA syntheses carried out in a parallel and substantially simultaneous fashion. The yield and quality of the products obtained from PEPS were comparable to those obtained by using the traditional polystyrene beaded support. Also, experiments with other geometries of the PEPS polymer such as, for example, non-woven felt, knitted net, sticks or microwell-plates have not indicated any limitations of the synthetic efficacy.

Two other methods proposed for the simultaneous synthesis of large numbers of peptides also apply to the preparation of multiple, different PNA molecules. The first of these methods (Geysen, et al., *Proc. Natl. Acad. Sci. USA*, 1984, 81, 3998) utilizes acrylic acid-grafted polyethylene-rods and 96-microtiter wells to immobilize the growing peptide chains and to perform the compartmentalized synthesis. While highly effective, the method is only applicable on a microgram scale. The second method (Houghten, *Proc. Natl. Acad. Sci. USA,* 1985, 82, 5131) utilizes a "tea bag" containing traditionally-used polymer beads. Other relevant proposals for multiple peptide or PNA synthesis in the context of the present invention include the simultaneous use of two different supports with different densities (Tregear, in *"Chemistry and Biology of Peptides"*, J. Meienhofer, ed., Ann Arbor Sci. Publ., Ann Arbor, 1972 pp. 175–178), combining of reaction vessels via a manifold (Gorman, *Anal. Biochem.,* 1984, 136, 397), multicolumn solid-phase synthesis (e.g. Krchnak, et al., *Int. J. Peptide Protein Res.,* 1989, 33, 209), and Holm and Meldal, in *"Proceedings of the 20th European Peptide Symposium"*, G. Jung and E. Bayer, eds., Walter de Gruyter & Co., Berlin, 1989 pp. 208–210), and the use of cellulose paper (Eichler, et al., *Collect. Czech. Chem. Commun.,* 1989, 54, 1746).

While the conventional cross-linked styrene/divinylbenzene copolymer matrix and the PEPS support are presently preferred in the context of solid-phase PNA synthesis, a non-limiting list of examples of solid supports which may be of relevance are: (1) Particles based upon copolymers of dimethylacrylamide cross-linked with N,N'-bisacryloylethylenediamine, including a known amount of N-tertbutoxycarbonyl-beta-alanyl-N'-acryloylhexamethylenediamine. Several spacer molecules are typically added via the beta alanyl group, followed thereafter by the amino acid residue subunits. Also, the beta alanyl-containing monomer can be replaced with an acryloyl sarcosine monomer during polymerization to form resin beads. The polymerization is followed by reaction of the beads with ethylenediamine to form resin particles that contain primary amines as the covalently linked functionality. The polyacrylamide-based supports are relatively more hydrophilic than are the polystyrene-based supports and are usually used with polar aprotic solvents including dimethylformamide, dimethylacetamide, N-methylpyrrolidone and the like (see Atherton, et al., *J. Am. Chem. Soc.,* 1975, 97, 6584, *Bioorg. Chem.* 1979, 8, 351), and J. C. S. Perkin I 538 (1981)); (2) a second group of solid supports is based on silica-containing particles such as porous glass beads and silica gel. One example is the reaction product of trichloro-[3-(4-chloromethyl)phenyl] propylsilane and porous glass beads (see Parr and Grohmann, *Angew. Chem. Internal. Ed.* 1972, 11, 314) sold under the trademark "PORASIL E" by Waters Associates, Framingham, Mass., USA. Similarly, a mono ester of 1,4-dihydroxymethylbenzene and silica (sold under the trademark "BIOPAK" by Waters Associates) has been reported to be useful (see Bayer and Jung, *Tetrahedron Lett.,* 1970, 4503); (3) a third general type of useful solid supports can be termed composites in that they contain two major ingredients: a resin and another material that is also substantially inert to the organic synthesis reaction conditions employed. One exemplary composite (see Scott, et al., *J. Chrom. Sci.,* 1971, 9, 577) utilized glass particles coated with a hydrophobic, cross-linked styrene polymer containing reactive chloromethyl groups, and was supplied by Northgate Laboratories, Inc., of Hamden, Conn., USA. Another exemplary composite contains a core of fluorinated ethylene polymer onto which has been grafted polystyrene (see Kent and Merrifield, Israel *J. Chem.* 1978, 17, 243) and van Rietschoten in *"Peptides 1974"*, Y. Wolman, Ed., Wiley and Sons, New York, 1975, pp. 113–116); and (4) contiguous solid supports other than PEPS, such as cotton sheets (Lebl and Eichler, *Peptide Res.* 1989, 2, 232) and hydroxypropylacrylate-coated polypropylene membranes (Daniels, et al., *Tetrahedron Lett.* 1989, 4345), are suited for PNA synthesis as well.

Whether manually or automatically operated, solid-phase PNA synthesis in the context of the present invention is normally performed batchwise. However, most of the syntheses may equally well be carried out in the continuous-flow mode, where the support is packed into columns (Bayer, et al., *Tetrahedron Lett.,* 1970, 4503 and Scott, et al., *J. Chromatogr. Sci.,* 1971, 9, 577). With respect to continuous-flow solid-phase synthesis, the rigid poly (dimethylacrylamide)-Kieselguhr support (Atherton, et al., *J. Chem. Soc. Chem. Commun.,* 1981, 1151) appears to be particularly successful, but another valuable configuration concerns the one worked out for the standard copoly (styrene-1%-divinylbenzene) support (Krchnak, et al., *Tetrahedron Lett.,* 1987, 4469).

While the solid-phase technique is presently preferred in the context of PNA synthesis, other methodologies or combinations thereof, for example, in combination with the solid-phase technique, apply as well: (1) the classical solution-phase methods for peptide synthesis (e.g., Bodanszky, *"Principles of Peptide Synthesis"*, Springer-Verlag, Berlin-New York 1984), either by stepwise assembly or by segment/fragment condensation, are of particular relevance when considering especially large scale productions (gram, kilogram, and even tons) of PNA compounds; (2) the so-called "liquid-phase" strategy, which utilizes soluble polymeric supports such as linear polystyrene (Shemyakin, et al., *Tetrahedron Lett.,* 1965, 2323) and polyethylene glycol (PEG) (Mutter and Bayer, *Angew. Chem., Int. Ed. Engl.,* 1974, 13, 88), is useful; (3) random polymerization (see, e.g., Odian, *"Principles of Polymerization"*, McGraw-Hill, New York (1970)) yielding mixtures of many molecular weights ("polydisperse") peptide or PNA molecules are particularly relevant for purposes such as screening for antiviral effects; (4) a technique based on the use of polymer-supported amino acid active esters (Fridkin, et al., *J. Am. Chem. Soc.,* 1965, 87, 4646), sometimes referred to as "inverse Merrifield synthesis" or "polymeric reagent synthesis", offers the advantage of isolation and purification of intermediate products, and may thus provide a particularly suitable method for the synthesis of medium-sized, optionally protected, PNA molecules, that can subsequently be used for fragment condensation into larger PNA molecules; (5) it is envisaged that PNA molecules may be assembled enzymatically by enzymes such as proteases or derivatives thereof with novel specificities (obtained, for example, by artificial means such as protein engineering). Also, one can envision the development of "PNA ligases" for the condensation of a number of PNA fragments into very large PNA molecules; (6) since antibodies can be generated to virtually any molecule of interest, the recently developed catalytic antibodies (abzymes), discovered simultaneously by the groups of Lerner (Tramantano, et al., *Science,* 1986, 234, 1566) and of Schultz (Pollack, et al., *Science,* 1986, 234, 1570), should also be considered as potential candidates for assembling PNA molecules. Thus, there has been considerable success in producing abzymes catalyzing acyl-transfer reactions (see for example Shokat, et al., *Nature*, 1989, 338, 269) and references therein). Finally, completely artificial enzymes, very recently pioneered by Stewart's group (Hahn, et al., *Science*, 1990, 248, 1544), may be developed to suit PNA synthesis. The design of generally applicable enzymes, ligases, and catalytic antibodies, capable of mediating specific coupling reactions, should be more readily achieved for PNA synthesis than for "normal" peptide synthesis since PNA molecules will often be comprised of only four different amino acids (one for each of the four native nucleobases) as compared to the twenty natural by occurring (proteinogenic) amino acids constituting peptides. In conclusion, no single strategy may be wholly suitable for the synthesis of a specific PNA molecule, and therefore, sometimes a combination of methods may work best.

The present invention also is directed to therapeutic or prophylactic uses for peptide nucleic acids. Likely therapeutic and prophylactic targets include herpes simplex virus (HSV), human papillomavirus (HPV), human immunodeficiency virus (HIV), *candidia albicans*, influenza virus, cytomegalovirus (CMV), intracellular adhesion molecules (ICAM), 5-lipoxygenase (5-LO), phospholipase $A_2$ ($PLA_2$), protein kinase C (PKC), and RAS oncogene. Potential applications of such targeting include treatments for ocular, labial, genital, and systemic herpes simplex I and II infections; genital warts; cervical cancer; common warts; Kaposi's sarcoma; AIDS; skin and systemic fungal infections; flu; pneumonia; retinitis and pneumonitis in immunosuppressed patients; mononucleosis; ocular, skin and systemic inflammation; cardiovascular disease; cancer; asthma; psoriasis; cardiovascular collapse; cardiac infarction; gastrointestinal disease; kidney disease; rheumatoid arthritis; osteoarthritis; acute pancreatitis; septic shock; and Crohn's disease.

For therapeutic or prophylactic treatment, the peptide nucleic acids of the invention can be formulated in a pharmaceutical composition, which may include carriers, thickeners, diluents, buffers, preservatives, surface active agents and the like. Pharmaceutical compositions may also include one or more active ingredients such as antimicrobial agents, antiinflammatory agents, anesthetics, and the like in addition to peptide nucleic acid.

The pharmaceutical composition may be administered in a number of ways depending on whether local or systemic treatment is desired, and on the area to be treated. Administration may be done topically (including ophthalmically, vaginally, rectally, intranasally), orally, by inhalation, or parenterally, for example by intravenous drip or subcutaneous, intraperitoneal or intramuscular injection.

Formulations for topical administration may include ointments, lotions, creams, gels, drops, suppositories, sprays, liquids and powders. Conventional pharmaceutical carriers, aqueous, powder or oily bases, thickeners and the like may be necessary or desirable. Coated condoms may also be useful.

Compositions for oral administration include powders or granules, suspensions or solutions in water or non-aqueous media, capsules, sachets, or tablets. Thickeners, flavorings, diluents, emulsifiers, dispersing aids or binders may be desirable.

Formulations for parenteral administration may include sterile aqueous solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons of ordinary skill can easily determine optimum dosages, dosing methodologies and repetition rates.

Treatments of this type can be practiced one a variety of organisms ranging from unicellular prokaryotic and eukaryotic organisms to multicellular eukaryotic organisms. Any organism that utilizes DNA-RNA transcription or RNA-protein translation as a fundamental part of its hereditary, metabolic or cellular control is susceptible to therapeutic and/or prophylactic treatment in accordance with the invention. Seemingly diverse organisms such as bacteria, yeast, protozoa, algae, all plants and all higher animal forms, including warm-blooded animals, can be treated. Further, since each cell of multicellular eukaryotes can be treated since they include both DNA-RNA transcription and RNA-protein translation as integral parts of their cellular activity. Furthermore, many of the organelles (e.g., mitochondria and chloroplasts) of eukaryotic cells also include transcription and translation mechanisms. Thus, single cells, cellular populations or organelles can also be included within the definition of organisms that can be treated with therapeutic or diagnostic phosphorothioate oligonucleotides. As used herein, therapeutics is meant to include the eradication of a disease state, by killing an organism or by control of erratic or harmful cellular growth or expression.

The present invention also pertains to the advantageous use of PNA molecules in solid-phase biochemistry (see, e.g., "*Solid-Phase Biochemistry—Analytical and Synthetic Aspects*", W. H. Scouten, ed., John Wiley & Sons, New York, 1983), notably solid-phase biosystems, especially bioassays or solid-phase techniques which concerns diagnostic detection/quantitation or affinity purification of complementary nucleic acids (see, e.g., "*Affinity Chromatography—A Practical Approach*", P. D. G. Dean, W. S. Johnson and F. A. Middle, eds., IRL Press Ltd., Oxford 1986; "*Nucleic Acid Hybridization—A Practical Approach*", B. D. Harnes and S. J. Higgins, IRL Press Ltd., Oxford 1987). Present day methods for performing such bioassays or purification techniques almost exclusively utilize "normal" or slightly modified oligonucleotides either physically adsorbed or bound through a substantially permanent covalent anchoring linkage to beaded solid supports such as cellulose, glass beads, including those with controlled porosity (Mizutani, et al., *J. Chromatogr.*, 1986, 356, 202), "Sephadex", "Sepharose", agarose, polyacrylamide, porous particulate alumina, hydroxyalkyl methacrylate gels, diol-bonded silica, porous ceramics, or contiguous materials such as filter discs of nylon and nitrocellulose. One example employed the chemical synthesis of oligo-dT on cellulose beads for the affinity isolation of poly A tail containing mRNA (Gilham in "*Methods in Enzymology,*" L. Grossmann and K. Moldave, eds., vol. 21, part D, page 191, Academic Press, New York and London, 1971). All the above-mentioned methods are applicable within the context of the present invention. However, when possible, covalent linkage is preferred over the physical adsorption of the molecules in question, since the latter approach has the disadvantage that some of the immobilized molecules can be washed out (desorbed) during the hybridization or affinity process. There is, thus, little control of the extent to which a species adsorbed on the surface of the support material is lost during the various treatments to which the support is subjected in the course of the bioassay/purification procedure. The severity of this problem will, of course, depend to a large extent on the rate at which equilibrium between adsorbed and "free" species is established. In certain cases it may be virtually impossible to perform a quantitative assay with acceptable accuracy and/or reproducibility. Loss of adsorbed species during treatment of the support with body fluids, aqueous reagents or washing media will, in general, be expected to be most pronounced for species of relatively low molecular weight. In contrast with oligonucleotides, PNA molecules are easier to attach onto solid supports because they contain strong nucleophilic and/or electrophilic centers. In addition, the direct assembly of oligonucleotides onto solid supports suffers from an extremely low loading of the immobilized molecule, mainly due to the low surface capacity of the materials that allow the successful use of the state-of-the-art phosphoramidite chemistry for the construction of oligonucleotides. (Beaucage and Caruthers, *Tetrahedron Lett.,* 1981, 22, 1859; Caruthers, *Science,* 1985, 232, 281). It also suffers from the fact that by using the alternative phosphite triester method (Letsinger and Mahadevan, *J. Am. Chem. Soc.* 1976, 98, 3655), which is suited for solid supports with a high surface/loading capacity, only relatively short oligonucleotides can be obtained. As for conventional solid-phase peptide synthesis, however, the latter supports are excellent materials for building up immobilized PNA molecules (the side-chain protecting groups are removed from the synthesized PNA chain without cleaving the anchoring linkage holding the chain to the solid support). Thus, PNA species benefit from the above-described solid-phase techniques with respect to the much higher (and still sequence-specific) binding affinity for complementary nucleic acids and from the additional unique sequence-specific recognition of (and strong binding to) nucleic acids present in double-stranded structures. They also can be loaded onto solid supports in large amounts, thus further increasing the sensitivity/capacity of the solid-phase technique. Further, certain types of studies concerning the use of PNA in solid-phase biochemistry can be approached, facilitated, or greatly accelerated by use of the recently-reported "light-directed, spatially addressable, parallel chemical synthesis" technology (Fodor, et al., *Science,* 1991, 251, 767), a technique that combines solid-phase chemistry and photolithography to produce thousands of highly diverse, but identifiable, permanently immobilized compounds (such as peptides) in a substantially simultaneous way.

Figure 13:
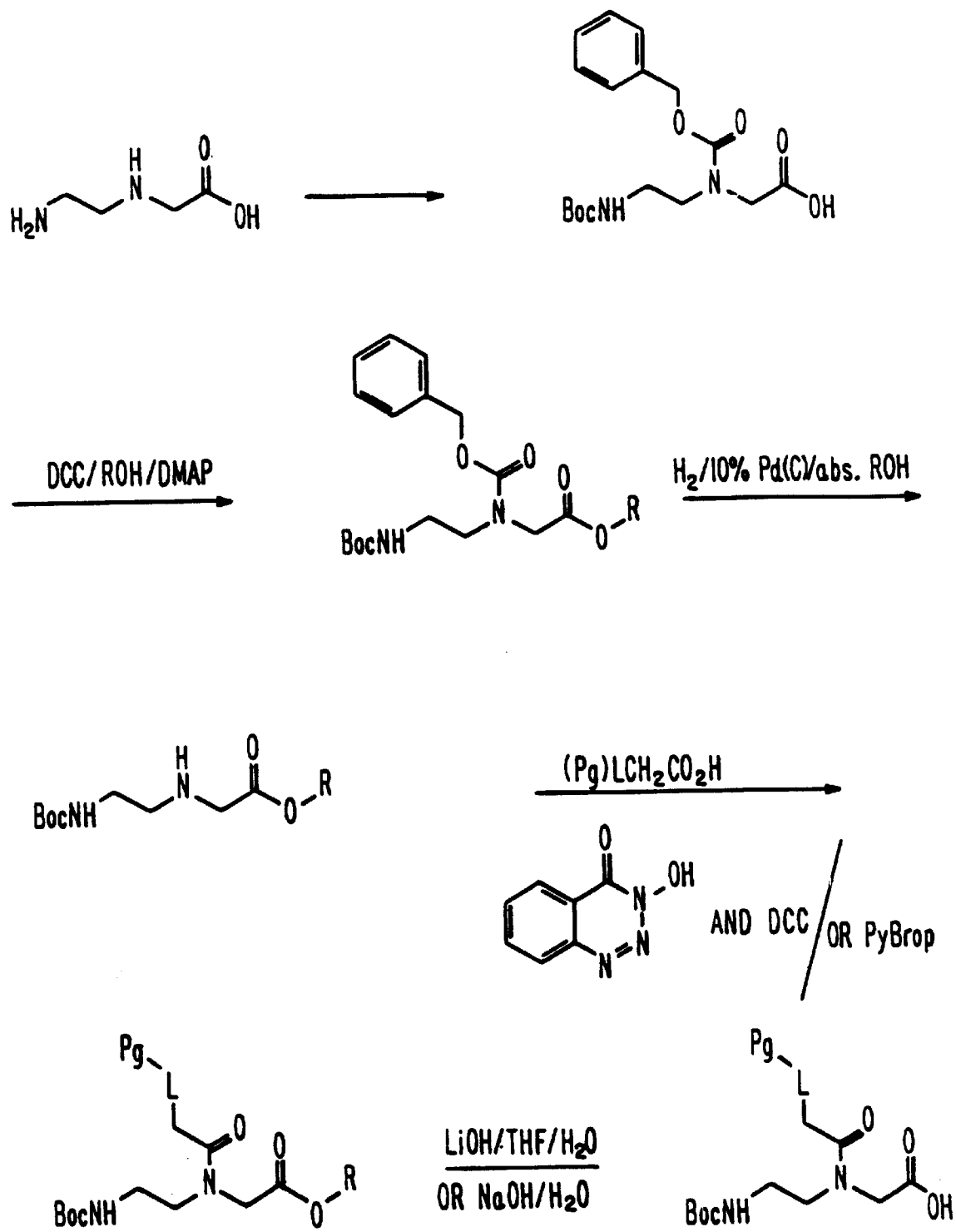
FIG. 13 provides a procedure for the synthesis of protected PNA synthons.

Additional objects, advantages, and novel features of this invention will become apparent to those skilled in the art upon examination of the following examples thereof, which are not intended to be limiting.
Synthesis of Monomeric Building Blocks The monomers preferably are synthesized by the general scheme outlined in FIG. 13. This involves preparation of either the methyl or ethyl ester of (Bocaminoethyl)glycine, by a protection/deprotection procedure as described in Examples 24–26. The synthesis of thymine monomer is described in Examples 27–28, and that of the protected cytosine monomer is described in Example 29.

Figure 14:
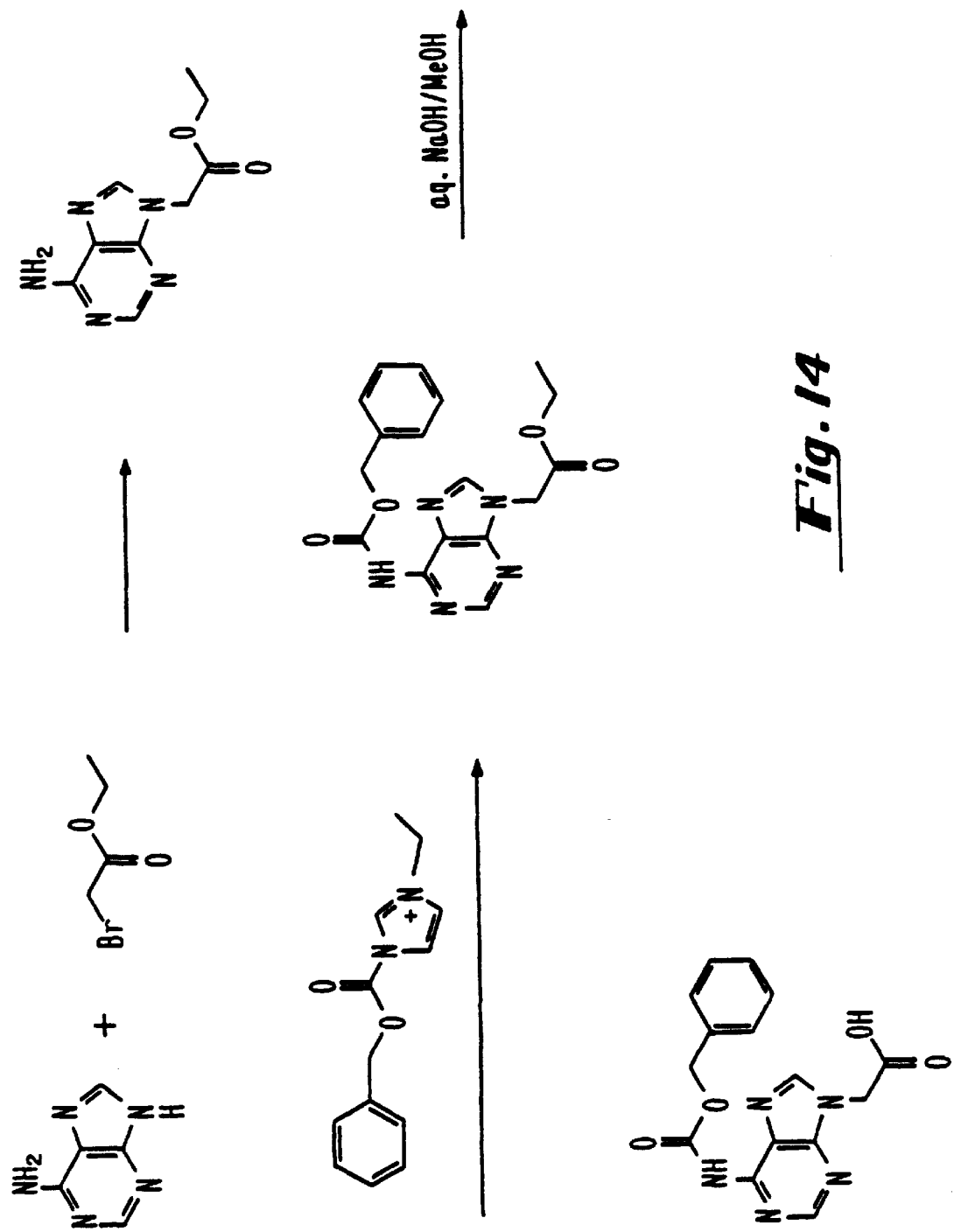
FIG. 14 provides a procedure for the synthesis of a protected adenine monomer synthon.

The synthesis of the protected adenine monomer (FIG. 14) involved alkylation with ethyl bromoacetate (Example 30) and verification of the position of substitution by X-ray crystallography, as being the wanted 9-position. The $N^6$-amino group then was protected with the benzyloxycarbonyl group by the use of the reagent N-ethyl-benzyloxycarbonylimidazole tetrafluoroborate (Example 31). Simple hydrolysis of the product ester (Example 32) gave $N^6$-benzyloxycarbonyl-9-carboxymethyl adenine, which then was used in the standard procedure (Examples 33–34, FIG. 13). The adenine monomer has been built into two different PNA-oligomers (Examples 56, 57, 71 and 73).

Figure 15:
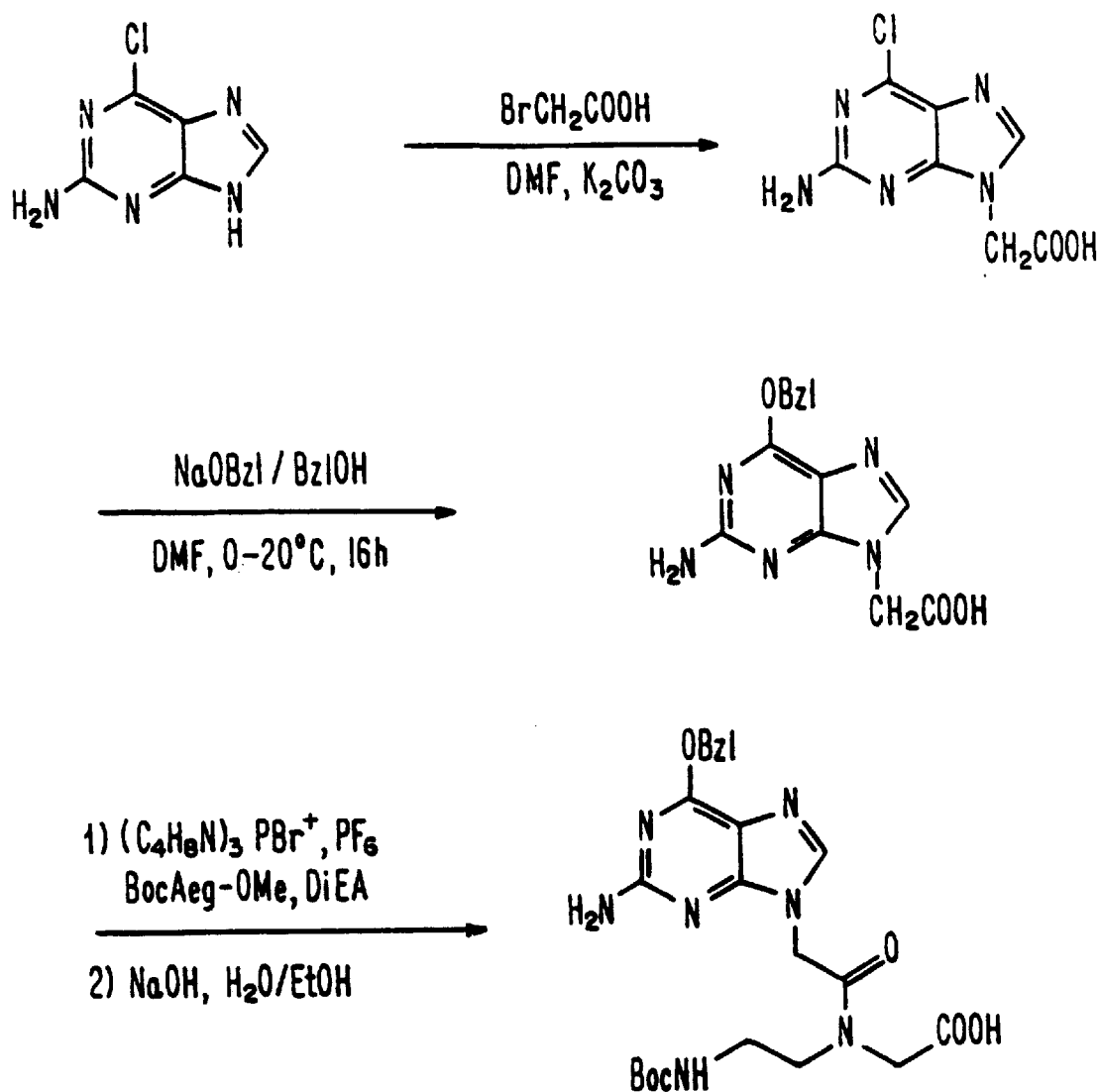
FIG. 15 provides a procedure for the synthesis of a protected guanine monomer synthon.

The synthesis of the protected G-monomer is outlined in FIG. 15. The starting material, 2-amino-6-chloropurine, was alkylated with bromoacetic acid (Example 35) and the chlorine atom was then substituted with a benzyloxy group (Example 36). The resulting acid was coupled to the (bocaminoethyl)glycine methyl ester (from Example 26) with agent PyBrop™, and the resulting ester was hydrolysed (Example 37). The $O^6$-benzyl group was removed in the final HF-cleavage step in the synthesis of the PNA-oligomer. Cleavage was verified by finding the expected mass of the final PNA-oligomer, upon incorporation into an PNA-oligomer using diisopropyl carbodiimide as the condensation agent (Examples 55 and 71).
Extended Backbones Alterations of the groups A, T and D (FIG. 16) is demonstrated by the synthesis of monomeric building blocks and incorporation into PNA-oligomers.

Figure 17:
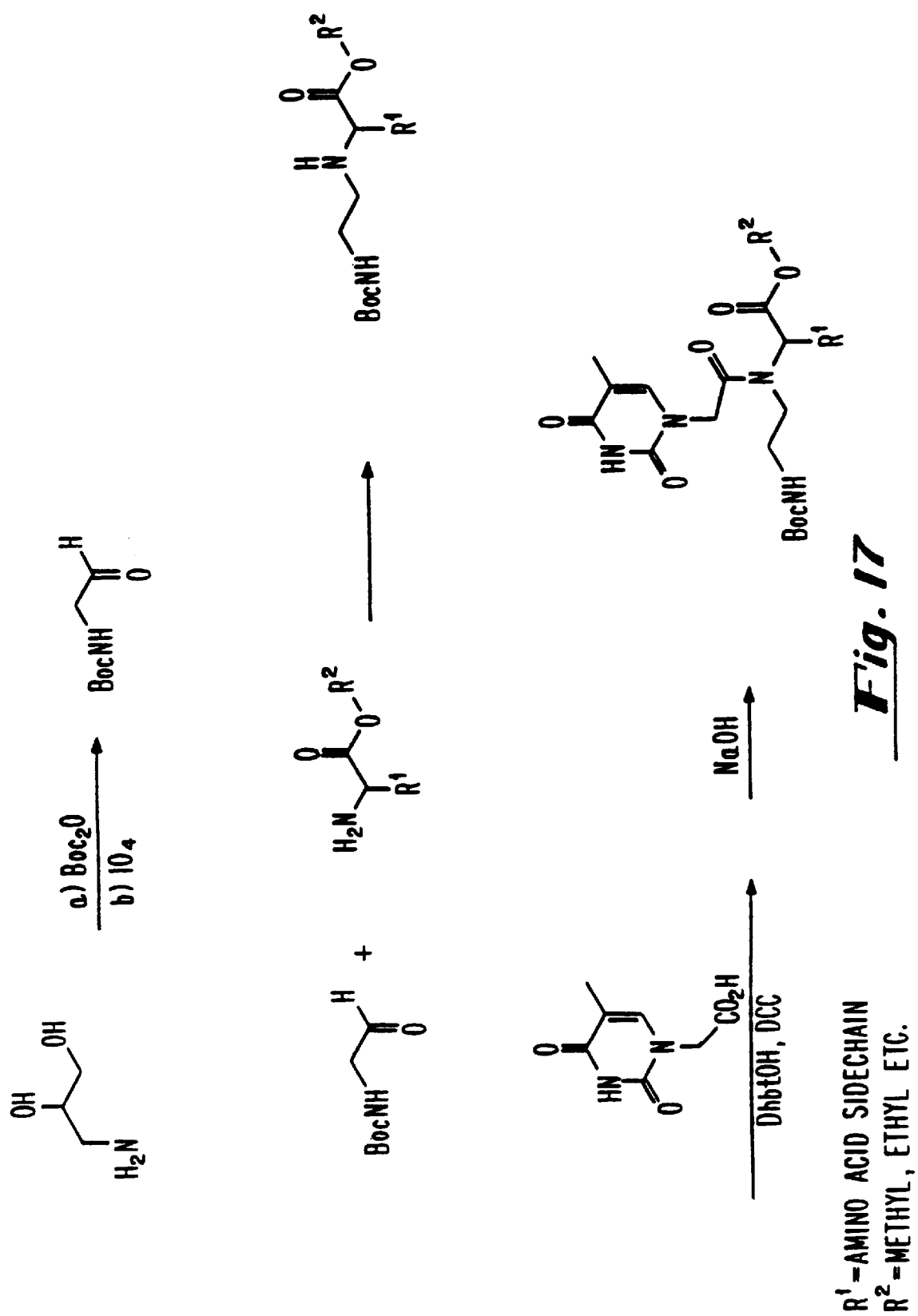
FIG. 17 provides a procedure for synthesis of thymine monomer synthons with side chains corresponding to the normal amino acids.

In one example, the T group was a $CH(CH_3)$ group. The synthesis of the corresponding monomer is outlined in FIG. 17. It involves preparation of Boc-protected 1-amino-2,3-propanediol (Example 38), which is cleaved by periodate to give bocaminoacetaldehyde, which is used directly in the next reaction. The bocaminoacetaldehyde can be condensed with a variety of amines; in Example 39, alanine ethyl ester was used. In Examples 40–42, the corresponding thymine monomers were prepared. The monomer has been incorporated into an 8-mer (Example 60) by the DCC-coupling protocol (Examples 56 and 57).

Figure 18A:
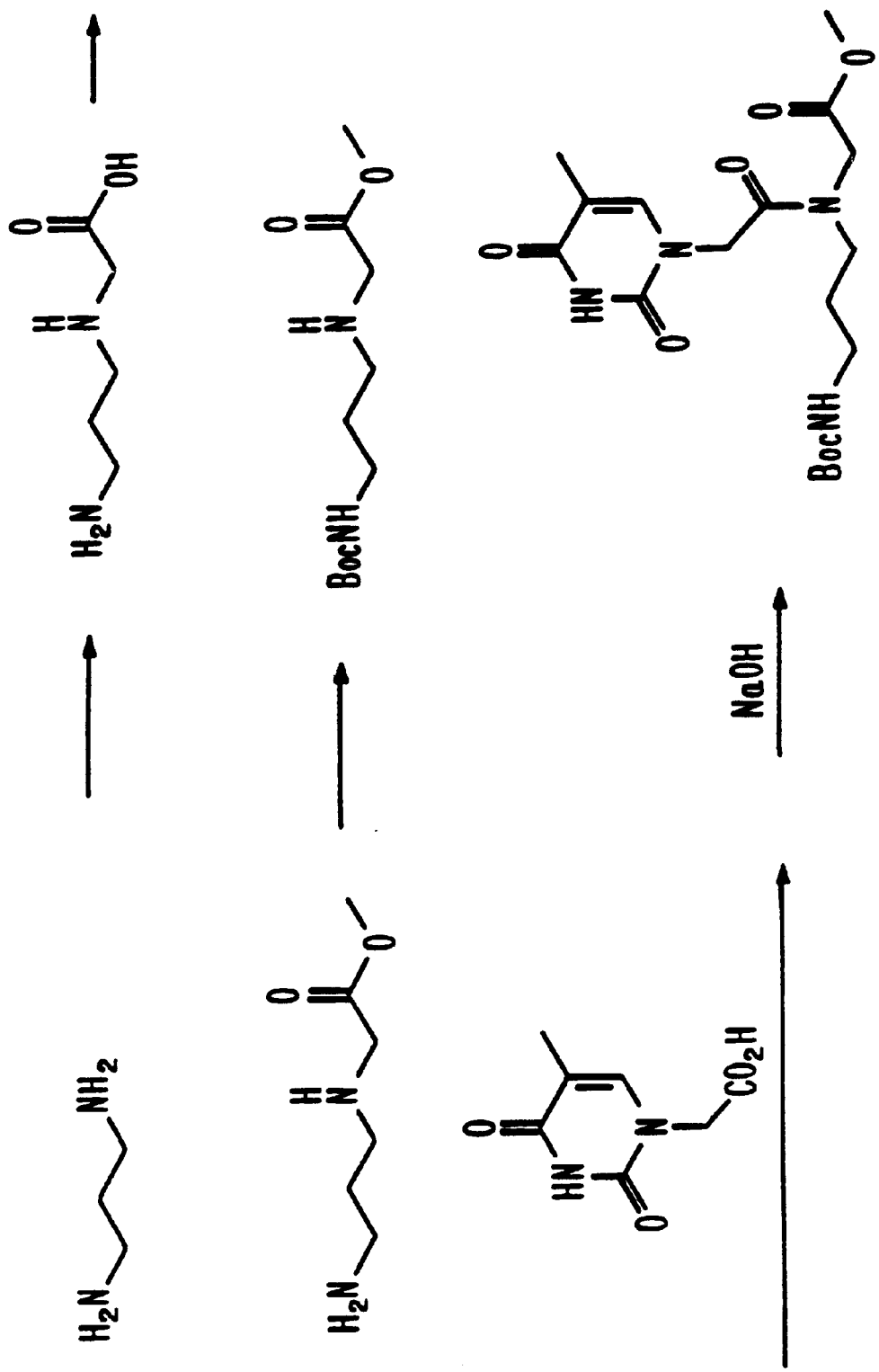
FIGS. 18(a) and 18(b) provide procedures for synthesis of an aminopropyl analogue and a propionyl analogue, respectively, of a thymine monomer synthon.
Figure 18B:
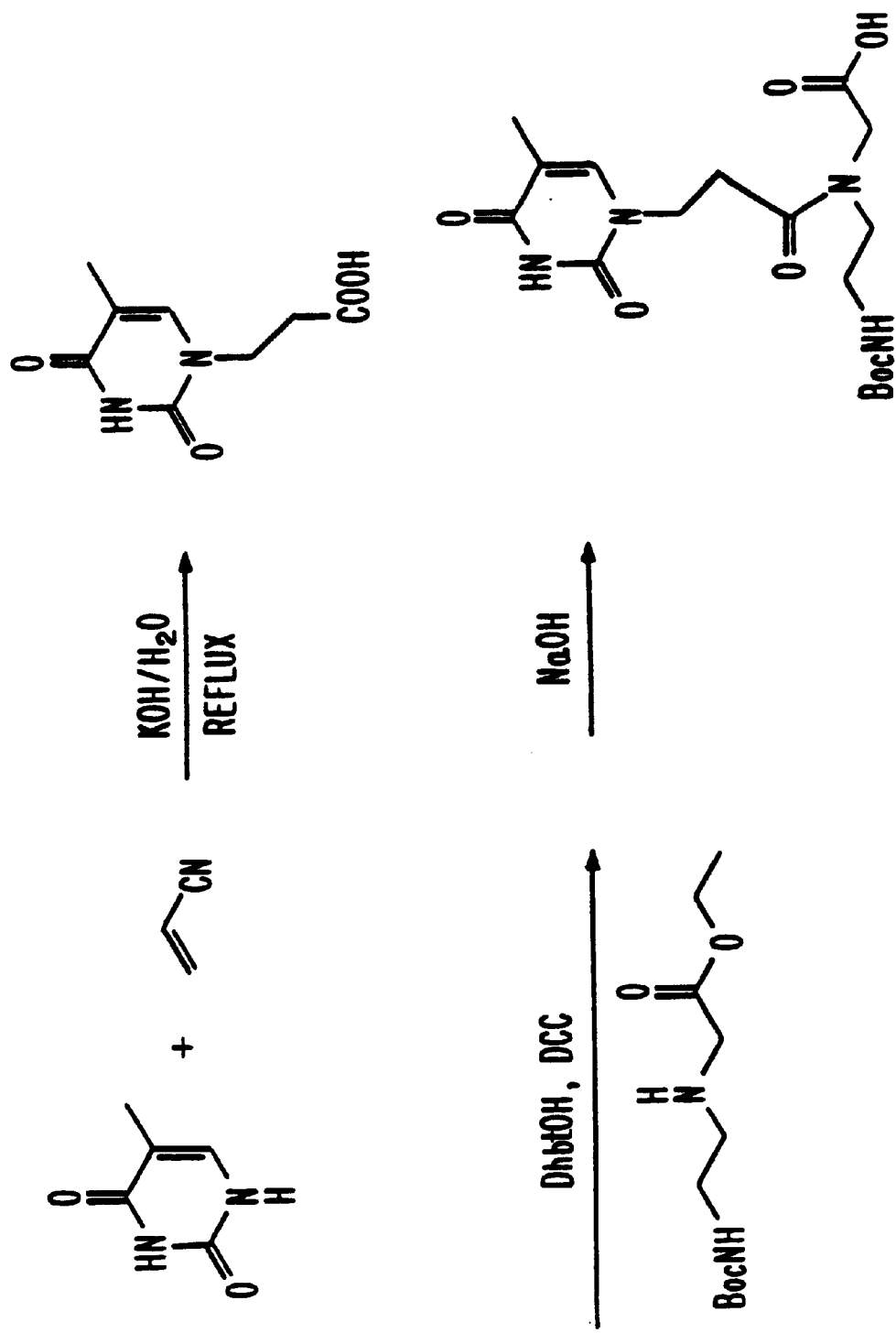

In another example, the D group is a $(CH_2)_3$ group. The synthesis of the corresponding monomer is outlined in FIG. 18.A and described in Examples 43–44.

In another example, the A group is a $(CH_2)_2CO$ group. The synthesis of the corresponding thymine monomer is outlined FIG. 18.B and Examples 46 through 48.

Figure 19:
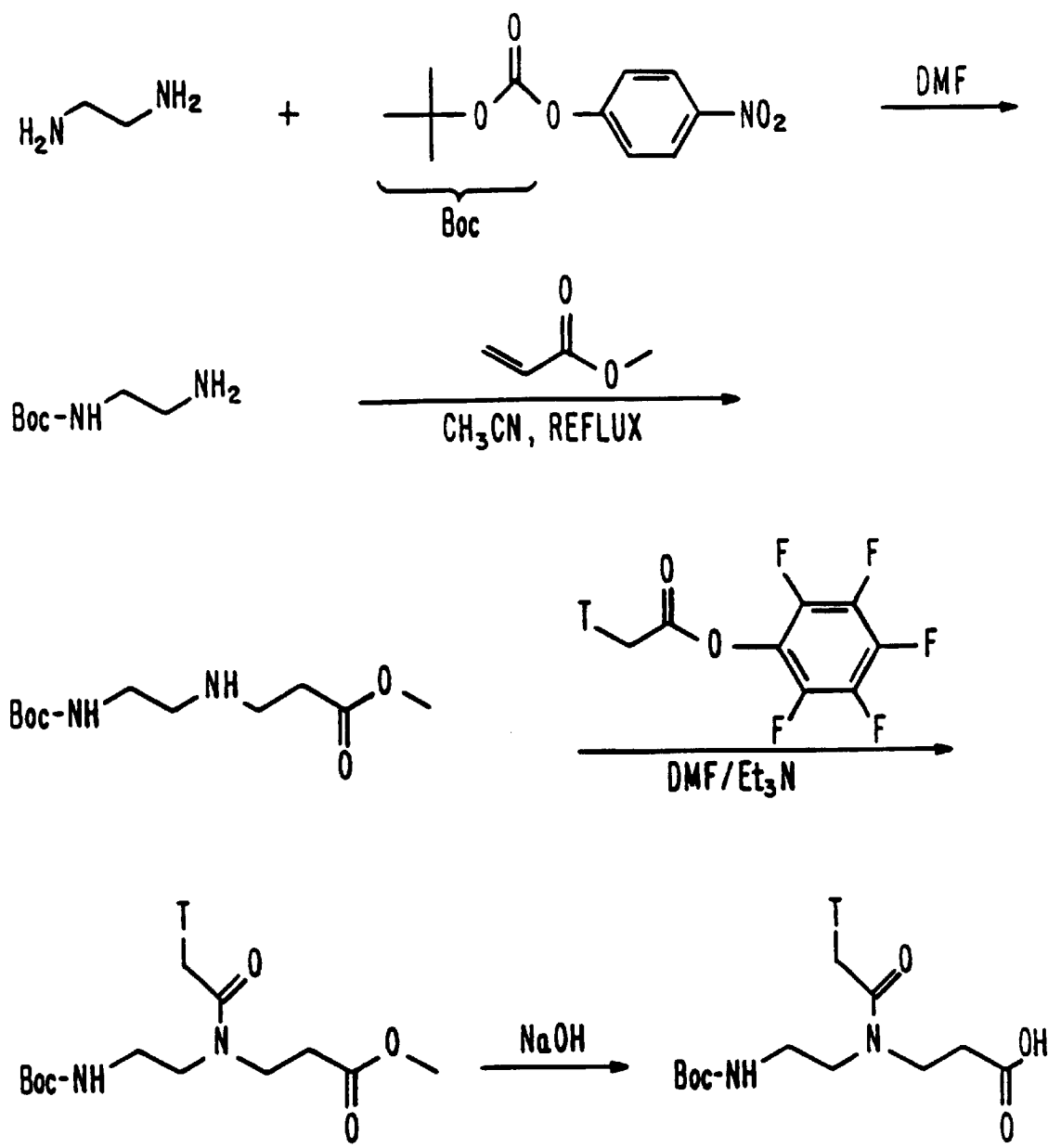
FIG. 19 provides a procedure for synthesis of an aminoethyl-β-alanine analogue of thymine monomer synthon.

In yet another example, the T group is a $(CH_2)_2$ group. The synthesis of the thymine and protected cytosine monomer is outlined in FIG. 19 and Examples 49 through 54. Hybridization experiments with a PNA-oligomer containing one unit is described in Examples 61 and 81, which shows a significant lowering of affinity but a retention of specificity.
General Remarks The following abbreviations are used in the experimental examples: DMF, N,N-dimethylformamide; DCC, N,N-dicyclohexyl carbodiimide; DCU, N,N-dicyclohexyl urea; THF, tetrahydrofuran; aeg, N-acetyl (2'-aminoethyl)glycine; pfp, pentafluorophenyl; Boc, tert-butoxycarbonyl; Z, benzyloxycarbonyl; NMR, nuclear magnetic resonance; s, singlet; d, doublet; dd, doublet of doublets; t; triplet; q, quartet; m, multiplet; b, broad; δ, chemical shift;

NMR spectra were recorded on either a JEOL FX 90Q spectrometer, or a Bruker 250 MHz with tetramethylsilane as internal standard. Mass spectrometry was performed on a MassLab VG 12-250 quadropole instrument fitted with a VG FAB source and probe. Melting points were recorded on Buchi melting point apparatus and are uncorrected. N,N-Dimethylformamide was dried over 4 Å molecular sieves, distilled and stored over 4 Å molecular sieves. Pyridine (HPLC quality) was dried and stored over 4 Å molecular sieves. Other solvents used were either the highest quality obtainable or were distilled before use. Dioxane was passed through basic alumina prior to use. Bocanhydride, 4-nitrophenol, methyl bromoacetate, benzyloxycarbonyl chloride, pentafluorophenol were all obtained through Aldrich Chemical Company. Thymine, cytosine, adenine were all obtained through Sigma.

Thin layer chromatography (Tlc) was performed using the following solvent systems: (1) chloroform:triethyl amine:methanol, 7:1:2; (2) methylene chloride:methanol, 9:1; (3) chloroform:methanol:acetic acid 85:10:5. Spots were visualized by UV (254 nm) or/and spraying with a ninhydrin solution (3 g ninhydrin in 1000 ml 1-butanol and 30 ml acetic acid), after heating at 120° C. for 5 min and, after spraying, heating again.

EXAMPLE 1 tert-Butyl 4-nitrophenyl Carbonate

Sodium carbonate (29.14 g; 0.275 mol) and 4-nitrophenol (12.75 g; 91.6 mmol) were mixed with dioxane (250 ml). Boc-anhydride (20.0 g; 91.6 mmol) was transferred to the mixture with dioxane (50 ml). The mixture was ref luxed for 1 h, cooled to 0° C., filtered and concentrated to 1/3, and then poured into water (350 ml) at 0° C. After stirring for ½ h., the product was collected by filtration, washed with water, and then dried over sicapent, in vacuo. Yield 21.3 g (97%). M.p. 73.0–74.5° C. (litt. 78.5–79.5° C.). Anal. for $C_{11}H_{13}NO_5$ found(calc.) C, 55.20(55.23); H, 5.61(5.48); N, 5.82(5.85).

EXAMPLE 2

(N'-Boc-2'-aminoethyl)glycine (2)

The title compound was prepared by a modification of the procedure by Heimer, et al. *Int. J. Pept.*, 1984, 23, 203–211 N-(2-Aminoethyl)glycine (1, 3.00 g; 25.4 mmol) was dissolved in water (50 ml), dioxane (50 ml) was added, and the pH was adjusted to 11.2 with 2 N sodium hydroxide. tert-Butyl-4-nitrophenyl carbonate (7.29 g; 30.5 mmol) was dissolved in dioxane (40 ml) and added dropwise over a period of 2 h, during which time the pH was maintained at 11.2 with 2 N sodium hydroxide. The pH was adjusted periodically to 11.2 for three more hours and then the solution was left overnight. The solution was cooled to 0° C. and the pH was carefully adjusted to 3.5 with 0.5 M hydrochloric acid. The aqueous solution was washed with chloroform (3×200 ml), the pH adjusted to 9.5 with 2N sodium hydroxide and the solution was evaporated to dryness, in vacuo (14 mmHg). The residue was extracted with DMF (25+2×10 ml) and the extracts filtered to remove excess salt. This results in a solution of the title compound in about 60% yield and greater than 95% purity by tlc (system 1 and visualised with ninhydrin, Rf=0.3). The solution was used in the following preparations of Boc-aeg derivates without further purification.

EXAMPLE 3

N-1-Carboxymethylthymine (4)

This procedure is different from the literature synthesis, but is easier, gives higher yields, and leaves no unreacted thymine in the product. To a suspension of thymine (3, 40.0 g; 0.317 mol) and potassium carbonate (87.7 g; 0.634 mmol) in DMF (900 ml) was added methyl bromoacetate (30.00 ml; 0.317 mmol). The mixture was stirred vigorously overnight under nitrogen. The mixure was filtered and evaporated to dryness, in vacuo. The solid residue was treated with water (300 ml) and 4 N hydrochloric acid (12 ml), stirred for 15 min at 0° C., filtered, and washed with water (2×75 ml). The precipitate was treated with water (120 ml) and 2N sodium hydroxide (60 ml), and was boiled for 10 minutes. The mixture was cooled to 0° C., filtered, and the pure title compound was precipitated by the addition of 4 N hydrochloric acid (70 ml). Yield after drying, in vacuo over sicapent: 37.1 g (64%). $^1$H-NMR: (90 MHz; DMSO-$d_6$): 11.33 ppm (s,1H,N$\underline{H}$); 7.49(d,J=0.92 Hz,1H,Ar$\underline{H}$); 4.38 (s,2H,C$\underline{H}_2$); 1.76 (d,J=0.92 Hz,T-C$\underline{H}_3$).

EXAMPLE 4

N-1-Carboxymethylthymine pentafluorophenyl Ester (5)

N-1-Carboxymethylthymine (4, 10.0 g; 54.3 mmol) and pentafluorophenol (10.0 g; 54.3 mmol) were dissolved in DMF (100 ml) and cooled to 5° C. in ice water. DCC (13.45 g; 65.2 mmol) then was added. When the temperature passed below 5° C., the ice bath was removed and the mixture was stirred for 3 h at ambient temperature. The precipitated DCU was removed by filtration and washed twice with DMF (2×10 ml). The combined filtrate was poured into ether (1400 ml) and cooled to 0° C. Petroleum ether (1400 ml) was added and the mixture was left overnight. The title compound was isolated by filtration and was washed thoroughly with petroleum ether. Yield: 14.8 g(78%). The product was pure enough to carry out the next reaction, but an analytical sample was obtained by recrystallization from 2-propanol. M.p. 200.5–206° C. Anal. for $C_{13}H_7F_5N_2O_4$. Found(calc.) C, 44.79(44.59); H, 2.14(2.01); N, 8.13(8.00). FAB-MS: 443 (M+1+glycerol), 351 (M+1). $^1$H-NMR (90 MHz; DMSO-$d_6$): 11.52 ppm (s,1H,N$\underline{H}$); 7.64 (s,1H,Ar$\underline{H}$); 4.99 (s,2H,C$\underline{H}_2$); 1.76 (s,3H,C$\underline{H}_3$).

EXAMPLE 5

1-(Boc-aeg)thymine (6)

To the DMF-solution from above was added triethyl amine (7.08 ml; 50.8 mmol) followed by N-1-carboxymethylthymine pentafluorophenyl ester (5, 4.45 g; 12.7 mmol). The resultant solution was stirred for 1 h. The solution was cooled to 0° C. and treated with cation exchange material ("Dowex 50W X-8", 40 g) for 20 min. The cation exchange material was removed by filtration, washed with dichloromethane (2×15 ml), and dichloromethane (150 ml) was added. The resulting solution was washed with saturated sodium chloride, dried over magnesium sulfate, and evaporated to dryness, in vacuo, first by a water aspirator and then by an oil pump. The residue was shaken with water (50 ml) and evaporated to dryness. This procedure was repeated once. The residue then was dissolved in methanol (75 ml) and poured into ether (600 ml) and petroleum ether (1.4 L). After stirring overnight, the white solid was isolated by filtration and was washed with petroleum ether. Drying over sicapent, in vacuo, gave 3.50 g (71.7%). M.p. 142–147° C. Anal. for $C_{16}H_{24}N_4O_7$. Found (calc.) C, 49.59(50.00); H, 6.34(6.29); N, 14.58(14.58). $^1$H-NMR (250 MHz, DMSO-$d_6$): Due to the limited rotation around the secondary amide bond several of the signals were doubled in the ratio 2:1, (indicated in the list by mj. for major and mi. for minor). 12.73 ppm (b,1H, —CO$_2$H); 11.27 ppm (s, mj., imide); 11.25 ppm (s, mi., imide); 7.30 ppm (s, mj., Ar$\underline{H}$); 7.26 ppm (s, mi., Ar$\underline{H}$); 6.92 ppm (unres. t, mj., BocNH); 6.73 ppm (unres. t; mi., BocNH); 4.64 ppm (s, mj., T-C$\underline{H}_2$—CO—); 4.47 ppm (s, mi., T-C$\underline{H}_2$—CO—); 4.19 ppm (s, mi., CONRC$\underline{H}_2$CO$_2$H); 3.97 ppm (s, mj., CONRC$\underline{H}_2$CO$_2$H); 3.41–2.89 ppm (unres. m, —CH$_2$CH$_2$— and water); 1.75 ppm (s,3H, T-CH$_3$); 1.38 ppm (s, 9H, t-Bu). $^{13}$C-NMR: 170.68 ppm (CO); 170.34 (CO); 167.47 (CO); 167.08 (CO); 164.29 (CO); 150.9 (C5"); 141.92 (C6"); 108.04 (C2'); 77.95 and 77.68 (Thy-C$\underline{H}_2$CO); 48.96, 47.45 and 46.70 (—$\underline{C}$H$_2$$\underline{C}$H$_2$— and NC$\underline{H}_2$CO$_2$H); 37.98 (Thy-C$\underline{H}_3$); 28.07 (t-Bu). FAB-MS: 407 (M+Na$^+$); 385 (M+H$^+$).

EXAMPLE 6

1-(Boc-aeg)thymine Pentafluorophenyl Ester (7, Boc-Taeg.OPfp)

1-(Boc-aeg)thymine (6) (2.00 g; 5.20 mmol) was dissolved in DMF (5 ml) and methylene chloride (15 ml) was added. Pentafluorophenol (1.05 g; 5.72 mmol) was added and the solution was cooled to 0° C. in an ice bath. DDC then was added (1.29 g; 6.24 mmol) and the ice bath was removed after 2 min. After 3 h with stirring at ambient temperature, the precipitated DCU was removed by filtration and washed with methylene chloride. The combined filtrate was washed twice with aqueous sodium hydrogen carbonate and once with saturated sodium chloride, dried over magnesium sulfate, and evaporated to dryness, in vacuo. The solid residue was dissolved in dioxane (150 ml) and poured into water (200 ml) at 0° C. The title compound was isolated by filtration, washed with water, and dried over sicapent, in vacuo. Yield: 2.20 g (77%). An analytical sample was obtained by recrystallisation from 2-propanol. M.p. 174–175.5° C. Analysis for $C_{22}H_{23}N_4O_7F_5$, found(calc.): C, 48.22(48.01); H, 4.64(4.21); N, 9.67(10.18). $^1$H-NMR (250 MHz, $CDCl_3$):Due to the limited rotation around the secondary amide bond several of the signals were doubled in the ratio 6:1 (indicated in the list by mj. for major and mi. for minor). 7.01 ppm (s, mi., ArH); 6.99 ppm (s, mj., ArH); 5.27 ppm (unres. t, BocN$\underline{H}$); 4.67 ppm (s, mj., T-CH$_2$—CO—); 4.60 ppm (s, mi., T-CH$_2$—CO—); 4.45 ppm (s, mj., CONRC$\underline{H}_2$CO$_2$Pfp); 4.42 ppm (s, mi., CONRC$\underline{H}_2$CO$_2$Pfp); 3.64 ppm (t,2H,BocNHCH$_2$C$\underline{H}_2$—); 3.87 ppm ("q",2H, BocNHC$\underline{H}_2$CH$_2$—); 1.44(s,9H,t-Bu). FAB-MS: 551 (10; M+1); 495 (10; M+1-tBu); 451 (80; –Boc).

EXAMPLE 7

N$^4$-Benzyloxycarbonyl Cytosine (9)

Over a period of about 1 h, benzyloxycarbonyl chloride (52 ml; 0.36 mol) was added dropwise to a suspension of cytosine (8, 20.0 g;0.18 mol) in dry pyridine (1000 ml) at 0° C. under nitrogen in oven-dried equipment. The solution then was stirred overnight, after which the pyridine suspension was evaporated to dryness, in vacuo. Water (200 ml) and 4 N hydrochloric acid were added to reach pH ~1. The resulting white precipitate was filtered off, washed with water and partially dried by air suction. The still-wet precipitate was boiled with absolute ethanol (500 ml) for 10 min, cooled to 0° C., filtered, washed thoroughly with ether, and dried, in vacuo. Yield 24.7 g (54%). M.p.>250° C. Anal. for $C_{12}H_{11}N_3O_3$. Found(calc.); C, 58.59(58.77); H, 4.55 (4.52); N, 17.17(17.13). No NMR spectra were recorded since it was not possible to get the product dissolved.

EXAMPLE 8

N$^4$-Benzyloxycarbonyl-N$^1$-carboxymethyl Cytosine (10)

In a three necked round bottomed flask equipped with mechanical stirring and nitrogen coverage was placed methyl bromacetate (7.82 ml;82.6 mmol) and a suspension of N$^4$-benzyloxycarbonyl-cytosine (9, 21.0 g;82. 6 mmol) and potassium carbonate (11.4 g;82.6 mmol) in dry DMF (900 ml). The mixture was stirred vigorously overnight, filtered, and evaporated to dryness, in vacuo. Water (300 ml) and 4 N hydrochloric acid (10 ml) were added, the mixture was stirred for 15 minutes at 0° C., filtered, and washed with water (2×75 ml). The isolated precipitate was treated with water (120 ml), 2N sodium hydroxide (60 ml), stirred for 30 min, filtered, cooled to 0° C., and 4 N hydrochloric acid (35 ml) was added. The title compound was isolated by filtration, washed thoroughly with water, recrystallized from methanol (1000 ml) and washed thoroughly with ether. This afforded 7.70 g (31%) of pure compound. The mother liquor from the recrystallization was reduced to a volume of 200 ml and cooled to 0° C. This afforded an additional 2.30 g of a material that was pure by tlc but had a reddish color. M.p. 266–274° C. Anal. for $C_{14}H_{13}N_3O_5$. Found(calc.); C, 55.41 (55.45); H, 4.23(4.32); N, 14.04(13.86). $^1$H-NMR (90 MHz; DMSO-$d_6$): 8.02 ppm (d,J=7.32 Hz,1H,H-6); 7.39 (s,5H, Ph); 7.01 (d,J=7.32 Hz,1H,H-5); 5.19 (s,2H,PhC$\underline{H}_2$—); 4.52 (s,2H).

EXAMPLE 9

N$^4$-Benzyloxycarbonyl-N$^1$-carboxymethyl-cytosine Pentafluorophenyl Ester (11)

N$^4$-Benzyloxycarbonyl-N$^1$-carboxymethyl-cytosine (10, 4.00 g; 13.2 mmol) and pentafluorophenol (2.67 g; 14.5 mmol) were mixed with DMF (70 ml), cooled to 0° C. with ice-water, and DCC (3.27 g; 15.8 mmol) was added. The ice bath was removed after 3 min and the mixture was stirred for 3 h at room temperature. The precipitated DCU was removed by filtration, washed with DMF, and the filtrate was evaporated to dryness, in vacuo (0.2 mmHg). The solid residue was treated with methylene chloride (250 ml), stirred vigorously for 15 min, filtered, washed twice with diluted sodium hydrogen carbonate and once with saturated sodium chloride, dried over magnesium sulfate, and evaporated to dryness, in vacuo. The solid residue was recrystallized from 2-propanol (150 ml) and the crystals were washed thoroughly with ether. Yield 3.40 g (55%). M.p. 241–245° C. Anal. for $C_{20}H_{12}N_3F_5O_5$. Found(calc.); C, 51.56(51.18); H, 2.77(2.58); N, 9.24(8.95). $^1$H-NMR (90 MHz; CDCl$_3$): 7.66 ppm (d,J=7.63 Hz,1H,H-6); 7.37 (s,5H,Ph); 7.31 (d,J=7.63 Hz,1H,H-5); 5.21 (s,2H,PhC$\underline{H}_2$—); 4.97 (s,2H,NC$\underline{H}_2$—). FAB-MS: 470 (M+1).

EXAMPLE 10

N$^4$-Benzyloxycarbonyl-1-Boc-aeg-cytosine (12)

To a solution of (N-Boc-2-aminoethyl)glycine (2) in DMF, prepared as described above, was added triethyl amine (7.00 ml; 50.8 mmol) and N$^4$-benzyloxycarbonyl-N$^1$-carboxymethyl-cytosine pentafluorophenyl ester (11, 2.70 g; 5.75 mmol). After stirring the solution for 1 h at room temperature, methylene chloride (150 ml), saturated sodium chloride (250 ml), and 4 N hydrochloric acid to pH ~1 were added. The organic layer was separated and washed twice with saturated sodium chloride, dried over magnesium sulfate, and evaporated to dryness, in vacuo, first with a water aspirator and then with an oil pump. The oily residue was treated with water (25 ml) and was again evaporated to dryness, in vacuo. This procedure then was repeated. The oily residue (2.80 g) was then dissolved in methylene chloride (100 ml), petroleum ether (250 ml) was added, and the mixture was stirred overnight. The title compound was isolated by filtration and washed with petroleum ether. Tlc (system 1) indicated substantial quantities of pentafluorophenol, but no attempt was made to remove it. Yield: 1.72 g (59%). M.p. 156° C.(decomp.). $^1$H-NMR (250 MHz, CDCl$_3$): Due to the limited rotation around the secondary amide bond several of the signals were doubled in the ratio 2:1,(indicated in the list by mj. for major and mi. for minor). 7.88 ppm (dd,1H,H-6); 7.39 (m,5H,Ph); 7.00

(dd,1H,H-5); 6.92 (b,1H,BocNH)-?; 6.74 (b,1H,ZNH)-?; 5.19 (s,2H,Ph—CH$_2$); 4.81 ppm (s, mj., Cyt-CH$_2$—CO—); 4.62 ppm (s, mi., Cyt-CH$_2$—CO—); 4.23 (s, mi., CONRCH$_2$CO$_2$H); 3.98 ppm (s, mj., CONRCH$_2$CO$_2$H); 3.42–3.02 (unres. m, —CH$_2$CH$_2$— and water);1.37 (s,9H,tBu). FAB-MS: 504 (M+1); 448 (M+1-tBu).

EXAMPLE 11

N$^4$-Benzyloxycarbonyl-1-Boc-aeg-cytosine Pentafluorophenyl Ester (13)

N$^4$-Benzyloxycarbonyl-1-Boc-aeg-cytosine (12, 1.50 g; 2.98 mmol) and pentafluorophenol (548 mg; 2.98 mmol) was dissolved in DMF (10 ml) Methylene chloride (10 ml) was added, the reaction mixture was cooled to 0° C. in an ice bath, and DCC (676 mg; 3.28 mmol) was added. The ice bath was removed after 3 min and the mixture was stirred for 3 h at ambient temperature. The precipitate was isolated by filtration and washed once with methylene chloride. The precipitate was dissolved in boiling dioxane (150 ml) and the solution was cooled to 15° C., whereby DCU precipitated. The DCU was removed by filtration and the resulting filtrate was poured into water (250 ml) at 0° C. The title compound was isolated by filtration, was washed with water, and dried over sicapent, in vacuo. Yield 1.30 g (65%). Analysis for C$_{29}$H$_{28}$N$_5$O$_8$F$_5$. Found(calc.); C, 52.63(52.02); H, 4.41(4.22); N, 10.55(10.46). $^1$H-NMR (250 MHz; DMSO-d$_6$): showed essentially the spectrum of the above acid, most probably due to hydrolysis of the ester. FAB-MS: 670 (M+1); 614 (M+1-tBu).

EXAMPLE 12

4-Chlorocarboxy-9-chloroacridine

4-Carboxyacridone (6.25 g; 26.1 mmol), thionyl chloride (25 ml), and 4 drops af DMF were heated gently under a flow of nitrogen until all solid material had dissolved. The solution then was refluxed for 40 min. The solution was cooled and excess thionyl chloride was removed in vacuo. The last traces of thionyl chloride were removed by coevaporation with dry benzene (dried over Na—Pb) twice. The remaining yellow powder was used directly in the next reaction.

EXAMPLE 13

4-(5-Methoxycarbonylpentylamidocarbonyl)-9-chloroacridine

Methyl 6-aminohexanoate hydrochloride (4.70 g; 25.9 mmol) was dissolved in methylene chloride (90 ml), cooled to 0° C., triethyl amine (15 ml) was added, and the resulting solution then was immediately added to the acid chloride from above. The roundbottomed flask containing the acid chloride was cooled to 0° C. in an ice bath. The mixture was stirred vigorously for 30 min at 0° C. and 3 h at room temperature. The resulting mixture was filtered to remove the remaining solids, which were washed with methylene chloride (20 ml). The red-brown methylene chloride filtrate was subsequently washed twice with saturated sodium hydrogen carbonate, once with saturated sodium chloride, dried over magnesium sulfate, and evaporated to dryness, in vacuo. To the resulting oily substance was added dry benzene (35 ml) and ligroin (60–80° C., dried over Na—Pb). The mixture was heated to reflux. Activated carbon and celite were added and mixture was refluxed for 3 min. After filtration, the title compound crystallised upon cooling with magnetic stirring. It was isolated by filtration and washed with petroleum ether. The product was stored over solid potassium hydroxide. Yield 5.0 g (50%).

EXAMPLE 14

4-(5-Methoxycarbonylpentyl)amidocarbonyl-9-[6'-(4''-nitrobenzamido)hexylamino]-aminoacridine 4-(5-Methoxycarbonylpentylamidocarbonyl)-9-chloroacridine (1.30 g; 3.38 mmol) and phenol (5 g) were heated to 80° C. for 30 min under a flow of nitrogen, after which 6-(4'-nitrobenzamido)-1-hexylamine (897 mg; 3.38 mmol) was added. The temperature raised to 120° C. for 2 h. The reaction mixture was cooled and methylene chloride (80 ml) was added. The resulting solution was washed three times with 2N sodium hydroxide (60 ml portions) and once with water, dried over magnesium sulfate, and evaporated to dryness, in vacuo. The resulting red oil (1.8 g) was dissolved in methylene chloride (40 ml), cooled to 0° C. Ether (120 ml) was added and the resultant solution was stirred overnight. This results in a mixture of solid material and an oil. The solid was isolated by filtration. The solid and the oil were redissolved in methylene chloride (80 ml) and added dropwise to cold ether (150 ml). After 20 minutes of stirring, the title compound was isolated by filtration in the form of orange crystals. The product was washed with ether and dried in vacuo over potassium hydroxide. Yield 1.60 g (77%). M.p. 145–147° C.

EXAMPLE 15

4-(5-Carboxypentyl)amidocarbonyl-9-[6'-(4''-nitrobenzamido)hexylamino]-aminoacridine 4-(5-Methoxycarbonylpentyl)amidocarbonyl-9-[6'-(4''-nitrobenzamido)hexylamino]-aminoacridine (503 mg; 0.82 mmol) was dissolved in DMF (30 ml), and 2 N sodium hydroxide (30 ml) was added. After stirring for 15 min, 2 N hydrochloric acid (35 ml) and water (50 ml) were added at 0° C. After stirring for 30 min, the solution was decanted, leaving an oily substance which was dissolved in boiling methanol (150 ml), filtered and concentrated to ⅓ volume. To the methanol solution were added ether (125 ml) and 5–6 drops of HCl in ethanol. The solution was decanted after 1 h of stirring at 0° C. The oily substance was redissolved in methanol (25 ml) and precipitated with ether (150 ml). The title compound was isolated as yellow crystals after stirring overnight. Yield 417 mg (80%). M.p. 1730 C. (decomp.).

EXAMPLE 16

(a) 4-(5-pentafluorophenyloxycarbonylpentyl)-amidocarbonyl-9-[6'-(4''-nitrobenzamido)-hexylamino]-aminoacridine(Acr$^1$Opfp)

The acid from above (300 mg; 0.480 mmol) was dissolved in DMF (2 ml) and methylene chloride (8 ml) was added. Pentafluorophenol (97 mg; 0.53 mmol), transferred with 2×2 ml of the methylene chloride, was added. The resulting solution was cooled to 0° C. after which DCC (124 mg; 0.60 mmol) was subsequently added. The ice bath was removed after 5 minutes and the mixture was left with stirring overnight. The precipitated DCU was removed by centrifugation and the centrifugate was evaporated to dryness, in vacuo, first by a water aspirator and then by an oil pump. The residue was dissolved in methylene chloride (20 ml), filtered, and evaporated to dryness, in vacuo. The residue was again dissolved in methylene chloride and petroleum ether (150 ml). A 1 ml portion of 5M HCl in ether was added. The solvent was removed by decanting after 30 min of stirring at 0° C. The residual oily substance was dissolved in methylene chloride (100 ml). Petroleum ether (150 ml) was added and the mixture was left with stirring overnight. The next day the yellow precipitated crystalline material was isolated by filtration and was washed with copious amounts of petroleum ether. Yield, after drying, 300 mg (78%). M.p. 97.5° C. (decomp.). All samples showed satisfactory elemental analysis, $^1$H- and $^{13}$C-NMR and mass spectra.

(b) Experimental for the Synthesis of PNA Compounds, cf. FIG. 8

Materials: Boc-Lys (ClZ), benzhydrylamine-copoly-(styrene-1%-divinylbenzene) resin (BHA resin), and p-methylbenzhydrylamine-copoly(styrene-1%-divinylbenzene)resin (MBHA resin) were purchased from Peninsula Laboratories. Other reagents and solvents were: Biograde trifluoroacetic acid from Halocarbon Products; diisopropylethylamine (99%; was not further distilled) and N-acetylimidazole (98%) from Aldrich; $H_2O$ was distilled twice; anhydrous HF from Union Carbide; synthesis grade N,N-dimethylformamide and analytical grade methylene chloride (was not further distilled) from Merck; HPLC grade acetonitrile from Lab-Scan; purum grade anisole, N,N'-dicyclohexylcarbodiimide, diisopropylcarbodiimide, puriss. grade 2,2,2-trifluoroethanol from Fluka and trifluoromethanesulfonic acid from flourad.

(b) General Methods and Remarks

Except where otherwise stated, the following applies. The PNA compounds were synthezised by the stepwise solid-phase approach (Merrifield, *J. Am. Chem. Soc.*, 1963, 85, 2149) employing conventional peptide chemistry utilizing the TFA-labile tert-butyloxycarbonyl (Boc) group for "temporary" N-protection (Merrifield, *J. Am. Chem. Soc.*, 1964, 86, 304) and the more acid-stable benzyloxycarbonyl (Z) and 2-chlorobenzyloxycarbonyl (ClZ) groups for "permanent" side chain protection. To obtain C-terminal amides, the PNAs were assembled onto the HF-labile BHA or MBHA resins (the MBHA resin has increased susceptibility to the final HF cleavage relative to the unsubstituted BHA resin (Matsueda, et al., *Peptides,* 1981, 2, 45). All reactions (except HF reactions) were carried out in manually operated standard solid-phase reaction vessels fitted with a coarse glass frit (Merrifield, et al., *Biochemistry,* 1982, 21, 5020). The quantitative ninhydrin reaction (Kaiser test), originally developed by Merrifield and co-workers (Sarin, et al., *Anal. Biochem.,* 1981, 117, 147) for peptides containing "normal" amino acids, was successfully apppplied (see Table I–III) using the "normally" employed effective extinction coefficient $\epsilon = 15000 \, M^{-1}cm^{-1}$ for all residues to determine the completeness of the individual couplings as well as to measure the number of growing peptide chains. The theoretical substitution $S_{n-1}$ upon coupling of residue number n (assuming both complete deprotection and coupling as well as neither chain termination nor loss of PNA chains during the synthetic cycle) is calculated from the equation:

$$S_n = S_{n-1} \times (1 + (S_{n-1} \times \Delta MW \times 10^{-3} \, mmol/mol))^{-1}$$

where $\Delta MW$ is the gain in molecular weight ($[\Delta MW]=g/mol$) and $S_{n-1}$ is the theoretical substitution upon coupling of the preceding residue n−1 ($[S]=mmol/g$). The estimated value (%) on the extent of an individual coupling is calculated relative to the measured substitution (unless S was not determined) and include correction for the number of remaining free amino groups following the previous cycle. HF reactions were carried out in a Diaflon HF apparatus from Toho Kasei (Osaka, Japan). Vydac $C_{18}$ (5 µm, 0.46×25 cm and 5 µm, 1.0×25 cm) reverse-phase columns, respectively were used for analytical and semi-preparative HPLC on an SP8000 instrument. Buffer A was 5 vol % acetonitrile in water containing 445 µl trifluoroacetic acid per liter, and buffer B was 60 vol % acetonitrile in water containing 390 µl trifluoroacetic acid per liter. The linear gradient was 0–100% of buffer B in 30 min, flow rates 1.2 ml/min (analytical) and 5 ml/min (semi-preparative). The eluents were monitored at 215 nm (analytical) and 230 nm (semi-preparative). Molecular weights of the PNAs were determined by $^{252}$Cf plasma desorption time-of-flight mass spectrometry from the mean of the most abundant isotopes.

EXAMPLE 17

Solid-Phase Synthesis of Acr$^1$-[Taeg]$_{15}$-NH$_2$ and Shorter Derivatives (a) Stepwise Assembly of Boc-[Taeg]$_{15}$-BHA Resin The synthesis was initiated on 100 mg of preswollen and neutralized BHA resin (determined by the quantitative ninhydrin reaction to contain 0.57 mmol NH$_2$/g) employing single couplings ("Synthetic Protocol 1") using 3.2 equivalents of BocTaeg-OPfp in about 33% DMF/CH$_2$Cl$_2$. The individual coupling reactions were carried out by shaking for at least 12 h in a manually operated 6 ml standard solid-phase reaction vessel and unreacted amino groups were blocked by acetylation at selected stages of the synthesis. The progress of chain elongation was monitored at several stages by the quantitative ninhydrin reaction (see Table I). Portions of protected Boc-[Taeg]$_5$-BHA, Boc-[Taeg]$_{10}$-BHA, and Boc-[Taeg]$_{15}$-BHA resins were taken out after assembling 5, 10, and 15 residues, respectively.

| Synthetic Step | Residue Coupled | Substitution After Deprotection (mmol/g) | | Remaining Free Amino Groups After (µmol/g) | | Estimated Extent of Coupling (%) |
|---|---|---|---|---|---|---|
| | | Measd | Theoretcl | Single Coupling | Acetylation | |
| "0" | | 0.57 | | | | |
| 1 | BocTaeg | ND | 0.50 | 1.30 | | <99.7 |
| 2 | BocTaeg | ND | 0.44 | 1.43 | | <99.9 |
| 3 | BocTaeg | 0.29 | 0.39 | 3.33 | | 99.3 |
| 4 | BocTaeg | 0.27 | 0.35 | 13.30 | | 96.3 |
| 5 | BocTaeg | 0.26 | 0.32 | 8.33 | | >99.9 |
| 6 | BocTaeg | ND | 0.30 | 7.78 | | >99.9 |
| 7 | BocaTeg | ND | 0.28 | 13.81 | 7.22 | <97.8 |
| 8 | BocTaeg | ND | 0.26 | 14.00 | | <99.9 |
| 9 | BocTaeg | ND | 0.24 | 30.33 | | 93.2 |
| 10 | BocTaeg | 0.16 | 0.23 | 11.67 | 2.67 | >99.9 |
| 11 | BocTaeg | ND | 0.21 | 4.58 | | >99.9 |
| 12 | BocTaeg | ND | 0.20 | 5.87 | | <99.4 |
| 13 | BocTaeg | ND | 0.19 | 1.67 | | >99.9 |
| 14 | BocTaeg | ND | 0.18 | 14.02 | | <93.1 |
| 15 | BocTaeg | 0.07 | 0.17 | 4.20 | 3.33 | >99.9 |

(b) Synthesis of Acr$^1$-[Taeg]$_{15}$-BRA Resin

Following deprotection of the residual Boc-[Taeg]$_{15}$-BHA resin (estimated dry weight is about 30 mg; ~0.002 mmol growing chains), the H-[Taeg]$_{15}$-BHA resin was reacted with about 50 equivalents (80 mg; 0.11 mmol) of Acr$^1$-OPfp in 1 ml of about 66% DMF/CH$_2$Cl$_2$ (i.e., a 0.11 M solution of the pentaflurophenylester) in a 3 ml solid-phase reaction vessel. As judged by a qualitative ninhydrin reaction, coupling of the acridine moiety was close to quantitative.

(c) Cleavage, Purification, and Identification of H-[Taeg]$_5$-NH$_2$

A portion of protected Boc-[Taeg]$_5$-BHA resin was treated with 50% trifluoroacetic acid in methylene chloride to remove the N-terminal Boc group (which is a precursor of the potentially harmful tert-butyl cation) prior to the HF cleavage. Following neutralization and washing (performed in a way similar to those of steps 2–4 in "Synthetic Protocol 1"), and drying for 2 h in vacuum, the resulting 67.1 mg (dry weight) of H-[Taeg]$_5$-BHA resin was cleaved with 5 ml of HF:anisole (9:1, v/v) stirring at 0° C. for 60 min. After removal of HF, the residue was stirred with dry diethyl ether (4×15 ml, 15 min each) to remove anisole, filtered under gravity through a fritted glass funnel, and dried. The PNA was then extracted into a 60 ml (4×15 ml, stirring 15 min each) 10% aqueous acetic acid solution. Aliquots of this solution were analyzed by analytical reverse-phase HPLC to establish the purity of the crude PNA. The main peak at 13.0 min accounted for about 93% of the total absorbance. The remaining solution was frozen and lyophilized to afford about 22.9 mg of crude material. Finally, 19.0 mg of the crude product was purified from five batches, each containing 3.8 mg in 1 ml of H$_2$O. The main peak was collected by use of a semi-preparative reverse-phase column. Acetonitrile was removed on a speed vac and the residual solution was frozen (dry ice) and subsequently lyophilized to give 13.1 mg of >99% pure H-[Taeg]$_5$—NH$_2$. The PNA molecule readily dissolved in water and had the correct molecular weight based on mass spectral determination. For (M+H)$^+$ the calculated m/z value was 1349.3 and the measured m/z value was 1347.8.

(d) Cleavage, Purification, and Identification of H-[Taeg]$_{10}$-NH$_2$

A portion of protected Boc-[Taeg]$_{10}$-BHA resin was treated as described in section (c) to yield 11.0 mg of crude material upon HF cleavage of 18.9 mg dry H-[Taeg]$_{10}$-BHA resin. The main peak at 15.5 min accounted for about 53% of the total absorbance. About 1 mg of the crude product was purified repeatedly (for reasons described below) to give approximately 0.1 mg of at least 80% but presumably >99% pure H-[Taeg]$_{10}$-NH$_2$. A rather broad tail eluting after the target peak and accounting for about 20% of the total absorbance could not be removed (only slightly reduced) upon the repeated purification. Judged by the mass spectrum, which only confirms the presence of the correct molecular weight H-[Taeg]$_{10}$-NH$_2$, the tail phenomonen is ascribed to more or less well-defined aggregational/conformational states of the target molecule. Therefore, the crude product is likely to contain more than the above-mentioned 53% of the target molecule. H-[Taeg]$_{10}$-NH$_2$ is readily dissolved in water. For (M+H)$^+$ the calculated m/z value was 2679.6 and the measured m/z value was 2681.5.

(e) Cleavage, Purification, and Identification of H-[Taeg]$_{15}$-NH$_2$

Figure 12A:
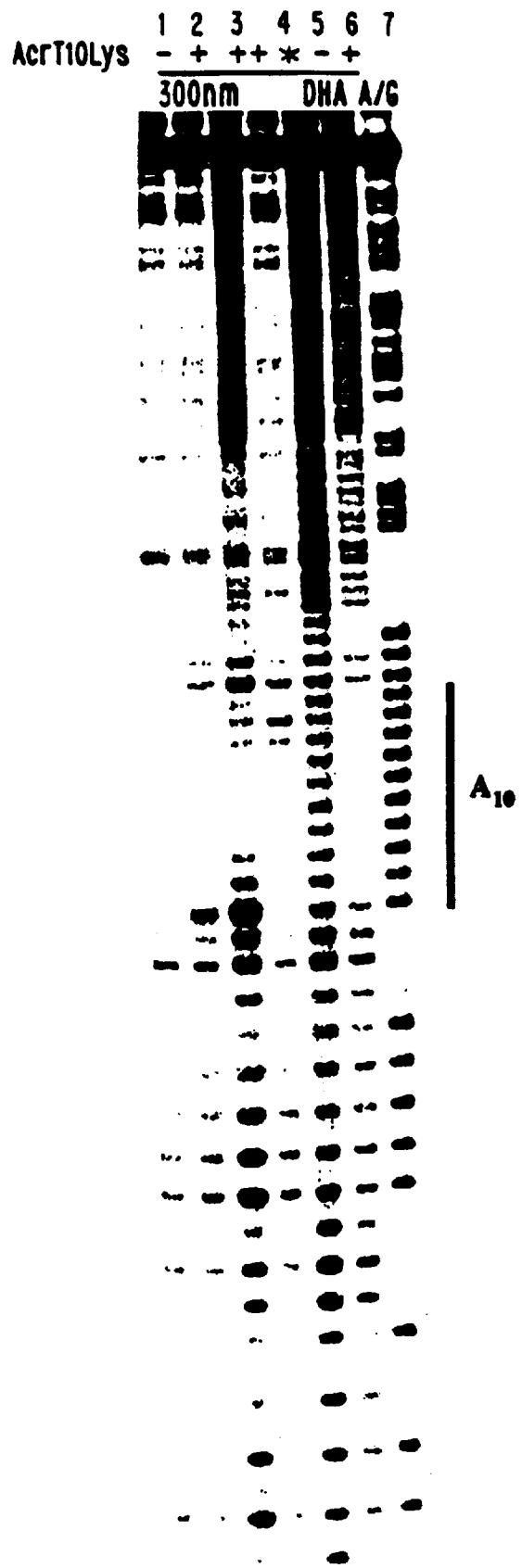
FIGS. 12A–C show chemical, photochemical and enzymatic probing of dsDNA-Acr-T10-LysNH$_2$ complex. Complexes between Acr-T10-LysNH$_2$ and a $^{32}$P-endlabeled DNA fragment containing a dA$_{10}$/dT$_{10}$ target sequence were probed by affinity photocleavage (FIG. 12a, lanes 1–3.

A portion of protected Boc-[Taeg]$_{15}$-BHA resin was treated as described in section (c) to yield 3.2 mg of crude material upon HF cleavage of 13.9 mg dry H-[Taeg]$_{15}$-BHA resin. The main peak at 22.6 min was located in a broad bulge accounting for about 60% of the total absorbance (FIG. 12a). Again (see the preceding section), this bulge is ascribed to aggregational/conformational states of the target molecule H-[Taeg]$_{15}$-NH$_2$ since mass spectral analysis of the collected "bulge" did not significantly reveal the presence of other molecules. All of the crude product was purified collecting the "bulge" to give approximately 2.8 mg material. For (M+Na)$^+$ the calculated m/z value was 4033.9 and the measured m/z value was 4032.9.

(f) Cleavage, Purification, and Identification of Acr$^1$-[Taeg]$_{15}$-NH$_2$

Figure 12B:
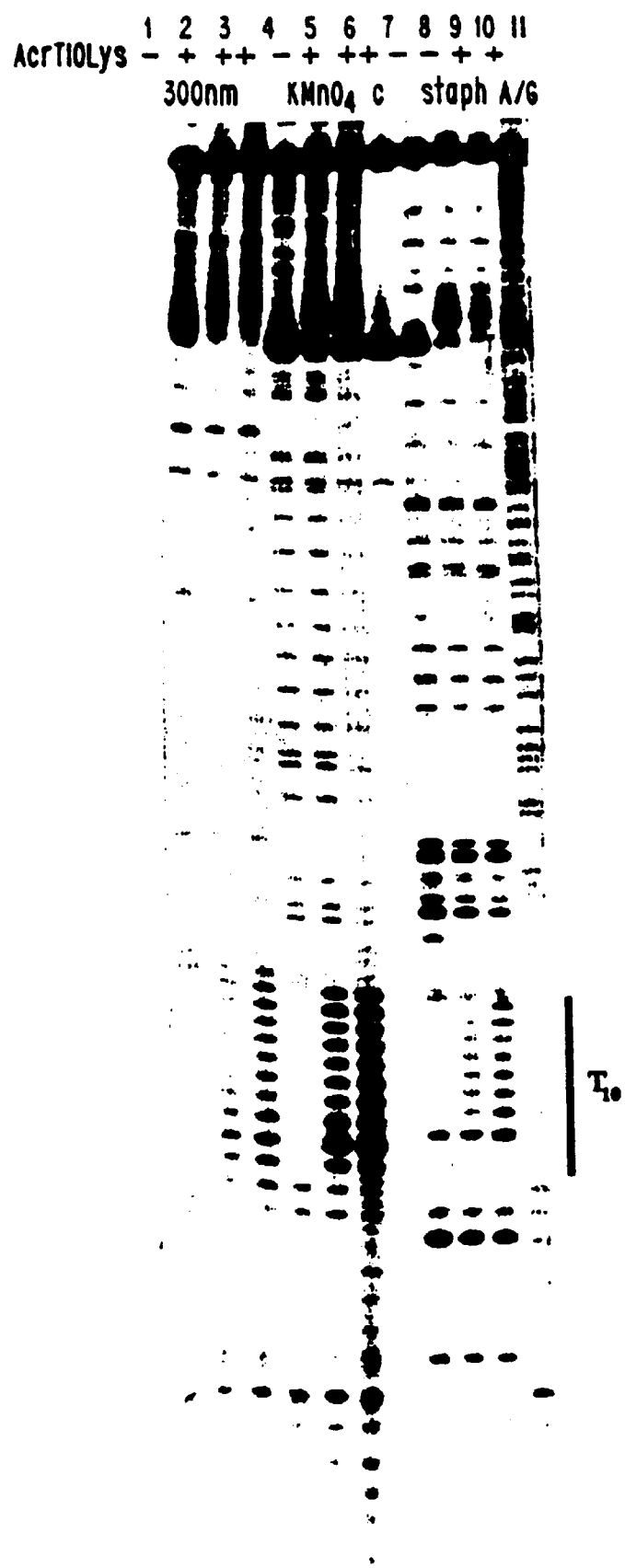
Figure 12C:
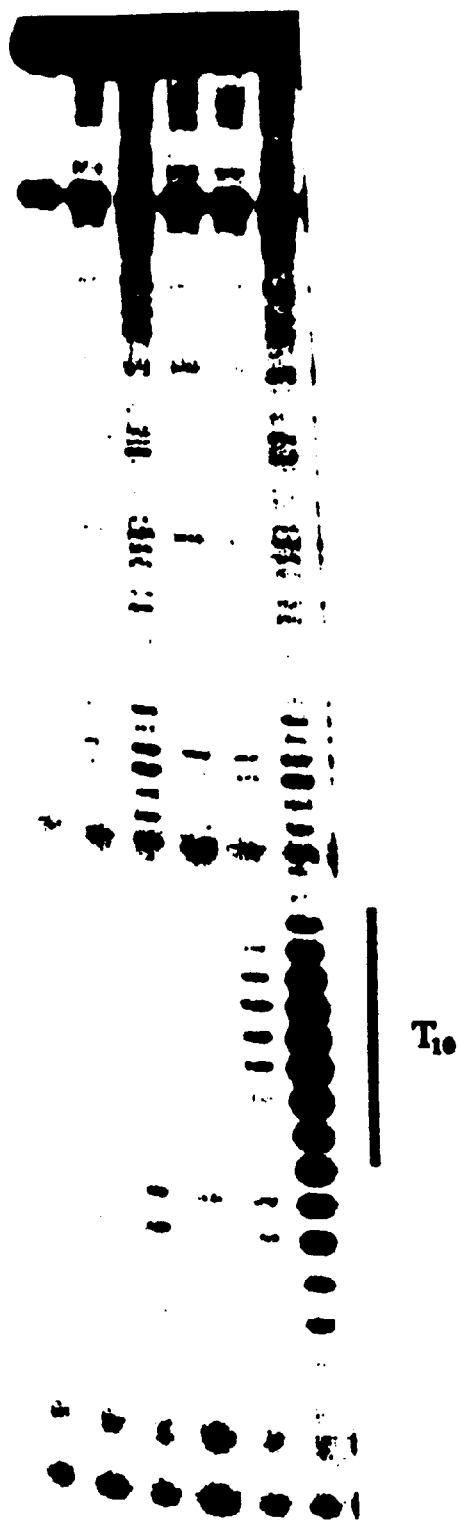

A portion of protected Acr$^1$-[Taeg]$_{15}$-BHA resin was treated as described in section (b) to yield 14.3 mg of crude material upon HF cleavage of 29.7 mg dry Acr$^1$-[Taeg]$_{15}$-BHA resin. Taken together, the main peak at 23.7 min and a "dimer" (see below) at 29.2 min accounted for about 40% of the total absorbance (FIG. 12b). The crude product was purified repeatedly to give approximately 1 mg of presumably >99% pure Acr$^1$-[Taeg]$_{15}$-NH$_2$ "contaminated" with self-aggregated molecules eluting at 27.4 min, 29.2 min, and finally as a huge broad bulge eluting with 100% buffer B (FIG. 12c). This interpretation is in agreement with the observation that those peaks grow upon standing (for hours) in aqueous acetic acid solution, and finally precipitate out quantitatively. For (M+H)$^+$ the calculated m/z value was 4593.6 and the measured m/z value was 4588.7.

(g) Synthetic Protocol 1

(1) Boc-deprotection with TFA/CH$_2$Cl$_2$ (1:1, v/v), 3 ml, 3×1 min and 1×30 min; (2) washing with CH$_2$Cl$_2$, 3 ml, 6×1 min; (3) neutralization with DIEA/CH$_2$Cl$_2$ (1:19, v/v), 3 ml, 3×2 min; (4) washing with CH$_2$Cl$_2$, 3 ml, 6×1 min, and drain for 1 min; (5) 2–5 mg sample of PNA-resin may be taken out and dried thoroughly for a quantitative ninhydrin analysis to determine the substitution; (6) addition of 3.2 equiv. (0.18 mmol; 100 mg) BocTaeg-OPfp dissolved in 1 ml CH$_2$Cl$_2$ followed by addition of 0.5 ml DMF (final concentration of pentafluorophenylester ~0.12 M); the coupling reaction was allowed to proceed for a total of 12–24 h shaking at room temperature; (7) washing with DMF, 3 ml, 1×2 min; (8) washing with CH$_2$Cl$_2$, 3 ml, 4×1 min; (9) neutralization with DIEA/CH$_2$Cl$_2$ (1:19, v/v), 3 ml, 2×2 min; (10) washing with CH$_2$Cl$_2$, 3 ml, 6×1 min; (11) 2–5 mg sample of protected PNA-resin is taken out for a rapid qualitative ninhydrin test and further 2–5 mg is dried thoroughly for a quantitative ninhydrin analysis to determine the extent of coupling (after cycles 7, 10, and 15 unreacted amino groups were blocked by acetylation with N-acetylimidazol in methylene chloride).

EXAMPLE 18

Solid-Phase Synthesis of Acr$^1$-[Taeg]$_{15}$-Lys-NH$_2$ and Shorter Derivatives (a) Stepwise Assembly of Boc-[Taeg]$_{15}$-Lys(ClZ)-BHA Resin The synthesis was initiated by a quantitative loading (standard DCC in situ coupling in neat CH$_2$Cl$_2$) of Boc-Lys (ClZ) onto 100 mg of preswollen and neutralized BHA resin (0.57 mmol NH$_2$/g). Further extension of the protected PNA chain employed single couplings ("Synthetic Protocol 2") for cycles 1 to 5 and cycles 10 to 15 using 3.2 equivalents of BocTaeg-OPfp in about 33% DMF/CH$_2$Cl$_2$. Cycles 5 to 10 employed an extra straight DCC (i.e., in situ) coupling of the free acid BocTaeg-OH in about 33% DMF/CH$_2$Cl$_2$. All coupling reactions were carried out by shaking for at least 12 h in a manually operated 6 ml standard solid-phase reaction vessel. Unreacted amino groups were blocked by acetylation at the same stages of the synthesis, as was done in Example 17. Portions of protected Boc-[Taeg]$_5$-Lys(ClZ)-BHA and Boc-[Taeg]$_{10}$-Lys(ClZ)-BHA resins were taken out after assembling 5 and 10 PNA residues, respectively. As judged by the analytical HPLC chromatogram of the crude cleavage product from the Boc-[Taeg]$_{10}$-Lys(ClZ)-BHA resin (see section (e)), an additional "free acid" coupling of PNA residues 5 to 10 gave no significant improvement of the synthetic yield as compared to the throughout single-coupled residues in Example 17.

(b) Synthesis of Acr$^1$-[Taeg]$_{10}$-Lys(ClZ)-BRA Resin

Following deprotection of a portion of Boc-[Taeg]$_{10}$-Lys (ClZ)-BHA resin (estimated dry weight is about 90 mg; ~0.01 mmol growing chains), the H-[Taeg]$_{15}$-BHA resin was reacted with about 20 equivalents (141 mg; 0.19 mmol) of Acr[1]-OPfp in 1 ml of about 66% DMF/$CH_2Cl_2$ in a 3 ml solid-phase reaction vessel. As judged by a qualitative ninhydrin reaction, coupling of the acridine moiety was close to quantitative.

(c) Synthesis of Acr[1]-[Taeg]$_{15}$-Lys(ClZ)-BRA Resin

Following deprotection of the residual Boc-[Taeg]$_{15}$-Lys (ClZ)-BHA resin (estimated dry weight about 70 mg; ~0.005 mmol growing chains), the H-[Taeg]$_{15}$-Lys(ClZ)-BHA resin was reacted with about 25 equivalents (91 mg; 0.12 mmol) of Acr[1]-OPfp in 1 ml of about 66% DMF/$CH_2Cl_2$ in a 3 ml solid-phase reaction vessel. As judged by a qualitative ninhydrin reaction, coupling of the acridine moiety was close to quantitative.

(d) Cleavage, Purification, and Identification of H-[Taeg]$_5$-Lys-$NH_2$

A portion of protected Boc-[Taeg]$_5$-Lys(ClZ)-BHA resin was treated as described in Example 17c to yield 8.9 mg of crude material upon HF cleavage of 19.0 mg dry H-[Taeg]$_5$-Lys(ClZ)-BHA resin. The main peak at 12.2 min (eluted at 14.2 min if injected from an aqueous solution instead of the 10% aqueous acetic acid solution) accounted for about 90% of the total absorbance. About 2.2 mg of the crude product was purified to give approximately 1.5 mg of 99% pure H-[Taeg]$_5$-Lys-$NH_2$.

(e) Cleavage, Purification, and Identification of H-[Taeg]$_{10}$-Lys-$NH_2$

A portion of protected Boc-[Taeg]$_{10}$-Lys(ClZ)-BHA resin was treated as described in Example 17c to yield 1.7 mg of crude material upon HF cleavage of 7.0 mg dry H-[Taeg]$_{10}$-Lys(ClZ)-BHA resin. The main peak at 15.1 min (eluted at 17.0 min if injected from an aqueous solution instead of the 10% aqueous acetic acid solution) accounted for about 50% of the total absorbance. About 1.2 mg of the crude product was purified to give approximately 0.2 mg of >95% pure H-[Taeg]$_{10}$-Lys-$NH_2$. FIG. 13a. For $(M+H)^+$ the calculated m/z value was 2807.8 and the measured m/z value was 2808.2.

(f) Cleavage, Purification, and Identification of Acr[1]-[Taeg]$_{10}$-Lys-$NH_2$ 99.1 mg protected Acr[1]-[Taeg]$_{10}$-Lys(ClZ)-BHA resin (dry weight) was cleaved as described in Example 17c to yield 42.2 mg of crude material. The main peak at 25.3 min (eluted at 23.5 min if injected from an aqueous solution instead of the 10% aqueous acetic acid solution) accounted for about 45% of the total absorbance. An 8.87 mg portion of the crude product was purified to give approximately 5.3 mg of >97% pure H-[Taeg]$_{10}$-Lys-$NH_2$. For $(M+H)^+$ the calculated m/z value was 2850.8 and the measured m/z value was 2849.8.

(g) Cleavage and Purification of Acr[1]-[Taeg]$_{15}$-Lys-$NH_2$

A 78.7 mg portion of protected Acr[1]-[Taeg]$_{15}$-Lys(ClZ)-BHA resin (dry weight) was cleaved as described in Example I section (c) to yield 34.8 mg of crude material. The main peak at 23.5 min (about the same elution time if injected from an aqueous solution instead of the 10% aqueous acetic acid solution) and a "dimer" at 28.2 min accounted for about 35% of the total absorbance. About 4.5 mg of the crude product was purified to give approximately 1.6 mg of presumably >95% pure H-[Taeg]$_{10}$-Lys-$NH_2$. This compound could not be free of the "dimer" peak, which grew upon standing in aqueous acetic acid solution.

(h) Synthetic Protocol 2

(1) Boc-deprotection with TFA/$CH_2Cl_2$ (1:1, v/v), 3 ml, 3×1 min and 1×30 min; (2) washing with $CH_2Cl_2$, 3 ml, 6×1 min; (3) neutralization with DIEA/$CH_2Cl_2$ (1:19, v/v), 3 ml, 3×2 min; (4) washing with $CH_2Cl_2$, 3 ml, 6×1 min, and drain for 1 min; (5) 2–5 mg sample of PNA-resin can be taken out and dried thoroughly for a qualitative ninhydrin analysis; (6) for cycles 1 to 5 and cycles 10 to 15 the coupling reaction was carried out by addition of 3.2 equiv. (0.18 mmol; 100 mg) BocTaeg-OPfp dissolved in 1 ml $CH_2Cl_2$ followed by addition of 0.5 ml DMF (final concentration of pentafluorophenylester ~0.12 M); the coupling reaction was allowed to proceed for a total of 12–24 h with shaking; cycles 5 to 10 employed an additional 0.12 M DCC coupling of 0.12 M BocTaeg-OH in 1.5 ml DMF/$CH_2Cl_2$ (1:2, v/v); (7) washing with DMF, 3 ml, 1×2 min; (8) washing with $CH_2Cl_2$, 3 ml, 4×1 min; (9) neutralization with DIEA/$CH_2Cl_2$ (1:19, v/v), 3 ml, 2×2 min; (10) washing with $CH_2Cl_2$, 3 ml, 6×1 min; (11) 2–5 mg sample of protected PNA-resin is taken out for a qualitative ninhydrin test (after cycles 7, 10, and 15 unreacted amino groups were blocked by acetylation with N-acetylimidazol in methylene chloride).

EXAMPLE 19

Improved Solid-Phase Synthesis of H-[Taeg]$_{10}$-Lys-$NH_2$

The protected PNA was assembled onto an MBHA resin, using approximately half the loading of the BHA resin used in the previous examples. Furthermore, all cycles except one was followed by acetylation of uncoupled amino groups. The following describes the synthesis in full detail:

(a) Preparation of Boc-Lys (ClZ)—NH—CH(p-$CH_3$—$C_6H_4$)—$C_6H_4$ Resin (MBHA Resin) with an Initial Substitution of 0.3 mmol/g The desired substitution of Boc-Lys (ClZ)-MBHA resin was 0.25–0.30 mmol/g. In order to get this value, 1.5 mmol of Boc-Lys(ClZ) was coupled to 5.0 g of neutralized and preswollen MBHA resin (determined by the quantitative ninhydrin reaction to contain 0.64 mmol $NH_2$/g) using a single "in situ" coupling (1.5 mmol of DCC) in 60 ml of $CH_2Cl_2$. The reaction was carried out by shaking for 3 h in a manually operated, 225 ml, standard, solid-phase reaction vessel. Unreacted amino groups were then blocked by acetylation with a mixture of acetic anhydride/pyridine/$CH_2Cl_2$ (1:1:2, v/v/v) for 18 h. A quantitative ninhydrin reaction on the neutralized resin showed that only 0.00093 mmol/g free amine remained (see Table I), i.e. 0.15% of the original amino groups. The degree of substitution was estimated by deprotection and ninhydrin analysis, and was found to be 0.32 mmol/g for the neutralized H-Lys(ClZ)-MBHA resin. This compares well with the maximum value of 0.28 mmol/g for a quantitative coupling of 0.30 mmol Boc-Lys(ClZ)/g resin (see Table II).

(b) Stepwise Assembly of Boc-[Taeg]$_3$-Lys(ClZ)-MBHA Resin

The entire batch of H-Lys(ClZ)-MBHA resin prepared in section (a) was used directly (in the same reaction vessel) to assemble Boc-[Taeg]$_3$-Lys(ClZ)-MBHA resin by single couplings ("Synthetic Protocol 3") utilizing 2.5 equivalents of BocTaeg-OPfp in neat $CH_2Cl_2$. The quantitative ninhydrin reaction was apppplied throughout the synthesis (see Table II).

(c) Stepwise Assembly of Boc-[Taeg]$_8$-Lys(ClZ)-MBHA Resin

About 4.5 g of wet Boc-[Taeg]$_3$-Lys(ClZ)-MBHA resin (~0.36 mmol growing chains; taken out of totally ~19 g wet resin prepared in section (b)) was placed in a 55 ml SPPS reaction vessel. Boc-[Taeg]$_8$-Lys(ClZ)-MBHA resin was assembled by single couplings ("Synthetic Protocol 4") utilizing 2.5 equivalents of BocTaeg-OPfp in about 30% DMF/$CH_2Cl_2$. The progress of the synthesis was monitored at all stages by the quantitative ninhydrin reaction (see. Table II).

(d) Stepwise Assembly of Boc-[Taeg]$_{10}$-Lys(ClZ)-MBHA Resin

About 1 g of wet Boc-[Taeg]$_8$-Lys(ClZ)-MBHA resin (~0.09 mmol growing chains; taken out of totally ~4 g wet resin prepared in section (c)) was placed in a 20 ml SPPS reaction vessel. Boc-[Taeg]$_{10}$-Lys(ClZ)-MBHA resin was assembled by the single-coupling protocol employed in the preceding section utilizing 2.5 equivalents of BocTaeg-OPfp in about 30% DMF/CH$_2$Cl$_2$. The reaction volume was 3 ml (vigorous shaking). The synthesis was monitored by the quantitative ninhydrin reation (see Table II).

| Syn-thetic Step | Residue Coupled | Substitution After Deprotection (mmol/g) | | Remaining Free Amino Groups After ($\mu$mol/g) | | Estimated Extent of Coupling (%) |
|---|---|---|---|---|---|---|
| | | Measd | Theoret | Single Coupling | Acetyl-ation | |
| "0" | BocLys (ClZ) | 0.32 | 0.28 | | 0.93 | |
| 1 | BocTaeg | 0.23 | 0.26 | 0.97 | 0.54 | >99.9 |
| 2 | BocTaeg | 0.21 | 0.24 | 0.92 | 0.46 | 99.8 |
| 3 | BocTaeg | 0.19 | 0.23 | 1.00 | 0.57 | 99.7 |
| 4 | BocTaeg | 0.18 | 0.21 | 1.85 | | 99.3 |
| 5 | BocTaeg | 0.17 | 0.20 | 2.01 | 0.19 | 99.9 |
| 6 | BocTaeg | 0.15 | 0.19 | 1.69 | 0.10 | 99.0 |
| 7 | BocaTeg | 0.11 | 0.18 | 1.11 | 0.66 | 99.1 |
| 8 | BocTaeg | 0.12 | 0.17 | 1.82 | 0.44 | 99.0 |
| 9 | BocTaeg | 0.10 | 0.17 | 5.63 | 0.56 | 94.8 |
| 10 | BocTaeg | 0.11 | 0.16 | 1.54 | 0.67 | 99.1 |

(e) Synthesis of Ac-[Taeg]$_{10}$-Lys(ClZ)-MBHA Resin

Following deprotection of a portion of Boc-[Taegl$_{10}$-Lys (ClZ)-MBHA resin (estimated dry weight is about 45 mg), the resin was next acetylated quantitatively with a 2 ml mixture of acetic anhydride/pyridine/CH$_2$Cl$_2$ (1:1:2, v/v/v) for 2 h in a 3 ml solid-phase reaction vessel.

(f) Cleavage, Purification, and Identification of H-[Taeg]$_{10}$-Lys-NH$_2$

A portion of protected Boc-[Taeg]$_{10}$-Lys(ClZ)-BHA resin was treated as described in Example 17c to yield about 24 mg of crude material upon HF cleavage of 76 mg dry H-[Taeg]$_5$-Lys(ClZ)-BHA resin. The main peak at 15.2 min (which includes impurities such as deletion peptides and various byproducts) accounted for about 78% of the total absorbance. The main peak also accounted for about 88% of the "main peak plus deletion peaks" absorbance, which is in good agreement with the overall estimated coupling yield of 90.1% obtained by summarizing the individual coupling yields in Table II. A 7.2 mg portion of the crude product was purified from two batches by use of a semi-preparative reserse-phase column, (collecting the main peak in a beaker cooled with dry ice/2-propanol). Each contained 3.6 mg in 1 ml of H$_2$O. The frozen solution was lyophilized directly (without prior removal of acetonitrile on a speed vac) to give 4.2 mg of 82% pure H-[Taeg]$_{10}$-Lys-NH$_2$.

(g) Cleavage, Purification, and Identification of Ac-[Taeg]$_{10}$-Lys —NH$_2$

A 400.0 mg portion of protected Ac-[Taeg]$_{10}$-Lys(ClZ)-BHA resin (dry weight) was cleaved as described in Example 17c, except for the TFA treatment to yield 11.9 mg of crude material. The main peak at 15.8 min accounted for about 75% of the total absorbance. A 4.8 mg portion of the crude product was purified to give approximately 3.5 mg of >95% pure Ac-[Taeg]$_{10}$-Lys-NH$_2$. For (M+H)$^+$ the calculated m/z value=2849.8 and the measured m/z value=2848.8.

(h) Synthetic Protocol 3

(1) Boc-deprotection with TFA/CH$_2$Cl$_2$ (1:1, v/v), 100 ml, 3×1 min and 1×30 min; (2) washing with CH$_2$Cl$_2$, 100 ml, 6×1 min; (3) neutralization with DIEA/CH$_2$Cl$_2$ (1:19, v/v), 100 ml, 3×2 min; (4) washing with CH$_2$Cl$_2$, 100 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (3.75 mmol; 2.064 g) BocTaeg-OPfp dissolved in 35 ml CH$_2$Cl$_2$ (final concentration of pentafluorophenylester ~0.1 M); the coupling reaction was allowed to proceed for a total of 20–24 h with shaking; (7) washing with DMF, 100 ml, 1×2 min (to remove precipitate of BocTaeg-OH); (8) washing with CH$_2$Cl$_2$, 100 ml, 4×1 min; (9) neutralization with DIEA/CH$_2$Cl$_2$ (1:19, v/v), 100 ml, 2×2 min; (10) washing with CH$_2$Cl$_2$, 100 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 100 ml mixture of acetic anhydride/pyridine/CH$_2$Cl$_2$ (1:1:2, v/v/v) for 2 h; (13) washing with CH$_2$Cl$_2$, 100 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

(i) Synthetic Protocol 4

(1) Boc-deprotection with TFA/CH$_2$Cl$_2$ (1:1, v/v), 25 ml, 3×1 min and 1×30 min; (2) washing with CH$_2$Cl$_2$, 25 ml, 6×1 min; (3) neutralization with DIEA/CH$_2$Cl$_2$ (1:19, v/v), 25 ml, 3×2 min; (4) washing with CH$_2$Cl$_2$, 25 ml, 6×1 min, and drain for 1 min; (5) 2–5 mg sample of PNA-resin is taken out and dried thoroughly for a quantitative ninhydrin analysis to determine the substitution; (6) addition of 2.5 equiv. (0.92 mmol; 0.506 g) BocTaeg-OPfp dissolved in 6 ml CH$_2$Cl$_2$ followed by addition of 3 ml DMF (final concentration of pentafluorophenylester ~0.1 M); the coupling reaction was allowed to proceed for a total of 20–24 hrs with shaking; (7) washing with DMF, 25 ml, 1×2 min; (8) washing with CH$_2$Cl$_2$, 25 ml, 4×1 min; (9) neutralization with DIEA/CH$_2$Cl$_2$ (1:19, v/v), 25 ml, 2×2 min; (10) washing with CH$_2$Cl$_2$, 25 ml, 6×1 min; (11) 2–5 mg sample of protected PNA-resin is taken out for a rapid qualitative ninhydrin test and a further 2–5 mg is dried thoroughly for a quantitative ninhydrin analysis to determine the extent of coupling; (12) blocking of unreacted amino groups by acetylation with a 25 ml mixture of acetic anhydride/pyridine/CH$_2$Cl$_2$ (1:1:2, v/v/v) for 2 h (except after the first cycle); (13) washing with CH$_2$Cl$_2$, 25 ml, 6×1 min; (14) 2×2–5 mg samples of protected PNA-resin are taken out, neutralized with DIEA/CH$_2$Cl$_2$ (1:19, v/v) and washed with CH$_2$Cl$_2$ for qualitative and quantitative ninhydrin analyses.

EXAMPLE 20

Solid-Phase Synthesis of H-[Taeg]$_5$-Caeg-[Taeg]$_4$-Lys-NH$_2$ (a) Stepwise Assembly of Boc-[Taeg]$_5$-C(z)aeg-[Taeg]$_4$-Lys (ClZ)-MBHA Resin About 2.5 g of wet Boc-[Taeg]$_3$-Lys(ClZ)-MBHA resin (~⅙ of the total remaining about 16 g wet resin; ~0.75 g dry resin ~0.15 mmol growing chains) was placed in a 6 ml SPPS reaction vessel. Boc-[Taeg]$_5$-Caeg-[Taeg]$_4$-Lys(ClZ)-MBHA resin was assembled by double coupling of all Taeg-residues utilizing the usual 2.5 equivalents of BocTaeg-OPfp in 2.5 ml about 30% DMF/CH$_2$Cl$_2$, except that the first residue was single-coupled. Incorporation of the C(Z)aeg-residue was accomplished by coupling with 2.0 equivalents of BocC(Z)aeg-OPfp in TFE/CH$_2$Cl$_2$ (1:2, v/v). The progress of the synthesis was monitored at all stages by the quantitative ninhydrin reaction (see Table III).

| Synthetic Step | Residue Coupled | Substitution After Deprotection (mmol/g) | | Remaining Free Amino Groups After ($\mu$mol/g) | | Acetyl- ation | Estimated Extent of Coupling |
|---|---|---|---|---|---|---|---|
| | | Measd. | Theoret. | 1st Coupl | 2nd Coupl | | |
| 3 | | 0.19 | 0.23 | 1.00 | | 0.57 | |
| 4 | BocTaeg | 0.17 | 0.21 | 4.88 | | 97.3 | 97.3 |
| 5 | BocC(Z)aeg | 0.11 | 0.20 | 70.20 | 27.98 | 1.33 | 78.4(46) |
| 6 | BocTaeg | 0.10 | 0.19 | 24.79 | 4.58 | 2.40 | 95.4(75) |
| 7 | BocTaeg | 0.09 | 0.18 | 8.55 | 1.61 | 0.20 | >99.9(93) |
| 8 | BocTaeg | 0.08 | 0.17 | 6.53 | 0.80 | 0.45 | 99.0(91) |
| 9 | BocTaeg | 0.07 | 0.16 | 9.26 | 3.66 | 0.61 | 94.8(86) |
| 10 | BocTaeg | 0.07 | 0.15 | 5.32 | 1.48 | 0.60 | 98.8(93) |

(b) Cleavage, Purification, and Identification of H-[Taeg]$_5$-Caeg-[Taeg]$_4$-Lys-NH$_2$ A portion of protected Boc-[Taeg]$_5$-Caeg-[Taeg]$_4$-Lys (ClZ)-BRA resin was treated as described in Example I section (c) to yield about 14.4 mg of crude material upon HF cleavage of 66.9 mg dry H-[Taeg]$_5$-Caeg-[Taeg]$_4$-Lys(Clz)-BHA resin. The main peak at 14.5 min accounted for >50% of the total absorbance. A 100.0 mg portion of the crude product was purified (8 batches; each dissolved in 1 ml H$_2$O) to give approximately 9.1 mng of 96% pure H-[Taeg]$_5$-Caeg-[Taeg]$_4$-Lys-NH$_2$ (FIG. 13b). For (M+H)$^+$ the calculated m/z value=2793.8 and the measured m/z value=2790.6.

EXAMPLE 21

Binding of Acr$^1$-(Taeg)$_{10}$-Lys-NH$_2$ to dA$_{10}$ (FIG. 11a)

Acr$^1$-(Taeg)$_{10}$-Lys (100 ng) was incubated for 15 min at room temperature with 50 cps 5'-[$^{32}$P]-end-labelled oligonucleotide [d(GATCCA$_{10}$G)) in 20 $\mu$l TE buffer (10 mM Tris-HCl, 1 mM EDTA, pH 7.4). The sample was cooled in ice (15 min) and analyzed by gel electrophoresis in polyacrylamide (PAGE). To 10 $\mu$l of the sample was added 2 $\mu$l 50% glycerol, 5 TBE (TBE=90 mM Tris-borate, 1 mM EDTA, pH 8.3), and the sample was analysed by PAGE (15% acrylamide, 0.5% bisacrylamide) in TBE buffer at 4° C. A 10 $\mu$l portion of the sample was lyophilized and redissolved in 10 $\mu$l 80% formamide, 1 TBE, heated to 90° C. (5 min), and analyzed by urea/PAGE (15% acrylamide, 0.5% bisacrylamide, 7 M urea) in TBE. [$^{32}$P]-containing DNA bands were visualized by autoradiography using intensifying screens and Agfa Curix RPI X-ray films exposed at −80° C. for 2 h.

Oligonucleotides were synthesized on a Biosearch 7500 DNA synthesizer, labelled with $\gamma$[$^{32}$P]-ATP (Amersham, 5000 Ci/mmol) and polynucleotide kinase, and purified by PAGE using standard techniques (Maniatis et al. (1986): A laboratory manual, Cold Spring Harbor Laboratories).

EXAMPLE 22

Formation of Strand Displacement Complex

A dA$_{10}$-dT$_{10}$ target sequence contained within a plasmid DNA sequence was constructed by cloning of two oligonucleotides (d(GATCCA$_{10}$G)+d(GATCCT$_{10}$G)) into the BamHI restriction enzyme site of pUC19 using the *Eschericia coli* JM101 strain by standard techniques (Maniatis et al., 1986). The desired plasmid (designated pT10) was isolated from one of the resulting clones and purified by the alkaline extraction procedure and CsCl centrifugation (Maniatis et al., 1986). A 3'-[$^{32}$P]-end-labelled DNA fragment of 248 bp containing the dA$_{10}$/dT$_{10}$ target sequence was obtained by cleaving the pT10 DNA with restriction enzymes EcoRI and PvuII, labelling of the cleaved DNA with $\alpha$[$^{32}$P]-DATP (4000 Ci/mmol, Amersham) using the Klenow fragment of *E. coli* DNA polymerase (Boehringer Mannheim), and purifying the 248 bp DNA fragment by PAGE (5% acrylamide, 0.06% bisacrylamide, TBE buffer). This DNA fragment was obtained with [$^{32}$P]-end-labelling at the 5'-end by treating the EcoRI-cleaved pT10 plasmid with bacterial alkaline phosphatase (Boehringer Mannheim), purifying the plasmid DNA by gel electrophoresis in low melting agarose, and labelling with $\gamma$[$^{32}$P] ATP and polynucleotide kinase. Following treatment with PvuII, the 248 bp DNA fragment was purified as above.

The complex between Acr$^1$-(Taeg)$_{10}$-Lys-NH$_2$ and the 248 bp DNA fragment was formed by incubating 50 ng of Acr$^1$-(Taeg)$_{10}$-Lys-NH$_2$ with 500 cps $^{32}$P-labelled 248 bp fragment and 0.5 $\mu$g calf thymus DNA in 100 $\mu$l buffer for 60 min at 37° C.

EXAMPLE 23

Probing of Strand Displacement Complex with (a) Staphylococcus Nuclease (FIG. 12b)

The strand displacement complex was formed in 25 mM Tris-HCl, 1 mM MgCl$_2$, 0.1 mM CaCl$_2$, pH 7.4 as described above. The comples was treated with Staphylococcus nuclease (Boehringer Mannheim) at 750 U/ml for 5 min at 20° C. and the reaction was stopped by addition of EDTA to 25 mM. The DNA was precipitated with 2 vols. of ethanol, 2% potassium acetate redissolved in 80% formamide, TBE, heated to 90° C. (5 min), and analyzed by high resolution PAGE (10% acrylamide, 0.3% bisacrylamide, 7 M urea) and autoradiography.

(b) Affinity photocleavage (FIGS. 12a+12b)

The complex was formed in TE buffer. A sample contained in an Eppendorf tube was irradiated from above at 300 nm (Philips TL 20 W/12 fluorescent light tube, 24 Jm$^{-2}$s$^{-1}$) for 30 min. The DNA was precipitated as above, taken up in 1 M piperidine, and heated to 90° C. for 20 min. Following lyophilization, the DNA was analysed by PAGE as above.

(c) Potassium Permanganate (FIG. 12b)

The complex was formed in 100 µl TE and 5 µl 20 mM $KMnO_4$ was added. After 15 s at 20° C., the reaction was stopped by addition of 50 µl 1.5 M sodium acetate, pH 7.0, 1 M 2-mercaptoethanol. The DNA was precipitated, treated with piperidine and analyzed, as above.

(d) Photofootprinting (FIG. 12b)

The complex was formed in 100 µl TE and diazo-linked acridine (0.1 µg/µl) (DHA, Nielsen et al. (1988) Nucl. Acids Res. 16, 3877–88) was added. The sample was irradiated at 365 nm (Philips TL 20 W/09N, 22 $Jm^{-2}s^{-1}$) for 30 min and treated as described for "affinity photocleavage".

(e) $S_1$-nuclease (FIG. 12c)

The complex was formed in 50 mM sodium acetate, 200 mM NaCl, 0.5% glycerol, 1 mM $ZnCl_2$, pH 4.5 and treated with nuclease $S_1$ (Boehringer Mannheim) at 0.5 U/ml for 5 min at 20° C. The reaction was stopped and treated further as described under "Staphylococcus nuclease".

EXAMPLE 24

N-Benzyloxycarbonyl-N-'(bocaminoethyl)glycine

Aminoethyl glycine (52.86 g; 0.447 mol) was dissolved in water (900 ml) and dioxane (900 ml) was added. The pH was adjusted to 11.2 with 2N NaOH. While the pH was kept at 11.2, tert-butyl-p-nitrophenyl carbonate (128.4 g; 0.537 mol) was dissolved in dioxane (720 ml) and added dropwise over the course of 2 hours. The pH was kept at 11.2 for at least three more hours and then left with stirring overnight. The yellow solution was cooled to 0° C. and the pH was adjusted to 3.5 with 2 N HCl. The mixture was washed with chloroform (4×100 ml), and the pH of the aqueous phase was readjusted to 9.5 with 2 N NaOH at 0° C. Benzyloxycarbonyl chloride (73.5 ml; 0.515 mol) was added over half an hour, while the pH was kept at 9.5 with 2 N NaOH. The pH was adjusted frequently over the next 4 hours, and the solution was left with stirring overnight. On the following day the solution was washed with ether (3×600 ml) and the pH of the solution was afterwards adjusted to 1.5 with 2 N HCl at 0° C. The title compound was isolated by extraction with ethyl acetate (5×1000 ml). The ethyl acetate solution was dried over magnesium sulfate and evaporated to dryness, in vacuo. This afforded 138 g, which was dissolved in ether (300 ml) and precipitated by the addition of petroleum ether (1800 ml). Yield 124.7 g (79%). M.p. 64.5–85° C. Anal. for $C_{17}H_{24}N_2O_6$ found(calc.) C, 58.40(57.94); H, 7.02(6.86); N, 7.94(7.95). $^1$H-NMR (250 MHz, $CDCl_3$) 7.33 & 7.32 (5H, Ph); 5.15 & 5.12 (2H, $PhCH_2$); 4.03 & 4.01 (2H, $NCH_2CO_2H$); 3.46 (b, 2H, $BocNHCH_2CH_2$); 3.28 (b, 2H, $BocNHCH_2CH_2$); 1.43 & 1.40 (9H, $^tBu$). HPLC (260 nm) 20.71 min. (80.2%) and 21.57 min. (19.8%). The UV-spectra (200 nm–300 nm) are identical, indicating that the minor peak consists of Bis-Z-AEG.

EXAMPLE 25

N'-Boc-aminoethyl Glycine Ethyl Ester

N-Benzyloxycarbonyl-N'-(bocaminoethyl)glycine (60.0 g; 0.170 mol) and N,N-dimethyl-4-aminopyridine (6.00 g) were dissolved in absolute ethanol (500 ml), and cooled to 0° C. before the addition of DCC (42.2 g; 0.204 mol). The ice bath was removed after 5 minutes and stirring was continued for 2 more hours. The precipitated DCU (32.5 g dried) was removed by filtration and washed with ether (3×100 ml). The combined filtrate was washed successively with diluted potassium hydrogen sulfate (2×400 ml), diluted sodium hydrogencarbonate (2×400 ml) and saturated sodium chloride (1×400 ml). The organic phase was filtered, then dried over magnesium sulfate, and evaporated to dryness, in vacuo, which yielded 66.1 g of an oily substance which contained some DCU.

The oil was dissolved in absolute ethanol (600 ml) and was added 10% palladium on carbon (6.6 g) was added. The solution was hydrogenated at atmospheric pressure, where the reservoir was filled with 2 N sodium hydroxide. After 4 hours, 3.3 L was consumed out of the theoretical 4.2 L. The reaction mixture was filtered through celite and evaporated to dryness, in vacuo, affording 39.5 g (94%) of an oily substance. A 13 g portion of the oily substance was purified by silica gel (600 g $SiO_2$) chromatography. After elution with 300 ml 20% petroleum ether in methylene chloride, the title compound was eluted with 1700 ml of 5% methanol in methylene chloride. The solvent was removed from the fractions with satisfactory purity, in vacuo and the yield was 8.49 g. Alternatively 10 g of the crude material was purified by Kugel Rohr distillation. $^1$H-NMR (250 MHz, $CD_3OD$); 4.77 (b. s, NH); 4.18 (q, 2H, $MeCH_2$—); 3.38 (s, 2H, $NCH_2CO_2Et$); 3.16 (t, 2H, $BocNHCH_2CH_2$); 2.68 (t, 2H, $BocNHCH_2CH_2$); 1.43 (s, 9H, $^tBu$) and 1.26 (t, 3H, $CH_3$) $^{13}$C-NMR 171.4 ($\underline{C}OEt$); 156.6 (CO); 78.3 (($CH_3$)$_3\underline{C}$); 59.9 ($CH_2$); 49.0 ($CH_2$); 48.1 ($CH_2$); 39.0 ($CH_2$); 26.9 ($\underline{C}H_2$) and 12.6 ($CH_3$).

EXAMPLE 26

N'-Boc-aminoethyl Glycine Methyl Ester

The above procedure was used, with methanol being substituted for ethanol. The final product was purified by column purification.

EXAMPLE 27

1-(Boc-aeg)thymine Ethyl Ester

N'-Boc-aminoethyl glycine ethyl ester (13.5 g; 54.8 mmol), DhbtOH (9.84 g; 60.3 mmol) and 1-carboxymethyl thymine (11.1 g; 60.3 mmol) were dissolved in DMF (210 ml). Methylene chloride (210 ml) then was added. The solution was cooled to 0° C. in an ethanol/ice bath and DCC (13.6 g; 65.8 mmol) was added. The ice bath was removed after 1 hour and stirring was continued for another 2 hours at ambient temperature. The precipitated DCU was removed by filtration and washed twice with methylene chloride (2×75 ml). To the combined filtrate was added more methylene chloride (650 ml). The solution was washed successively with diluted sodium hydrogen carbonate (3×500 ml), diluted potassium hydrogen sulfate (2×500 ml), and saturated sodium chloride (1×500 ml). Some precipitate was removed from the organic phase by filtration, The organic phase was dried over magnesium sulfate and evaporated to dryness, in vacuo. The oily residue was dissolved in methylene chloride (150 ml), filtered, and the title compound was precipitated by the addition of petroleum ether (350 ml) at 0° C. The methylene chloride/petroleum ether procedure was repeated once. This afforded 16.0 g (71%) of a material which was more than 99% pure by HPLC.

EXAMPLE 28

1-(Boc-aeg)thymine

The material from above was suspended in THF (194 ml, gives a 0.2 M solution), and 1 M aqueous lithium hydroxide (116 ml) was added. The mixture was stirred for 45 minutes at ambient temperature and then filtered to remove residual DCU. Water (40 ml) was added to the solution which was then washed with methylene chloride (300 ml). Additional water (30 ml) was added, and the alkaline solution was washed once more with methylene chloride (150 ml). The aqueous solution was cooled to 0° C. and the pH was adjusted to 2 by the dropwise addition of 1 N HCl (approx. 110 ml). The title compound was extracted with ethyl acetate (9×200 ml), the combined extracts were dried over magnesium sulfate and were evaporated to dryness, in vacuo. The residue was evaporated once from methanol, which after drying overnight afforded a colorless glassy solid. Yield 9.57 g (64%). HPLC>98% $R_T$=14.8 min. Anal. for $C_{16}H_{24}N_4O_7 \cdot 0.25\ H_2O$ Found (calc.) C, 49.29(49.42); H, 6.52(6.35); N, 14.11(14.41). Due to the limited rotation around the secondary amide, several of the signals were doubled in the ratio 2:1 (indicated in the list by mj. for major and mi. for minor). $^1$H-NMR (250 MHz, DMSO-$d_6$): 12.75 (b.s., 1H, CO$_2$H); 11.28 (s, "1H", mj., imide NH); 11.26 (s, "1H", mi. imide NH); 7.30 (s, "1H", mj., T H-6); 7.26 (s, "1H", mi. ,T H-6); 6.92 (b.t., "1H", mj., BocNH); 6.73 (b.t., "1H", mi. BocNH); 4.64 (s, "2H", mj., CH$_2$CON); 4.46 (s, "2H", mj., CH$_2$CON); 4.19 (s, "2H", mi., CH$_2$CO$_2$H); 3.97 (s, "2H", mj., CH$_2$CO$_2$H); 3.63–3.01 (unresolved m, includes water, CH$_2$CH$_2$); 1.75 (s, 3H, CH$_3$) and 1.38 (s, 9H, $^t$Bu).

EXAMPLE 29

N$^4$-Benzyloxycarbonyl-1-(Boc-aeg)cytosine

N'-Boc-aminoethyl glycine ethyl ester (5.00 g; 20.3 mmol), DhbtoH (3.64 g; 22.3 mmnol) and N$^4$-benzyloxycarbonyl-1-carboxymethyl cytosine (6.77 g; 22.3 mmol) were suspended in DMF (100 ml). Methylene chloride (100 ml) then was added. The solution was cooled to 0° C. and DCC (5.03 g; 24.4 mmol) was added. The ice bath was removed after 2 h and stirring was continued for another hour at ambient temperature. The reaction mixture then was evaporated to dryness, in vacuo. The residue was suspended in ether (100 ml) and stirred vigorously for 30 min. The solid material was isolated by filtration and the ether wash procedure was repeated twice. The material was then stirred vigorously for 15 min with dilute sodium hydrogencarbonate (aprox. 4% solution, 100 ml), filtered and washed with water. This procedure was then repeated once, which after drying left 17.0 g of yellowish solid material. The solid was then boiled with dioxane (200 ml) and filtered while hot. After cooling, water (200 ml) was added. The precipitated material was isolated by filtration, washed with water, and dried. According to HPLC (observing at 260 nm) this material has a purity higher than 99%, besides the DCU. The ester was then suspended in THF (100 ml), cooled to 0° C., and 1 N LiOH (61 ml) was added. After stirring for minutes, the mixture was filtered and the filtrate was washed with methylene chloride (2×150 ml). The alkaline solution then was cooled to 0° C. and the pH was adjusted to 2.0 with 1 N HCl. The title compound was isolated by filtration and was washed once with water, leaving 11.3 g of a white powder after drying. The material was suspended in methylene chloride (300 ml) and petroleum ether (300 ml) was added. Filtration and wash afforded 7.1 g (69%) after drying. HPLC showed a purity of 99% $R_T$=19.5 min, and a minor impurity at 12.6 min (approx. 1%) most likely the Z-de protected monomer. Anal. for $C_{23}H_{29}N_5O_8$ found(calc.) C, 54.16(54.87); H, 5.76(5.81) and N, 13.65(13.91). $^1$H-NMR (250 MHz, DMSO-$d_6$). 10.78 (b.s, 1H, COH); 7.88 (2 overlapping dublets, 1H, Cyt H-5); 7.41–7.32 (m, 5H, Ph); 7.01 (2 overlapping doublets, 1H, Cyt H-6); 6.94 & 6.78 (unres. triplets, 1H, BocNH); 5.19 (s, 2H, PhCH$_2$); 4.81 & 4.62 (s, 2H, CH$_2$CON); 4.17 & 3.98 (s, 2H, CH$_2$CO$_2$H); 3.42–3.03 (m, includes water, C H$_2$CH$_2$) and 1.38 & 1.37 (s, 9H, $^t$Bu). $^{13}$C-NMR. 150.88; 128.52; 128.18; 127.96; 93.90; 66.53; 49.58 and 28.22. IR: Frequency in cm$^{-1}$ (intensity). 3423 (26.4), 3035 (53.2), 2978(41.4), 1736(17.3), 1658(3.8), 1563(23.0), 1501(6.8) and 1456 (26.4).

EXAMPLE 30

9-Carboxymethyl Adenine Ethyl Ester

Adenine (10.0 g, 74 mmol) and potassium carbonate (10.29 g, 74.0 mmol) were suspended in DMF and ethyl bromoacetate (8.24 ml, 74 mmol) was added. The suspension was stirred for 2.5 h under nitrogen at room temperature and then filtered. The solid residue was washed three times with DMF (10 ml). The combined filtrate was evaporated to dryness, in vacuo. The yellow-orange solid material was poured into water (200 ml) and 4 N HCl was added to pH≈6. After stirring at 0° C. for 10 min, the solid was filtered off, washed with water, and recrystallized from 96% ethanol (150 ml). The title compound was isolated by filtration and washed thoroughly with ether. Yield 3.4 g (20%). M.p. 215.5–220° C. Anal. for $C_9H_{11}N_5O_2$ found(calc.): C, 48.86 (48.65); H, 5.01(4.91); N, 31.66(31.42). $^1$H-NMR (250 MHz; DMSO-$d_6$): (s, 2H, H-2 & H-8), 7.25 (b. s., 2H, NH$_2$), 5.06 (s, 2H, NCH$_2$), 4.17 (q, 2H, J=7.11 Hz, OCH$_2$) and 1.21 (t, 3H, J=7.13 Hz, NCH$_2$). $^{13}$C-NMR. 152.70, 141.30, 61.41, 43.97 and 14.07. FAB-MS. 222 (MH+). IR: Frequency in cm$^{-1}$ (intensity). 3855 (54.3), 3274(10.4), 3246(14.0), 3117 (5.3), 2989(22.3), 2940(33.9), 2876(43.4), 2753(49.0), 2346 (56.1), 2106(57.1), 1899(55.7), 1762(14.2), 1742(14.2), 1742(1.0), 1671(1.8), 1644(10.9), 1606(0.6), 1582(7.1), 1522(43.8), 1477(7.2), 1445(35.8) and 1422(8.6). The position of alkylation was verified by X-ray crystallography on crystals, which were obtained by recrystallization from 96% ethanol.

Alternatively, 9-carboxymethyl adenine ethyl ester can be prepared by the following procedure. To a suspension of adenine (50.0 g, 0.37 mol) in DMF (1100 ml) in 2 L three-necked flask equipped with a nitrogen inlet, a mechanical stirrer and a dropping funnel was added 16.4 g (0.407 mol) haxane washed sodium hydride-mineral oil dispersion. The mixture was stirred vigorously for 2 hours, whereafter ethy bromacetate 75 ml, 0.67 mol) was added dropwise over the course of 3 hours. The mixture was stirred for one additional hour, whereafter tic indicated complete conversion of adenine. The mixture was evaporated to dryness at 1 mmHg and water (500 ml) was added to the oily residue which caused crystallisation of the title compound. the solid was recrystallised from 06% ethanol (600 ml). Yield after drying 53.7 (65.6%). HPLC (215 nm) purity >99.5%.

EXAMPLE 31

N$^6$-Benzyloxycarbonyl-9-carboxymethyl Adenine Ethyl Ester

9-Carboxymethyladenine ethyl ester (3.40 g, 15.4 mmol) was dissolved in dry DMF (50 ml) by gentle heating, cooled to 20° C., and added to a solution of N-ethyl-benzyloxycarbonylimidazole tetrafluoroborate (62 mmol) in methylene chloride (50 ml) over a period of 15 min with ice-cooling. Some precipitation was observed. The ice bath was removed and the solution was stirred overnight. The reaction mixture was treated with saturated sodium hydrogen carbonate (100 ml). After stirring for 10 min, the phases were separated and the organic phase was washed successively with one volume of water, dilute potassium hydrogen sulfate (twice), and with saturated sodium chloride. The solution was dried over magnesium sulfate and evaporated to dryness, in vacuo, which afforded 11 g of an oily material. The material was dissolved in methylene chloride (25 ml), cooled to 0° C., and precipitated with petroleumeum ether (50 ml). This procedure was repeated once to give 3.45 g (63%) of the title compound. M.p. 132–35° C. Analysis for $C_{17}H_{17}N_5O_4$ found (calc.): C, 56.95(57.46); H, 4.71(4.82); N, 19.35(19.71). $^1$H-NMR (250 MHz; CDCl$_3$): 8.77 (s, 1H, H-2 or H-8); 7.99 (s, 1H, H-2 or H-8); 7.45–7.26 (m, 5H, Ph); 5.31 (s, 2H, N—C$\underline{H}_2$); 4.96 (s, 2H, Ph—C$\underline{H}_2$); 4.27 (q, 2H, J=7.15 Hz, C$\underline{H}_2$CH$_3$) and 1.30 (t, 3H, J=7.15 Hz, CH$_2$C$\underline{H}_3$). $^{13}$C-NMR: 153.09; 143.11; 128.66; 67.84; 62.51; 44.24 and 14.09. FAB-MS: 356 (MH+) and 312 (MH+—CO$_2$). IR: frequency in cm$^{-1}$ (intensity). 3423 (52.1); 3182 (52.8); 3115(52.1); 3031(47.9); 2981(38.6); 1747(1.1); 1617(4.8); 15.87(8.4); 1552(25.2); 1511(45.2); 1492(37.9); 1465(14.0) and 1413(37.3).

EXAMPLE 32

N$^6$-Benzyloxycarbonyl-9-carboxymethyl Adenine

N$^6$-Benzyloxycarbonyl-9-carboxymethyladenine ethyl ester (3.20 g; 9.01 mmol) was mixed with methanol (50 ml) cooled to 0° C. Sodium Hydroxide Solution (50 ml; 2N) was added, whereby the material quickly dissolved. After 30 min at 0° C., the alkaline solution was washed with methylene chloride (2×50ml). The aqueous solution was brought to pH 1.0 with 4 N HCl at 0° C., whereby the title compound precipitated. The yield after filtration, washing with water, and drying was 3.08 g (104%). The product contained salt and elemental analysis reflected that. Anal. for $C_{15}H_{13}N_5O_4$ found(calc.): C, 46.32(55.05); H, 4.24(4.00); N, 18.10 (21.40) and C/N, 2.57(2.56). $^1$H-NMR(250 MHz; DMSO-d$_6$): 8.70 (s, 2H, H-2 and H-8); 7.50–7.35 (m, 5H, Ph); 5.27 (s, 2H, N—C$\underline{H}_2$); and 5.15 (s, 2H, Ph—C$\underline{H}_2$). $^{13}$C-NMR. 168.77, 152.54, 151.36, 148.75, 145.13, 128.51, 128.17, 127.98, 66.76 and 44.67.IR (KBr) 3484(18.3); 3109(15.9); 3087(15.0); 2966(17.1); 2927(19.9); 2383(53.8); 1960 (62.7); 1739(2.5); 1688(5.2); 1655(0.9); 1594(11.7); 1560 (12.3); 1530(26.3); 1499(30.5); 1475(10.4); 1455(14.0); 1429(24.5) and 1411(23.6). FAB-MS: 328 (MH+) and 284 (MH+—CO$_2$). HPLC (215 nm, 260 nm) in system 1: 15.18 min, minor impurities all less than 2%.

EXAMPLE 33

N$^6$-Benzyloxycarbonyl-1-(BOc-aeg)adenine Ethyl Ester

N'-Boc-aminoethyl glycine ethyl ester (2.00 g; 8.12 mmol), DhbtOH (1.46 g; 8.93 mmol) and N$^6$-benzyloxycarbonyl-9-carboxymethyl adenine (2.92 g; 8.93 mmol) were dissolved in DMF (15 ml). Methylene chloride (15 ml) then was added. The solution was cooled to 0° C. in an ethanol/ice bath. DCC (2.01 g; 9.74 mmol) was added. The ice bath was removed after 2.5 h and stirring was continued for another 1.5 hour at ambient temperature. The precipitated DCU was removed by filtration and washed once with DMF (15 ml), and twice with methylene chloride (2×15 ml). To the combined filtrate was added more methylene chloride (100 ml). The solution was washed successively with dilute sodium hydrogen carbonate (2×100 ml), dilute potassium hydrogen sulfate (2×100 ml), and saturated sodium chloride (1×100 ml). The organic phase was evaporated to dryness, in vacuo, which afforded 3.28 g (73%) of a yellowish oily substance. HPLC of the raw product showed a purity of only 66% with several impurities, both more and less polar than the main peak. The oil was dissolved in absolute ethanol (50 ml) and activated carbon was added. After stirring for 5 minutes, the solution was filtered. The filtrate was mixed with water (30 ml) and was left with stirring overnight. The next day, the white precipitate was removed by filtration, washed with water, and dried, affording 1.16 g (26%) of a material with a purity higher than 98% by HPLC. Addition of water to the mother liquor afforded another 0.53 g with a purity of approx. 95%. Anal. for $C_{26}H_{33}N_7O_7\cdot H_2O$ found(calc.) C, 55.01(54.44; H, 6.85 (6.15) and N, 16.47(17.09). $^1$H-NMR (250 MHz, CDCl$_3$) 8.74 (s, 1H, Ade H-2); 8.18 (b. s, 1H, ZNH); 8.10 & 8.04 (s, 1H, H-8); 7.46–7.34 (m, 5H, Ph); 5.63 (unres. t, 1H, BocNH); 5.30 (s, 2H, PhCH$_2$); 5.16 & 5.00 (s, 2H, C H$_3$CON);. 4.29 & 4.06 (s, 2H, CH$_2$CO$_2$H); 4.20 (q, 2H, OC $\underline{H}_2$CH$_3$); 3.67–3.29 (m, 4H, C$\underline{H}_2\underline{CH}_2$); 1.42 (s, 9H, $^t$Bu) and 1.27 (t, 3H, OCH$_2$CH$_3$). The spectrum shows traces of ethanol and DCU.

EXAMPLE 34

N$^6$-Benzyloxycarbonyl-1-(Boc-aeg)adenine

N$^6$-Benzyloxycarbonyl-1-(Boc-aeg)adenine ethyl ester (1.48 g; 2.66 mmol) was suspended in THF (13 ml) and the mixture was cooled to 0° C. Lithium hydroxide (8 ml; 1 N) was added. After 15 min of stirring, the reaction mixture was filtered, extra water (25 ml) was added, and the solution was washed with methylene chloride (2×25 ml). The pH of the aqueous solution was adjusted to pH 2.0 with 1 N HCl. The precipitate was isolated by filtration, washed with water, and dried, and drief affording 0.82 g (58%). The product repecipitated twice with methylene chloride/petroleum ether, 0.77 g (55%) after drying. M.p. 119° C. (decomp.) Anal. for $C_{24}H_{29}N_7O_7\cdot H_2O$ found(calc.) C, 53.32(52.84); H, 5.71 (5.73); N, 17.68(17.97). FAB-MS. 528.5 (MH+). $^1$H-NMR (250 MHz, DMSO-d$_6$). 12.75 (very b, 1H, CO$_2$H); 10.65 (b. s, 1H, ZNH); 8.59 (d, 1H, J=2.14 Hz, Ade H-2); 8.31 (s, 1H, Ade H-8); 7.49–7.31 (m, 5H, Ph); 7.03 & 6.75 (unresol. t, 1H, BocNH); 5.33 & 5.16 (s, 2H, CH$_2$CON); 5.22 (s, 2H, PhCH$_2$); 4.34–3.99 (s, 2H, CH$_2$CO$_2$H); 3.54–3.03 (m's, includes water, CH$_2$CH$_2$) and 1.39 & 1.37 (s, 9H, $^t$Bu). $^{13}$C-NMR. 170.4; $\overline{166.6}$; 152.3; 151.5; 149.5; 145.2; 128.5; 128.0; 127.9; 66.32; 47.63; 47.03; 43.87 and 28.24.

EXAMPLE 35

2-Amino-6-chloro-9-carboxymethylpurine

To a suspension of 2-amino-6-chloropurine (5.02 g; 29.6 mmol) and potassium carbonate (12.91 g; 93.5 mmol) in DMF (50 ml) was added bromoacetic acid (4.70 g; 22.8 mmol). The mixture was stirred vigorously for 20 h. under nitrogen. Water (150 ml) was added and the solution was filtered through Celite to give a clear yellow solution. The solution was acidified to a pH of 3 with 4 N hydrochloric acid. The precipitate was filtered and dried, in vacuo, over sicapent. Yield (3.02 g; 44.8%). $^1$H-NMR(DMSO-d6): d=4.88 ppm (s,2H); 6.95 (s,2H); 8.10 (s,1H).

EXAMPLE 36

2-Amino-6-benzyloxy-9-carboxymethylpurine

Sodium (2.0 g; 87.0 mmol) was dissolved in benzyl alcohol (20 ml) and heated to 130° C. for 2 h. After cooling to 0° C., a solution of 2-amino-6-chloro-9-carboxymethylpurine (4.05 g; 18.0 mmol) in DMF (85 ml) was slowly added, and the resulting suspension stirred overnight at 20° C. Sodium hydroxide solution (1N, 100 ml) was added and the clear solution was washed with ethyl acetate (3×100 ml). The water phase then was acidified to a pH of 3 with 4 N hydrochloric acid. The precipitate was taken up in ethyl acetate (200 ml), and the water phase was extracted with ethyl acetate (2×100 ml). The combined organic phases were washed with saturated sodium chloride solution (2×75 ml), dried with anhydrous sodium sulfate, and taken to dryness by evaporation, in vacuo. The residue was recrystallized from ethanol (300 ml). Yield after drying, in vacou, over sicapent: 2.76 g (52%). M.p. 159–65° C. Anal. (calc., found) C(56.18; 55.97); H(4.38; 4.32); N(23.4; 23.10). $^1$H-NMR (DMSO-$d_6$): 4.82 ppm.(s,2H); 5.51 (s,2H); 6.45 (s,2H); 7.45 (m,5H); 7.82 (s,1H).

EXAMPLE 37

N-([2-Amino-6-benzyloxy-purine-9-yl]-acetyl)-N-(2-Boc-aminoethyl)-glycine [BocGaeg-OH monomer]

2-Amino-6-benzyloxy-9-carboxymethyl-purine (0.50 g; 1.67 mmol), methyl-N(2-[tert-butoxycarbonylamino]ethyl)-glycinate (0.65 g; 2.80 mmol), diisopropylethyl amine (0.54 g; 4.19 mmol), and bromo-tris-pyrrolidino-phosphonium-hexafluoro-phosphate (PyBroP®) (0.798 g; 1.71 mmol) were stirred in DMF (2 ml) for 4 h. The clear solution was poured into an ice-cooled solution of sodium hydrogen carbonate (1 N; 40 ml) and extracted with ethyl acetate (3×40 ml). The organic layer was washed with potassium hydrogen sulfate solution (1 N; 2×40 ml), sodium hydrogen carbonate (1 N; 1×40 ml) and saturated sodium chloride solution (60 ml). After drying with anhydrous sodium sulfate and evaporation, in vacuo, the solid residue was recrystallized from ethyl acetate/hexane (20 ml (2:1)) to give the methyl ester in 63% yield (MS-FAB 514 (M+1). Hydrolysis was accomplished by dissolving the ester in ethanol/water (30 ml (1:2)) containing conc. sodium hydroxide (1 ml). After stirring for 2 h, the solution was filtered and acidified to a pH of 3, by the addition of 4 N hydrochloric acid. The title compound was obtained by filtration. Yield: 370 mg (72% for the hydrolysis). Purity by HPLC was more than 99%. Due to the limited rotation around the secondary amide several of the signals were doubled in the ratio 2:1 (indicated in the list by mj. for major and mi. for minor). $^1$H-NMR(250, MHz, DMSO-$d_6$): d=1.4 ppm. (s,9H); 3.2 (m,2H); 3.6 (m,2H); 4.1 (s, mj., CONRC$\underline{H}_2$COOH); 4.4 (s, mi., CONRC$\underline{H}_2$COOH); 5.0 (s, mi., Gua-C$\underline{H}_2$CO—); 5.2 (s, mj., Gua-C$\underline{H}_2$CO); 5.6 (s,2H); 6.5 (s,2H); 6.9 (m, mi., BocNH); 7.1 (m, mj., BocNH); 7.5 (m.,3H); 7.8 (s,1H); 12,8 (s;1H). $^{13}$C-NMR. 170.95; 170.52; 167.29; 166.85; 160.03; 159.78; 155.84; 154.87; 140.63; 136.76; 128.49; 128.10; 113.04; 78.19; 77.86; 66.95; 49.22; 47.70; 46.94; 45.96; 43.62; 43.31 and 28.25.

EXAMPLE 38

3-Boc-amino-1,2-propanediol

3-Amino-1,2-propanediol (40.00 g, 0.440 mol, 1.0 eq.) was dissolved in water (1000 ml) and cooled to 0° C. Di-tert-butyl dicarbonate (115.0 g, 0.526 mol, 1.2 eq.) was added in one portion. The reaction mixture was heated to room temperature on a water bath during stirring. The pH was maintained at 10.5 with a solution of sodium hydroxide (17.56 g, 0.440 mol, 1.0 eq.) in water (120 ml). When the addition of aqueous sodium hydroxide was completed, the reaction mixture was stirred overnight at room temperature. Subsequently, ethyl acetate (750 ml) was added to the reaction mixture, followed by cooling to 0° C. The pH was adjusted to 2.5 with 4 N sulphuric acid with vigorous stirring. The phases were separated and the water phase was washed with additional ethyl acetate (6×350 ml). The volume of the organic phase was reduced to 900 ml by evaporation under reduced pressure. The organic phase then was washed with a saturated aqueous solution of potassium hydrogen sulfate diluted to twice its volume (1×1000 ml) and with saturated aqueous sodium chloride (1×500 ml). The organic phase was dried (MgSO$_4$) and evaporated under reduced pressure to yield 50.12 g (60%) of the title compound. The product could be solidified by evaporation from methylene chloride and subsequent freezing. $^1$H-NMR (CDCl$_3$/TMS): d=1.43 (s, 9H, Me$_3$C), 3.25 (m, 2H, CH$_2$), 3.57 (m, 2H, CH$_2$), 3.73 (m, 1H, CH). $^{13}$C-NMR (CDCl$_3$/TMS): d=28.2 (Me$_3$C), 42.6 (CH$_2$), 63.5, 71.1 (CH$_2$OH, CHOH), 79.5 (Me$_3$C), 157.0 (C=O).

EXAMPLE 39

2-(BoC-amino)ethyl-L-alanine Methyl Ester

3-Boc-amino-1,2-propanediol (20.76 g, 0.109 mol, 1 eq.) was suspended in water (150 ml). Potassium m-periodate (24.97 g, 0.109 mol, 1 eq.) was added and the reaction mixture was stirred for 2 h at room temperature under nitrogen. The reaction mixture was filtered and the water phase extracted with chloroform (6×250 ml) The organic phase was dried (MgSO$_4$) and evaporated to afford an almost quantitative yield of Boc-aminoacetaldehyde as a colourless oil, which was used without further purification in the following procedure.

Palladium-on-carbon (10%, 0.8 g) was added to MeOH (250 ml) under nitrogen with cooling (0° C.) and vigorous stirring. Anhydrous sodium acetate (4.49 g, 54.7 mmol, 2 eqv) and L-alanine methyl ester, hydrochloride (3.82 g, 27.4 mmol, 1 eqv) were added. Boc-aminoacetaldehyde (4.79 g, 30.1 mmol, 1.1 eqv) was dissolved in MeOH (150 ml) and added to the reaction mixture. The reaction mixture was hydrogenated at atmospheric pressure and room temperature until hydrogen uptake had ceased. The reaction mixture was filtered through celite, which was washed with additional MeOH. The MeOH was removed under reduced pressure. The residue was suspended in water (150 ml) and pH adjusted to 8.0 by dropwise addition of 0.5 N NaOH with vigorous stirring. The water phase was extracted with methylene chloride (4×250 ml). The organic phase was dried (MgSO$_4$), filtered through celite, and evaporated under reduced pressure to yield 6.36 g (94%) of the title compound as a clear, slightly yellow oil. MS (FAB-MS): m/z (%)=247 (100, M+1), 191 (90), 147 (18). $^1$H-NMR (250 MHz, CDCl$_3$). 1.18 (d, J=7.0 Hz, 3H, Me), 1.36 (s, 9H, Me$_3$C), 1.89 (b, 1H, NH), 2.51 (m, 1H, CH$_2$), 2.66 (m, 1H, CH$_2$), 3.10 (m, 2H, CHZ), 3.27 (q, J=7.0 Hz, 1H, CH), 3.64 (s, 3H, OMe), 5.06 (b, 1H, carbamate NH). $^{13}$C-NMR. d=18.8 (Me), 28.2 (Me$_3$C), 40.1, 47.0 (CH$_2$), 51.6 (OMe), 56.0 (CH), 155.8 (carbamate C=O), 175.8 (ester C=O).

EXAMPLE 40

N-(Boc-aminoethyl)-N-(1-thyminylacetyl)-L-alanine Methyl Ester

To a solution of Boc-aminoethyl-(L)-alanine methyl ester (1.23 g, 5.0 mmol) in DMF (10 ml) was added Dhbt-OH (0.90 g, 5.52 mmol) and 1-thyminylacetic acid (1.01 g, 5.48 mmol). When the 1-thyminylacetic acid was dissolved, dichloromethane (10 ml) was added and the solution was cooled on an ice bath. After the reaction mixture had reached 0° C., DCC (1.24 g, 6.01 mmol) was added. Within 5 min after the addition, a precipitate of DCU was seen. After a further 5 min, the ice bath was removed. Two hours later, TLC analysis showed the reaction to be finished. The mixture was filtered and the precipitate washed with dichloromethane (100 ml). The resulting solution was extracted twice with 5% sodium hydrogen carbonate (150 ml) and twice with saturated potassium hydrogen sulfate (25 ml) in water (100 ml). After a final extraction with saturated sodium chloride (150 ml), the solution was dried with magnesium sulfate and evaporated to give a white foam. The foam was purified by column chromatography on silica gel using dichloromethane with a methanol gradient as eluent. This yielded a pure compound (>99% by HPLC) (1.08 g, 52.4%). FAB-MS: 413 (M+1) and 431 (M+1+water). $^1$H-NMR (CDCl$_3$): 4.52 (s, 2 H, CH'$_2$); 3.73 (s, 3 H, OMe); 3.2–3.6 (m, 4 H, ethyl CH$_2$'s); 1.90 (s, 3 H, Me in T); 1.49 (d, 3 H, Me in Ala, J=7.3 Hz); 1.44 (s, 9 H, Boc).

EXAMPLE 41

N-(Boc-aminoethyl)-N-(1-thyminylacetyl)-L-alanine

The methyl ester of the title compound (2.07 g, 5.02 mmol) was dissolved in methanol (100 ml), and cooled on an ice bath. 2 M sodium hydroxide (100 ml) was added. After stirring for 10 min, the pH of the mixture was adjusted to 3 with 4 M hydrogen chloride. The solution was subsequently extracted with ethyl acetate (3×100 ml). The combined organic extracts were dried over magnesium sulfate. After evaporation, the resulting foam was dissolved in ethyl acetate (400 ml) and a few ml of methanol to dissolve the solid material. Petroleum ether then was added until precipitation started. After standing overnight at −20° C., the precipitate was removed by filtration. This gave 1.01 g (50.5%) of pure compound (>99% by HPLC). The compound can be recrystallized from 2-propanol. FAB-MS: 399 (M+1). $^1$H-NMR (DMSO-d$_6$): 11.35 (s, 1 H, COO); 7.42 (s, 1 H, H'$_6$); 4.69 (s, 2 H, CH'$_2$); 1.83 (s, 3 H, Me in T); 1.50–1.40 (m, 12 H, Me in Ala+Boc).

EXAMPLE 42

(a) N-(Boc-aminoethyl)-N-(1-thyminylacetyl)-D-alanine Methyl Ester

To a solution of Boc-aminoethyl alanine methyl ester (2.48 g, 10.1 mmol) in DMF (20 ml) was added Dhbt-OH (1.80 g, 11.0 mmol) and thyminylacetic acid (2.14 g, 11.6 mmol). After dissolution of the 1-thyminylacetic acid, methylene chloride (20 ml) was added and the solution cooled on an ice bath. When the reaction mixture had reached 0° C., DCC (2.88 g, 14.0 mmol) was added. Within 5 min after the addition a precipitate of DCU was seen. After 35 min the ice bath was removed. The reaction mixture was filtered 3.5 h later and the precipitate washed with methylene chloride (200 ml). The resulting solution was extracted twice with 5% sodium hydrogen carbonate (200 ml) and twice with saturated potassium hydrogen sulfate in water (100 ml). After a final extraction with saturated sodium chloride (250 ml), the solution was dried with magnesium sulfate and evaporated to give an oil. The oil was purified by short column silica gel chromatography using methylene chloride with a methanol gradient as eluent. This yielded a compound which was 96% pure according to HPLC (1.05 g, 25.3%) after precipitation with petroleum ether. FAB-MS: 413 (M+1). $^1$H-NMR (CDCl$_3$): 5.64 (t, 1 H, BocNH, J=5.89 Hz); 4.56 (d, 2 H, CH'$_2$); 4.35 (q, 1 H, CH in Ala, J=7.25 Hz); 3.74 (s, 3 H, OMe); 3.64–3.27 (m, 4 H, ethyl H's); 1.90 (s, 3 H, Me in T); 1.52–1.44 (t, 12 H, Boc+Me in Ala).

(b) N-(Boc-aminoethyl)-N-(1-thyminylacetyl)-D-alanine

The methyl ester of the title compound (1.57 g, 3.81 mmol) was dissolved in methanol (100 ml) and cooled on an ice bath. Sodium hydroxide .(100 ml; 2 M) was added. After stirring for 10 min the pH of the mixture was adjusted to 3 with 4 M hydrogen chloride. The solution then was extracted with ethyl acetate (3×100 ml). The combined organic extracts were dried over magnesium sulfate. After evaporation, the oil was dissolved in ethyl acetate (200 ml). Petroleum ether was added (to a total volume of 600 ml) until precipitation started. After standing overnight at −20° C., the precipitate was removed by filtration. This afforded 1.02 g (67.3%) of the title compound, which was 94% pure according to HPLC. FAB-MS: 399 (M+1). $^1$H-NMR: 11.34 (s, 1 H, COOH); 7.42 (s, 1 H, H'$_6$); 4.69 (s, 2 H, CH'$_2$); 4.40 (q, 1 H, CH in Ala, J=7.20 Hz); 1.83 (s, 3 H, Me in T); 1.52–1.40 (m, 12 H, Boc+Me in Ala).

EXAMPLE 43

N-(N'-Boc-3'-aminopropyl)-N-[(1-thyminyl)acetyl] glycine Methyl Ester

N-(N'-Boc-3'-aminopropyl)glycine methyl ester (2.84 g, 0.0115 mol) was dissolved in DMF (35 ml), followed by addition of DhbtOH (2.07 g, 0.0127 mol) and 1-thyminylacetic acid (2.34 g, 0.0127 mol). Methylene chloride (35 ml) was added and the mixture cooled to 0° C. on an ice bath. After addition of DCC (2.85 g, 0.0138 mol), the mixture was stirred at 0° C. for 2 h, followed by 1 h at room temperature. The precipitated DCU was removed by filtration, washed with methylene chloride (25 ml), and a further amount of methylene chloride (150 ml) was added to the filtrate. The organic phase was extracted with sodium hydrogen carbonate (1 volume saturated diluted with 1 volume water, 6×250 ml), potassium sulfate (1 volume saturated diluted with 4 volumes water, 3×250 ml), and saturated aqueous sodium chloride (1×250 ml), dried over magnesium sulfate, and evaporated to dryness, in vacuo. The solid residue was suspended in methylene chloride (35 ml) and stirred for 1 h. The precipitated DCU was removed by filtration and washed with methylene chloride (25 ml). The filtrate was evaporated to dryness, in vacuo, and the residue purified by column chromatography on silica gel, eluting with a mixture of methanol and methylene chloride (gradient from 3–7% methanol in methylene chloride). This afforded the title compound as a white solid (3.05 g, 64%). M.p. 76–79° C. (decomp.). Anal. for C$_{18}$H$_{28}$N$_4$O$_7$, found (calc.) C, 52.03 (52.42) H, 6.90 (6.84); N, 13.21 (13.58). The compound showed satisfactory $^1$H and $^{13}$C-NMR spectra.

EXAMPLE 44

N-(N'-Boc-3'-aminopropyl)-N-[(1-thyminyl)acetyl] glycine

N-(N'-Boc-3'-aminopropyl)-N-[(1-thyminyl)acetyl] glycine methyl ester (3.02 g, 0.00732 mol) was dissolved in methanol (25 ml) and stirred for 1.5 h with 2 M sodium hydroxide (25 ml). The methanol was removed by evaporation, in vacuo, and pH adjusted to 2 with 4 M hydrochloric acid at 0° C. The product was isolated as white crystals by filtration, washed with water (3×10 ml), and dried over sicapent, in vacuo. Yield 2.19 g (75%). Anal. for C$_{17}$H$_{26}$N$_4$O$_7$, H$_2$O, found (calc.) C, 49.95 (49.03); H, 6.47

(6.29); N, 13.43 (13.45). The compound showed satisfactory $^1$H and $^{13}$C-NMR spectra.

EXAMPLE 45

3-(1-Thyminyl)-propanoic Acid Methyl Ester

Thymine (14.0 g, 0.11 mol) was suspended in methanol. Methyl acrylate (39.6 ml, 0.44 mol) was added, along with catalytic amounts of sodium hydroxide. The solution was refluxed in the dark for 45 h, evaporated to dryness, in vacuo, and the residue dissolved in methanol (8 ml) with heating. After cooling on an ice bath, the product was precipitated by addition of ether (20 ml), isolated by filtration, washed with ether (3×15 ml), and dried over sicapent, in vacuo. Yield 11.23 g (48%). M.p. 112–119° C. Anal. for $C_9H_{12}N_2O_4$, found (calc.) C, 51.14 (50.94); H, 5.78 (5.70); N, 11.52 (13.20). The compound showed satisfactory $^1$H and $^{13}$C-NMR spectra.

EXAMPLE 46

3-(1-Thyminyl)-propanoic Acid 3-(1-Thyminyl)-propanoic acid methyl ester (1.0 g, 0.0047 mol) was suspended in 2 M sodium hydroxide (15 ml), boiled for 10 min. The pH was adjusted to 0.3 with conc. hydrochloric acid. The solution was extracted with ethyl acetate (10×25 ml). The organic phase was extracted with saturated aqueous sodium chloride, dried over magnesium sulfate, and evaporated to dryness, in vacuo, to give the title compound as a white solid (0.66 g, 71%). M.p. 118–121° C. Anal. for $C_8H_{10}N_2O_4$, found (calc.) C, 48.38 (48.49) H, 5.09 (5.09); N, 13.93 (14.14). The compound showed satisfactory $^1$H and $^{13}$C-NMR spectra.

EXAMPLE 47

N-(N'-Doc-aminoethyl)-N-[(1-thyminyl)propanoyl] glycine Ethyl Ester

N-(N'-Boc-aminoethyl)glycine ethyl ester (1.0 g, 0.0041 mol) was dissolved in DMF (12 ml). DhbtOH (0.73 g, 0.0045 mol) and 3-(1-thyminyl)-propanoic acid (0.89 g, 0.0045 mol) were added. Methylene chloride (12 ml) then was added and the mixture was cooled to 0° C. on an ice bath. After addition of DCC (1.01 g, 0.0049 mol), the mixture was stirred at 0° C. for 2 h, followed by 1 h at room temperature. The precipitated DCU was removed by filtration, washed with methylene chloride (25 ml), and a further amount of methylene chloride (50 ml) was added to the filtrate. The organic phase was extracted with sodium hydrogen carbonate (1 volume saturated diluted with 1 volume water, 6×100 ml), potassium sulfate (1 volume saturated diluted with 4 volumes water, 3×100 ml), and saturated aqueous sodium chloride (1×100 ml), dried over magnesium sulfate, and evaporated to dryness, in vacuo. The solid residue was suspended in methylene chloride (15 ml), and stirred for 1 h. The precipitated DCU was removed by filtration and washed with methylene chloride. The filtrate was evaporated to dryness, in vacuo, and the residue purified by column chromatography on silica gel, eluting with a mixture of methanol and methylene chloride (gradient from 1 to 6% methanol in methylene chloride). This afforded the title compound as a white solid (1.02 g, 59%). Anal. for $C_{19}H_{30}N_4O_7$, found (calc.) C, 53.15 (53.51); H, 6.90 (7.09); N, 12.76 (13.13). The compound showed satisfactory $^1$H and $^{13}$C-NMR spectra.

EXAMPLE 48

N-(N'-Boc-aminoethyl)-N-[(1-thyminyl)propanoyl] glycine

N-(N'-Boc-aminoethyl)-N-[(1-thyminyl)propanoyl) glycine ethyl ester (0.83 g, 0.00195 mol) was dissolved in methanol (25 ml). Sodium hydroxide (25 ml; 2 M) was added. The solution was stirred for 1 h. The methanol was removed by evaporation, in vacuo, and the pH adjusted to 2 with 4 M hydrochloric acid at 0° C. The product was isolated by filtration, washed with ether (3×15 ml), and dried over sicapent, in vacuo. Yield 0.769 g, 99%). M.p. 213° C. (decomp.).

EXAMPLE 49

Mono-Boc-ethylenediamine (2)

tert-Butyl-4-nitrophenyl carbonate (1) (10.0 g; 0.0418 mol) dissolved in DMF (50 ml) was added dropwise over a period of 30 min to a solution of ethylenediamine (27.9 ml; 0.418 mol) and DMF (50 ml) and stirred overnight. The mixture was evaporated to dryness, in vacuo, and the resulting oil dissolved in water (250 ml). After cooling to 0° C., pH was adjusted to 3.5 with 4 M hydrochloric acid. The solution then was filtered and extracted with chloroform (3×250 ml). The pH was adjusted to 12 at 0° C. with 2 M sodium hydroxide, and the aqueous solution extracted with methylene chloride (3×300 ml). After treatment with sat. aqueous sodium chloride (250 ml), the methylene chloride solution was dried over magnesium sulfate. After filtration, the solution was evaporated to dryness, in vacuo, resulting in 4.22 g (63%) of the product (oil). $^1$H-NMR (90 MHz; CDCl$_3$): δ1.44 (s, 9H); 2.87 (t, 2H); 3.1 (q, 2H); 5.62 (s, broad).

EXAMPLE 50

(N-Boc-aminoethyl)-β-alanine Methyl Ester, HCl

Mono-Boc-ethylenediamine (2) (16.28 g; 0.102mol) was dissolved in acetonitrile (400 ml) and methyl acrylate (91.50 ml; 1.02 mol) was transferred to the mixture with acetonitrile (200 ml). The solution was refluxed overnight under nitrogen in the dark to avoid polymerization of methyl acrylate. After evaporation to dryness, in vacuo, a mixture of water and ether (200+200 ml) was added, and the solution was filtered and vigorously stirred. The aqueous phase was extracted one more time with ether and then freeze dried to yield a yellow solid. Recrystallization from ethyl acetate yielded 13.09 g (46%) of the title compound. M.p. 138–140° C. Anal. for $C_{11}H_{23}N_2O_4Cl$, found (calc.) C, 46.49 (46.72); H, 8.38 (8.20); N, 9.83 (9.91); Cl, 12.45 (12.54). $^1$H-NMR (90 MHz; DMSO-d$_6$): δ1.39 (s, 9H); 2.9 (m, 8H); 3.64 (s, 3H).

EXAMPLE 51

N-[(1-Thyminyl)acetyl]-N'-Boc-aminoethyl-β-alanine Methyl Ester (N-Boc-amino-ethyl)-β-alanine methyl ester, HCl (3) (2.0 g; 0.0071 mol) and 1-thyminylacetic acid pentafluorophenyl ester (5) (2.828 g; 0.00812 mol) were dissolved in DMF (50 ml). Triethyl amine (1.12 ml; 0.00812 mol) was added and the mixture stirred overnight. After addition of methylene chloride (200 ml) the organic phase was extracted with aqueous sodium hydrogen carbonate (3×250 ml), half-sat. aqueous potassium hydrogen sulfate (3×250 ml), and sat. aqueous sodium chloride (250 ml) and dried over magnesium sulfate. Filtration and evaporation to dryness, in vacuo, resulted in 2.9 g (99%) yield (oil). $^1$H-NMR (250 MHz; CDCl$_3$): due to limited rotation around the secondary amide several of the signals were doubled; δ1.43 (s, 9H); 1.88 (s, 3H); 2.63 (t, 1H); 2.74 (t, 1H); 3.25–3.55 (4×t, 8H); 3.65

(2×t, 2H); 3.66 (s, 1.5); 3.72 (s, 1.5); 4.61 (s, 1H); 4.72 (s, 2H); 5.59 (s, 0.5H); 5.96 (s, 0.5H); 7.11 (s, 1H); 10.33 (s, 1H).

EXAMPLE 52

N-[(1-Thyminyl)acetyl]-N'-Boc-aminoethyl-β-alanine

N-[(1-Thyminyl)acetyl]-N'-Boc-aminoethyl-β-alanine methyl ester (3.0 g; 0.0073 mol) was dissolved in 2 M sodium hydroxide (30 ml), the pH adjusted to 2 at 0° C. with 4 M hydrochloric acid, and the solution stirred for 2 h. The precipitate was isolated by filtration, washed three times with cold water, and dried over sicapent, in vacuo. Yield 2.23 g (77%). M.p. 170–176° C. Anal. for $C_{17}H_{26}N_4O_7$, $H_2O$, found (calc.) C, 49.49 (49.03); H, 6.31 (6.78); N, 13.84 (13.45). $^1$H-NMR (90 MHz; DMSO-$d_6$): δ1.38 (s, 9H); 1.76 (s, 3H); 2.44 and 3.29 (m, 8H); 4.55 (s, 2H); 7.3 (s, 1H); 11.23 (s, 1H). FAB-MS: 399 (M+1).

EXAMPLE 53

N-[(1-($N^4$-Z)-cytosyl)acetyl]-N'-Boc-aminoethyl-β-alanine Methyl Ester (N-Boc-amino-ethyl)-β-alanine methyl ester, HCl (3) (2.0 g; 0.0071 mol) and 1-(N-4-Z)-cytosylacetic acid pentafluorophenyl ester (5) (3.319 g; 0.0071 mol) were dissolved in DMF (50 ml). Triethyl amine (0.99 ml; 0.0071 mol) was added and the mixture stirred overnight. After addition of methylene chloride (200 ml), the organic phase was extracted with aqueous sodium hydrogen carbonate (3×250 ml), half-sat. aqueous potassium hydrogen sulfate (3×250 ml), and sat. aqueous sodium chloride (250 ml), and dried over magnesium sulfate. Filtration and evaporation to dryness, in vacuo, resulted in 3.36 g of solid compound which was recrystallized from methanol. Yield 2.42 g (64%). M.p. 158–161° C. Anal. for $C_{25}H_{33}N_5O_8$, found (calc.) C, 55.19 (56.49); H, 6.19 (6.26); N, 12.86 (13.18). 1H-NMR (250 MHz; $CDCl_3$): due to limited rotation around the secondary amide several of the signals were doubled; δ1.43 (s, 9H); 2.57 (t, 1H); 3.60–3.23 (m's, 6H); 3.60 (s, 1,5H); 3.66 (s, 1.5H); 4.80 (s, 1H); 4.88 (s, 1H); 5.20 (s, 2H); 7.80–7.25 (m's, 7H). FAB-MS: 532 (M+1).

EXAMPLE 54

N-[(1-($N^4$-Z)-cytosyl)acetyl]-N'-Boc-aminoethyl-β-alanine

N-[(1-(N-4-Z)-cytosyl)acetyl]-N'-Boc-aminoethyl-β-alanine methyl ester (0.621 g; 0.0012 mol) was dissolved in 2 M sodium hydroxide (8.5 ml) and stirred for 2 h. Subsequently, pH was adjusted to 2 at 0° C. with 4 M hydrochloric acid and the solution stirred for 2 h. The precipitate was isolated by filtration, washed three times with cold water, and dried over sicapent, in vacuo. Yield 0.326 g (54%). The white solid was recrystallized from 2-propanol and washed with petroleum ether. Mp.163° C. (decomp.). Anal. for $C_{24}H_{31}N_5O_8$, found (calc.) C, 49.49 (49.03); H, 6.31 (6.78); N, 13.84 (13.45). $^1$H-NMR (250 MHz; $CDCl_3$): due to limited rotation around the secondary amide several of the signals were doubled; δ1.40 (s, 9H); 2.57 (t, 1H); 2.65 (t, 1H); 3.60–3.32 (m's, 6H); 4.85 (s, 1H); 4.98 (s, 1H); 5.21 (s, 2H); 5.71 (s, 1H, broad); 7.99–7.25 (m's, 7H). FAB-MS: 518 (M+1).

EXAMPLE 55

Example of a PNA-oligomer with a Guanine Residue (a) Solid-Phase Synthesis of H-[Taeg]$_5$-[Gaeg]-[Taeg]$_4$-Lys-NH$_2$ The protected PNA was assembled onto a Boc-Lys(ClZ) modified MBHA resin with a substitution of approximately 0.15 mmol/g (determined by quantitative Ninhydrin reaction). Capping of uncoupled amino groups was only carried out before the incorporation of the BocGaeg-OH monomer.

(b) Stepwise Assembly of H-[Taeg]$_5$-[Gaeg]-[Taeg]$_4$-Lys-NH$_2$ (Synthetic Protocol)

Synthesis was initiated on 102 mg (dry weight) of pre-swollen (overnight in DCM) and neutralized Boc-Lys(ClZ)-MBHA resin. The steps performed were as follows: (1) Boc-deprotection with TFA/DCM (1:1, v/v), 1×2 min and 1×½ h, 3 ml; (2) washing with DCM, 4×20 sec, 3 ml; washing with DMF, 2×20 sec, 3 ml; washing with DCM, 2×20 sec, 3 ml, and drain for 30 sec; (3) neutralization with DIEA/DCM (1:19 v/v), 2×3 min, 3 ml; (4) washing with DCM, 4×20 sec, 3 ml, and drain for 1 min.; (5) addition of 4 equiv. diisopropyl carbodiimide (0.06 mmol; 9.7 μl) and 4 equiv. (0.06 mmol; 24 mg) BocTaeg-OH or (0.06 mmol; 30 mg) BocGaeg-OH dissolved in 0.6 ml DCM/DMF (1:1, v/v) (final concentration of monomer 0.1 M), the coupling reaction was allowed to proceed for ½ h shaking at room temperature; (6) drain for 20 sec; (7) washing with DMF, 2×20 sec and 1×2 min, 3 ml; washing with DCM 4×20 sec, 3 ml; (8) neutralization with DIEA/DCM (1:19 v/v), 2×3 min, 3 ml; (9) washing with DCM 4×20 sec, 3 ml, and drain for 1 min.; (10) qualitative Kaiser test; (11) blocking of unreacted amino groups by acetylation with Ac$_2$O/pyridine/DCM (1:1:2, v/v), 1×½ h, 3 ml; and (12) washing with DCM, 4×20 sec, 2×2 min and 2×20 sec, 3 ml. Steps 1–12 were repeated until the desired sequence was obtained. All qualitative Kaiser tests were negative (straw-yellow colour with no coloration of the beads) indicating near 100% coupling yield. The PNA-oligomer was cleaved and purified by the normal procedure. FAB-MS: 2832.11 [M*+1] (calc. 2832.15)

EXAMPLE 56

Solid-Phase Synthesis of H-Taeg-Aaeg-[Taeg]$_8$-Lys-NH$_2$ (a) Stepwise Assembly of Boc-Taeg-A(Z)aeg-[Taeg]$_8$-Lys(ClZ)-MBHA Resin About 0.3 g of wet Boc-[Taeg]$_8$-Lys(ClZ)-MBHA resin was placed in a 3 ml SPPS reaction vessel. Boc-Taeg-A(Z)aeg-[Taeg]$_8$-Lys(ClZ)-MBHA resin was assembled by in situ DCC coupling (single) of the A(Z)aeg residue utilizing 0.19 M of BocA(Z)aeg-OH together with 0.15 M DCC in 2.5 ml 50% DMF/CH$_2$Cl$_2$ and a single coupling with 0.15 M BocTaeg-OPfp in neat CH$_2$Cl$_2$ ("Synthetic Protocol 5"). The synthesis was monitored by the quantitative ninhydrin reaction, which showed about 50% incorporation of A(Z)aeg and about 96% incorporation of Taeg.

(b) Cleavage, Purification, and Identification of H-Taeg-Aaeg-[Taeg]$_8$-Lys-NH$_2$ The protected Boc-Taeg-A(Z)aeg-[Taeg]$_8$-Lys(ClZ)-BAH resin was treated as described in Example 40c to yield about 15.6 mg of crude material upon HF cleavage of 53.1 mg dry H-Taeg-A(Z)aeg-[Taeg]$_8$-Lys(ClZ)-BHA resin. The main peak at 14.4 min accounted for less than 50% of the total absorbance. A 0.5 mg portion of the crude product was purified to give approximately 0.1 mg of H-Taeg-Aaeg-[Taeg]$_8$-Lys-NH$_2$. For (MH$^+$)$^+$ the calculated m/z value was 2816.16 and the measured m/z value was 2816.28.

(c) Synthetic Protocol 5

(1) Boc-deprotection with TFA/CH$_2$Cl$_2$ (1:1, v/v), 2.5 ml, 3×1 min and 1×30 min; (2) washing with CH$_2$Cl$_2$, 2.5 ml, 6×1 min; (3) neutralization with DIEA/CH$_2$Cl$_2$ (1:19, v/v), 2.5 ml, 3×2 min; (4) washing with $CH_2Cl_2$, 2.5 ml, 6×1 min, and drain for 1 min; (5) 2–5 mg sample of PNA-resin is taken out and dried thoroughly for a quantitative ninhydrin analysis to determine the substitution; (6) addition of 0.47 mmol (0.25 g) BocA(Z)aeg-OH dissolved in 1.25 ml DMF followed by addition of 0.47 mmol (0.1 g) DCC in 1.25 ml $CH_2Cl_2$ or 0.36 mmol (0.20 g) BocTaeg-OPfp in 2.5 ml $CH_2Cl_2$; the coupling reaction was allowed to proceed for a total of 20–24 hrs shaking; (7) washing with DMF, 2.5 ml, 1×2 min; (8) washing with $CH_2Cl_2$, 2.5 ml, 4×1 min; (9) neutralization with $DIEA/CH_2Cl_2$ (1:19, v/v), 2.5 ml, 2×2 min; (10) washing with $CH_2Cl_2$, 2.5 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/pyridine/$CH_2Cl_2$ (1:1:2, v/v/v) for 2 h (except after the last cycle); and (13) washing with $CH_2Cl_2$, 2.5 ml, 6×1 min; (14) 2×2–5 mg samples of protected PNA-resin are taken out, neutralized with $DIEA/CH_2Cl_2$ (1:19, v/v) and washed with $CH_2C_2$ for ninhydrin analyses.

EXAMPLE 57

Solid-Phase Synthesis of H-[Taeg]$_2$-Aaeg-[Taeg]$_5$-Lys-NH$_2$ (a) Stepwise Assembly of Boc-[Taeg]$_2$-A(Z)aeg-[Taeg]$_5$-Lys(ClZ)-KBHA Resin About 0.5 g of wet Boc-[Taeg]$_5$-Lys(ClZ)-MBHA resin was placed in a 5 ml SPPS reaction vessel. Boc-[Taeg]$_2$-A(Z)aeg-[Taeg]$_5$-Lys(ClZ)-MBHA resin was assembled by in situ DCC coupling of both the A(Z)aeg and the Taeg residues utilising 0.15 M to 0.2 M of protected PNA monomer (free acid) together with an equivalent amount of DCC in 2 ml neat $CH_2Cl_2$ ("Synthetic Protocol 6"). The synthesis was monitored by the quantitative ninhydrin reaction which showed a total of about 82% incorporation of A(Z)aeg after coupling three times (the first coupling gave about 50% incorporation; a fourth HOBt-mediated coupling in 50% DMF/$CH_2Cl_2$ did not increase the total coupling yield significantly) and quantitative incorporation (single couplings) of the Taeg residues.

(b) Cleavage, Purification and Identification of H-[Taeg]$_2$-Aaeg-[Taeg]$_5$-Lys-NH$_2$ The protected Boc-[Taeg]$_2$-A(Z) aeg-[Taeg]$_5$-Lys (ClZ)-BHA resin was treated as described in Example 40c to yield about 16.2 mg of crude material upon HF cleavage of 102.5 mg dry H-[Taeg]$_2$-A(Z)aeg-[Taeg]$_5$-Lys(ClZ)-BHA resin. A small portion of the crude product was purified. For $(MH^+)^+$, the calculated m/z value was 2050.85 and the measured m/z value was 2050.90

(c) Synthetic Protocol 6

(1) Boc-deprotection with TFA/$CH_2Cl_2$ (1:1, v/v), 2 ml, 3×1 min and 1×30 min; (2) washing with $CH_2Cl_2$, 2 ml, 6×1 min; (3) neutralization with $DIEA/CH_2Cl_2$ (1:19, v/v), 2 ml, 3×2 min; (4) washing with $CH_2Cl_2$, 2 ml, 6×1 min, and drain for 1 min; (5) 2–5 mg sample of PNA-resin was taken out and dried thoroughly for a quantitative ninhydrin analysis to determine the substitution; (6) addition of 0.44 mmol (0.23 g) BocA(Z)aeg-OH dissolved in 1.5 ml $CH_2Cl_2$ followed by addition of 0.44 mmol (0.09 g) DCC in 0.5 ml $CH_2Cl_2$ or 0.33 mmol (0.13 g) BocTaeg-OH in 1.5 ml $CH_2Cl_2$ followed by addition of 0.33 mmol (0.07 g) DCC in 0.5 ml $CH_2Cl_2$; the coupling reaction was allowed to proceed for a total of 20–24 hrs with shaking; (7) washing with DMF, 2 ml, 1×2 min; (8) washing with $CH_2Cl_2$, 2 ml, 4×1 min; (9) neutralization with $DIEA/CH_2Cl_2$ (1:19, v/v), 2 ml, 2×2 min; (10) washing with $CH_2Cl_2$, 2 ml, 6×1 min; (11) 2–5 mg sample of protected PNA-resin is taken out and dried thoroughly for a quantitative ninhydrin analysis to determine the extent of coupling; (12) blocking of unreacted amino groups by acetylation with a 25 ml mixture of acetic anhydride/pyridine/$CH_2Cl_2$ (1:1:2, v/v/v) for 2 h (except after the last cycle); (13) washing with $CH_2Cl_2$, 2 ml, 6×1 min; and (14) 2×2–5 mg samples of protected PNA-resin were taken out, neutralized with $DIEA/CH_2Cl_2$ (1:19, v/v) and washed with $CH_2Cl_2$ for ninhydrin analyses.

EXAMPLE 58

The PNA-oligomer H-T4C2TCT-LysNH$_2$ was prepared as described in Example 93. Hybridization experiments with this sequence should resolve the issue of orientation, since it is truly asymmetrical. Such experiments should also resolve the issues of pH-dependency of the Tm, and the stoichiometry of complexes formed.

Hybridization experiments with the PNA-oligomer H-T$_4$C$_2$TCTC-LysNH$_2$ were performed as follows:

| Row | Hybridized With | pH | Tm | § |
|---|---|---|---|---|
| 1 | 5'-(dA)$_4$(dG)$_2$(dA) (dG) (dA) (dG) (SEQ ID NO: 19) | 7.2 | 55.5 | 2:1 |
| 2 | 5'-(dA)$_4$(dG)$_2$(dA) (dG) (dA) (dG) | 9.0 | 26.0 | 2:1 |
| 3 | 5'-(dA)$_4$(dG)$_2$(dA) (dG) (dA) (dG) | 5.0 | 88.5 | 2:1 |
| 4 | 5'-(dG) (dA) (dG) (dA) (dG)$_2$(dA)$_4$(SEQ ID NO: 20) | 7.2 | 38.0 | 2:1 |
| 5 | 5'-(dG) (dA) (dG) (dA) (dG)$_2$(dA)$_4$ | 9.0 | 31.5 | — |
| 6 | 5'-(dG) (dA) (dG) (dA) (dG)$_2$(dA)$_4$ | 5.0 | 52.5 | — |
| 7 | 5'-(dA)$_4$(dG) (dT) (dA) (dG) (dA) (dG) (SEQ ID NO: 21) | 7.2 | 39.0 | — |
| 8 | 5'-(dA)$_4$(dG) (dT) (dA) (dG) (dA) (dG) | 9.0 | <20 | — |
| 9 | 5'-(dA)$_4$(dG) (dT) (dA) (dG) (dA) (dG) | 5.0 | 51.5 | — |
| 10 | 5'-(dA)$_4$(dG) (dT) (dG) (dA) (dG) (SEQ ID NO: 22) | 7.2 | 31.5 | — |
| 11 | 5'-(dA)$_4$(dG)$_2$(dT) (dG) (dA) (dG) | 5.0 | 50.5 | — |
| 12 | 5'-(dG) (dA) (dG) (dA)dT) (dG) (dA)$_4$(SEQ ID NO: 23) | 7.2 | 24.5 | — |
| 13 | 5'-(dG) (dA) (dG) (dA)dT) (dG) (dA)$_4$ | 9.0 | <20 | — |
| 14 | 5'-(dG) (dA) (dG) (dA)dT) (dG) (dA)$_4$ | 5.0 | 57.0 | — |
| 15 | 5'-(dG) (dA) (dG) (dT) (dG)$_2$(dA)$_4$(SEQ ID NO: 24) | 7.2 | 25.0 | — |
| 16 | 5'-(dG) (dA) (dG) (dT) (dG)$_2$(dA)$_4$ | 5.0 | 39.5 | — |
|   |   |   | 52.0 |   |

§ = stoichiometry determined by UV-mixing curves
— = not determined

These results show that a truly mixed sequence gave rise to well defined melting curves. The PNA-oligomers can actually bind in both orientations (compare row 1 and 4), although there is preference for the N-terminal/5'-orientation. Introducing a single mismatch opposite either T or C caused a lowering of $T_m$ by more than 16° C. at pH 7.2; at pH 5.0 the $T_m$-value was lowered more than 27° C. This shows that there is a very high degree a sequence-selectivity which should be a general feature for all PNA C/T sequences.

As indicated above, there is a very strong pH-dependency for the $T_m$-value, indicating that Hoogsteen basepairing is important for the formation of hybrids. Therefore, it is not surprising that the stoichiometry was found to be 2:1.

The lack of symmetry in the sequence and the very large lowering of $T_m$ when mismatches are present show that the Watson-Crick strand and the Hoogsteen strand are parallel when bound to complementary DNA. This is true for both of the orientations, i.e., 5'/N-terminal and 3'/N-terminal.

EXAMPLE 59

The results of hybridization experiments with H-T$_5$GT$_4$-LysNH$_2$ to were performed as follows:

| Row | Deoxyoligonucleotide | Tm |
|---|---|---|
| 1 | 5'-(dA)$_5$(dA) (dA)$_4$-3'(SEQ ID NO: 3) | 55.0 |
| 2 | 5'-(dA)$_5$(dG) (dA)$_4$-3'(SEQ ID NO: 8) | 47.0 |
| 3 | 5'-(dA)$_5$(dG) (dA)$_4$-3'(SEQ ID NO: 8) | 56.5 |
| 4 | 5'-(dA)$_5$(dT) (dA)$_4$-3'(SEQ ID NO: 25) | 46.5 |
| 5 | 5'-(dA)$_4$(dG) (dA)$_5$-3'(SEQ ID NO: 10) | 48.5 |
| 6 | 5'-(dA)$_4$(dC) (dA)$_5$-3'(SEQ ID NO: 26) | 55.5 |
| 7 | 5'-(dA)$_4$(dT) (dA)$_5$-3'(SEQ ID NO: 27) | 47.0 |

As shown by comparing rows 1, 3, and 6 with rows 2, 4, 5, and 7, G can in this mode discriminate between C/A and G/T in the DNA-strand, i.e., sequence discrimination is observed. The complex in row 3 was furthermore determined to be 2 PNA: 1 DNA complex by UV-mixing curves.

EXAMPLE 60

The masses of some synthesized PNA-oligomers, as determined by FAB mass spectrometry, are as follows:

| SEQUENCE | CALC. | FOUND |
|---|---|---|
| H-T$_4$C$_2$TCTC-LysNH$_2$ | 2747.15 | 2746.78 |
| H-T$_5$GT$_4$-LysNH$_2$ | 2832.15 | 2832.11 |
| H-T$_7$-LysNH$_2$ | 2008.84 | 2540.84 |
| H-T$_9$-LysNH$_2$ | 2541.04 | 2540.84 |
| H-T$_{10}$-LysNH | 2807.14 | 2806.69 |
| H-T$_2$CT$_5$-LysNH$_2$ | 2259.94 | 2259.18 |
| H-T$_3$(L-alaT)T$_4$-LysNH$_4$ | 2287.95 | 2288.60 |
| H-T$_4$(Ac)T$_5$-LysNH$_2$ | 2683.12 | 2683.09 |

EXAMPLE 61

Hybridization data for a PNA-oligomer with a single unit with an extended backbone (the β-alanine modification) is as follows:

| PNA | DNA | $T_m$ |
|---|---|---|
| H-T$_{10}$-LysnH$_2$ | (dA)$_{10}$ | 73° C. |
| H-T$_4$(βT)T$_5$-.LysNH$_2$ | (dA)$_{10}$ | 57° C. |
| H-T$_4$(βT)T$_5$-.LysNH$_2$ | (dA)$_4$(dG) (dA)$_5$ | 47° C. |
| H-T$_4$(βT)T$_5$-.LysNH$_2$ | (dA)$_4$(dG) (dA)$_5$ | 49° C. |
| H-T$_4$(βT)T$_5$-.LysNH$_2$ | (dA)$_4$(dG) (dA)$_5$ | 47° C. |

Although the melting temperature decreases, the data demonstrates that base specific recognition is retained.

EXAMPLE 62

An example with a "no base" substitution.

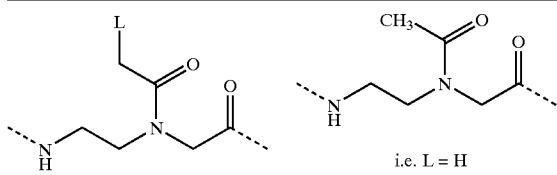

i.e. L = H

| PNA | DNA | $T_m$ |
|---|---|---|
| H—T$_{10}$-LysNH$_2$ (SEQ ID NO: 44) | (dA)$_{10}$ (SEQ ID NO: 3) | 73° C. |
| H—T$_4$(Ac)T$_5$-LysNH$_2$ (SEQ ID NO: 48) | (dA)$_{10}$ (SEQ ID NO: 3) | 49° C. |
| H—T$_4$(Ac)T$_5$-LysNH$_2$ (SEQ ID NO: 48) | (dA)$_4$(dG)(dA)$_5$ (SEQ ID NO: 10) | 37° C. |
| H—T$_4$(Ac)T$_5$-LysNH$_2$ (SEQ ID NO: 48) | (dA)$_4$(dC)(dA)$_5$ (SEQ ID NO: 26) | 41° C. |
| H—T$_4$(Ac)T$_5$-LysNH$_2$ (SEQ ID NO: 48) | (dA)$_4$(dT)(dA)$_5$ (SEQ ID NO: 27) | 41° C. |
| H—T$_4$(Ac)T$_5$-LysNH$_2$ (SEQ ID NO: 48) | (dA)$_5$(dG)(dA)$_4$ (SEQ ID NO: 8) | 36° C. |
| H—T$_4$(Ac)T$_5$-LysNH$_2$ (SEQ ID NO: 48) | (dA)$_5$(dC)(dA)$_4$ (SEQ ID NO: 28) | 40° C. |
| H—T$_4$(Ac)T$_5$-LysNH$_2$ (SEQ ID NO: 48) | (dA)$_5$(dT)(dA)$_4$ (SEQ ID NO: 25) | 40° C. |

EXAMPLE 63

Iodination Procedure

A 5 μg portion of Tyr-PNA-T$_{10}$-Lys-NH$_2$ is dissolved in 40 μl 100 mM Na-phosphate, pH 7.0, and 1 mCi Na $^{125}$I and 2 μl chloramine-T (50 mM in CH$_3$CN) are added. The solution is left at 20° C. for 10 min and then passed through a 0.5+5 cm Sephadex G10 column. The first 2 fractions (100 μl each) containing radioactivity are collected and purified by HPLC: reversed phase C-18 using a 0–60% CH$_3$CN gradient in 0.1% CF$_3$COOH in H$_2$O. The $^{125}$I-PNA elutes right after the PNA peak. The solvent is removed under reduced pressure.

EXAMPLE 64

Figure 20:
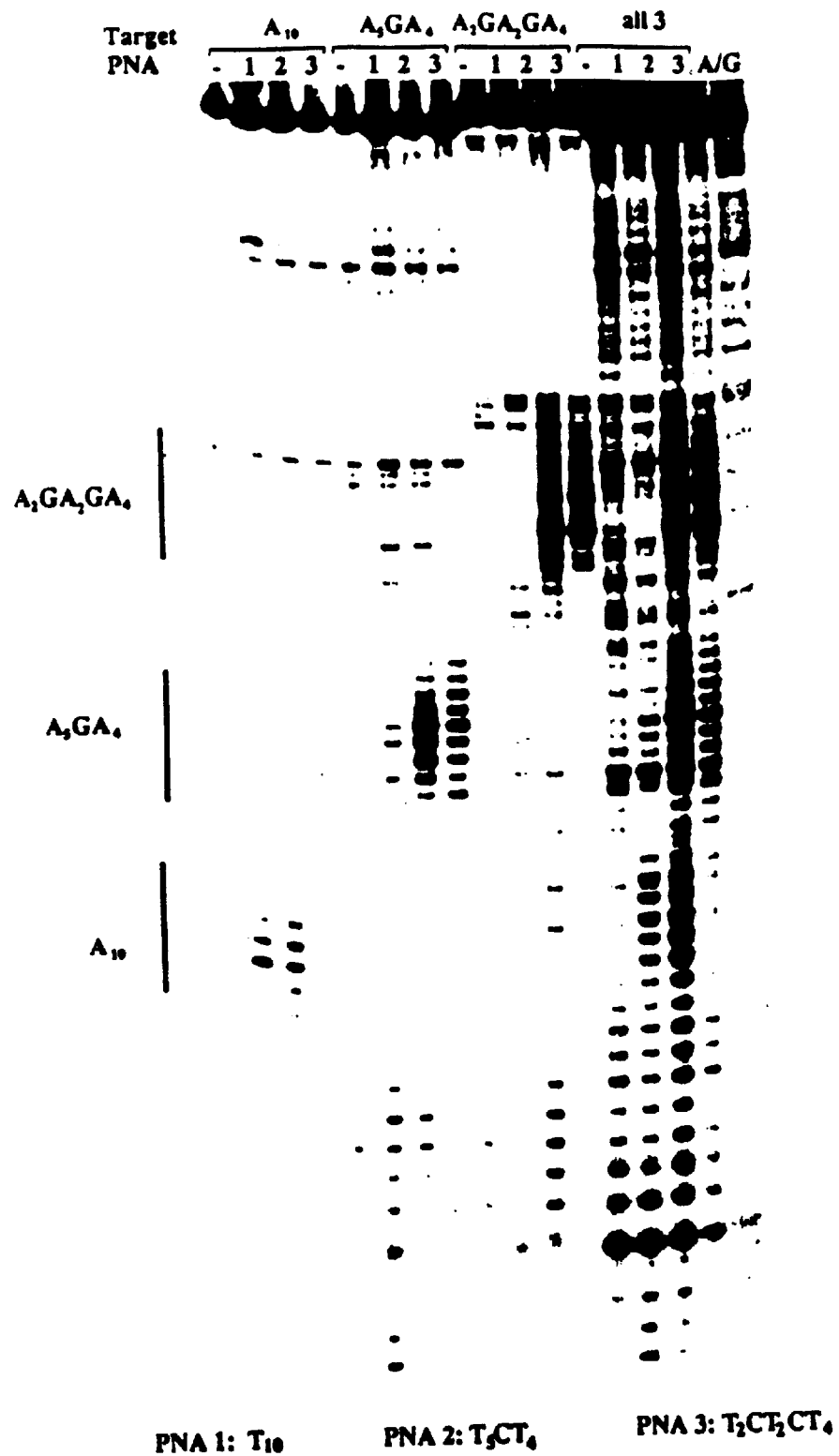
FIG. 20 shows a PAGE autoradiograph demonstrating that PNAs-$T_{10}$, -$T_9C$ and -$T_8C_2$ bind to double stranded DNA with high sequence specificity.

Binding of PNAs-T$_{10}$/T$_9$C/T$_8$C$_2$ to Double Stranded DNA Targets A$_{10}$/A$_9$G/A$_8$G$_2$ (FIG. 20)

A mixture of 200 cps $^{32}$P-labeled EcoRI-PvuII fragment (the large fragment labeled at the 3'-end of the EcoRI site) of the indicated plasmid, 0.5 μg carrier calf thymus DNA, and 300 ng PNA in 100 μl buffer (200 mM NaCl, 50 mM Na-acetate, pH 4.5, 1 mM ZnSO$_4$) was incubated at 37° C. for 120 min. A 50 unit portion of nuclease S$_1$ was added and incubated at 20° C. for 5 min. The reaction was stopped by addition of 3 μl 0.5 M EDTA and the DNA was precipitated by addition of 250 μl 2% potassium acetate in ethanol. The DNA was analyzed by electrophoresis in 10% polyacrylamide sequencing gels and the radiolabeled DNA bands visualized by autoradiography.

The target plasmids were prepared by cloning of the appropriate oligonucleotides into pUC19. Target $A_{10}$: oligonucleotides $GATCCA_{10}G$ & $GATCCT_{10}G$ cloned into the BamHI site (plasmid designated pT10). Target $A_5GA_4$: oligonucleotides $TCGACT_4CT_5G$ (SEQ ID NO: 29) & $TCGACA_5GA_4G$ (SEQ ID NO: 30) cloned into the SalI site (plasmid pT9C). Target $A_2GA_2GA_4$: oligonucleotides $GA2GA_2GA_4TGCA$ (SEQ ID NO:30) & $GT_4CT_2CT_2CTGCA$ (SEQ ID NO: 32) into the PstI site (plasmid pT8C2). The positions of the targets in the gel are indicated by bars to the left. A/G is an A+G sequence ladder of target P10.

EXAMPLE 65

Inhibition of Restriction Enzyme Cleavage by PNA (FIG. 23)

A 2 μg portion of plasmid pT10 was mixed with the indicated amount of PNA-$T_{10}$ in 20 μl TE buffer (10 mM Tris-HCl, mM EDTA, pH 7.4) and incubated at 37° C. for 120 min. 2 μl 10× buffer (10 mM Tris-HCl, pH 7.5, 10 mM, $MgCl_2$, 50 mM NaCl, 1 mM DTT). PvuII (2 units) and BamHI (2 units) were added and the incubation was continued for 60 min. The DNA was analyzed by gel electrophoresis in 5% polyacrylamide and the DNA was visualized by ethidium bromide staining.

EXAMPLE 66

Kinetics of PNA-$T_{10}$—dsDNA Strand Displacement Complex Formation (FIG. 21)

A mixture of 200 cps $^{32}$P-labeled EcoRI-PvuII fragment of pT10 (the large fragment labeled at the 3'-end of the EcoRI site), 0.5 μg carrier calf thymus DNA, and 300 ng of PNA-$T_{10}$-$LysNH_2$ in 100 μl buffer (200 mM NaCl, 50 mM Na-acetate, pH 4.5, 1 mM $ZnSO_4$) were incubated at 37° C. At the times indicated, 50 U of $S_1$ nuclease was added to each of 7 samples and incubation was continued for 5 min at 20° C. The DNA was then precipitated by addition of 250 μl 2% K-acetate in ethanol and analyzed by electrophoresis in a 10% polyacrylamide sequencing gel. The amount of strand displacement complex was calculated from the intensity of the $S_1$-cleavage at the target sequence, as measured by densitometric scanning of autoradiographs.

EXAMPLE 67

Figure 22:
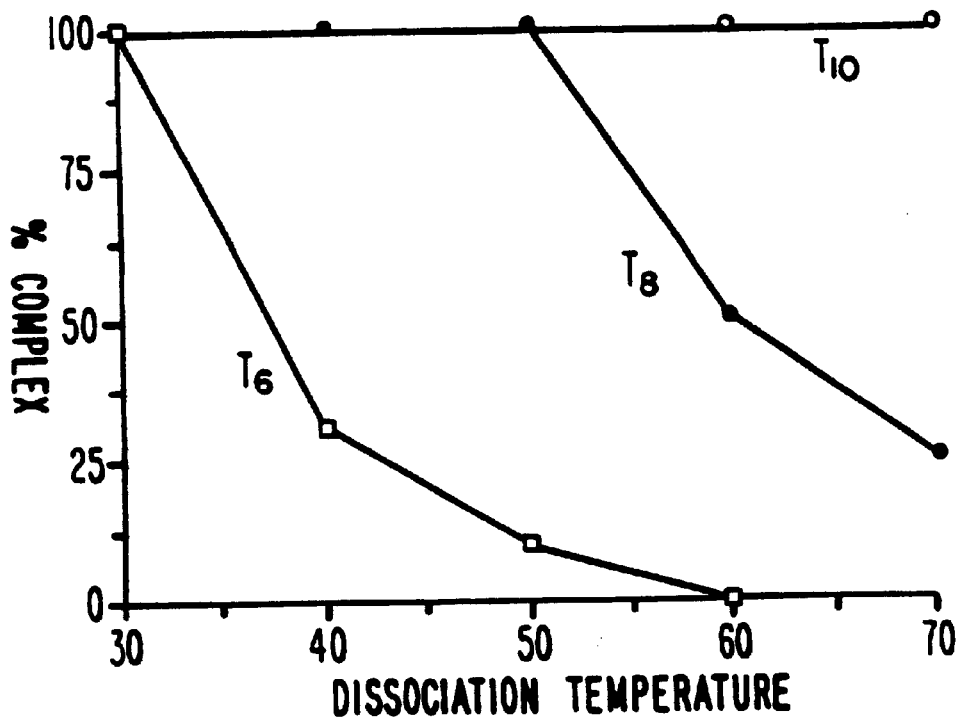
FIG. 22 shows a graph based on densitometric scanning of PAGE autoradiographs demonstrating the thermal stabilities of PNAS of varying lengths bound to an $A_{10}/T_{10}$) double stranded DNA target.

Stability of PNA-dsDNA Complexes (FIG. 22)

A mixture of 200 cps $^{32}$P-pT10 fragment, 0.5 μg calf thymus DNA and 300 ng of the desired PNA (either $T_{10}$-$LysNH_2$, $T_8$-$LysNH_2$ or $T_6$-$LysNH_2$) was incubated in 100 μl 200 mM NaCl, 50 mM Na-acetate, pH 4.5, 1 mM $ZnSO_4$ for 60 min at 37° C. A 2 μg portion of oligonucleotide $GATCCA_{10}G$ was added and each sample was heated for 10 min at the temperature indicated, cooled in ice for 10 min and warmed to 20° C. A 50 U portion of $S_1$ nuclease was added and the samples treated and analyzed and the results quantified.

EXAMPLE 68

Inhibition of Transcription by PNA

A mixture of 100 ng plasmid DNA (cleaved with restriction enzyme PvuII (see below) and 100 ng of PNA in 15 μl 10 mM Tris-HCl, 1 mM EDTA, pH 7.4 was incubated at 37° C. for 60 min. Subsequently, 4 μl 5× concentrated buffer (0.2 M Tris-HCl (pH 8.0), 40 mM $MgCl_2$, 10 mM spermidine, 125 mM NaCl) were mixed with 1 μl NTP-mix (10 mM ATP, 10 mM CTP, 10 mM GTP, 1 mM UTP, 0.1 μCi/μl $^{32}$P-UTP, 5 mM DTT, 2 μg/ml tRNA, 1 μg/ml heparin) and 3 units RNA polymerase. Incubation was continued for 10 min at 37° C. The RNA was then precipitated by addition of 60 μl 2% postassium acetate in 96% ethanol at −20° C. and analyzed by electrophoresis in 8% polyacrylamide sequencing gels. RNA transcripts were visualized by autoradiography. The following plasmids were used: pT8C2-KS/pA8G2-KS: oligonucleotides $GA_2GA_2GA_4GTGAC$ (SEQ ID NO: 33) & $GT_4CT_2CT_2CTGCA$ (SEQ ID NO: 34) cloned into the PstI site of pBluescript-KS$^+$; pT10-KS/pA10-KS (both orientations of the insert were obtained). pT10 UV5: oligonucleotides $GATCCA_{10}G$ & $GATCCT_{10}G$ cloned into the BamHI site of a pUC18 derivative in which the lac UV5 E.coli promoter had been cloned into the EcoRI site (Jeppesen, et al., Nucleic Acids Res., 1988, 16, 9545).

Figure 25:
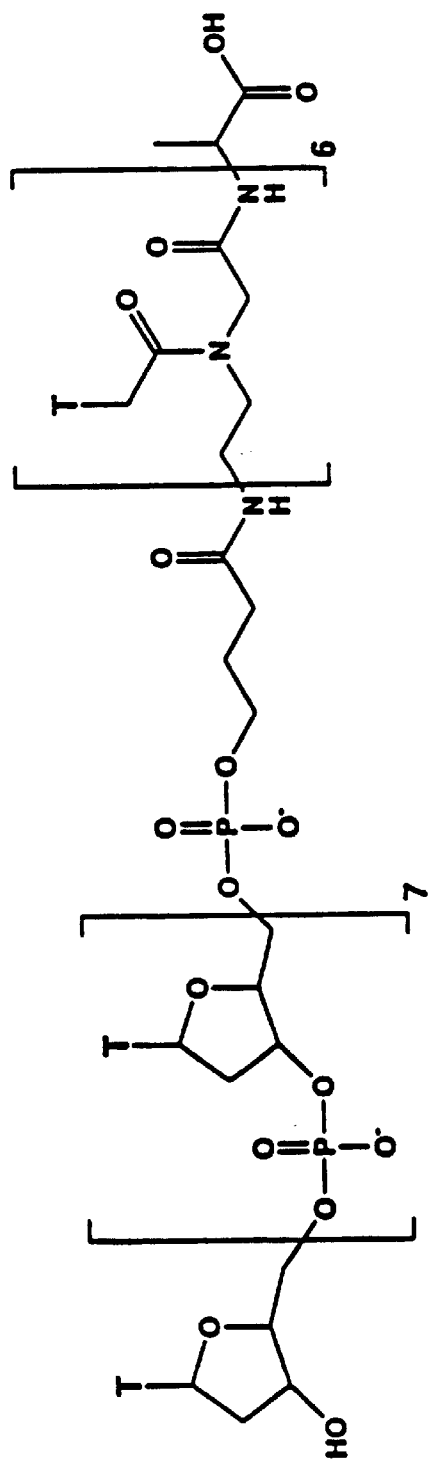
FIG. 25 shows a peptide nucleic acid according to the invention.

Using $T_3$-RNA polymerase, transcription elongation arrest was obtained with PNA-$T_8C_2$-$LysNH_2$ and the pA8G2-KS plasmid having the PNA recognition sequence on the template strand, but not with pT8C2-KS having the PNA recognition sequence on the non-template strand. Similar results were obtained with PNA-T10-LysNH, and the plasmids pA10-KS and pT10-KS. (see, FIG. 25) Using E.coli RNA polymerase and the pT10 UV5 plasmid ($A_{10}$-sequence on the template strand) transcription elongation arrest was obtained with PNA-$T_{10}$-$LysNH_2$.

EXAMPLE 69

Biological Stability of PNA

A mixture of PNA-$T_5$ (10 μg) and a control, "normal" peptide (10 μg) in 40 μl 50 mM Tris-HCl, pH 7.4 was treated with varying amounts of peptidase from porcine intestinal mucosa or protease from Streptomyces caespitosus for 10 min at 37° C. The amount of PNA and peptide was determined by HPLC analysis (reversed phase C-18 column: 0–60% acetonitrile, 0.1% trifluoroacetic acid).

At peptidase/protease concentrations where complete degradation of the peptide was observed (no HPLC peak) the PNA was still intact.

EXAMPLE 70

Inhibition of Gene Expression

A preferred assay to test the ability of peptide nucleic acids to inhibit expression of the E2 mRNA of papillomavirus is based on the well-documented transactivation properties of E2. Spalholtz, et al., *J. Virol.*, 1987, 61, 2128–2137. A reporter plasmid (E2RECAT) was constructed to contain the E2 responsive element, which functions as an E2 dependent enhancer. E2RECAT also contains the SV40 early promoter, an early polyadenylation signal, and the chloramphenicol acetyl transferase gene (CAT). Within the context of this plasmid, CAT expression is dependent upon expression of E2. The dependence of CAT expression on the presence of E2 has been tested by transfection of this plasmid into C127 cells transformed by BPV-1, uninfected C127 cells and C127 cells cotransfected with E2RECAT and an E2 expression vector.

A. Inhibition of BPV-1 E2 Expression

BPV-1 transformed C127 cells are plated in 12 well plates. Twenty four hours prior to transfection with E2RE1, cells are pretreated by addition of antisense PNAs to the growth medium at final concentrations of 5, 15 and 30 mM. The next day cells are transfected with 10 μg of E2RE1CAT by calcium phosphate precipitation. Ten micrograms of E2RE1CAT and 10 μg of carrier DNA (PUC 19) are mixed with 62 μl of 2 M $CaCl_2$ in a final volume of 250 μl of $H_2O$, followed by addition of 250 μl of 2×HBSP (1.5 mM $Na_2PO_2$. 10 mM KCl, 280 mM NaCl, 12 mM glucose and 50 mM HEPES, pH 7.0) and incubated at room temperature for 30 minutes. One hundred microliters of this solution is added to each test well and allowed to incubate for 4 hours at 37° C. After incubation, cells are glycerol shocked for 1 minute at room temperature with 15% glycerol in 0.75 mM $Na_2PO_2$, 5 mM KCl, 140 mM NaCl, 6 mM glucose and 25 mM HEPES, pH 7.0. After shocking, cells are washed 2 times with serum free DMEM and refed with DMEM containing 10% fetal bovine serum and antisense oligonucleotide at the original concentration. Forty eight hours after transfection cells are harvested and assayed for CAT activity.

For determination of CAT activity, cells are washed 2 times with phosphate buffered saline and collected by scraping. Cells are resuspended in 100 μl of 250 mM Tris-HCl, pH 8.0 and disrupted by freeze-thawing 3 times. Twenty four microliters of cell extract is used for each assay. For each assay the following are mixed together in an 1.5 ml Eppendorf tube and incubated at 37° C. for one hour: 25 μl of cell extract, 5 μl of 4 mM acetyl coenzyme A, 18 μl $H_2O$ and 1 μl $^{14}$C-chloramphenicol, 40–60 mCi/mM. After incubation, chloramphenicol (acetylated and nonacetylated forms) is extracted with ethyl acetate and evaporated to dryness. Samples are resuspended in 25 μl of ethyl acetate, spotted onto a TLC plate and chromatographed in chloroform:methanol (19:1). Chromatographs are analyzed by autoradiography. Spots corresponding to acetylated and nonacetylated $^{14}$C-chloramphenicol are excised from the TLC plate and counted by liquid scintillation for quantitation of CAT activity. Peptide nucleic acids that depress CAT activity in a dose dependent fashion are considered positives.

B. Inhibition of HPV E2 Expression

The assay for inhibition of human papillomavirus (HPV) E2 by peptide nucleic acids is essentially the same as that for BPV-1 E2. For HPV assays appropriate HPVs are co-transfected into either CV-1 or A431 cells with PSV2NEO using the calcium phosphate method described above. Cells which take up DNA are selected for by culturing in media containing the antibiotic G418. G418-resistant cells are then analyzed for HPV DNA and RNA. Cells expressing E2 are used as target cells for antisense studies. For each PNA, cells are pretreated as above, transfected with E2RE1CAT, and analyzed for CAT activity as above. Peptide nucleic acids are considered to have a positive effect if they can depress CAT activity in a dose dependent fashion.

EXAMPLE 71

Synthesis of PNA 15-mer Containing Four Naturally Occurring Nucleobases; R-[Taeg]-[Aaeg]-[Gaeg]-[Taeg]-[Taeg]-[Aaeg]-[Taeg]-[Caeg]-[Taeg]-[Caeg]-[Taeg]-[Aaeg]-[Taeg]-[caeg]-[Taeg]-LYS-NH2

The protected PNA was assembled onto a Boc-Lys(ClZ) modified MBHA resin with a substitution of approximately 0.145 mmol/g. Capping of uncoupled amino groups was only carried out before the incorporation of the BocGaeg-OH monomer.

Synthesis was initiated on 100 mg (dry weight) of neutralised Boc-Lys(ClA)-MBHA resin that had been preswollen overnight in DCM. The incorporation of the monomers followed the protocol of Example 32, except at step 5 for the incorporation of the BocAaeg-OH monomer. Step 5 for the present synthesis involved addition of 4 equiv. diisopropyl carbodiimide (0.06 ml; 9.7 μl) and 4 equiv. BocAaeg-OH (0.06 mmol; 32 mg) dissolved in 0.6 ml DCM/DMF (1:1, v/v) (final concentration of monomer 0.1M). The coupling reaction was allowed to proceed for 1×15 min and 1×60 min. (recoupling).

All qualitative Kaiser tests were negative (straw-yellow color with no coloration of the beads). The PNA-oligomer was cleaved and purified by the standard procedure. FAB-MS average mass found(calc.) (M+H) 4145.1 (4146.1).

EXAMPLE 72

| Hybridization of H-TAGTTATCTCTATCT-LysNH$_2$ | | |
|---|---|---|
| DNA - target | pH | Tm |
| 5'----3' | 5 | 60.5 |
| 5'----3' | 7.2 | 43.0 |
| 5'----3' | 9 | 38.5 |
| 3'----5' | 5 | 64.5/49.0 |
| 3'----5' | 7.2 | 53.5 |
| 3'----5' | 9 | 51.5 |

The fact that there is almost no loss in Tm in going from pH 7.2 to 9.0 indicates that Hoogsteen basepairing is not involved. The increase in Tm in going from 7.2 to 5 is large for the parallel orientation and is probably due to the formation of a 2:1 complex. It is believed that the most favorable orientation in the Watson-Crick binding motif is the 3'/N-orientation and that in the Hoogsteen motif the 5'/N-orientation is the most stable. Thus, it may be the case that the most stable complex is with the two PNA's strands anti parallel.

There is apparently a very strong preference for a parallel orientation of the Hoogsteen strand. This seems to explain why even at pH 9 a 2:1 complex is seen with the 5'/N-orientation. Furthermore, it explains the small loss in going from pH 7.2 to 9 in the 3'/N, as this is probably a 1:1 complex.

EXAMPLE 73

Solid-Phase Synthesis of H-[Taeg]$_2$-Aaeg-Taeg-Caeg-Aaeg-Taeg-Caeg-Taeg-Caeg-Lys-NH2

(a) Stepwise Assembly of Boc-[Taeg]2-A(Z)aeg-Taeg-C(Z)aeg-A(Z)aeg-Taeg-C(Z)aeg-Taeg-C(Z)aeg-Lys(ClZ)-MKBA Resin About 1 g of wet Boc-Lys(Clz)-MBHA (0.28 mmol Lys/g) resin was placed in a 5 ml SPPS reaction vessel. Boc-[Taeg]2-A(Z)aeg-Taeg-C(Z)aeg-A(Z)aeg-Taeg-C(Z)aeg-Taeg-C(Z)aeg-Lys(ClZ)-MBHA resin was assembled by in situ DCC coupling of the five first residues utilizing 0.16 M of BocC[Z]-OH, BocTaeg-OH or BocA(Z)aeg-OH, together with 0.16 M DCC in 2.0 ml 50% DMF/$CH_2Cl_2$ ("Synthetic Protocol 9") and by analogous in situ DIC coupling of the five last residues ("Synthetic Protocol 10"). Each coupling reaction was allowed to proceed for a total of 20–24 hrs with shaking. The synthesis was monitored by the ninhydrin reaction, which showed nearly quantitative incorporation of all residues except of the first A(Z)aeg residue, which had to be coupled twice. The total coupling yield was about 96% (first coupling, about 89% efficiency).

(b) Cleavage, Purification, and Identification of H-[Taeg]2-Aaeg-Taeg-Caeg-Aaeg-Taeg-Caeg-Taeg-Caeg-Lys-NH2

The protected Boc-[Taeg]2-A (Z)aeg-Taeg-C(Z)aeg-A(Z)aeg-Taeg-C(Z)aeg-Taeg-C(Z)aeg-Lys(ClZ)-MBHA resin was treated as described in Example 17c to yield about 53.4 mg of crude material upon HF cleavage of 166.1 mg dry Boc-[Taeg]2-A(Z)aeg-Taeg-C(Z)aeg-A(Z)aeg-Taeg-C(Z)aeg-Taeg-C(Z)aeg-Lys(ClZ)-MBHA resin. The crude product (53.4 mg) was purified to give 18.3 mg of H-[Taeg]2-Aaeg-Taeg-Caeg-Aaeg-Taeg-Caeg-Taeg-Caeg-Lys-NH2. For (M+H)+, the calculated m/z value=2780.17 and the measured m/z value=2780.07.

EXAMPLE 74

Hybridization Properties of H-TTA TCA TCT C-Lys-NH2

The title compound hybridized with the following oligonucleotides:

| Oligodeoxynucleotide | | pH | Tm(° C.) |
|---|---|---|---|
| 5'-AAT AGT AGT G-3 | (SEQ ID NO: 35) | 5 | 31.5† |
| 5'-ATT AGT AGT G-3' | (SEQ ID NO: 36) | 7.2 | 28.5† |
| 5'-AAT AGT AGT G-3' | (SEQ ID NO: 35) | 9 | 28.0† |
| 5'-GTG ATG ATA A-3' | (SEQ ID NO: 37) | 7.2 | 30.5 |
| 5'-GTG ATG ATA A-3' | (SEQ ID NO: 37) | 9 | 28.0 |

†Low hypochromicity

EXAMPLE 75

Synthesis of a PNA With Two Parallel Strings Tied Together

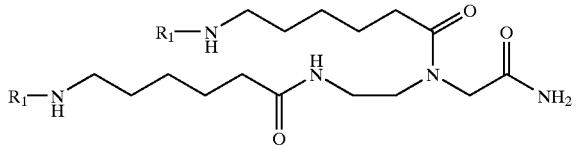

A 375 mg portion of MBHA resin (loading 0.6 mmol/g) was allowed to swell over night in dichloromethane (DCM). After an hour in DMF/DCM, the resin was neutralized by washing 2 times with 5% diisopropylethylamine in DCM (2 min.), followed by washing with DCM (2ml; 6×1 min.); N,N'-di-Boc-aminoethyl glycine (41.9 mg; 0.132 mmol) disolved in 2 ml DMF was added to the resin, followed by DCC (64.9 mg; 0.315 mmol) dissolved in 1 ml of DCM. After 2.5 hours, the resin was washed with DMF 3 times (1 min.) and once with DCM (1 min.). The unreacted amino groups were then capped by treatment with acetic anhydride/DCM/pyridine (1 ml/2 ml/2 ml) for 72 hours. After washing with DCM (2 ml; 4×1 min), a Kaiser test showed no amino groups were present. The resin was deprotected and washed as described above. This was followed by reaction with 6-(Bocamino)-hexanoic acid DHBT ester (255.8 mg; 67 mmol) dissolved in DMF/DCM 1:1 (4 ml) overnight. After washing and neutraliation, a Kaiser test and an isatin test were performed. Both were negative. After capping, the elongenation of the PNA-chains was performed according to standard procedures for DCC couplings. All Kaiser tests performed after the coupling reactions were negative (Yellow). Qualitative Kaiser tests were done after deprotection of PNA units number 1, 2, 4, and 6. Each test was blue. The PNA oligomers were cleaved and purified by standard procedures. The amount of monomer and DCC used for each coupling was as follows (total volume 4.5 ml):

| Coupling | Monomer (T) | DCC |
|---|---|---|
| 1. | 173 mg | 95 mg |
| 2. | 176 mg | 101 mg |
| 3. | 174 mg | 97 mg |
| 4. | 174 mg | 103 mg |
| 5. | 178 mg | 97 mg |
| 6. | 173 mg | 99 mg |
| 7. | 174 mg | 95 mg |
| 8. | 175 mg | 96 mg |

For the PNA having the Structure (70) where $R_{70}=T_6$, there was 24.5 mg of crude product, which resulted in 6.9 mg. after purification. For the PNA where $R_1=T_8$, there was 28.8 mg of crude product, which resulted in 2.8 mg. after purification. The products had a high tendency of aggregation, as indicated by a complex HPLC chromatogram after a few hours at room temperature in concentration above 1 mg/ml. The PNA-$(T_6)_2$ and PNA-$(T_8)_2$ were hybridised to $(dA)_6$ and $(dA)_8$, respectively, with recorded Tm of 42° C. and 59° C., respectively.

EXAMPLE 76

Solid-Phase Synthesis of H-[Taeg]$_5$-Lys(ClZ)-MBHA Resin

The PNA oligomer was assembled onto 500 mg (dry weight) of MBHA resin that had been preswollen overnight in DCM. The resin was initially substituted with approximately 0.15 mmol/g Boc-Lys(ClZ) as determined by quantitative ninhydrin reaction. The stepwise synthesis of the oligomer followed the synthetic protocol described in Example 32 employing 0.077 g (0.2 mmol) BocTaeg-OH and 31.3 μl (0.2 mmol) diisopropyl carbodiimide in 2.0 ml 50% DMF/CH$_2$Cl$_2$ in each coupling. Capping of uncoupled amino groups was carried out before deprotection in each step. All qualitative Kaiser tests were negative indicating near 100% coupling yield.

EXAMPLE 77

Solid-Phase Synthesis of H-[Taeg]$_4$-[apgT]-[Taeg]$_5$-Lys-NH$_2$

Synthesis was initiated on approximately ¼ of the wet H-[Taeg]5-Lys(ClZ)-MBHA resin from Example 76. In situ diisopropyl carbodiimide (DIC) couplings of both Boc-(apgT)-OH and BocTaeg-OH were carried out in 1.2 ml 50% DMF/CH$_2$Cl$_2$ using 0.048 g (0.12 mmol) and 0.046 g (0.12 mmol) monomer, respectively, and 18.7 μl (0.12 mmol) diusopropyl carbodiimide in each coupling. All qualitative Kaiser tests were negative, indicating near 100% coupling yield. The PNA oligomer was cleaved and purified by standard procedures. For (M+H)+, the calculated m/z value was 2820.15 and the measured m/z value was 2820.92.

EXAMPLE 78

Solid-Phase Synthesis of R-[Taeg]$_4$-[proT]-[Taeg]$_5$-Lys-NH$_2$

Synthesis was initiated on approximately ¼ of the wet H-[Taeg]$_5$-Lys(ClZ)-MBHA resin from Example 76. In situ diisopropyl carbodiimide couplings of BocTaeg-OH were carried out in 1.2 ml 50% DMF/CH$_2$Cl$_2$ using 0.046 g (0.12 mmol) monomer and 18.7 μl (0.12 mmol) diisopropyl carbodiimide in each coupling. Due to solubility problems, Boc-(proT)-OH 0.048 g (0.12 mmol) was suspended in 2.5 ml 50% DMF/DMSO prior to coupling, the suspension filtered, and approximately 2 ml of the filtrate used in the overnight coupling. All qualitative Kaiser tests were negative, indicating near 100% coupling yield. The PNA oligomer was cleaved and purified by standard procedures.

EXAMPLE 79

Hybridization properties of H-[Taeg]$_4$-[proT]-[Taeg]$_5$Lys-NH$_2$

| Oligodeoxynucleotide | Tm (° C.) |
|---|---|
| 5'-AAA AAA AAA A (SEQ ID NO:3) | 53.5 |
| 5'-AAA AGA AAA A (SEQ ID NO:10) | 44.0 |
| 5'-AAA AAG AAA A (SEQ ID NO:8) | 43.5 |
| 5'-AAA ACA AAA A (SEQ ID NO:26) | 46.5 |
| 5'-AAA AAC AAA A (SEQ ID NO:28) | 46.5 |
| 5'-AAA ATA AAA A (SEQ ID NO:27) | 46.5 |
| 5'-AAA AAT AAA A (SEQ ID NO:25) | 46.0 |

EXAMPLE 80

Solid-Phase Synthesis of H-[Taeg]$_4$-[bc]-[Taeg]$_5$-Lys-NH$_2$

The PNA oligomer was assembled onto 100 mg (dry weight) MBHA resin that had been preswollen overnight in DCM. The resin was initially substituted with approximately 0.25 mmol/g Boc-Lys(ClZ) as determined by quantitative ninhydrin reaction. The stepwise synthesis of the oligomer followed synthetic Protocol 9 employing 0.023 g (0.06 mmol) BocTaeg-OH, 0.062 g (0.12 mmol) BocbC(Z)—OH and 0.012 g (0.06 mmol) DCC in 1.2 ml 50% DMF/CH$_2$Cl$_2$ in each coupling. Capping of uncoupled amino groups was carried out before deprotection in each step. All qualitative Kaiser tests were negative, indicating near 100% coupling yield. The PNA-oligomer was cleaved and purified by standard procedures.

EXAMPLE 81

Hybridization Properties of H-T$_4$bCT$_5$-Lys-NH$_2$

| Oligodeoxynucleotide | | Tm(° C.) |
|---|---|---|
| 5'-AAA AAA AAA A | (SEQ ID NO: 3) | 43.5 |
| 5-'AAA AGA AAA A | (SEQ ID NO: 10) | 58.0 |
| 5'-AAA AAG AAA A | (SEQ ID NO: 8) | 60.0 |
| 5'-AAA ACA AAA A | (SEQ ID NO: 26) | 34.5 |
| 5'-AAA AAC AAA A | (SEQ ID NO: 28) | 34.5 |
| 5'-AAA ATA AAA A | (SEQ ID NO: 27) | 34.0 |
| 5'-AAA AAT AAA A | (SEQ ID NO: 25) | 36.0 |

EXAMPLE 82

Stepwise Assembly of H-[Taeg]-[Taeg]-[Taeg]-[Taeg]-[Aaeg]-[Taeg]-[Taeg]-[Taeg]-[Taeg]-[Taeg]-LYS—NH$_2$ Synthesis was initiated on a Boc-[Taeg]$_5$-Lys(ClZ)-MBHA resin (from example 76) that had been preswollen overnight in DCM. The resin resembled approximately 100 mg (dry Weight) of Boc-Lys(ClZ)-MBHA resin (loading 0.15 mmol/g). The incorporation of the monomers followed the protocol of example 55, except for step 5 (incorporation of the BocA(Z)aeg-OH monomer). New step 5 (incorporation of A(Z)aeg) involved addition of 4 equiv. diisopropyl carbodiimide (0.06 mmol; 9.7 μl) and 4 equiv. BocA(Z)aeg-OH (0.06 mmol; 32 mg) dissolved in 0.6 ml DCM/DMF (1:1, v/v) (final concentration of monomer 0.1 M). The coupling reaction was allowed to proceed for 1×15 min. and 1×60 min. (recoupling).

Capping of uncoupled amino groups was only carried out before the incorporation of the BocA(Z)aeg-OH monomer. The coupling reaction was monitored by qualitative ninhydrin reaction (Kaiser test). All qualitative Kaiser tests were negative (straw-yellow color with no coloration of the beads). The PNA oligomer was cleaved and purified by standard procedures.

EXAMPLE 84

Hybridization Properties of H-T$_4$AT$_5$-LysNH$_2$

| Oligodeoxynucleotide | | Tm(° C.) |
|---|---|---|
| 5'-AAA AAA AAA A | (SEQ ID NO: 3) | 59.5 |
| 5-'AAA AGA AAA A | (SEQ ID NO: 10) | 45.0 |
| 5'-AAA AAG AAA A | (SEQ ID NO: 8) | 45.5 |
| 5'-AAA ACA AAA A | (SEQ ID NO: 26) | 48.0 |
| 5'-AAA AAC AAA A | (SEQ ID NO: 28) | 48.0 |
| 5'-AAA ATA AAA A | (SEQ ID NO: 27) | 52.0 |
| 5'-AAA AAT AAA A | (SEQ ID NO: 25) | 52.5 |

EXAMPLE 85

Stepwise Assembly of H-[Taeg]-[Taeg]-[Taeg]-[Taeg]-[Gaeg]-[Gaeg]-[Taeg]-[Gaeg]-[Taeg]-[Gaeg]-LYS—NH$_2$ The protected PNA was assembled onto a Boc-Lys(ClZ) modified MBHA resin with a substitution of 0.15 mmol/g. The incorporation of the monomers followed the protocol of example 32, except that the capping step 11 and the washing step 12 were omitted. After the incorporation and deprotection of the first, second, and fourth G(Bzl)aeg-monomer there were some difficulties getting the resin to swell properly. Three hours of shaking in neat DCM gave acceptable swelling. For the incorporation of residues Taeg-4, G(Bzl) aeg-6, and Taeg-7 to Taeg-10, recoupling was necessary to obtain near quantitative coupling yields. Taeg$_4$ (2× in 50% DMF/DCM), Gaeg$_6$ (2× in 50% DMF/DCM), Taeg$_7$ (2× in 50% DMF/DCM, 1× in 50% NMP/DCM and 1× in neat DCM), Taeg$_8$ (1× in 50% DMF/DCM and 2× in neat DCM), Taeg$_9$ (2× in 50% DMF/DCM), Taeg$_{10}$ (2× in 50% DMF/DCM). All qualitative Kaiser tests were negative (straw-yellow color with no coloration of the beads). The PNA oligomer was cleaved and purified by standard procedures.

EXAMPLE 86

Hybridization properties of crude (approx. 50%) H-T$_4$G$_2$TGTG-LysNH$_2$

| Oligodeoxynucleotide | Tm |
|---|---|
| 5'- A$_4$C$_2$ACAC (SEQ ID NO: 38) | 38 |
| 5'- CACAC$_2$A$_4$ (SEQ ID NO: 39) | 55 |

EXAMPLE 87

Large Scale Solid-Phase Synthesis of H-[Taeg]$_6$-Lys-NH$_2$, H-[Taeg]$_7$-Lys-NH$_2$, H-[Taeg]$_8$-Lys-NH$_2$, H-[Taeg]$_9$-Lys-NH$_2$, and H-[Taeg]$_{10}$-Lys-NH$_2$ (a) Stepwise Assembly of Boc-[Taeg]$_{10}$-Lys(ClZ)-MBHA Resin and Shorter Fragments About 9 g of wet Boc-[Taeg]$_3$-Lys(ClZ)-MBHA (see, Example 19b) resin was placed in a 60 ml SPPS reaction vessel. Boc-[Taeg]₅-Lys(ClZ)-MBHA resin was assembled by single coupling of both residues with 0.15 M of BocTaeg-OPfp in 10 ml neat CH₂Cl₂ ("Synthetic Protocol 8"). Both coupling reactions were allowed to proceed overnight. The synthesis was monitored by the ninhydrin reaction, which showed close to quantitative incorporation of both residues. After deprotection of the N-terminal Boc group, about 4.5 g of H-[Taeg]₅-Lys(ClZ)-MBHA was placed in a 20 ml SPPS reaction vessel and elongated to Boc-[Taeg]₈-Lys(ClZ)-MBHA by single in situ DCC coupling of all residues (close to quantitative, except for residue number eight) overnight with 0.2 M of BocTaeg-OH together with 0.2 M DCC in 7.5 ml neat CH₂Cl₂ ("Synthetic Protocol 9"). Before coupling of Taeg residues number seven and eight, respectively, small portions of H-[Taeg]₆-Lys(ClZ)-MBHA and H-[Taeg]₇-Lys(ClZ)-MBHA, respectively, were taken out for HF cleavage.

Taeg residue number eight was coupled twice (overnight) to give close to quantitative incorporation. After deprotection of the N-terminal Boc group, a large portion of H-[Taeg]₈-Lys(ClZ)-MBHA was taken out for HF cleavage. Boc-[Taeg]₁₀-Lys(ClZ)-MBHA resin was assembled by double in situ DCC coupling of 0.16 M BocTaeg-OH, together with 0.16 M DCC in 2.0 ml 50% DMF/CH₂Cl₂ ("Synthetic Protocol" 9). Before coupling of the final residue, a small portion of H-[Taeg]₉-Lys(ClZ)-MBHA was taken out for HF cleavage.

(b) cleavage, Purification, and Identification of H-[Taeg]₆-Lys-NH₂

The protected Boc-[Taeg]₆-Lys(ClZ)-MBHA resin was treated as described in Example 17c to yield about 14.0 mg of crude material upon HF cleavage of 52.4 mg dry H-Taeg)₆-Lys(ClZ)-MBHA resin. The crude product was not purified (about 99% purity).

(c) Cleavage, Purification, and Identification of H-[Taeg]₇-Lys-NH₂

The protected Boc-[Taeg]₇-Lys(ClZ)-MBHA resin was treated as described in Example 17c to yield about 5.2 mg of crude material upon HF cleavage of 58.4 mg dry H-Taeg)₇-Lys(ClZ)-MBHA resin.

(d) Cleavage, Purification, and Identification of H-[Taeg]₈-Lys-NH₂

The protected Boc-[Taeg]₈-Lys(ClZ)-MBHA resin was treated as described in Example 17c to yield about 114 mg of crude material upon HF cleavage of about 604 mg dry H-Taeg)₈-Lys(ClZ)-MBHA resin.

(e) Cleavage, Purification, and Identification of H-[Taeg]₉-Lys-NH₂

The protected Boc-[Taeg]₉-Lys(ClZ)-MBHA resin was treated as described in Example 17c to yield about 19.3 mg of crude material upon HF cleavage of 81.0 mg dry H-Taeg)₉-Lys(ClZ)-MBHA resin.

(f) Cleavage, Purification, and Identification of H-[Taeg]₁₀-Lys-NH₂

The protected Boc-[Taeg]₁₀-Lys(ClZ)-MBHA resin was treated as described in Example 17c to yield about 141 mg of crude material upon HF cleavage of about 417 mg dry H-Taeg)₁₀-Lys(ClZ)-MBHA resin.

(g) Synthetic Protocol 8 (General Protocol)

(1) Boc-deprotection with TFA/CH₂Cl₂ (1:1, v/v), 3×1 min and 1×30 min; (2) washing with CH₂Cl₂, 6×1 min; (3) neutralization with DIEA/CH₂Cl₂ (1:19, v/v), 3×2 min; (4) washing with CH₂Cl₂, 6×1 min , and drain for 1 min; (5) at some stages of the synthesis, 2–5 mg sample of PNA-resin is taken out and dried thoroughly for a ninhydrin analysis to determine the substitution; (6) addition of Boc-protected PNA monomer (Pfp ester); the coupling reaction was allowed to proceed for a total of X hrs shaking; (7) washing with DMF, 1×2 min; (8) washing with CH₂Cl₂, 4×1 min; (9) neutralization with DIEA/CH₂Cl₂ (1:19, v/v), 2×2 min; (10) washing with CH₂Cl₂, 6×1 min; (11) occasionally, 2–5 mg sample of protected PNA-resin is taken out and dried thoroughly for a ninhydrin analysis to determine the extent of cbupling; (12) at some stages of the synthesis, unreacted amino groups are blocked by acetylation with a mixture of acetic anhydride/pyridine/CH₂Cl₂ (1:1:2, v/v/v) for 2 h followed by washing with CH₂Cl₂, 6×1 min, and, occasionally, ninhydrin analysis.

EXAMPLE 88

Solid-Phase Synthesis of H-[Taeg]4-Caeg-[Taeg]5-Lys-NH₂

(a) Stepwise Assembly of Boc-[Taeg]4-C[Z]aeg-[Taeg]5-Lys(ClZ)-MBHA Resin

About 1 g of wet Boc-[Taeg]5-Lys(ClZ)-MBHA resin was placed in a 5 ml SPPS reaction vessel. Boc-[Taeg9 4-C[Z] aeg-[Taeg]5-Lys(ClZ)-MBHA resin was assembled by in situ DCC coupling of all residues utilizing 0.16 M of BocC[Z]aeg-OH together with 0.16 M DCC in 2.0 ml 50% DMF/CH₂Cl₂ or 0.16 M BocTaeg-OH together with 0. 16 M DCC in 2.0 ml 50% DMF/CH₂C₂ ("synthetic Protocol 9"). Each coupling reaction was allowed to proceed f(or a total of 20–24 hrs with shaking. The synthesis was monitor ed by t he ninhydrin reaction, which showed about 98% incorporation of C[Z]aeg and close to quantitative incorporation of all the Taeg residues.

(b) Cleavage, Purification, and Identification of H-[Taeg]4-C[Z]aeg-[Taeg]5-Lys-NH₂

The protected Boc-[Taeg]4-C[Z]aeg-[Taeg]5-Lys(ClZ)-MBHA resin was treated as described in Example 17c to yield about 22.5 mg of crude material upon HF cleavage of 128.2 mg dry H-[Taeg]4-C[Z]aeg-[Taeg]5-Lys(ClZ)-MBHA resin. Crude product (5.8 mg) was purified to give 3.1 mg of H-[Taeg]4-Caeg-[Taeg]5-Lys-NH₂.

(c) Synthetic Protocol 9 (General Protocol)

(1) Boc-deprotection with TFA/CH₂Cl₂ (1:1, v/v), 3×1 min and 1×30 min; (2) washing with CH₂Cl₂, 6×1 min; (3) neutralization with DIEA/CH₂Cl₂ (1:19, v/v), 3×2 min; (4) washing with CH₂Cl₂, 6×1 min, and drain for 1 min; (5) at some stages of the synthesis, 2–5 mg sample of PNA-resin is taken out and dried thoroughly for a ninhydrin analysis to determine the substitution; (6) addition of Boc-protected PNA monomer (free acid) in X ml DMF followed by addition of DCC in X ml CH₂Cl₂; the coupling reaction was allowed to proceed for a total of Y hrs shaking; (7) washing with DMF, 1×2 min; (8) washing with CH₂Cl₂, 4×1 min; (9) neutralization with DIEA/CH₂Cl₂ (1:19, v/v), 2×2 min; (10) washing with CH₂Cl₂, 6×1 min; (11) occasionally, 2–5 mg sample of protected PNA-resin is taken out and dried thoroughly for a ninhydrin analysis to determine the extent of coupling; (12) at some stages of the synthesis, unreacted amino groups are blocked by acetylation with a mixture of acetic anhydride/pyridine/CH₂Cl₂ (1:1:2, v/v/v) for 2 h followed by washing with CH₂Cl₂, 6×1 min, and, occasionally, ninhydrin analysis.

EXAMPLE 89

Solid-Phase Synthesis of H-[Taeg]4-(NBaeg)-[Taeg] S-Lys-NH₂. (NB=COCH3)

(a) Stepwise Assembly of Boc-[Taeg]4-(NBaeg)-[Taeg]5-Lys(ClZ)-MBHA Resin

About 1 g of wet Boc-[Taeg]5-Lys(ClZ)-MBHA resin was placed in a 5 ml SPPS reaction vessel. Boc-[Taeg]4-

(NBaeg)-Taeg]5-Lys(ClZ)-MBHA resin was assembled by in situ DCC coupling utilizing 0.16 M of Boc(NBaeg)-OH together with 0.16 M DCC in 2.0 ml neat $CH_2Cl_2$ or 0.16 M BocTaeg-OH together with 0.16 M DCC in 2.0 ml 50% DMF/$CH_2Cl_2$ ("Synthetic Protocol 9"). Each coupling reaction was allowed to proceed for a total of 20–24 hrs with shaking. The NBaeg residue was coupled three times and the Taeg residues were all coupled once. The synthesis was monitored by the ninhydrin reaction which showed >99% total incorporation of NBaeg (about 88% after the first coupling and about 93% after the second coupling) and close to quantitative incorporation of all the Taeg residues.

(b) Cleavage, Purification, and Identification of H-[Taeg]4-(NBaeg)-[Taeg]5-Lys-$NH_2$ The protected Boc-[Taeg]4-(NBaeg)-[Taeg]5-Lys(ClZ)-MBHA resin was treated as described in Example 17c to yield about 33.6 mg of crude material upon HF cleavage of 108.9 mg dry H-[Taeg]4-(NBaeg)-[Taeg]5-Lys(ClZ)-MBHA resin. Crude product (20.6 mg) was purified to give 4.6 mg of H-[Taeg]4-(NBaeg)-[Taeg]5-Lys-$NH_2$. For (M+H)+, the calculated m/z value was 2683.12 and the measured m/z value was 2683.09.

EXAMPLE 90

Solid-Phase Synthesis of H-[Taeg]4-aeg-[Taeg]5-Lys-$NH_2$ (a) Stepwise Assembly of Boc-[Taeg]4-aeg-[Taeg]5-Lys (ClZ)-MBHA Resin About 1 g of wet Boc-[Taeg]5-Lys(ClZ)-MBHA resin was placed in a 5 ml SPPS reaction vessel. Boc-[Taeg]4-aeg-[Taeg]5-Lys(ClZ)-MBHA resin was assembled by in situ DCC single coupling of all residues utilizing: (1) 0.16 M of Bocaeg-OH together with 0.16 M DCC in 2.0 ml 50% DMF/$CH_2Cl_2$ or (2) 0.16 M BocTaeg-OH together with (2) 0.16 M DCC in 2.0 ml 50% DMF/$CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-aeg-[Taeg]5-Lys-$NH_2$ The protected Boc-[Taeg]4-aeg-[Taeg]5-Lys(ClZ)-MBHA resin was treated as described in Example 17c to yield about 22.2 mg of crude material upon HF cleavage of 126.0 mg dry H-[Taeg]4-aeg-[Taeg]5-Lys(ClZ)-MBHA resin. Crude product (22.2 mg) was purified to give 7.6 mg of H-[Taeg]4-aeg-[Taeg]5-Lys-$NH_2$. For (M+H)+, the calculated m/z value was 2641.11 and the measured m/z value was 2641.16.

EXAMPLE 91

Solid-Phase Synthesis of H-[Taeg]4-Gly-[Taeg]5-Lys-$NH_2$ (a) Stepwise Assembly of Boc-[Taeg]4-Gly-[Taeg]5-Lys (ClZ)-KBHA Resin About 1 g of wet Boc-[Taeg]5-Lys(ClZ)-MBHA resin was placed in a 5 ml SPPS reaction vessel. Boc-[Taeg]4-Gly-[Taeg]5-Lys(ClZ)-MBHA resin was assembled by in situ DCC single coupling of all residues utilizing: (1) 0.16 M of BocGly-OH together with 0.16 M DCC in 2.0 ml 50% DMF/$CH_2Cl_2$ or (2) 0.16 M BocTaeg-OH together with 0.16 M DCC in 2.0 ml 50% DMF/$CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-Gly-[Taeg]5-Lys-$NH_2$ The protected Boc-[Taeg]4-Gly-[Taeg]5-Lys(ClZ)-MBHA resin was treated as described in Example 18c to yield about 45.0 mg of crude material upon HF cleavage of 124.1 mg dry H-[Taeg]4-Gly-[Taeg]5-Lys(ClZ)-MBHA resin. Crude product (40.4 mg) was purified to give 8.2 mg of H-[Taeg]4-Gly-[Taeg]5-Lys-$NH_2$.

EXAMPLE 92

Solid-Phase Synthesis of H-[Taeg]4-Gly2-[Taeg]5-Lys-$NH_2$ (a) Stepwise Assembly of Boc-[Taeg]4-Gly2-[Taeg]5-Lys (ClZ)-MBHA Resin About 1 g of wet Boc-[Taeg]5-Lys(ClZ)-MBHA resin was placed in a 5 ml SPPS reaction vessel. Boc-[Taeg]4-[C[Z]aeg]2-Taeg-C[Z]aeg-Taeg-C[Z]aeg-Lys(ClZ)-MBHA resin was assembled by in situ DCC single coupling of all residues utilizing: (1) 0.16 M of BocGly-OH together with 0.16 M DCC in 2.0 ml 50% DMF/$CH_2Cl_2$ or (2) 0.16 M BocTaeg-OH together with 0.16 M DCC in 2.0 ml 50% DMF/$CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-Gly2-[Taeg]5-Lys-$NH_2$ The protected Boc-[Taeg]4-Gly2-[Taeg]5-Lys(ClZ)-MBHA resin was treated as described in Example 17c to yield about 32.6 mg of crude material upon HF cleavage of 156.6 mg dry H-[Taeg]4-Gly2-[Taeg]5-Lys(ClZ)-MBHA resin. Crude product (30 mg) was purified to give 7.8 mg of H-[Taeg]4-Gly2-[Taeg]5-Lys-$NH_2$. For (M+H)+, the calculated m/z value was 2655.09 and the measured m/z value was 2655.37.

EXAMPLE 93

Solid-Phase Synthesis of H-[Taeg]4-[caeg]2-Taeg-caeg-Taeg-Caeg-Lys-$NH_2$ (a) Stepwise Assembly of Boc-[Taeg]4-[C[Z]aeg]2-Taeg-C[Z]aeg-Taeg-C[Z]aeg-Lys(ClZ)-KBHA Resin About 1.5 g of wet Boc-Lys(ClZ)-MBHA (0.28 mmol Lys/g) resin was placed in a 5 ml SPPS reaction vessel. Boc-[Taeg]4-[C[Z]aeg]2-Taeg-C[Z]aeg-Taeg-C[Z]aeg-Lys (ClZ)-MBHA resin was assembled by in situ DCC single coupling of all residues utilizing: (1) 0.16 M of BocC[Z]-OH together with 0.16 M DCC in 2.0 ml 50% DMF/$CH_2Cl_2$ or (2) 0.16 M BocTaeg-OH together with 0.16 M DCC in 2.0 ml 50% DMF/$CH_2Cl_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-[Taeg]4-[Caeg]2-Taeg-Caeg-Taeg-Caeg-Lys-$NH_2$ The protected Boc-[Taeg]4-[C[Z]aeg]2-Taeg-C[Z]aeg-Taeg-C[Z]aeg-Lys(ClZ)-MBHA resin was treated as described in Example 17c to yield about 52.1 mg of crude material upon HF cleavage of 216.7 mg dry H-[Taeg]4-[C[Z]aeg]2-Taeg-C[Z]aeg-Taeg-C[Z]aeg-Lys(ClZ)-MBHA resin. Crude product (30.6 mg) was purified to give 6.2 mg of H-[Taeg]4-[Caeg]2-Taeg-Caeg-Taeg-Caeg-Lys-$NH_2$. For (M+H)+ the calculated m/z value was 2747.15 and the measured m/z value was 2746.78.

EXAMPLE 94

Solid-Phase Synthesis of H-Caeg-Taeg-Caeg-Taeg-[Caeg]3-Taeg-Caeg-Taeg-Lys-$NH_2$ (a) Stepwise Assembly of Boc-C[Z]aeg-Taeg-C[Z]aeg-Taeg-[C[Z]aeg]3-Taeg-C[Z]aeg-Taeg-Lys(ClZ)-MBHA Resin About 1.5 g of wet Boc-Lys(ClZ)-MBHA (0.28 mmol Lys/g) resin was placed in a 5 ml SPPS reaction vessel.

Boc-C[Z]aeg-Taeg-C[Z]aeg-Taeg-[C[Z]aeg]3-Taeg-C[Z] aeg-Taeg-Lys(ClZ)-MBHA resin was assembled by in situ DCC single coupling of all residues utilizing: (1) 0.16 M of BocC[Z]-OH together with 0.16 M DCC in 2.0 ml 50% DMF/CH$_2$Cl$_2$ or (2) 0.16 M BocTaeg-OH together with 0.16 M DCC in 2.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues.

(b) Cleavage, Purification, and Identification of H-Caeg-Taeg-Caeg-Taeg-[Caeg]3-Taeg-Caeg-Taeg-Lys-NH 2

The protected Boc-C [Z]aeg-Taeg-C [Z]aeg-Taeg-[C [Z]aeg]3-Taeg-C(Z)aeg-TaegLys(ClZ)-MBHA resin was treated as described in Example 17c to yield about 56.1 mg of crude material upon HF cleavage of 255.0 mg dry H-C[Z]aeg-Taeg-C[Z]aeg-Taeg-[C[Z]aeg]3-Taeg-C[Z]aeg-TaegLys(ClZ)-MBHA resin. Crude product (85.8 mg) was purified to give 46.2 mg of H-Caeg-Taeg-Caeg-Taeg-[Caeg]3-Taeg-Caeg-Taeg-LysNH$_2$. For (M+H)+ the calculated m/z value was 2717.15 and the measured m/z value was 2716.93.

EXAMPLE 95

Solid-Phase Synthesis of H-[Taeg]2-[Caeg]3-[Taeg]2-[Caeg]2-Lys-NH$_2$, H-Caeg-[Taeg]2-[Caeg]3-[Taeg]2-[Caeg]2-Lys-NH$_2$, and H-Tyr-[Taeg]2-[Caeg]3-[Taeg]2-[Caeg]2-Lys-NH$_2$ (a) Stepwise Assembly of Boc-[Taeg]2-[C(Z)aeg]3-[Taeg]2-[C(Z)aeg]2-Lys(ClZ)-MBHA Resin, Boc-Caeg-[Taeg]2-[C(Z)aeg]3-[Taeg]2-[C(Z)aeg]2-Lys(ClZ)-MBHA Resin, and Boc-Tyr(BrZ)-[Taeg]2-[C(Z)aeg]3-[Taeg]2-[C(Z)aeg]2-Lys(ClZ)-MBHA Resin About 3 g of wet Boc-Lys(ClZ)-MBHA (0.28 mmol Lys/g) resin was placed in a 20 ml SPPS reaction vessel. Boc-[Taeg]2-[C(Z)aeg]3-[Taeg]2-[C(Z)aeg]2-Lys(ClZ)-MBHA resin was assembled by in situ DCC single coupling of all residues utilizing: (1) 0.16 M of BocC[Z]-OH together with 0.16 M DCC in 3.0 ml 50% DMF/CH$_2$Cl$_2$ or (2) 0.16 M BocTaeg-OH together with 0.16 M DCC in 3.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues. After deprotection of the N-terminal Boc group, half of the PNA-resin was coupled quantitatively onto Tyr(BrZ)-OH and a small portion was coupled quantitatively onto one more Caeg residue. Both couplings employed the above-mentioned synthetic protocol.

(b) Cleavage, Purification, and Identification of H-[Taeg]2-[Caeg]3-[Taeg]2-[Caeg]2-Lys-NH$_2$ The protected Boc-[Taeg]2-[C(Z)aeg]3-[Taeg]2-[C(Z)aeg]2-Lys(ClZ)-MBHA resin was treated as described in Example 17c to yield about 50.9 mg of crude material upon HF cleavage of 182.5 mg dry H-[Taeg]2-[C(Z)aeg]3-[Taeg]2-[C(Z)aeg]2-Lys(ClZ)-MBHA resin. Crude product (50.9) mg was purified to give 13.7 mg of H-[Taeg]2-[Caeg]3-[Taeg]2-[Caeg]2-LysNH$_2$. For (M+H)+ the calculated m/z value was 2466.04; the m/z value was not measured.

(c) Cleavage, Purification, and Identification of H-Tyr-[Taeg]2-[Caeg]3-[Taeg]2-[Caeg]2-Lys-NH$_2$ The protected Boc-Tyr(BrZ)-[Taeg]2-[C(Z)aeg]3-[Taeg]2-[C(Z)aeg]2-Lys(ClZ)-MBHA resin was treated as described in Example 17c to yield about 60.8 mg of crude material upon HF cleavage of 188.8 mg dry H-Tyr(BrZ)-[Taeg]2-[C(Z)aeg)3-[Taeg]2-[C(Z)aeg]2-Lys(ClZ)-MBHA resin. Crude product (60.8 mg) was purified to give 20.7 mg of H-Tyr-[Taeg]2-[Caeg]3-[Taeg]2-[Caeg]2-LysNH$_2$. For (M+H)+ the calculated m/z value was 2629.11 and the measured m/z value was 2629.11.

(d) Cleavage, Purification, and Identification of H-Caeg-[Taeg]2-[Caeg]3-[Taeg]2-[Caeg]2-Lys-NH$_2$ The protected Boc-C(Z)aeg-[Taeg]2-[C(Z)aeg]3-[Taeg]2-[C(Z)aeg]2-Lys(ClZ)-MBHA resin was treated as described in Example 17c to yield about 11.7 mg of crude material upon HF cleavage of 42.0 mg dry H-C(Z)aeg-[Taeg]2-[C(Z)aeg]3-[Taeg]2-[C(Z)aeg]2-Lys(ClZ)-MBHA resin. Crude product (11.6 mg) was purified to give 3.1 mg of H-Caeg-[Taeg]2-[Caeg]3-[Taeg]2-[Caeg]2-LysNH$_2$. For (M+H)+ the calculated m/z value was 2717.15; the m/z value was not measured.

EXAMPLE 96

Solid-Phase Synthesis of H-[Caeg]2-[Taeg]2-[Caeg]3-[Taeg]2-LYS—NH$_2$, H-Taeg-[Caeg]2-[Taeg]2-[Caeg]3-[Taeg]2-Lys-NN$_2$, and H-Tyr-[Caeg]2-[Taeg]2-[Caeg]3-[Taeg]2-Lys-NH$_2$ (a) Stepwise Assembly of Boc-[C(Z)aeg]2-[Taeg]2-[C(Z)aeg]3-[Taeg]2-Lys(ClZ)-MBHA Resin, Boc-Taeg-[C(Z)aeg]2-[Taeg]2-[C(Z)aeg]3-[Taeg]2-Lys(ClZ)-MBHA Resin, and Boc-Tyr(BrZ)-[C(Z)aeg]2-[Taeg]2-[C(Z)aeg]3-[Taeg]2-Lys(ClZ)-MBHA Resin About 3 g of wet Boc-Lys(ClZ)-MBHA (0.28 mmol Lys/g) resin was placed in a 20 ml SPPS reaction vessel. Boc-[Taeg]2-[C(Z)aeg]3-[Taeg]2-[C(Z)aeg]2-Lys(ClZ)-MBHA resin was assembled by in situ DCC single coupling of all residues utilizing: (1) 0.16 M of BocC[Z]—OH together with 0.16 M DCC in 3.0 ml 50% DMF/CH$_2$Cl$_2$ or (2) 0.16 M BocTaeg-OH together with 0.16 M DCC in 3.0 ml 50% DMF/CH$_2$Cl$_2$ ("Synthetic Protocol 9"). Each coupling reaction was allowed to proceed for a total of 20–24 hrs with shaking. The synthesis was monitored by the ninhydrin reaction, which showed close to quantitative incorporation of all the residues. After deprotection of the N-terminal Boc group, half of the PNA-resin was coupled quantitatively onto Tyr(BrZ)—OH and a small portion was coupled quantitatively onto one more Taeg residue. Both couplings employed the above-mentioned synthetic protocol.

(b) Cleavage, Purification, and Identification of H-[C(Z)aeg]2-[Taeg]2-[C(Z)aeg]3-[Taeg]2-Lys-NH$_2$ The protected Boc-[C(Z)aeg]2-[Taeg]2-[C(Z)aeg]3-[Taeg]2-Lys(ClZ)-MBHA resin was treated as described in Example 17c to yield about 57.6 mg of crude material upon HF cleavage of 172.7 mg dry H-[C(Z)aeg]2-[Taeg]2-[C(Z)aeg]3-[Taeg]2-Lys(ClZ)-MBHA resin. Crude product (57.6 mg) was purified to give 26.3 mg of H-[Caeg]2-[Taeg]2-[Caeg]3-[Taeg]2-Lys-NH$_2$. For (M+H)+ the calculated m/z value was 2466.04; the m/z value was not measured.

(c) Cleavage, Purification, and Identification of H-Tyr-[C(Z)aeg]2-[Taeg]2-[C(Z)aeg]3-[Taeg]2-Lys-NH$_2$ The protected Boc-Tyr(BrZ)-[C(Z)aeg]2-[Taeg]2-[C(Z)aeg]3-[Taeg]2-Lys(ClZ)-MBHA resin was treated as described in Example 17c to yield about 57.6 mg of crude material upon HF cleavage of 172.7 mg dry H-Tyr(BrZ)-[C(Z)aeg]2-[Taeg]2-[C(Z)aeg]3-[Taeg]2-Lys(ClZ)-MBHA resin. Crude product (47.1 mg) was purified to give 13.4 mg of H-Tyr-[Caeg]2-[Taeg]2-[Caeg]3-[Taeg]2-Lys-NH$_2$. For (M+H)+ the calculated m/z value was 2629.11 and the measured m/z value was 2629.11.

(d) Cleavage, Purification, and Identification of H-Taeg-[C(Z)aeg]2-[Taeg]2-[C(Z)aeg]3-[Taeg]2-Lys-NH$_2$ The protected Boc-Taeg-[C(Z)aeg]2-[Taeg]2-[C(Z)aeg]3-[Taeg]2-Lys(ClZ)-MBHA resin was treated as described in Example 17c to yield about 53.4 mg of crude material upon HF cleavage of 42.4 mg dry H-Taeg-[C(Z)aeg]2-[Taeg]2-[C(Z)aeg]3-[Taeg]2-Lys(Cl Z)-MBHA resin. Crude product (11.9 mg) was purified to give 4.3 mg of H-Taeg-[Caeg]2-[Taeg]2-[Caeg]3-[Taeg]2-Lys-$NH_2$. For (M+H)+ the calculated m/z value was 2732.15; the m/z value was not measured.

(c) Synthetic Protocol 10 (General Protocol)

Same protocol as "Synthetic Protocol 9", except that DCC has been replaced with DIC.

EXAMPLE 97

SYNTHESIS OF THE BACKBONE MOIETY FOR SCALE UP BY REDUCTIVE AMINATION (a) Preparation of (bocamino)acetaldehyde 3-Amino-1,2-propanediol (80.0 g; 0.88 mol) was dissolved in water (1500 ml) and the solution was cooled to 4° C., whereafter Boc anhydride (230 g; 1.05 mol) was added at once. The solution was gently heated to room temperature with a water bath. The pH was kept at 10.5 by the dropwise addition of sodium hydroxide. Over the course of the reaction a total of 70.2 g NaOH, dissolved in 480 ml water, was added. After stirring overnight, ethyl acetate (1000 ml) was added and the mixture was cooled to 0° C. and the pH was adjusted to 2.5 by the addition of 4 M hydrochloric acid. The ethyl acetate layer was removed and the acidic aqueous solution was extracted with more ethyl acetate (8×500 ml). The combined ethyl acetate solution was reduced to a volume of 1500 ml using a rotary evaporator. The resulting solution was washed with half saturated potassium hydrogen sulphate (1500 ml) and then with saturated sodium chloride. It then was dried over magnesium sulphate and evaporated to dryness, in vacuo. Yield. 145.3 g (86%).

3-Bocamino-1,2-propanediol (144.7 g; 0.757 mol) was suspended in water (750 ml) and potassium periodate (191.5 g; 0.833 mol) was added. The mixture was stirred under nitrogen for 2.5 h and the precipitated potassium iodate was removed by filtration and washed once with water (100 ml). The aqueous phase was extracted with chloroform (6×400 ml). The chloroform extracts were dried and evaporated to dryness, in vacuo. Yield 102 g (93%) of an oil. The (bocamino)acetaldehyde was purified by kugelrohr distillation at 84° C. and 0.3 mmHg in two portions. The yield 79 g (77%) of a colorless oil.

(b) Preparation of (N'-bocaminoethyl)glycine Methyl Ester

Palladium on carbon (10%; 2.00 g) was added to a solution of (bocamino)acetaldehyde (10.0 g; 68.9 mmol) in methanol (150 ml) at 0° C. Sodium acetate (11.3 g; 138 mmol) in methanol (150 ml), and glycine methyl ester hydrochloride (8.65 g; 68.9 mmol) in methanol (75 ml) then were added. The mixture was hydrogenated at atmospheric pressure for 2.5 h, then filtered through celite and evaporated to dryness, in vacuo. The material was redissolved in water (150 ml) and the pH was adjusted to 8.0 with 0.5 N NaOH. The aqueous solution was extracted with methylene chloride (5×150 ml). The combined extracts were dried over sodium sulphate and evaporated to dryness, in vacuo. This resulted in 14.1 g (88%) of (N'-bocaminoethyl)glycine methyl ester. The crude material was purified by kugelrohr destination at 120° C. and 0.5 mmHg to give 11.3 g (70%) of a colorless oil. The product had a purity that was higher than the material produced in example 26 according to tlc-analysis (10% methanol in methylene chloride).

Alternatively, sodium cyanoborohydride can be used as reducing agent instead of hydrogen (with Pd(C) as catalyst), although the yield (42%) was lower.

(c) Preparation of (N'-bocaminoethyl)glycine Ethyl Ester

The title compound was prepared by the above procedure with glycine ethyl ester hydrochloride substituted for glycine methyl ester hydrochloride. Also, the solvent used was ethanol. The yield was 78%.

EXAMPLE 98

Solid-Phase Synthesis of H-Tyr-[Taeg]$_{10}$-Lys-$NH_2$ (a) Stepwise Assembly of Boc-Tyr(Brz)-[Taeg]$_{10}$-Lys(ClZ)-MBHA Resin About 0.2 g of wet Boc-[Taeg]$_{10}$-Lys(ClZ)-MBHA resin was placed in a 5 ml SPPS reaction vessel. Boc-Tyr(BrZ)-[Taeg]$_{10}$-Lys(ClZ)-MBHA resin was assembled by standard in situ DCC coupling utilizing 0.32 M of BocCTyr(BrZ)-OH together with 0.32 M DCC in 3.0 ml neat $CH_2Cl_2$ overnight. The ninhydrin reaction showed about 97% incorporation of BocTyr(BrZ).

(b) Cleavage, Purification, and Identification of H-Tyr-[Taeg]$_{10}$-Lys —$NH_2$ The protected Boc-Tyr (BrZ)-[Taeg]]$_{10}$-Lys (ClZ)-MBHA resin was treated as described in Example 17c to yield about 5.5 mg of crude material upon HF cleavage of 20.7 mg dry H-Tyr(BrZ)-[Taeg]$_{10}$-Lys(ClZ)-MBHA resin. The crude product was purified to give 2.5 mg of H-Tyr-[Taeg]$_{10}$-Lys-$NH_2$.

EXAMPLE 99

Solid-Phase Synthesis of Dansyl-[Taeg]$_{10}$-Lys-$NH_2$ (a) Stepwise Assembly of Dansyl-[Taeg]$_{10}$-Lys(ClZ)-MBMA Resin About 0.3 g of wet Boc-[Taeg]$_{10}$-Lys(ClZ)-MBHA resin was placed in a 5 ml SPPS reaction vessel. Dansyl-[Taeg]$_{10}$-Lys(ClZ)-MBHA resin was assembled by coupling of 0.5 M dansyl-Cl in 2.0 ml neat pyridine overnight. The ninhydrin reaction showed about 95% incorporation of dansyl.

(b) Cleavage, Purification, and Identification of Dansyl-[Taeg]$_{10}$-Lys-$NH_2$ The protected dansyl-[Taeg]$_{10}$-Lys(ClZ)-MBHA resin was treated as described in Example 17c to yield about 12 mg of crude material upon HF cleavage of 71.3 mg dry dansyl-[Taeg]$_{10}$-Lys(ClZ)-MBHA resin. The crude product was purified to give 5.4 mg of dansyl-[Taeg]$_{10}$-Lys-$NH_2$.

EXAMPLE 100

Solid-Phase Synthesis of Gly-Gly-His-[Taeg]$_{10}$-Lys-$NH_2$ (a) Stepwise Assembly of Boc-Gly-Gly-His(Tos)-[Taeg]$_{10}$-Lys(ClZ)-MBHA Resin About 0.05 g of Boc-[Taeg]$_{10}$-Lys(ClZ)-MBHA resin was placed in a 5 ml SPPS reaction vessel. Boc-Gly-Gly-His (Tos)-[Taeg]$_{10}$-Lys(ClZ)-MBHA resin was assembled by standard double in situ DCC coupling of Boc-protected amino acid (0.1 M) in 2.5 ml 25% DMF/$CH_2Cl_2$, except for the first coupling of BocHis(Tos), which was done by using a preformed symmetrical anhydride (0.1M) in 25% DMF/$CH_2Cl_2$. All couplings were performed overnight and ninhydrin reactions were not carried out.

(b) Cleavage, Purification, and Identification of Gly-Gly-His-[Taeg]$_{10}$-Lys-$NH_2$ The protected Boc-Gly-Gly-His(Tos)-[Taeg]$_{10}$-Lys(ClZ)-MBHA resin was treated as described in Example 17c to yield about 10.3 mg of crude material (about 40% purity) upon HF cleavage of 34.5 mg dry Boc-Gly-Gly-His(Tos)-[Taeg]$_{10}$-Lys(ClZ)-MBHA resin. A small portion of the crude product (taken out before lyophilization) was purified to give 0.1 mg of Gly-Gly-His-[Taeg]$_{10}$-Lys-$NH_2$.

EXAMPLE 101

Solid-Phase Synthesis of H-[Taeg]$_5$-[caeg]$_2$-NH$_2$ (a) stepwise Assembly of Boc-[Taeg]$_5$-[C(Z)aeg]$_2$-MBHA Resin About 0.2 g of MBHA resin was placed in a 3 ml SPPS reaction vessel and neutralized. The loading was determined to be about 0.64 mmol/g. BocC(Z)aeg-OPfp was coupled onto the resin using a concentration of 0.13 M in 2.5 ml 25% phenol//CH$_2$Cl$_2$. The ninhydrin analysis showed a coupling yield of about 40%. The remaining free amino groups were acetylated as usual. Boc-(Taeg)$_5$-[C(Z)aeg]$_2$-MBHA resin was assembled by single in situ DCC coupling of the next residue utilizing 0.11 M of BocC(Z)aeg-OH together with 0.11 M DCC in 2.5 ml 50% DMF/CH$_2$Cl$_2$ and by coupling with 0.13 M BocTaeg-OPfp in neat CH$_2$Cl$_2$ for the remaining residues ("Synthetic Protocol 8"). Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_5$-[caeg]$_2$—NH$_2$ The protected Boc-[Taeg]$_5$-[C(Z)aeg]$_2$-MBHA resin was treated as described in Example 17c to yield about 21.7 mg of crude material (>80% purity) upon HF cleavage of 94.8 mg dry H-[Taeg]$_5$-[C(Z)aeg]$_2$-MBHA resin. Crude product (7.4 mg) was purified to give 2.0 mg of H-[Taeg]$_5$-[Caeg]$_2$—NH$_2$ (>99% purity).

EXAMPLE 102

Solid-Phase Synthesis of H-[Taeg]$_5$-Caeg-[Taeg]$_4$—NH$_2$ (a) Stepwise Assembly of Boc-[Taeg]$_3$-C(Z)aeg-[Taeg]$_4$-MBHA Resin About 0.2 g of the above-mentioned MBHA resin was placed in a 5 ml SPPS reaction vessel and neutralized. Boc-[Taeg]$_3$-C(Z)aeg-[Taeg]$_4$-MBHA resin was assembled by single in situ DCC coupling of the C(Z)aeg residue utilizing 0.13 M of BocC[Z]aeg-OH together with 0.13 M DCC in 2.5 ml 50% DMF/CH$_2$Cl$_2$ and by coupling the Taeg residues with 0.13 M BocTaeg-OPfp in 2.5 ml neat CH$_2$Cl$_2$. Each coupling reaction was allowed to proceed with shaking overnight. The synthesis was monitored by the ninhydrin reaction, which showed close to quantitative incorporation of all the residues.

(b) Cleavage, Purification, and Identification of H-[Taeg]$_3$-Caeg-[Taeg]$_4$-NH$_2$ The protected Boc-[Taeg]$_3$-C(Z)aeg-[Taeg]$_4$-MBHA resin was treated as described in Example 17c to yield about 44.4 mg of crude material upon HF cleavage of about 123 mg dry H-[Taeg]$_3$-C(Z)aeg-[Taeg]$_4$-MBHA resin. Crude product (11.0 mg) was purified to give 3.6 mg of H-[Taeg]$_3$-Caeg-[Taeg]$_4$—NH$_2$.

EXAMPLE 103

Solid-Phase Synthesis of H-Taeg-Caeg-[Taeg]$_8$-LysNH$_2$ (a) Stepwise Assembly of Boc-Taeg-C(Z)aeg-[Taeg]$_8$-Lys(ClZ)-MBHA Resin About 0.3 g of wet Boc-[Taeg]$_8$-Lys(ClZ)-MBHA resin was placed in a 3 ml SPPS reaction vessel. Boc-Taeg-C(Z)aeg-[Taeg]$_3$-Lys(ClZ)-MBHA resin was assembled by single in situ DCC coupling overnight of the C(Z)aeg residue ("Synthetic Protocol" 9) utilizing 0.2 M of BocC[Z]aeg-OH together with 0.2 M DCC in 2.5 ml 50% DMF/CH$_2$Cl$_2$ (incorporation was about 80% as judged by ninhydrin analysis; remaining free amino groups were acetylated) and by overnight coupling the Taeg residue with 0.15 M BocTaeg-OPfp in 2.5 ml neat CH$_2$Cl$_2$ (nearly quantitatively).

(b) cleavage, Purification, and Identification of H-Taeg-Caeg-[Taeg]$_8$-LysNH$_2$ The protected Boc-Taeg-C(Z)aeg-[Taeg]$_8$-Lys(ClZ)-MBHA resin was treated as described in Example 17c to yield about 22.3 mg of crude material upon HF cleavage of about 76.5 mg dry H-Taeg-C(Z)aeg-[Taeg]$_8$-Lys(ClZ)-MBHA resin. Crude product (6.7 mg) was purified to give 2.6 mg of H-Taeg-Caeg-[Taeg]$_8$-LysNH$_2$. For (M+H)$^+$ the calculated m/z value was 2792.15 and the measured m/z value was 2792.21.

EXAMPLE 104

Solid-Phase Synthesis of H-Caeg-[Taeg]$_5$-Lys-NH$_2$ and H-[Taeg]$_2$-Caeg-[Taeg]$_5$-Lys-NH$_2$ (a) Stepwise Assembly of Boc-[Taeg]$_2$-C(Z)aeg-[Taeg]$_5$-Lys(ClZ)-KBHA Resin About 0.5 g of wet Boc-[Taeg]$_5$-Lys(ClZ)-MBHA resin was placed in a 5 ml SPPS reaction vessel. Boc-[Taeg]$_2$-C(Z)aeg-[Taeg]$_5$-Lys(ClZ)-MBHA resin was assembled by single in situ DCC coupling of all residues utilizing: (1) 0.12 M of BocC[Z]aeg-OH together with 0.12 M DCC in 3.0 ml 50% DMF/CH$_2$Cl$_2$ or (2) 0.12 M BocTaeg-OH together with 0.12 M DCC in 3.0 ml 50% DMF/CH$_2$Cl$_2$ ("Synthetic Protocol 9"). Each coupling reaction was allowed to proceed overnight with shaking. The synthesis was monitored by the ninhydrin reaction, which showed close to quantitative incorporation of all the residues. During the synthesis, a small portion of H-C(Z)aeg-[Taeg]$_5$-Lys(ClZ)-MBHA resin was taken out for HF cleavage.

(b) Cleavage, Purification, and Identification of H-Caeg-[Taeg]$_5$-Lys-NH$_2$

The protected Boc-C[Z]aeg-[Taeg]$_5$-Lys(ClZ)-MBHA resin was treated as described in Example 17c to yield about 3.0 mg of crude material upon HF cleavage of 37.5 mg dry H-C[Z]aeg-[Taeg]$_5$-Lys(ClZ)-MBHA resin. About 0.7 mg of the crude product was purified to give about 0.5 mg of H-Caeg-[Taeg]$_5$-Lys-NH$_2$.

(c) Cleavage, Purification, and Identification of H-[Taeg]$_2$-Caeg-[Taeg]$_5$-Lys-NH$_2$ The protected Boc-[Taeg]$_2$-C[Z]aeg-[Taeg]$_5$-Lys(ClZ)-MBHA resin was treated as described in Example 17c to yield about 37.7 mg of crude material upon HF cleavage of 118.6 mg dry H-[Taeg]$_2$-C[Z]aeg-[Taeg]$_5$-Lys(ClZ)-MBHA resin.

EXAMPLE 105

Solid-Phase Synthesis of H-[Caeg]$_5$-Lys-NH$_2$, H-[Caeg]$_6$-Lys-NH$_2$, H-[Caeg]$_8$-Lys-NH$_2$, and H-[Caeg]$_{10}$-Lys-NH$_2$ (a) Stepwise Assembly of Boc-[C(Z)aeg]$_{10}$-Lys(ClZ)-MBHA Resin and Shorter Fragments About 5 g of wet Boc-Lys(ClZ)-MBHA resin (substitution=0.3 mmol Lys/g) was placed in a 30 ml SPPS reaction vessel. Boc-[C(Z)aeg]$_{10}$-Lys(ClZ)-MBHA resin was assembled by single in situ DCC coupling of the first three residues with 0.1 M of BocC(Z)aeg-OH together with 0.1 M DCC in 10 ml 50% DMF/CH$_2$Cl$_2$ ("Synthetic Protocol 9") and by single in situ DIC coupling of the remaining seven residues with 0.1 M of BocC(Z)aeg-OH together with 0.1 M DIC in 10 ml 50% DMF/CH$_2$Cl$_2$ ("Synthetic Protocol 10"). All the coupling reactions were allowed to proceed overnight. The synthesis was monitored by the ninhydrin reaction, which showed close to quantitative incorporation of all residues. During the synthesis, portions of the shorter fragments H-[C(Z)aeg]$_5$-Lys(ClZ)-MBHA resin, H-[C(Z)aeg]$_6$-Lys(ClZ)-MBHA resin, H-[C(Z)aeg $_7$-Lys(ClZ)-MBHA resin, H-[C(Z)aeg]$_8$-Lys(ClZ)-MBHA resin, and H-[C(Z)aeg]$_9$-Lys(ClZ)-MBHA resin were taken out for HF cleavage.

(b) Cleavage, Purification, and Identification of H-[Caeg]$_5$-Lys-NH$_2$

The protected Boc-[C(Z)aeg]$_5$-Lys(ClZ)-MBHA resin was treated as described in Example 17c to yield about 10.8 mg of crude material upon HF cleavage of 60.1 mg dry H-[C(Z)aeg]$_5$-Lys(ClZ)-MBHA resin.

(c) Cleavage, Purification, and Identification of H-[Caeg]$_6$-Lys-NH$_2$

The protected Boc-[C(Z)aeg]$_6$-Lys(ClZ)-MBHA resin was treated as described in Example 17c to yield about 13.4 mg of crude material upon HF cleavage of 56.2 mg dry H-[C(Z)aeg]$_6$-Lys(ClZ)-MBHA resin.

(d) Cleavage, Purification, and Identification of H-[Caeg]$_8$-Lys-NH$_2$

The protected Boc-[C(Z)aeg]$_8$-Lys (ClZ)-MBHA resin was treated as described in Example 17c to yield about 16.8 mg of crude material upon HF cleavage of 65.6 mg dry H-[C(Z)aeg]$_8$-Lys(ClZ)-MBHA resin.

(e) Cleavage, Purification, and Identification of H-[Caeg]$_{10}$-Lys-NH$_2$

The protected Boc-(C(Z)aeg]$_{10}$-Lys(ClZ)-MBHA resin was treated as described in Example 17c to yield about 142.4 mg of crude material upon HF cleavage of 441 mg dry H-[C(Z)aeg]$_{10}$-Lys(ClZ)-MBHA resin.

EXAMPLE 106

Solid-Phase Synthesis of H-[Taeg]$_2$-Caeg-[Taeg]$_2$-Caeg-[Taeg]$_4$-Lys-NH$_2$ (a) Stepwise Assembly of Boc-[Taeg]$_2$-C(Z)aeg-[Taeg]$_2$-C(Z)aeg-[Taeg]$_4$-Lys(ClZ)-MBHA Resin About 0.3 g of wet H-[Taeg]$_2$-C(Z)aeg-[Taeg]$_4$-Lys(ClZ)-MBHA resin from the earlier synthesis of Boc-[Taeg]$_5$-C(Z)aeg-[Taeg]$_4$-Lys(ClZ)-MBHA resin was placed in a 5 ml SPPS reaction vessel. After coupling of the next residue five times, a total incorporation of BocC(Z)aeg of 87% was obtained. The five repeated couplings were carried out with 0.18 M BocC(Z)aeg-OPfp in 2 ml of TFE/CH$_2$Cl$_2$ (1:2, v/v), 2 ml of TFE/CH$_2$Cl$_2$ (1:2, v/v), 2 ml of TFE/CH$_2$Cl$_2$ (1:2, v/v) with two drops of dioxane and two drops of DIEA (this condition gave only a few per cent coupling yield), 2 ml of TFE/CH$_2$Cl$_2$ (1:2, v/v) plus 0.5 g phenol, and 1 ml of CH$_2$Cl$_2$ plus 0.4 g of phenol, respectively. The two final Taeg residues were incorporated close to quantitatively by double couplings with 0.25 M BocTaeg-OPfp in 25% phenol/CH$_2$Cl$_2$. All couplings were allowed to proceed overnight.

(b) Cleavage, Purification, and Identification of H-[Taeg]$_2$-Caeg-[Taeg]$_2$-Caeg-[Taeg]$_4$-Lys-NH$_2$ The protected Boc-[Taeg]$_2$-C(Z)aeg-[Taeg]$_2$-C(Z)aeg-[Taeg]$_4$-Lys(ClZ)-MBHA resin was treated as described in Example 17c to yield about 7 mg of crude material upon HF cleavage of 80.7 mg dry H-[Taeg]$_2$-C(Z)aeg-[Taeg]$_2$-C(Z)aeg-[Taeg]$_4$-Lys(ClZ)-MBHA resin. The crude product was purified to give 1.2 mg of H-[Taeg]$_2$-Caeg-[Taeg]$_2$-Caeg-[Taeg]$_4$- Lys-NH$_2$ (>99.9% purity).

EXAMPLE 107

Synthesis of a PNA With Two Anti Parallel Strands Tied Together

Figure 26:
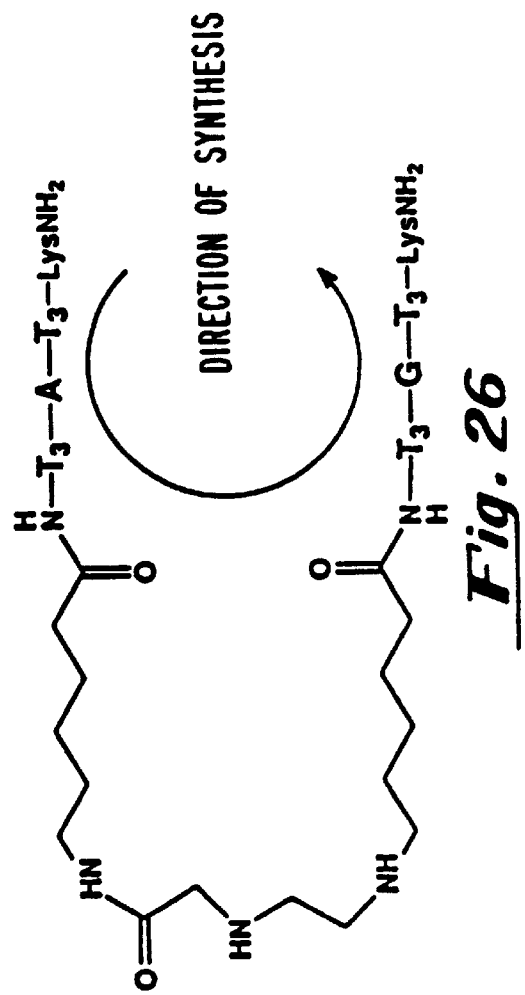
FIG. 26 shows the direction of synthesis for a peptide nucleic acid according to the invention.

Synthesis of H-[Taeg]-[Taeg]-[Taeg]-[Gaeg]-[Taeg]-[Taeg]-[Taeg]-[6-AHA]-[aeg]-[6-AHA]-[Taeg]-[Taeg]-[Taeg]-[Aaeg]-[Taeg]-[Taeg]-[Taeg]-LYS-NH$_2$. (6-AHA=6-aminohexanoic Acid) (FIG. 26)

The protected PNA was assembled onto a Boc-Lys(ClZ) modified MBHA resin with a substitution of approximately 0.30 mmol/g. Capping of uncoupled amino groups was only carried out before the incorporation of the BocGaeg-OH monomer. Synthesis was initiated on 1.00 g (dry weight) of preswollen (overnight in DCM) and neutralized Boc-Lys (ClZ)-MBHA resin. The incorporation of the monomers followed the protocol of Example 32 and Example 71. The coupling reaction was monitored by qualitative ninhydrin reaction (kaiser test). In case of a positive Kaiser test, the coupling reaction was repeated until the test showed no coloration of the beads. Final deprotection, cleavage from support, and purification were performed according to standard procedures.

EXAMPLE 108

Alternative protecting group strategy for PNA-synthesis (FIG. 27)

(a) Synthesis of Test Compounds 2-amino-6-O-benzyl purine. To a solution of 2.5 g (0.109 mol) of sodium in 100 ml of benzyl alcohol was added 10.75 g (0.063 mol) of 2-amino-6-chloropurine. The mixture was stirred for 12 h at 120 0° C. The solution was cooled to room temperature and neutralized with acetic acid and extracted with 10 portions of 50 ml of 0.2 N sodium hydroxide. The collected sodium hydroxide phases were washed with 100 ml of diethyl ether and neutralized with acetic acid, whereby precipitation starts. The solution was cooled to 0° C. and the yellow precipitate was collected by filtration. Recrystallization from ethanol gave 14.2 g 92% of pure white crystals of the target compound. 1H-NMR (250 MHz—DMSO-d6) d ppm: 8-H, 7.92; benzyl aromatic, 7.60–7.40; 2NH$_2$, 6.36; benzyl CH2, 5.57.

(2-amino-6-O-benzyl purinyl)methylethanoate. A mixture of 5 g (0.0207 mol) of 2-amino-6-O-benzyl-purine, 30 ml of DMF and 2.9 g (0.021 mol) of potassium carbonate was stirred at room temperature. Methyl bromoacetate (3.2 g; 1.9 ml; 0.0209 mol) was added dropwise. The solution was filtrated after 4 h and the solvent was removed under reduced pressure (4 mmHg, 40° C.). The residue was recrystallized two times from ethyl acetate to give 3.7 g (57%) of the target compound. 1H-NMR (250 MHz, DMSO-d6) d ppm: 8-H, 7.93; benzyl aromatic 7.4–7.6; 2—NH$_2$, 6.61; benzyl CH2, 5.03; CH2, 5.59; OCH3, 3.78.

(2N-p-Toluene sulfonamido-6-O-benzyl purinyl)methyl ethanoate. To a solution of 0.5 g (1.6 mmol) of (2-amino-6-O-benzyl purinyl)methyl ethanoate in 25 ml methylene chloride was added 0.53 g (1.62 mmol) of p-toluenesulfonic anhydride and 0.22 g (1.62 mmol) of potassium carbonate. The mixture was stirred at room temperature. The mixture was filtered and the solvent was removed at reduced pressure (15 mmHg, 40° C.). Diethyl ether was added to the oily residue. The resulting solution was stirred overnight, whereby the target compound (0.415 mg; 55%) precipitated and was collected by filtration. 1H-NMR (250 MHz, DMSO-d6) d ppm: 8-H, 8.97; aromatic 7.2–7.8; benzyl CH2, 5,01; CH2, 4.24; OCH3, 3.73; CH3, 2.43.

(b) Stability of the Tosyl Protected Base-residue in TFA and HF

The material was subjected to the standard deprotection conditions (TFA-deprotection) and the final cleavage conditions with HF. The products were then subjected to HPLC-analysis using a 4 $\mu$ RCM 8×10 Nova pack column and solvents A (0.1% TFA in water) and B (0.1% TFA in acetonitrile) according to the following time gradient with a flow of 2 ml/min.

| Time | % A | % B |
|------|-----|-----|
| 0 | 100 | 0 |
| 5 | 100 | 0 |
| 35 | 0 | 100 |
| 37 | 0 | 100 |
| 39 | 100 | 0 |

The following retention times were found: (a) Compound 1: 30.77 min; (b) compound 2: 24.22 min; and (c) compound 3: 11.75 min. The analysis showed that the O6-benzyl group was removed both by TFA and HF, whereas there was no cleavage of the tosyl group in TFA, but quantitative removal in HF under the standard cleavage conditions.

EXAMPLE 109

5-Bromouracil-N$^1$-methyl Acetate

5-Bromouracil (5.00 g; 26.2 mmol) and potassium carbonate (7.23 g; 52.3 mmol) were suspended in DMF (75 ml). Methyl bromoacetate (2.48 ml; 26.1 mmol) was added over a period of 5 min. The suspension was stirred for 2 h at room temperature, and then filtered. The solid residue was washed twice with DMF, and the combined filtrates were evaporated to dryness in vacuo. The residue was an oil containing the title compound, DMF and some unidentified impurities. It is not necessary to purify the title compound before hydrolysis. $^1$H-NMR (DMSO-d$_6$, 250 MHz); 8.55 (impurity); 8.27 (CBr=C$\underline{H}$N); 8.02 (impurity); 4.76 (impurity); 4.70 (impurity); 4.62 (NC$\underline{H}_2$COOCH$_3$); 3.78 (COOC$\underline{H}_3$); 2.96 (DMF); 2.80 (DMF). $^{13}$C-NMR (DMSO-d$_6$, 250 MHz); 168.8 ($\underline{C}$OOCH$_3$); 172.5 (CH=CBr$\underline{C}$ON); 161.6 (DMF); 151.9 (N$\underline{C}$ON); 145.0 (CO—CBr=$\underline{C}$HN); 95.6 (CO $\underline{C}$Br=CHN); 52.6 (impurity); 52.5 (O$\underline{C}$H$_3$); 49.7 (impurity); 48.8 (N$\underline{C}$H$_2$COOMe); 43.0 (impurity); 36.0 (DMF). UV(Methanol; $_{max}$nm); 226; 278. IR (KBr;cm$^{-1}$__; 3158s (_NH); 1743vs (_C=O, COOMe); 170lvs (_C=O, CONH); 1438vs ($\partial$ CH, CH$_3$O); 1223vs (_C—O, COOMe); 864 m ($\partial$ CH, Br=C—H). FAB-MS m/z (assignment): 265/263 (M+H).

EXAMPLE 110

(5-Bromouracil)acetic Acid

Water (30 ml) was added to the oil of the crude product from Example 109 and the mixture was dissolved by adding sodium hydroxide (2M, 60 ml). After stirring at 0° C. for 10 min, hydrochloric acid (4M, 45 ml) was added to pH=2 and the title compound precipitated. After 50 min, the solid residue was isolated by filtration, washed once with cold water, and then dried in vacuo over sicapent. Yield: 2.46 g (38%). Mp, 250°–251° C. Anal. for C$_6$H$_5$BrN$_2$O$_4$. Found (calc.): C, 28.78 (28.94); H, 2.00 (2.02); Br, 32.18 (32.09); N, 11.29 (11.25). $^1$H-NMR (DMSO-d$_6$, 250 MHz): 12,55 (1H.s,COO$\underline{H}$); 11.97 (1H,s,N$\underline{H}$); 8.30 (1H,s,C=C—$\underline{H}$); 4.49 (2H,s,NC$\underline{H}_2$COOH). $^{13}$C-NMR (DMSO-d$_6$, 250 MHz); 169.4 ($\underline{C}$OOH); 159.8 (NH$\underline{C}$OCBr=CH); 150.04 (N $\underline{C}$ON); 145.8 (CO$\underline{C}$Br=$\underline{C}$HN); 94.6 (CO$\underline{C}$Br=CHN); 48.8 (N$\underline{C}$H$_2$COOH). UV (Methanol; $_{max}$nm); 226; 278. IR (KBr; cm$^{-1}$); 3187s (_NH); 1708vs (_C=O,COOH); 1687vs; 1654VS (_C=O, CONH); 1192s (_C—O, COOH); 842 m ($\partial$ CH, Br—C=C—H). FAB-MS m/z (assignment, relative intensity); 251/249 (M +H,5).

EXAMPLE 111

N-(Boc-aminoethyl)-N-(5-bromouracil) methylenecarbonoylglycine Ethyl Ester

Boc-aminoethylglycine ethyl ester (1.80 g; 7.30 mmol) was dissolved in DMF (10 ml). Dhbt-OH (1.31 g; 8.03 mmol) was added, whereby a precipitate was formed. DMF (2×10 ml) was added until the precipitate was dissolved. The product of Example 110 (2.00 g; 8.03 mmol) was added slowly to avoid precipitation. Methylene chloride (30 ml) was added, and the mixture was cooled to 0° C. and then filtered. The precipitate, DCU, was washed twice with methylene chloride. To the combined filtrate was added methylene chloride (100 ml). The mixture was washed with half saturated NaHCO$_3$-solution (3×100 ml, H$_2$O:saturated NaHCO$_3$-solution 1:1 v/v), then with dilute KHSO$_4$-solution (2×100 ml, H$_2$O:saturated KHSO$_4$-solution 4:1 v/v), and finally with saturated NaCl-solution (1×100 ml). The organic phase was dried over magnesium sulphate, filtered, and evaporated to dryness in vacuo (about 15 mmHg and then about 1 mmHg). The residue was suspended in methylene chloride (35 ml), stirred for 45 min at room temperature, and filtered (the precipitate was DCU). Petroleum ether (2 volumes) was added dropwise to the filtrate at 0° C., whereby an oil precipitated. The liquor was decanted and the remaining oil dissolved in methylene chloride (20–50 ml). Precipitated was effected by the addition of petroleum ether (2 volumes). This procedure was repeated 5 times until an impurity was removed. The impurity can be seen at TLC with 10% MeOH/CH$_2$Cl$_2$ as the developing solvent. The resulting oil was dissolved in methylene chloride (25 ml) and evaporated to dryness in vacuo, which caused solidification of the title compound. Yield: 2.03 g ((58%). Mp. 87°–90° C. Anal. for C$_{17}$H$_{25}$BrN$_4$O$_7$. Found (calc.): C, 42.33 (42.78); H, 5.15 (5.28); Br, 17.20 (16.74); N, 1.69 (11.74). $^1$H-NMR (DMSO-d$_6$, 250 MHz, J in Hz): 1.93 & 11.92 (1H,s,C=ONH$\underline{C}$=O); 8.09 & 8.07 (1H,s, C=C—$\underline{H}$); 7.00 & 6.80 (1H,t,b,BocN$\underline{H}$); 4.80 & 4.62 (2H,s,NC$\underline{H}_2$CON); 4.35 & 4.24 (2H,s,NC$\underline{H}_2$COOEt); 4.27–4.15 (2H,m's, COOC$\underline{H}_2$CH$_3$O); 3.47–3.43 (2H,m's, BocNHCH$_2$C$\underline{H}_2$N); 3.28–3.25 & 3.12–3.09 (2H,m's, BocNHC$\underline{H}_2$CH—$_2$N); 1.46 & 1.45 (9H,s,$^t$Bu); 1.26 & 1.32 (3H,t,J=7.1, COOCH$_2$C$\underline{H}_3$). $^{13}$C-NMR (DMSO-d$_6$, 250 MHz); 169.3 & 169.0 ($^t$BuO$\underline{C}$=O); 167.4 & 167.1 ( $\underline{C}$OOEt); 159.8 (C=C—$\underline{C}$ON); 155.9 (NCH$_2$$\underline{C}$ON); 150.4 (N$\underline{C}$ON); 145.9 (COCBr—$\underline{C}$HN); 94.5 (CO$\underline{C}$Br=CHN); 78.2 (Me$_3$$\underline{C}$); 61.3 & 60.7 (CO$\underline{C}$H$_2$CH$_3$); 49.1 & 48.0 (N $\underline{C}$H$_2$COOH); 48.0 & 47.0 (N$\underline{C}$H$_2$CON); 38.6 (BocNHCH$_2$ $\underline{C}$H$_2$N); 38.2 (BocNH$\underline{C}$H$_2$CH$_2$N); 26.3 (C($\underline{C}$H$_3$)$_3$); 14.1 (COCH$_2$$\underline{C}$H$_3$). UV (Methanol; $_{max}$NM): 226; 280. IR (KBr, CM$^{-1}$); 3200 ms, broad (_NH); 168vs, vbroad (_C=O, COOH, CONH); 1250s (_C—O, COOEt); 1170s (_C—O, COO$^t$Bu); 859m ($\partial$ CH, Br—C=C—H). FAB-MS m/z (assignment, relative intensity): 479/477 (M+H, 5); 423/421 (M+2H-$^t$Bu, 8); 379/377 (M+2H–Boc, 100); 233/231 (M–backbone, 20).

EXAMPLE 112

N-(Boc-aminoethyl)-N-(5-bromouracyl-N$^1$-methylenecarbonoyl)-glycine

The product of Example 111 (1.96 g; 4.11 mmol) was dissolved in methanol (30 ml) by heating, and then cooled to 0° C. Sodium hydroxide (2M, 30 ml) was added, and the mixture stirred for 30 min. HCl (1M, 70 ml) was added to pH=2.0. The water phase was extracted with ethyl acetate (3×65 ml+7×40 ml). The combined ethyl acetate extractions were washed with saturated NaCl-solution (500 ml). The ethyl acetate phase was dried over magnesium sulphate, filtered and evaporated to dryness in vacuo. Yield: 1.77 g (96%). Mp. 92°–97° C. Anal. for C$_{15}$H$_{21}$BrN$_4$O$_7$. Found (calc.): C, 40.79 (40.10); H, 5.15 (4.71); Br, 14.64 (17.70); N, 11.35 (12.47). $^1$H-NMR (DMSO-d$_6$, 250 MHz, J in Hz):

12.83 (1H,s,COO$\underline{H}$); 11.93 & 11.91 (1H,s,C=ON$\underline{H}$C=O); 8.10 & 8.07 (1H,s,C=C—$\underline{H}$); 7.00 & 6.81 (1H,t,b,BocN$\underline{H}$); 4.79 & 4.61 (2H,s,NC$\underline{H}_2$CON); 4.37 & 4.25 (2H,s,NC$\underline{H}_2$COOH); 3.46–3.39 (2H,m's, BocNHCH$_2$C$\underline{H}_2$N); 3.26–3.23 & 3.12–3.09 (2H,m's, BocNHC$\underline{H}_2$CH$_2$N); 1.46 (9H,s,$^t$Bu). $^{13}$C-NMR 9DMSO-d$_6$,250 MHz); 170.4 ($^t$BuO$\underline{C}$=O); 166.9($\underline{C}$OOH); 159.7 (C=C—$\underline{C}$ON); 155.8 (NCH$_2$$\underline{C}$ON); 150.4 (N$\underline{C}$ON); 145.9 (COCBr=$\underline{C}$HN); 94.4 (CO$\underline{C}$Br=CHN); 78.1 (Me$_3$$\underline{C}$); 49.1 & 48.0 (N$\underline{C}$H$_2$COOH); 47.7 & 47.8 (N$\underline{C}$H$_2$CON); 38.6 (BocNHC$_2$$\underline{C}$H$_2$N); 38.1 (Boc NH$\underline{C}$H$_2$CH$_2$N); 28.2 (C($\underline{C}$H$_3$)$_3$). UV (Methanol; $_{max}$nm); 226; 278. IR (KBr,cm$^{-1}$): 3194 ms, broad (_NH); 1686vs, vbroad (_C=O COOH, CONH); 1250s (_C—O, COOH); 1170s (_C—O,COO$^t$Bu); 863m ($\partial$ CH, Br—C=C—H). FAB-MS m/z (assignment, relative intensity): 449/451 (M+H, 70); 349/351 (M+2H–Boc, 100); 231/233 (M–backbone, 20).

EXAMPLE 113

Uracil-N$^1$-methyl Acetate

Uracil (10.0 g; 89.2 mmol) and potassium carbonate (24.7 g; 178 mmol) were suspended in DMF (250 ml). Methyl bromoacetate (8.45 ml; 89.2 mmol) was added over a period of 5 min. The suspension was stirred overnight under nitrogen at room temperature, and then filtered. TLC (10% methanol in ethylene chloride) indicated incomplete conversion of uracil. The solid residue was washed twice with DMF, and the combined filtrates were evaporated to dryness in vacuo. The precipitate was suspended in water (60 ml) and HCl (2.5 ml, 4M) was added to pH=2. The suspension was stirred for 30 min at 0° C., and then filtered. The precipitated title compound was washed with water and dried, in vacuo, over sicapent. Yield: 9.91 g (60%). Mp. 1820–183° C. Anal. for C$_6$H$_8$N$_2$O$_4$. Found (calc.): C, 45.38 (45.66); H, 4.29 (4.38); N, 15.00 (15.21). $^1$H-NMR (DMSO-d$_6$, 250 MHz, J in Hz): 1.47 (1H,s, N$\underline{H}$); 7.68 (1H,d,J$_{H—C=C—H}$=7.9), CH=C$\underline{H}$N); 5.69 (1H,d,J$_{H—C—C—H}$=7.9), C$\underline{H}$=CHN); 4.59 (2H,s,NC$\underline{H}_2$COOMe); 3.76 (3H,s,COOC$\underline{H}_3$). $^{13}$C-NMR (DMSO-d$_6$, 250 MHz); 168.8 ($\underline{C}$OOMe); 164.0 (C=C—$\underline{C}$ON); 151.1 (N$\underline{C}$ON); 146.1 (COCH=$\underline{C}$HN); 101.3 (CO$\underline{C}$H=CHN); 52.5 (COO$\underline{C}$H$_3$); 48.7 (N$\underline{C}$H$_2$COOMe). UV (Methanol; $_{max}$nm): 226; 261. IR (KBr; cm$^{-1}$); 3164s (_NH); 1748vs (_C=O, COOMe); 1733vs (_C=O, CONH); 1450vs ($\partial$ CH, CH$_3$O); 1243VS (_C—O,COOMe); 701m ($\partial$ CH, H—C=C—H). FAB-MS m/z (assignment); 185 (M+H).

EXAMPLE 114

Uracilacetic Acid

Water (90 ml) was added to the product of Example 113 (8.76 g; 47.5 mmol), followed by sodium hydroxide (2M, 40 ml). The mixture was heated for 40 min, until all the methyl ester has reacted. After stirring at 0° C. for 15 min, hydrochloric acid (4M, 25 ml) was added to pH=2. The title compound precipitated and the mixture was filtered after 2–3 h. The precipitate was washed once with the mother liquor and twice with cold water and dried in vacuo over sicapent. Yield: 6.66 g (82%). Mp. 288°–289° C. Anal. for C$_6$H$_6$N$_2$O$_4$. Found (calc.): C, 42.10 (42.36), H, 3.43 (3.55); N, 16.25 (16.47)/$^1$H-NMR (DMSO-d$_6$), 250 MHz, J in Hz): 13.19 (1H,s,COO$\underline{H}$); 11.41 (1H,s,N$\underline{H}$); 7.69 (1H,d,J$_{H—C=C—H}$=7.8, J$_{H—C—C—N—H}$=2.0, coc$\underline{h}$=chn); 4.49 (2H,s, NC$\underline{H}_2$COOH). $^{13}$C-NMR (DMSO-d$_6$, 2509 MHz); 169.9 ($\underline{C}$OOH); 163.9 (CH=CH$\underline{C}$ON); 151.1 (N$\underline{C}$ON); 146.1 (CO$\underline{C}$H=$\underline{C}$HN); 100.9 (CO$\underline{C}$H=CHN); 48.7 NC$\underline{C}_2$COOH.

UV (Methanol; $_{max}$nm): 246; 263. IR (KBr; cm$^{-1}$) 3122s (_NH); 1703vs (_C=O, COOH); 1698vs, 1692vs (_C=O, CONH); 1205s (_C—O,COOH); 676 ($\partial$ CH, H—C=C—H). FAB-MS m/z (assignment): 171 (M+H).

EXAMPLE 115

N-(Bocaminoethyl)-N-(uracil-N$^1$-methylenecarbonoyl)glycine Ethyl Ester (Bocaminoethyl)glycine ethyl ester (2.00 g; 8.12 mmol) was dissolved in DMF (10 ml). Dhbt-OH (1.46 g; 8.93 mmol) was added and a precipitate was formed. DMF (2×10 ml) was added until all was dissolved. The product of Example 114 (1.52 g; 8.93 mmol) was added slowly to avoid precipitation. Methylene chloride (30 ml) was added, and the mixture was cooled to 0° C., whereafter DDC (2.01 g; 9.74 mmol) was added. The mixture was stirred for 1 h at 0° C., at 2 h at room temperature, and then filtered. The precipitated DCU was washed twice with methylene chloride. To combined filtrate was added methylene chloride (100 ml), and the solution washed with half-saturated NaHCO3-solution (3×100 ml, H$_2$O:saturated NaHCO$_3$-solution 1:1 v/v), then with dilute KHSO$_4$solution (2×100 ml, H$_2$O:saturated KHSO$_4$-solution 4:1 v/v) and finally with saturated NaCl-solution (1×100 ml). The organic phase was dried over magnesium sulphate, filtered and evaporated to dryness in vacuo (about 15 mmHg and then about 1 mmHg). The residue was suspended in methylene chloride (32 ml), and stirred for 35 min at room temperature, and 30 min at 0° C., and then filtered. The precipitate (DCU) was washed with methylene chloride. Petroleum ether (2 volumes) was added dropwise to the combined filtrate at 0° C., which caused separation of an oil. The mixture was decanted, the remaining oil was then dissolved in methylene chloride (20 ml), and then again precipitated by addition of petroleum ether (2 volumes). This procedure was repeated 5 times until an impurity was removed. The impurity can be seen by TLC with 10% MeOH/CH$_2$Cl$_2$ as the developing solvent. The resulting oil was dissolved in methylene chloride (20 ml) and evaporated to dryness in vacuo, which caused solidification of the title compound. Yield: 1.71 g (53%). Mp. 68.50°–75.7° C. Anal for C$_{17}$H$_{26}$N$_4$O$_7$. Found (calc.): C, 50.61 (51.25); H, 6.48 (6.58); N, 13.33 (14.06). $^1$H-NMR (DMSO-d$_6$,250 MHZ,J in Hz): 11.36 (1H,s,C=ON$\underline{H}$C=O); 7.51 & 7.47 (1H,d,J$_{H—C=C—H}$+6.1; COCH=X—$\underline{H}$); 7.00 & 6.80 (1H,t,b, BocN$\underline{H}$); 5.83 & 5.66 (1H,d,J$_{H—C=C—H}$=5.7, COC$\underline{H}$=CH); 4.78 & 4.60 (2H,s, NC$\underline{H}_2$CON); 4.37 & 4.12 (2H,s,NC$\underline{h}_2$COOEt); 4.30–4.15 (2H,m's,COOC$\underline{H}_2$CH$_3$); 3.49–3.46 (2H,m's, BocNHCH$_2$C$\underline{H}_2$N); 3.27 3.23 & 3.11–3.09 (2H, m's, BocNHC$\underline{H}_2$CH$_2$N; 1.46 (9H, s, $^t$Bu); 1.39–1.23 (3H, m's, COOCH$_2$C$\underline{H}_3$). $^{13}$C-NMR (DMSO-d$_6$, 250 MHz): 169.4 & 169.0 ($^t$BuO$\underline{C}$=O); 167.6 & 167.3 ($\underline{C}$OOEt); 163.8 (CH=CH$\underline{C}$ON); 155.8 (NCH$_2$$\underline{C}$ON); 151.0 (N$\underline{C}$ON); 146.3 (CO$\underline{C}$H=$\underline{C}$HN); 100.8 (CO$\underline{C}$H=CHN); 78.1 (Me$_3$$\underline{C}$); 61.2 & 60.6 (COO$\underline{C}$H$_2$CH$_3$); 49.1 (N$\underline{C}$H$_2$COOEt); 47.8 & 47.0 (N$\underline{C}$H$_2$CON); 38.6 (BocNHCH$_2$$\underline{C}$H$_2$N); 38.1 & 37.7 (BocNH$\underline{C}$H$_2$N); 28.2 (C($\underline{C}$H$_3$)$_3$); 14.1 (CO—OCH$_2$$\underline{C}$H$_3$. UV (Methanol; $_{max}$ nm); 226; 264. IR (KBr; cm$^{-1}$): 3053m (_NH); 1685vs, vbroad (_C=O, COOH, CONH); 1253s (_C—O, COOEt); 1172s (_C—O, COO$^t$Bu); 718w ($\partial$ CH, C—C—C—H), FAB-MS m/z (assignment, relative intensity); 399 (M+H, 35); 343 (M+2H–$^t$Bu, 100); 299 (M+2H–Boc, 100); 153 (M–backbone, 30).

EXAMPLE 116

N-(Bocaminoethyl)-N-(uracilmethylenecarbonoyl) glycine

The product of Example 115 (1.56 g; 3.91 mmol) was dissolved in methanol (20 ml) and then cooled to 0° C.

Sodium hydroxide (2M, 20 ml) was added, and the mixture was stirred for 75 min at 0° C. Hydrochloric acid (1M, 46 ml) was added to pH=2.0. The water phase was extracted was ethyl acetate (3×50 ml+7×30 ml). The combined ethyl acetate extractions were washed with saturated NaCl solution (360 ml). The ethyl acetate phase was dried over magnesium sulphate, filtered, and evaporated to dryness, in vacuo. The residue was dissolved in methanol and evaporated to dryness, in vacuo. Yield: 0.55 g (38%). Mp 164°–170° C. Anal. for $C_{15}H_{22}N_4O_7$. Found (calc.): C, 46.68 (48.65); H, 6.03 (5.99); N, 1461 (15.13). $^1$H-NMR (DMSO-$d_6$, 250 MHz, J in Hz); 12.83 (1H, s, COO$\underline{H}$); 11.36 (1H, s, C=ON$\underline{H}$C=O); 7.52–7.45 (1H, m's, COCH=C $\underline{H}$N); 7.00 & 6.82 (1H, t,b, BocN$\underline{H}$); 5.67–5.62 (1H, M's, COC$\underline{H}$=CHN); 4.76 & 4.58 (2H, s, NC$\underline{H}_2$CON); 4.26 & 4.05 (2H, s, NC$\underline{H}_2$COOH); 3.46–3.39 (2H, m's, BocNHCH$_2$C$\underline{H}_2$N); 3.25–3.23 & 3.15–3.09 (2H, m's, Boc-NHC$\underline{H}_2$CH$_2$N); 1.46 (9H, s, $^t$Bu). $^{13}$C-NMR (DMSO-$d_6$, 250 MHz); 170.5 ($^t$BuO$\underline{C}$=O); 167.2 (COOH); 163.9 (C=C—$\underline{C}$ON); 155.8 (NCH$_2$$\underline{C}$ON); 151.1 (N$\underline{C}$ON); 146.4 (COCH=$\underline{C}$HN); 100.8 (CO$\underline{C}$H=CHN); 78.1 (Me$_3$$\underline{C}$); 49.1 & 47.8 (N$\underline{C}$H$_2$ COOH); 47.6 & 46.9 (N$\underline{C}$H$_2$CON); 38.6 (BocNHCH$_2$$\underline{C}$H$_2$N); 38.1 & 37.6 (BocNH$\underline{C}$H$_2$CH$_2$N); 28.2 (C($\underline{C}$H$_3$)$_3$). UV (Methanol; $_{max}$ nm); 226; 264. IR (KBr; cm$^{-1}$); 3190 (_NH); 1685vs, vbroad (_C=O, COOH, CONH); 1253s (_C—O, COOH); 1171s (_C—O, COO$^t$BU); 682w ($\partial$ CH, H—C=C—H). FAB-MS m/z (assignment, relative intensity): 371 (M+H, 25); 271 (M+H–Boc, 100).

EXAMPLE 117

H-U10-LysNH$_2$

Synthesis of the title compound was accomplished by using "Synthetic Protocol 10". The synthesis was initiated on approximately 100 mg Lys (ClZ)-MHBA-resin. The crude product (12 mg) was pure enough for hybridization studies. The hybrid between 5'-(dA)10 and H-U10 had Tm of 67.5° C.

EXAMPLE 118

Deprotection and Cleavage of H-[Cacg]$_{10}$-Lys-NH$_2$ by Trifluoromethansulfonic Acid (TFMSA). An Alternative Method to Deprotection and Cleavage by Hydrogen Fluoride (HF)

(a) Deprotection of Side-Chain Protecting Groups by a "Low-Acidity" TFMSA-TFA-DMS Procedure A portion of ca. 0.4 g wet Boc-[Cacg]$_{10}$-Lys(ClZ)-MBHA resin (prepared in one of the previous examples) was placed in a 5 ml solid-phase reaction vessel. The n-Terminal Boc group was removed by the following protocol: (1) 50% TFA/CH$_2$Cl$_2$, 2×1 min and 1×30 min; (2) 100% TFA, 2×1 min and drain. In order to deprotect the benzyl-based side-chain protecting groups a so-called "low-acidity" TFMSA procedure was carried out as follows: A stock solution (a) containing 5 ml of TFA-DMS-m-cresol (2:6:2, v/v/v) and a stock solution (B) containing TFA-TFMSA (8:2, v/v) were prepared. Next, the following steps were carried out: (3) 1 ml of stock solution (A) is added to the PNA-resin in the reaction vessel with shaking for 2 min. No drain; (4) 1 ml of stock solution (B) (cooled with ice/water) is added in portions of 200 μl every 10th minute over a period of 40 min, and shaking is continued for another 50 min; (5) drain and washing with 100% TFA, 5×1 min. and drain.

(b) Cleavage from the Resin by a "High-Acidity" TFMSA-TFA Procedure

In order to cleave the above-mentioned deprotected PNA from the resin a so-called "high acidity" TFMSA procedure was carried out as follows: A stock solution (C) containing m-cresol-TFA (2:8, v/v) was prepared. Next, the following steps were carried out: (6) 1 ml of stock solution (C) was added to the deprotected PNA-resin in the SPPS vessel with shaking for 2 min; (7) 1 ml of stock solution (B) (cooled with ice/water) is added in portions of 200 μl over a period of 30 min and shaking is continued for another 150 min; (5) the 2 ml solutin in the reaction vessel is "blown out" through the filter into a 20 ml solution of diethylether cooled with dry ice/isopropanol. In order to complete the precipitation process, 200 μl of anhydrous pyridine is added dropwise to the acid-ether mixture; (8) centrifugalization at 3000 rpm for 5 min; (9) the supernatant is decanted and the precipitate is washed three times with cold diethylether, dried, dissolved in water, and lyophilized.

(c) Purification and Identification of H-[Caeg]$_{10}$-Lys-NH$_2$

An analytical HPLC chromatogram showed a nice crude product of good purity and a profile almost identical to that obtained from the HF cleavage of H-[Caeg]$_{10}$-Lys-NH$_2$, except that an additional peak, of course, arising from pyridine TFMSA salt elutes early in the chromatogram. Purification and identification was carried out by the usual procedures.

Those skilled in the art will appreciate that numerous changes and modifications may be made to the preferred embodiments of the invention and that such changes and modifications may be made without departing from the spirit of the invention. It is therefore intended that the appended claims cover all such equivalent variations as fall within the true spirit and scope of the invention.

What is claimed is:

1. A compound having one of the following formulas:

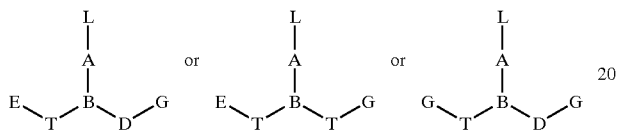

wherein:
L is a naturally occurring nucleobase, a non-naturally occurring nucleobase, a DNA intercalator, or a nucleobase-binding group, and amino groups are, optionally, protected by amino protecting groups;
A is a single bond or a group of the formula:

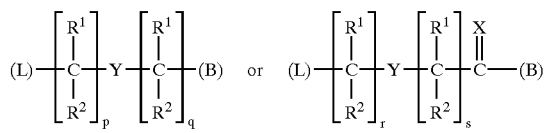

where:
X is O, S, Se, $NR^3$, $CH_2$ or $C(CH_3)_2$;
Y is:
  a single bond, O or S when s or q is zero; or
  a single bond, O, S or $NR^4$ when s or q is an integer from 1 to 5;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, $(C_1-C_4)$alkyl, hydroxy- or alkoxy- or alkylthio-substituted $(C_1-C_4)$ alkyl, hydroxy, alkoxy, alkylthio, amino and halogen; and
each $R^3$ and $R^4$ is independently selected from the group consisting of hydrogen, $(C_1-C_4)$alkyl, hydroxy- or alkoxy- or alkylthio-substituted $(C_1-C_4)$ alkyl, hydroxy, alkoxy, alkylthio and amino;
B is N or $R^3N^+$, where $R^3$ is as defined above;
each T is $CR^6R^7$, $CHR^6CHR^7$ or $CR^6R^7CH_2$, where $R^6$ is hydrogen and $R^7$ is selected from the group consisting of the side chains of naturally occurring alpha amino acids, or $R^6$ and $R^7$ are independently selected from the group consisting of hydrogen, $(C_2-C_6)$alkyl, aryl, aralkyl, heteroaryl, hydroxy, $(C_1-C_6)$alkoxy, $(C_1-C_6)$ alkylthio, $NR^3R^4$ and $SR^5$, where $R^3$ and $R^4$ are as defined above, and $R^5$ is hydrogen or $(C_1-C_6)$alkyl, hydroxy-, alkoxy-, or alkylthio-substituted $(C_1-C_6)$ alkyl, or $R^6$ and $R^7$ taken together complete an alicyclic or heterocyclic system;

D is $CR^6R^7$, $CH_2CR^6R^7$ or $CHR^6CHR^7$, where $R^6$ and $R^7$ are as defined above;
each E is, independently, COON or CSOH, or an activated or protected derivative thereof; and
each G is, independendy, $NHR^3$ or $NPgR^3$, where $R^3$ is as defined above, and Pg is an amino protecting group.

2. A compound having one of the following formulas:

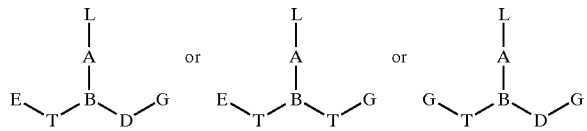

wherein:
L is a purine nucleobase and amino groups are, optionally, protected by amino protecting groups;
A is a single bond or a group of the formula:

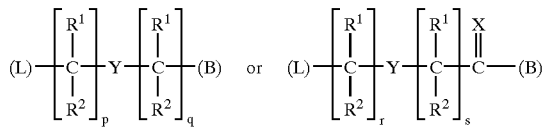

where:
X is O, S, Se, $NR^3$, $CH_2$ or $C(CH_3)_2$;
Y is:
  a single bond, O or S when s or q is zero; or
  a single bond, O, S or $NW^4$ when s or q is an integer from 1 to 5;
each of p and q is zero or an integer from 1 to 5, the sum p+q being not more than 10;
each of r and s is zero or an integer from 1 to 5, the sum r+s being not more than 10;
each $R^1$ and $R^2$ is independently selected from the group consisting of hydrogen, $(C_1-C_4)$alkyl, hydroxy- or alkoxy- or alkylthio-substituted $(C_1-C_4)$ alkyl, hydroxy, alkoxy, alkylthio, amino and halogen; and
each $R^3$ and $R^4$ is independently selected from the group consisting of hydrogen, $(C_1-C_4)$alkyl, hydroxy- or alkoxy- or alkylthio-substitited $(C_1-C_4)$ alkyl, hydroxy, alkoxy, alkylthio and amino;
B is N or $R^3N^+$, where $R^3$ is as defined above;
each T is $CR^6R^7$, $CHR^6CHR^7$ or $CR^6R^7CH_2$, where $R^6$ is hydrogen and $R^7$ is selected from the group consisting of the side chains of naturally occurring alpha amino acids other than lysine, or $R^6$ and $R^7$ are independently selected from the group consisting of hydrogen, $(C_2-C_6)$alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen or ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

D is $CR^6R^7$, $CH_2CR^6R^7$ or $CHR^6CHR^7$, where $R^6$ and $R^7$ are as defined above;

each E is, independently, COOH or CSOH, or an activated or protected derivative thereof; and each G is, independently, $NHR^3$ or $NPgR^3$, where $R^3$ is as defined above, and Pg is an amino protecting group.

3. A compound having one of the following formulas:

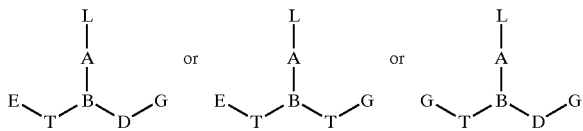

wherein:

L is a pyrimidine nucleobase and amino groups are, optionally, protected by amino protecting groups;

A is a single bond or a group of the formula:

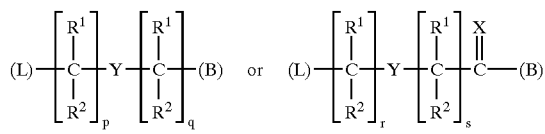

where:

X is O, S, Se, $NR^3$, $CH_2$ or $C(CH_3)_2$;

Y is:
a single bond, O or S when s or q is zero; or
a single bond, O, S or $NR^4$ when s or q is an integer from 1 to 5;

each of p and q is zero or an integer from 1 to 5, the sum p+q being not more than 10;

each of r and s is zero or an integer from 1 to 5, the sum r+s being not more than 10;

each $R^1$ and $R^2$ is independently selected from the group consisting of hydrogen, ($C_1$–$C_4$)alkyl, hydroxy- or alkoxy- or alkylthio-substituted ($C_1$–$C_4$) alkyl, hydroxy, alkoxy, alkylthio, amino and halogen; and each $R^3$ and $R^4$ is independently selected from the group consisting of hydrogen, ($C_1$–$C_4$)alkyl, hydroxy- or alkoxy- or alkylthio-substituted ($C_1$–$C_4$) alkyl, hydroxy, alkoxy, alkylthio and amino;

B is N or $R^3N^+$, where $R^3$ is as defined above;

each T is $CR^6R^7$, $CHR^6CHR^7$ or $CR^6R^7CH_2$, where $R^6$ is hydrogen and $R^7$ is selected from the group consisting of the side chains of naturally occurring alpha amino acids other than lysine, or $R^6$ and $R^7$ are independently selected from the group consisting of hydrogen, ($C_2$–$C_6$)alkyl, aryl, aralkyl, heteroaryl, hydroxy, ($C_1$–$C_6$)alkoxy, ($C_1$–$C_6$)alkylthio, $NR^3R^4$ and $SR^5$, where $R^3$ and $R^4$ are as defined above, and $R^5$ is hydrogen or ($C_1$–$C_6$)alkyl, hydroxy-, alkoxy-, or alkylthio-substituted ($C_1$–$C_6$)alkyl, or $R^6$ and $R^7$ taken together complete an alicyclic or heterocyclic system;

D is $CR^6R^7$, $CH_2CR^6R^7$ or $CHR^6CHR^7$, where $R^6$ and $R^7$ are as defined above;

each E is, independently, COOH or CSOH, or an activated or protected derivative thereof; and each G is, independently, $NHR^3$ or $NPgR^3$, where $R^3$ is as defined above, and Pg is an amino protecting group.

4. The compound of claim 1 having formula:

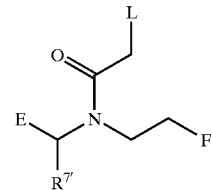

wherein:

L is selected from the group consisting of the nucleobases thymine, adenine, cytosine, guanine, uracil, 5-methylcytosine, 6-thioguanine 7-deazaguanine, 7-deaza,8-azaguanine, 2,6-diaminopurine, and 5-bromouracil, and protected derivatives thereof;

$R^{7'}$ is hydrogen;

E is COOH or an activated or protected derivative thereof; and

F is $NH_2$ or NHPg, where Pg is an amino protecting group.

5. The compound of claim 1 wherein Pg is tert-butoxycarbonyl or 9-fluorenylmethoxycarbonyl.

6. The compound of claim 4 wherein Pg is tert-butoxycarbonyl or 9-fluorenylmethoxycarbonyl.

7. The compound of claim 1 having the formula:

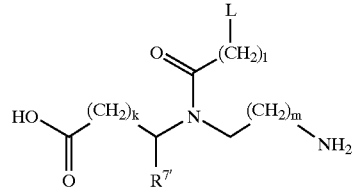

wherein:

L is selected from the group consisting of heterocyclic moieties, naturally occurring nucleobases, and non-naturally occurring nucleobases;

$R^7$ is selected from the group consisting of hydrogen and the side chains of naturally occurring alpha amino acids other than lysine;

l is zero or an integer from 1 to 5; and k and m are, independently, zero or 1.

8. The compound of claim 7 wherein $R^{7'}$ is hydrogen.

9. The compound of claim 7 wherein L is a naturally occurring nucleobase or a non-naturally occurring nucleobase.

10. The compound of claim 1 wherein L is a naturally occurring nucleobase or a non-naturally occurring nucleobase.

11. The compound of claim 2 wherein L is adenine.

12. The compound of claim 2 wherein L is guanine.

13. The compound of claim 2 wherein L is 6-thioguanine.

14. The compound of claim 2 wherein L is 7-deazaguanine.

15. The compound of claim 2 wherein L is 7-deaza,8-azaguanine.

16. The compound of claim 2 wherein L is 2,6-diaminopurine.

17. The compound of claim 3 wherein L is thymine.

18. The compound of claim 3 wherein L is cytosine.

19. The compound of claim 3 wherein L is uracil.

20. The compound of claim 3 wherein L is 5-methylcytosine.

21. The compound of claim 3 wherein L is 5-bromouracil.

22. The compound of claim 4 wherein L is thymine.

23. The compound of claim 22 wherein Pg is tert-butoxycarbonyl or 9-fluorenylmethoxycarbonyl.

24. The compound of claim 4 wherein L is adenine or a protected derivative thereof.

25. The compound of claim 24 wherein Pg is tert-butoxycarbonyl or 9-fluorenylmethoxycarbonyl.

26. The compound of claim 25 wherein Pg is tert-butoxycarbonyl and adenine is protected with a benzyloxycarbonyl protecting group.

27. The compound of claim 4 wherein L is cytosine or a protected derivative thereof.

28. The compound of claim 27 wherein Pg is tert-butoxycarbonyl or 9-fluorenylmethoxycarbonyl.

29. The compound of claim 4 wherein L is guanine or a protected derivative thereof.

30. The compound of claim 29 wherein Pg is tert-butoxycarbonyl or 9-fluorenylmethoxycarbonyl.

31. The compound of claim 4 wherein L is uracil.

32. The compound of claim 31 wherein Pg is tert-butoxycarbonyl or 9-fluorenylmethoxycarbonyl.

33. The compound of claim 4 wherein L is 5-methylcytosine or a protected derivative thereof.

34. The compound of claim 33 wherein Pg is tert-butoxycarbonyl or 9-fluorenylmethoxycarbonyl.

35. The compound of claim 4 wherein L is 6-thioguanine or a protected derivative thereof.

36. The compound of claim 35 wherein Pg is tert-butoxycarbonyl or 9-fluorenylmethoxycarbonyl.

37. The compound of claim 4 wherein L is 7-deazaguanine or a protected derivative thereof.

38. The compound of claim 37 wherein Pg is tert-butoxycarbonyl or 9-fluorenylmethoxycarbonyl.

39. The compound of claim 4 wherein L is 7-deaza,8-azaguanine or a protected derivative thereof.

40. The compound of claim 39 wherein Pg is tert-butoxycarbonyl or 9-fluorenylmethoxycarbonyl.

41. The compound of claim 4 wherein L is 2,6-diaminopurine or a protected derivative thereof.

42. The compound of claim 41 wherein Pg is tert-butoxycarbonyl or 9-fluorenylmethoxycarbonyl.

43. The compound of claim 4 wherein L is 5-bromouracil.

44. The compound of claim 43 wherein Pg is tert-butoxycarbonyl or 9-fluorenylmethoxycarbonyl.

45. A monomer synthon having the formula:

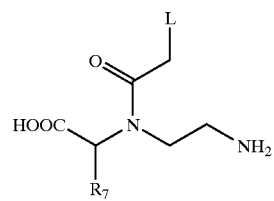

wherein $R_7$ is selected from the group consisting of hydrogen and the side chains of naturally occurring amino acids other than lysine and L is selected from the group consisting of thymine, adenine, cytosine, guanine and uracil, and said monomer synthon having one of amino-protection, acid terminal activation or both amino-protection and acid terminal activation.

46. The monomer synthon of claim 45 wherein L is adenine.

47. The monomer synthon of claim 45 wherein L is guanine.

48. The monomer synthon of claim 45 wherein L is thymine.

49. The monomer synthon of claim 45 wherein L is cytosine.

50. The monomer synthon of claim 45 wherein L is uracil.

51. The monomer synthon of claim 45 wherein $R_7$ is hydrogen.

52. The monomer synthon of claim 45 wherein $R_7$ is the side chain of a naturally occurring alpha amino acid other than lysine.

53. A monomer synthon having the formula:

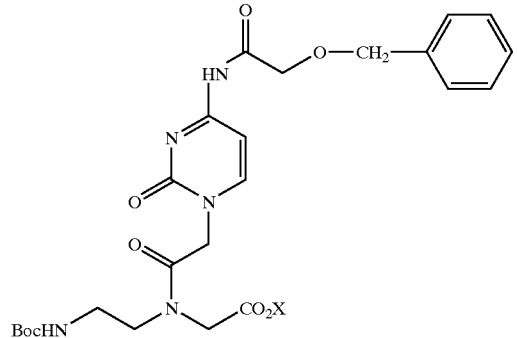

wherein X is hydrogen or pentafluorophenyl and Boc is tert-butoxycarbonyl.

54. The monomer synthon of claim 51 wherein L is adenine.

55. The compound of claim 51 wherein L is guanine.

56. The compound of claim 51 wherein L is thymine.

57. The compound of claim 51 wherein L is cytosine.

58. The compound of claim 51 wherein L is uracil.

* * * * *

UNITED STATES PATENT AND TRADEMARK OFFICE
CERTIFICATE OF CORRECTION

PATENT NO. : 6,710,163 B1
DATED : March 23, 2004
INVENTOR(S) : Ole Buchardt et al.

It is certified that error appears in the above-identified patent and that said Letters Patent is hereby corrected as shown below:

Column 100,
Line 17, delete "COON" insert -- COOH --;
Line 19, delete "independendy" and insert -- independently --;
Line 46, delete "$NW^4$" and insert -- $NR^4$ --;

Column 102,
Line 44, "$R^7$" and insert -- $R^{7'}$ --.

Signed and Sealed this

Second Day of May, 2006

JON W. DUDAS
*Director of the United States Patent and Trademark Office*

SEQUENCE LISTING

<160> NUMBER OF SEQ ID NOS: 48

<210> SEQ ID NO 1
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 1
gatccaaaaa aaaaag                                                    16

```
<210> SEQ ID NO 2
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 2
gatccttttt tttttg                                                    16

<210> SEQ ID NO 3
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 3
aaaaaaaaaa                                                           10

<210> SEQ ID NO 4
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 4
aaaaagaaaa aaaaaaaaag                                                20

<210> SEQ ID NO 5
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 5
aagaagaaaa aaaaaaaagg                                                20

<210> SEQ ID NO 6
<211> LENGTH: 8
<212> TYPE: DNA
<213> ORGANISM: Artificial Sequence
<220> FEATURE:
<223> OTHER INFORMATION: Oligonucleotide Primer

<400> SEQUENCE: 6 aaaaaaaa                                                              8

<210> SEQ ID NO 7
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 7
tttttttttt                                                           10

<210> SEQ ID NO 8
<211> LENGTH: 10
<212> TYPE: DNA
<213> ORGANISM: Artificial Sequence
<220> FEATURE:
```

<223> OTHER INFORMATION: Oligonucleotide Primer

<400> SEQUENCE: 8
aaaaagaaaa                                                              10

<210> SEQ ID NO 9
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 9
aagaagaaaa                                                              10

<210> SEQ ID NO 10
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 10
aaaagaaaaa                                                              10

<210> SEQ ID NO 11
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 11
aaaagaagaa                                                              10

<210> SEQ ID NO 12
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 12
ttttctttt                                                               10

<210> SEQ ID NO 13
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 13
ttttcttctt                                                              10

<210> SEQ ID NO 14
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 14
tttttctttt                                                              10

```
<210> SEQ ID NO 15
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 15
tttttcttct                                                              10

<210> SEQ ID NO 16
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 16
ttcttctttt                                                              10

<210> SEQ ID NO 17
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 17
tttttttttt ttttt                                                        15

<210> SEQ ID NO 18
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 18
aaaaaaaaaa aaaaa                                                        15

<210> SEQ ID NO 19
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 19
aaaaggagag                                                              10

<210> SEQ ID NO 20
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 20
gagaggaaaa                                                              10

<210> SEQ ID NO 21
<211> LENGTH: 10
<212> TYPE: DNA
<213> ORGANISM: Artificial Sequence
<220> FEATURE:
<223> OTHER INFORMATION: Oligonucleotide Primer
```

```
<400> SEQUENCE: 21
aaaagtagag                                                               10

<210> SEQ ID NO 22
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 22
aaaaggtgag                                                               10

<210> SEQ ID NO 23
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 23
gagatgaaaa                                                               10

<210> SEQ ID NO 24
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 24
gagtggaaaa                                                               10

<210> SEQ ID NO 25
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 25
aaaaataaaa                                                               10

<210> SEQ ID NO 26
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 26
aaaacaaaaa                                                               10

<210> SEQ ID NO 27
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 27
aaaataaaaa                                                               10

<210> SEQ ID NO 28
<211> LENGTH: 10
```

```
<212> TYPE: DNA
<213> ORGANISM: Artificial Sequence
<220> FEATURE:
<223> OTHER INFORMATION: Oligonucleotide Primer

<400> SEQUENCE: 28
aaaaacaaaa                                                              10

<210> SEQ ID NO 29
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 29
tcgacttttc tttttg                                                       16

<210> SEQ ID NO 30
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 30
tcgacaaaaa gaaaag                                                       16

<210> SEQ ID NO 31
<211> LENGTH: 15
<212> TYPE: DNA
<213> ORGANISM: Artificial Sequence
<220> FEATURE:
<223> OTHER INFORMATION: Oligonucleotide Primer

<400> SEQUENCE: 31
gaagaagaaa atgca                                                        15

<210> SEQ ID NO 32
<211> LENGTH: 17
<212> TYPE: DNA
<213> ORGANISM: Artificial Sequence
<220> FEATURE:
<223> OTHER INFORMATION: Oligonucleotide Primer

<400> SEQUENCE: 32
gttttcttct ttctgca                                                      17

<210> SEQ ID NO 33
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 33
gaagaagaaa agtgac                                                       16

<210> SEQ ID NO 34
<211> LENGTH: 16
<212> TYPE: DNA
<213> ORGANISM: Artificial Sequence
<220> FEATURE:
<223> OTHER INFORMATION: Oligonucleotide Primer

<400> SEQUENCE: 34
```

```
gttttcttct tctgca                                                   16
```

<210> SEQ ID NO 35
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 35

```
aatagtagtg                                                          10
```

<210> SEQ ID NO 36
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 36

```
attagtagtg                                                          10
```

<210> SEQ ID NO 37
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 37

```
gtgatgataa                                                          10
```

<210> SEQ ID NO 38
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 38

```
aaaaccacac                                                          10
```

<210> SEQ ID NO 39
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 39

```
cacaccaaaa                                                          10
```

<210> SEQ ID NO 40
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 40

```
ctaggttttt ttttcctag                                                20
```

<210> SEQ ID NO 41
<211> LENGTH: 20
<212> TYPE: DNA
<213> ORGANISM: Artificial Sequence

```
<220> FEATURE:
<223> OTHER INFORMATION: Oligonucleotide Primer

<400> SEQUENCE: 41
gatccaaaaa aaaaaggatc                                               20

<210> SEQ ID NO 42
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 42
ggatccaaaa aaaaaaggat cc                                            22

<210> SEQ ID NO 43
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 43
cctaggtttt tttttttccta gg                                           22

<210> SEQ ID NO 44
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 44
tttttttttt                                                          10

<210> SEQ ID NO 45
<211> LENGTH: 8
<212> TYPE: DNA
<213> ORGANISM: Artificial Sequence
<220> FEATURE:
<223> OTHER INFORMATION: Oligonucleotide Primer

<400> SEQUENCE: 45 tttttttt                                                             8

<210> SEQ ID NO 46
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 46
tttttctttt                                                          10

<210> SEQ ID NO 47
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 47
ttcttctttt                                                          10
```

-continued

```
<210> SEQ ID NO 48
<211> LENGTH: 10
<212> TYPE: DNA
<213> ORGANISM: Artificial Sequence
<220> FEATURE:
<223> OTHER INFORMATION: Oligonucleotide Primer

<400> SEQUENCE: 48
ttttattttt                                                              10
```